(12) United States Patent
Ricci

(10) Patent No.: US 11,379,541 B2
(45) Date of Patent: Jul. 5, 2022

(54) SYSTEM AND METHOD FOR ADAPTING A CONTROL FUNCTION BASED ON A USER PROFILE

(71) Applicant: AutoConnect Holdings LLC, Newbury, MA (US)

(72) Inventor: Christopher P. Ricci, Saratoga, CA (US)

(73) Assignee: AutoConnect Holdings LLC, Wellesley, MA (US)

( * ) Notice: Subject to any disclaimer, the term of this patent is extended or adjusted under 35 U.S.C. 154(b) by 0 days.

(21) Appl. No.: 17/233,369

(22) Filed: Apr. 16, 2021

(65) Prior Publication Data

US 2021/0232643 A1 Jul. 29, 2021

Related U.S. Application Data

(63) Continuation of application No. 16/289,518, filed on Feb. 28, 2019, which is a continuation-in-part of (Continued)

(51) Int. Cl.
*B60W 50/08* (2020.01)
*B60W 50/10* (2012.01)
(Continued)

(52) U.S. Cl.
CPC .......... *G06F 16/951* (2019.01); *A61B 5/0077* (2013.01); *A61B 5/4809* (2013.01);
(Continued)

(58) Field of Classification Search
CPC ... A61B 5/0077; A61B 5/4809; A61B 5/6808; A61B 5/7405; A61B 5/742; A61B 7/04;
(Continued)

(56) References Cited

U.S. PATENT DOCUMENTS 5,726,916 A 3/1998 Smyth
5,838,251 A 11/1998 Brinkmeyer et al.
(Continued)

FOREIGN PATENT DOCUMENTS

JP 2004341956 12/2004
KR 20100013527 2/2010

OTHER PUBLICATIONS

U.S. Appl. No. 13/678,673, filed Nov. 16, 2012, Ricci.
(Continued)

*Primary Examiner* — Charles J Han
(74) *Attorney, Agent, or Firm* — Fish & Richardson P.C.

(57) ABSTRACT

The vehicle control system/method for adapting a control function based on a user profile may comprise: a gesture recognition module; a user profile module; a function control module; a processor; a non-transitory storage element coupled to the processor; encoded instructions stored in the non-transitory storage element, wherein the encoded instructions when implemented by the processor, configure the system to: identify a user; retrieve a user profile for the identified user; receive at a gesture recognition module, an input indicating a gesture from the user; identify a control function request corresponding to the gesture input; send a verification of the control function request; and receive at a function control module characteristics parsed from the user profile that effect the control function request by the user profile module to adapt a control function command for an adapted control function output by the function control module.

21 Claims, 42 Drawing Sheets

Related U.S. Application Data application No. 14/253,321, filed on Apr. 15, 2014, now abandoned.

(60) Provisional application No. 61/811,981, filed on Apr. 15, 2013, provisional application No. 61/865,954, filed on Aug. 14, 2013, provisional application No. 61/870,698, filed on Aug. 27, 2013, provisional application No. 61/891,217, filed on Oct. 15, 2013, provisional application No. 61/904,205, filed on Nov. 14, 2013, provisional application No. 61/924,572, filed on Jan. 7, 2014, provisional application No. 61/926,749, filed on Jan. 13, 2014.

(51) Int. Cl.

| | |
|---|---|
| B60W 50/14 | (2020.01) |
| G06F 3/01 | (2006.01) |
| G06F 16/951 | (2019.01) |
| H04W 48/04 | (2009.01) |
| H04W 36/34 | (2009.01) |
| H04N 21/2225 | (2011.01) |
| H04N 21/239 | (2011.01) |
| H04N 21/226 | (2011.01) |
| H04N 21/4363 | (2011.01) |
| H04N 21/436 | (2011.01) |
| H04N 21/258 | (2011.01) |
| H04N 21/454 | (2011.01) |
| H04N 21/6408 | (2011.01) |
| H04N 21/643 | (2011.01) |
| H04W 4/60 | (2018.01) |
| H04W 76/11 | (2018.01) |
| G06F 16/25 | (2019.01) |
| G06F 16/182 | (2019.01) |
| G06F 16/583 | (2019.01) |
| G06F 16/2457 | (2019.01) |
| H04W 4/48 | (2018.01) |
| B60R 25/10 | (2013.01) |
| G06F 21/31 | (2013.01) |
| G06F 21/32 | (2013.01) |
| H04L 67/10 | (2022.01) |
| G06Q 30/00 | (2012.01) |
| G08G 1/0967 | (2006.01) |
| H04W 12/06 | (2021.01) |
| G08B 13/196 | (2006.01) |
| G08B 21/06 | (2006.01) |
| G08B 29/18 | (2006.01) |
| G06Q 10/00 | (2012.01) |
| H04W 12/088 | (2021.01) |
| G07C 9/00 | (2020.01) |
| G07C 5/08 | (2006.01) |
| G06V 20/59 | (2022.01) |
| G06V 40/20 | (2022.01) |
| G06V 40/16 | (2022.01) |
| G08B 25/01 | (2006.01) |
| H04W 4/12 | (2009.01) |
| G05D 23/19 | (2006.01) |
| G06F 3/0481 | (2022.01) |
| G06F 3/04842 | (2022.01) |
| G06F 21/00 | (2013.01) |
| G06Q 10/02 | (2012.01) |
| G06Q 30/02 | (2012.01) |
| G06Q 30/06 | (2012.01) |
| G06Q 50/30 | (2012.01) |
| G08B 21/02 | (2006.01) |
| H04L 67/12 | (2022.01) |
| B60R 25/00 | (2013.01) |
| G07C 5/02 | (2006.01) |
| G01C 21/36 | (2006.01) |
| H04L 67/55 | (2022.01) |
| B60R 25/01 | (2013.01) |
| B60K 35/00 | (2006.01) |
| G08G 1/01 | (2006.01) |
| B60C 1/00 | (2006.01) |
| G06F 3/06 | (2006.01) |
| A61B 5/00 | (2006.01) |
| A61B 7/04 | (2006.01) |
| B60Q 9/00 | (2006.01) |
| H04W 76/19 | (2018.01) |
| G05D 1/00 | (2006.01) |
| G08G 1/07 | (2006.01) |
| H04L 9/40 | (2022.01) |
| G05D 1/02 | (2020.01) |
| G08G 1/0968 | (2006.01) |
| G08G 1/16 | (2006.01) |
| H04W 4/70 | (2018.01) |
| H04W 4/80 | (2018.01) |
| B60R 25/20 | (2013.01) |
| G01S 19/42 | (2010.01) |
| H04L 67/306 | (2022.01) |
| B60H 1/00 | (2006.01) |
| B60N 2/02 | (2006.01) |
| B60R 25/102 | (2013.01) |
| B60R 25/25 | (2013.01) |
| G06F 9/451 | (2018.01) |
| G06F 3/04886 | (2022.01) |
| G09G 5/37 | (2006.01) |
| H04L 51/02 | (2022.01) |
| H04W 4/021 | (2018.01) |
| G01C 21/34 | (2006.01) |
| G06F 3/0482 | (2013.01) |
| G08G 1/00 | (2006.01) |
| G08B 21/18 | (2006.01) |
| H04W 4/40 | (2018.01) |
| H04W 4/30 | (2018.01) |
| G06F 3/0488 | (2022.01) |
| B60Q 1/52 | (2006.01) |
| H04N 7/18 | (2006.01) |
| B60W 50/00 | (2006.01) |
| H04W 12/68 | (2021.01) |
| G06V 40/10 | (2022.01) |
| H04W 84/00 | (2009.01) |
| B60R 11/04 | (2006.01) |
| G02B 27/00 | (2006.01) |
| H04L 67/00 | (2022.01) |

(52) U.S. Cl.
CPC ............ *A61B 5/6808* (2013.01); *A61B 5/742* (2013.01); *A61B 5/7405* (2013.01); *A61B 7/04* (2013.01); *B60C 1/00* (2013.01); *B60H 1/00742* (2013.01); *B60K 35/00* (2013.01); *B60N 2/0244* (2013.01); *B60Q 9/00* (2013.01); *B60R 25/00* (2013.01); *B60R 25/01* (2013.01); *B60R 25/102* (2013.01); *B60R 25/1004* (2013.01); *B60R 25/20* (2013.01); *B60R 25/25* (2013.01); *B60W 50/085* (2013.01); *B60W 50/10* (2013.01); *B60W 50/14* (2013.01); *G01C 21/3484* (2013.01); *G01C 21/365* (2013.01); *G01C 21/3667* (2013.01); *G01C 21/3691* (2013.01); *G01C 21/3697* (2013.01); *G01S 19/42* (2013.01); *G05D 1/0016* (2013.01); *G05D 1/0276*

(2013.01); *G05D 23/1917* (2013.01); *G06F 3/013* (2013.01); *G06F 3/017* (2013.01); *G06F 3/0481* (2013.01); *G06F 3/0482* (2013.01); *G06F 3/04842* (2013.01); *G06F 3/04886* (2013.01); *G06F 3/0622* (2013.01); *G06F 3/0637* (2013.01); *G06F 3/0673* (2013.01); *G06F 9/451* (2018.02); *G06F 16/183* (2019.01); *G06F 16/24575* (2019.01); *G06F 16/25* (2019.01); *G06F 16/252* (2019.01); *G06F 16/583* (2019.01); *G06F 21/00* (2013.01); *G06F 21/31* (2013.01); *G06F 21/32* (2013.01); *G06Q 10/00* (2013.01); *G06Q 10/02* (2013.01); *G06Q 10/20* (2013.01); *G06Q 30/00* (2013.01); *G06Q 30/012* (2013.01); *G06Q 30/0265* (2013.01); *G06Q 30/0266* (2013.01); *G06Q 30/0633* (2013.01); *G06Q 30/0639* (2013.01); *G06Q 30/0641* (2013.01); *G06Q 30/0645* (2013.01); *G06Q 50/30* (2013.01); *G06V 20/59* (2022.01); *G06V 20/593* (2022.01); *G06V 40/166* (2022.01); *G06V 40/168* (2022.01); *G06V 40/172* (2022.01); *G06V 40/20* (2022.01); *G06V 40/28* (2022.01); *G07C 5/02* (2013.01); *G07C 5/08* (2013.01); *G07C 5/0825* (2013.01); *G07C 5/0833* (2013.01); *G07C 9/00563* (2013.01); *G08B 13/19647* (2013.01); *G08B 21/0205* (2013.01); *G08B 21/06* (2013.01); *G08B 21/18* (2013.01); *G08B 25/016* (2013.01); *G08B 29/188* (2013.01); *G08G 1/01* (2013.01); *G08G 1/07* (2013.01); *G08G 1/0968* (2013.01); *G08G 1/096725* (2013.01); *G08G 1/096741* (2013.01); *G08G 1/096775* (2013.01); *G08G 1/096805* (2013.01); *G08G 1/096811* (2013.01); *G08G 1/096844* (2013.01); *G08G 1/164* (2013.01); *G08G 1/207* (2013.01); *G09G 5/37* (2013.01); *H04L 51/02* (2013.01); *H04L 63/0236* (2013.01); *H04L 63/0428* (2013.01); *H04L 63/102* (2013.01); *H04L 67/10* (2013.01); *H04L 67/12* (2013.01); *H04L 67/26* (2013.01); *H04L 67/306* (2013.01); *H04N 21/2225* (2013.01); *H04N 21/2265* (2013.01); *H04N 21/2393* (2013.01); *H04N 21/25816* (2013.01); *H04N 21/43615* (2013.01); *H04N 21/43637* (2013.01); *H04N 21/454* (2013.01); *H04N 21/6408* (2013.01); *H04N 21/64322* (2013.01); *H04W 4/021* (2013.01); *H04W 4/12* (2013.01); *H04W 4/30* (2018.02); *H04W 4/40* (2018.02); *H04W 4/48* (2018.02); *H04W 4/60* (2018.02); *H04W 4/70* (2018.02); *H04W 4/80* (2018.02); *H04W 12/06* (2013.01); *H04W 12/088* (2021.01); *H04W 36/34* (2013.01); *H04W 48/04* (2013.01); *H04W 76/11* (2018.02); *H04W 76/19* (2018.02); *H05K 999/00* (2013.01); *H05K 999/99* (2013.01); *A61B 2503/04* (2013.01); *B60K 2370/11* (2019.05); *B60K 2370/146* (2019.05); *B60K 2370/15* (2019.05); *B60K 2370/193* (2019.05); *B60K 2370/52* (2019.05); *B60Q 1/52* (2013.01); *B60R 11/04* (2013.01); *B60R 25/2081* (2013.01); *B60R 25/257* (2013.01); *B60W 2050/0067* (2013.01); *B60W 2050/0085* (2013.01); *G01C 21/362* (2013.01); *G02B 27/0093* (2013.01); *G05D 1/021* (2013.01); *G06F 3/0488* (2013.01); *G06F 2203/04803* (2013.01); *G06V 40/15* (2022.01); *G06V 40/16* (2022.01); *G09G 2380/10* (2013.01); *H04L 67/34* (2013.01); *H04N 7/181* (2013.01); *H04W 12/68* (2021.01); *H04W 84/005* (2013.01)

(58) Field of Classification Search
CPC .. A61B 2503/04; B60C 1/00; B60H 1/00742; B60K 2370/11; B60K 2370/146; B60K 2370/15; B60K 2370/193; B60K 2370/52; B60K 35/00; B60N 2/0244; B60Q 1/52; B60Q 9/00; B60R 11/04; B60R 25/00; B60R 25/01; B60R 25/1004; B60R 25/102; B60R 25/20; B60R 25/2081; B60R 25/25; B60R 25/257; B60W 2050/0067; B60W 2050/0085; B60W 50/085; B60W 50/10; B60W 50/14; G01C 21/3484; G01C 21/362; G01C 21/365; G01C 21/3667; G01C 21/3691; G01C 21/3697; G01S 19/42; G02B 27/0093; G05D 1/0016; G05D 1/021; G05D 1/0276; G05D 23/1917; G06F 16/183; G06F 16/24575; G06F 16/25; G06F 16/252; G06F 16/583; G06F 16/951; G06F 21/00; G06F 21/31; G06F 21/32; G06F 2203/04803; G06F 3/013; G06F 3/017; G06F 3/0481; G06F 3/0482; G06F 3/04842; G06F 3/0488; G06F 3/04886; G06F 3/0622; G06F 3/0637; G06F 3/0673; G06F 9/451; G06K 2009/00939; G06K 9/00221; G06K 9/00255; G06K 9/00268; G06K 9/00288; G06K 9/00335; G06K 9/00355; G06K 9/00832; G06K 9/00838; G06Q 10/00; G06Q 10/02; G06Q 10/20; G06Q 30/00; G06Q 30/012; G06Q 30/0265; G06Q 30/0266; G06Q 30/0633; G06Q 30/0639; G06Q 30/0641; G06Q 30/0645; G06Q 50/30; G07C 5/02; G07C 5/08; G07C 5/0825; G07C 5/083; G07C 9/00563; G08B 13/19647; G08B 21/0205; G08B 21/06; G08B 21/18; G08B 25/016; G08B 29/188; G08G 1/01; G08G 1/07; G08G 1/096725; G08G 1/096741; G08G 1/096775; G08G 1/0968; G08G 1/096805; G08G 1/096811; G08G 1/096844; G08G 1/164; G08G 1/207; G09G 2380/10; G09G 5/37; H04L 51/02; H04L 63/0236; H04L 63/0428; H04L 63/102; H04L 67/10; H04L 67/12; H04L 67/26; H04L 67/306; H04L 67/34; H04N 21/2225; H04N 21/2265; H04N 21/2393; H04N 21/25816; H04N 21/43615; H04N 21/43637; H04N 21/454; H04N 21/6408; H04N 21/64322; H04N 7/181; H04W 12/06; H04W 12/088; H04W 12/68; H04W 36/34; H04W 4/021; H04W 4/12; H04W 4/21; H04W 4/30; H04W 4/48; H04W 4/60; H04W 4/70; H04W 4/80; H04W 48/04; H04W 76/11; H04W 76/19; H04W 84/005; H04W 84/18; H05K 999/00
See application file for complete search history.

(56) References Cited

U.S. PATENT DOCUMENTS

| | | | |
|---|---|---|---|
| 6,124,805 | A | 9/2000 | Gabbard |
| 6,542,794 | B2 | 4/2003 | Obradovich |
| 6,587,755 | B1 | 7/2003 | Smith et al. |
| 8,187,182 | B2 | 5/2012 | Kahn et al. |
| 8,866,745 | B1 | 10/2014 | Schrick |
| 8,979,159 | B2 | 3/2015 | Ricci |
| 9,330,567 | B2 | 5/2016 | Ricci |
| 2002/0184091 | A1 | 12/2002 | Pudar |
| 2003/0090392 | A1 | 5/2003 | Schuessler |
| 2004/0039504 | A1 | 2/2004 | Coffee et al. |
| 2004/0141634 | A1* | 7/2004 | Yamamoto ............ B60K 37/06 382/104 |
| 2007/0100514 | A1 | 5/2007 | Park |
| 2009/0299572 | A1 | 12/2009 | Fujikawa et al. |
| 2010/0023204 | A1 | 1/2010 | Basir et al. |
| 2010/0162319 | A1 | 6/2010 | Piepenbrink et al. |
| 2010/0235744 | A1 | 9/2010 | Schultz et al. |
| 2011/0046939 | A1 | 2/2011 | Balasaygun |
| 2011/0246301 | A1 | 10/2011 | Bae et al. |
| 2012/0001771 | A1 | 1/2012 | Roth et al. |
| 2012/0116609 | A1 | 5/2012 | Jung et al. |
| 2012/0231738 | A1 | 9/2012 | Khamharn |
| 2012/0271500 | A1* | 10/2012 | Tsimhoni ............... B62D 1/046 701/23 |
| 2012/0323474 | A1 | 12/2012 | Breed |
| 2013/0151088 | A1 | 6/2013 | Ricci |
| 2013/0204457 | A1* | 8/2013 | King ................... G06K 9/00355 701/1 |
| 2013/0241720 | A1 | 9/2013 | Ricci et al. |
| 2013/0245882 | A1 | 9/2013 | Ricci |
| 2013/0282946 | A1 | 10/2013 | Ricci |
| 2013/0293364 | A1 | 11/2013 | Ricci et al. |
| 2013/0293452 | A1 | 11/2013 | Ricci et al. |
| 2014/0028542 | A1 | 1/2014 | Lovitt et al. |
| 2014/0156133 | A1 | 6/2014 | Cullinane et al. |
| 2014/0221781 | A1 | 8/2014 | Schrauf et al. |
| 2014/0223384 | A1 | 8/2014 | Graumann |
| 2014/0253471 | A1* | 9/2014 | Bakalor ............... G06F 3/04883 345/173 |
| 2014/0292665 | A1* | 10/2014 | Lathrop ................. G06F 3/013 345/173 |
| 2014/0309871 | A1* | 10/2014 | Ricci ..................... B60R 25/00 701/36 |
| 2015/0006012 | A1 | 1/2015 | Kammel |
| 2015/0025740 | A1* | 1/2015 | Cartarius ............. B60W 50/10 701/36 |

OTHER PUBLICATIONS

U.S. Appl. No. 13/678,691, filed Nov. 16, 2012, Ricci.
U.S. Appl. No. 13/678,710, filed Nov. 16, 2012, Ricci.
U.S. Appl. No. 13/678,722, filed Nov. 16, 2012, Ricci.
U.S. Appl. No. 13/678,726, filed Nov. 16, 2012, Ricci.
U.S. Appl. No. 13/678,735, filed Nov. 16, 2012, Ricci.
U.S. Appl. No. 13/678,745, filed Nov. 16, 2012, Ricci.
U.S. Appl. No. 13/678,753, filed Nov. 16, 2012, Ricci.
U.S. Appl. No. 13/678,762, filed Nov. 16, 2012, Ricci.
U.S. Appl. No. 13/678,773, filed Nov. 16, 2012, Ricci.
U.S. Appl. No. 13/679,204, filed Nov. 16, 2012, Ricci.
U.S. Appl. No. 13/679,234, filed Nov. 16, 2012, Ricci.
U.S. Appl. No. 13/679,292, filed Nov. 16, 2012, Ricci.
U.S. Appl. No. 13/679,350, filed Nov. 16, 2012, Ricci et al.
U.S. Appl. No. 13/679,358, filed Nov. 16, 2012, Ricci et al.
U.S. Appl. No. 13/679,363, filed Nov. 16, 2012, Ricci et al.
U.S. Appl. No. 13/679,368, filed Nov. 16, 2012, Ricci.
U.S. Appl. No. 13/679,369, filed Nov. 16, 2012, Ricci.
U.S. Appl. No. 13/679,400, filed Nov. 16, 2012, Ricci.
U.S. Appl. No. 13/679,412, filed Nov. 16, 2012, Ricci.
U.S. Appl. No. 13/679,441, filed Nov. 16, 2012, Ricci.
U.S. Appl. No. 13/679,443, filed Nov. 16, 2012, Ricci.
U.S. Appl. No. 13/679,459, filed Nov. 16, 2012, Ricci et al.
U.S. Appl. No. 13/679,476, filed Nov. 16, 2012, Ricci et al.
U.S. Appl. No. 13/679,680, filed Nov. 16, 2012, Ricci.
U.S. Appl. No. 13/679,815, filed Nov. 16, 2012, Ricci.
U.S. Appl. No. 13/679,857, filed Nov. 16, 2012, Ricci.
U.S. Appl. No. 13/679,864, filed Nov. 16, 2012, Ricci.
U.S. Appl. No. 13/679,875, filed Nov. 16, 2012, Ricci.
U.S. Appl. No. 13/679,878, filed Nov. 16, 2012, Ricci.
U.S. Appl. No. 13/679,887, filed Nov. 16, 2012, Ricci.
[No Author Listed], "2013 MKZ Owner's Manual," Lincoln Motor Company, Sep. 2012, 474 pages.
[No Author Listed], "A Technical Companion to Windows Embedded Automotive 7," Windows Embedded Automotive 7, Jul. 2010, 100 pages.
[No Author Listed], "MyFord Touch Defines Intuitive Driver Experience: Advanced Capabilities All Voice-Controlled Now," Ford Motor Company, Jan. 7, 2010, 7 pages.
[No Author Listed], "MyFord Touch/ MyLincoln Touch Handbook," Ford Motor Company, Jun. 2010, 52 pages.
[No Author Listed], "SYNC Handbook: Quick Access to Frequently Used Features and Services," Ford Motor Company et al., Apr. 2009, 23 pages.
[No Author Listed], "SYNC with MyFord Touch + Audio by Sony," Ford Motor Company, Jun. 2013, 1 page.
[No Author Listed], "User Guide: MyFord Touch," Ford Motor Company, Feb. 2012, 12 pages.
[No Author Listed], "User's Manual," Ford Motor Company, Feb. 16, 2011, 102 pages.
Browne [online], "Which Cars Are Made With a Remote Start System?," upon information and belief, available no later than Dec. 1, 2020, retrieved from URL <https://itstillruns.com/program-am6-remote-starter-7451748,html>, 3 pages.
Cripps [online], "Hottie in seat 17D? Send her a drink!," Updated Apr. 24, 2013, retrieved Jul. 12, 2021, retrieved from URL <https://www.cnn.com/travel/article/virgin-seat-to-seat-service/index.html>, 2 pages.
Estrada [online], "Should You Pay for In-Car Navigation, or Use Your Phone?," Jul. 30, 2012, retrieved on Jul. 12, 2021, retrieved from URL <https://www.carsdirect.com/buying-guides/should-you-pay-for-in-car-navigation-or-use-your-phone>, 2 pages.
Everett [online], "Virgin launch in-flight flirting system," Apr. 25, 2013, retrieved on Jul. 12, 2021, retrieved from URL <https://www.cosmopolitan.com/uk/love-sex/relationships/a19867/in-flight-flirting-virgin-entertainment-drink-system/>, 3 pages.
ford.com, [online] "About SYNC," Dec. 1, 2010, retrieved on Aug. 19, 2020, retrieved from URL <http://www.ford.com/technology/sync/about>, 1 page.
Hollister [online], "Exclusive: VW's Terminal Mode prototype with a Nokia N97 at the helm, we go hands-on," Sep. 29, 2010, retrieved on Jul. 12, 2021, retrieved from URL <https://www.engadget.com/2010-09-29-exclusive-vws-terminal-mode-prototype-has-a-nokia-n97-at-the-h.html#/>, 7 pages.
Howard [online], "MirrorLink phone-to-dashboard screen mirroring gets rolling with 2 Sony car radios," Aug. 15, 2012, retrieved on Jul. 12, 2021, retrieved from URL <https://www.extremetech.com/extreme/134400-mirrorlink-phone-to-dashboard-connector-gets-rolling-with-2-sony-car-radios>, 4 pages.
Hyundai [online], "BlueLink: User's Manual," May 22, 2013, retrieved on Jul. 12, 2021, retrieved from URL <https://www.manualslib.com/manual/667719/Hyundai-Bluelink.html?page=14>, 1 page.
Levere [online], "Business Travel; Passengers on Jetblue will be able to watch live satellite-television programming from their seats," Jul. 21, 1999, retrieved on Jul. 12, 2021, retrieved from URL <https://www.nytimes.com/1999/07/21/business/business-travel-passengers-jetblue-will-be-able-watch-live-satellite-television.html>, 3 pages.
Oemdtc, [online] "12M02—Warranty Extension Covering Accessory Protocol Interface Module (APIM) Software and Hardware—2011-2014 Ford & Lincoln," May 11, 2016, retrieved on Aug. 19, 2020, retrieved from URL <https://ford.oemdtc.com/1745/12m02-warranty-extension-covering-accessory-protocol-interface-modlue-apim-software-and-hardware-2011-2014-ford-lincoln>, 54 pages.

(56) References Cited

OTHER PUBLICATIONS

Quain [online], "Parental Controls Come to the Car," Apr. 12, 2009, retrieved on Jul. 12, 2021, retrieved from URL <https://wheels.blogs.nytimes.com/2009/04/12/parental-controls-come-to-the-car/>, 2 pages.
Rao [online], "American Airlines and Gogo Roll Out In-Flight Personal Device Video Streaming to 767 Fleet," Aug. 3, 2011, retrieved on Jul. 12, 2021, retrieved from URL <https://techcrunch.com/2011/08/03/american-airlines-rolls-out-in-flight-personal-device-video-streaming-to-767-fleet/>, 2 pages.
Rettie [online], "BMW's Car-to-x Communications," Oct. 21, 2011, retrieved on Jul. 12, 2021, retrieved from URL<https://www.roadandtrack.com/new-cars/car-technology/news/a3276/bmws-car-to-x-communications-27582/>, 3 pages.
RMT [online], "The Difference Between Active and Passive GPS Tracking Devices," May 25, 2009, retrieved on Jul. 12, 2021, retrieved from URL <https://rmtracking.com/blog/2009/05/25/the-difference-between-active-and-passive-gps-tracking-devices/>, 2 pages.
Vartabedian [online], "Remote helps a car keep its cool," May 28, 2008, retrieved on Jul. 12, 2021, retrieved from URL <https://www.latimes.com/archives/la-xpm-2008-may-28-hy-wheels28-story.html>, 6 pages.

\* cited by examiner

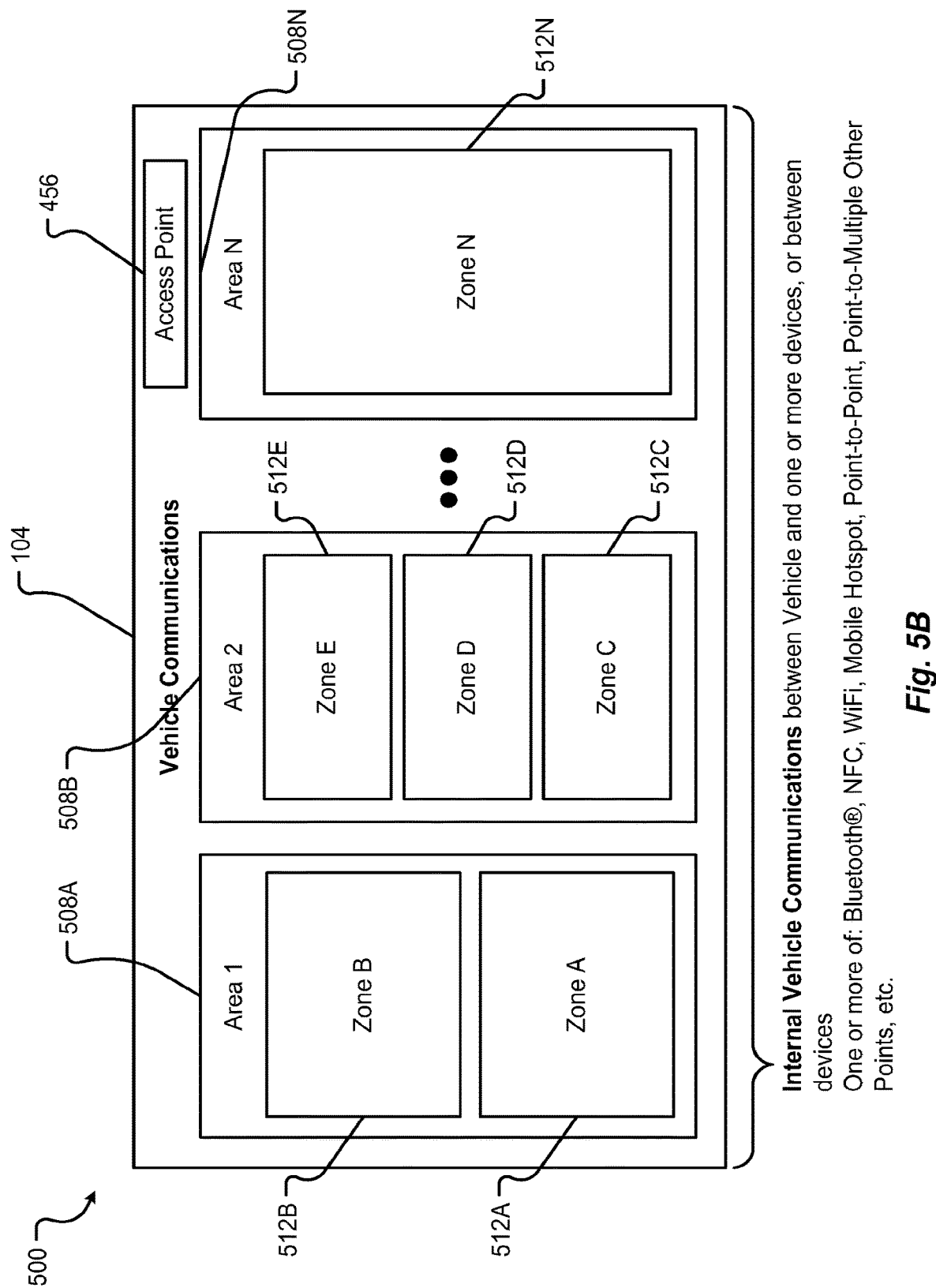

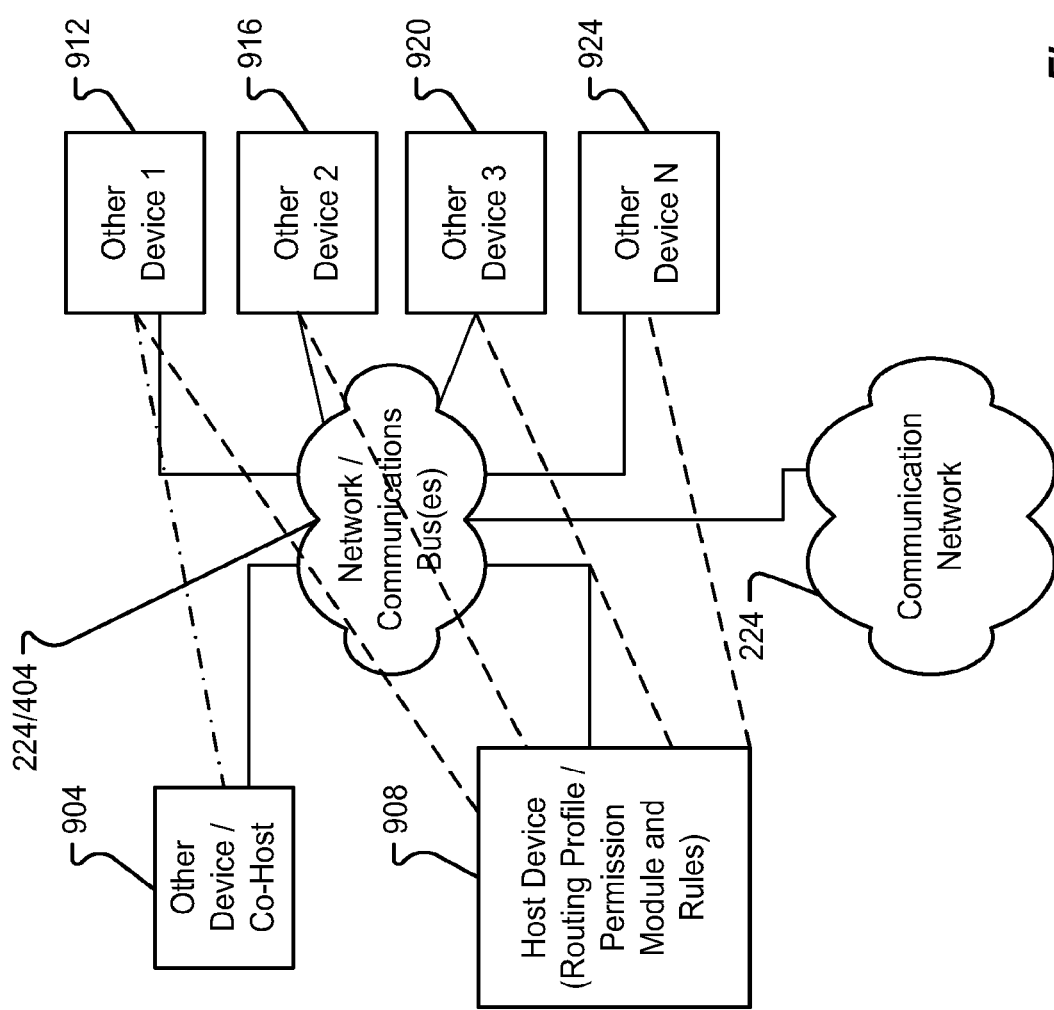

Tap

Long Press

Drag

Flick

Pinch

Spread

Vehicle Systems

| | |
|---|---|
| Ignition 2202 | Cruise Control 2224 |
| Transmission 2204 | Parking System 2226 |
| Braking 2206 | Steering 2228 |
| Acceleration 2208 | Alarms 2230 |
| Doors 2210 | Wipers 2232 |
| Hood 2212 | Headlights/Exterior Lights 2234 |
| Trunk 2214 | Interior Lighting 2236 |
| Windows 2216 | Mirrors 2238 |
| Tire Pressure 2220 | Sunroof 2240 |
| Locks 2222 | Convertible 2242 |

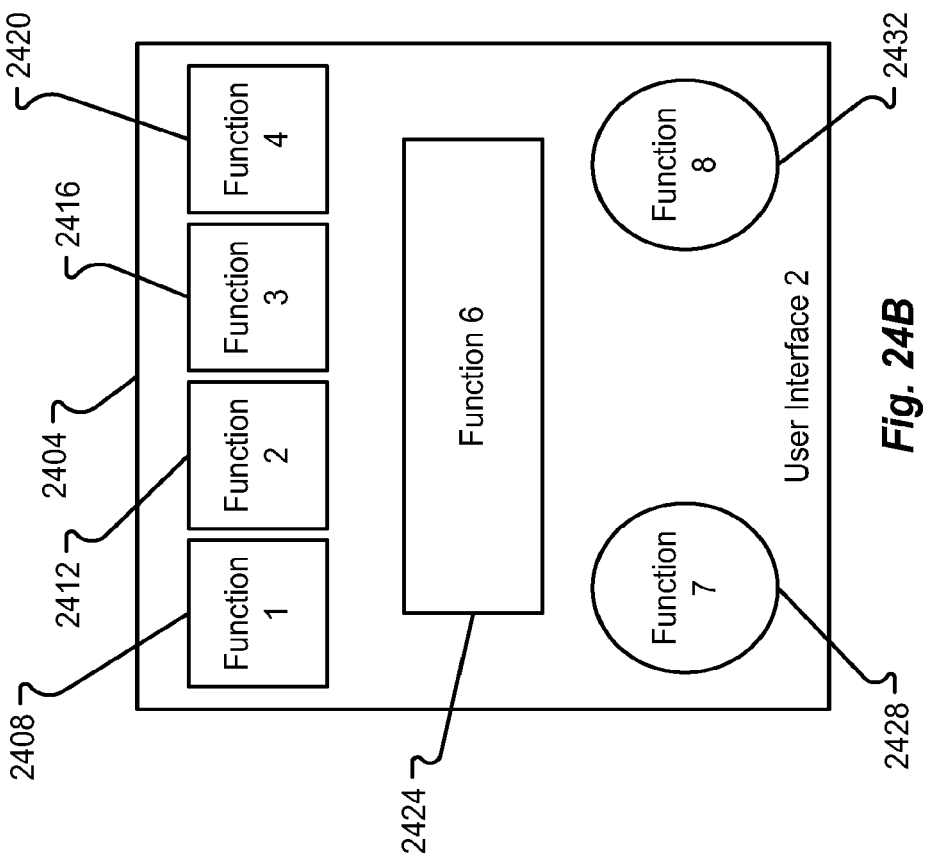
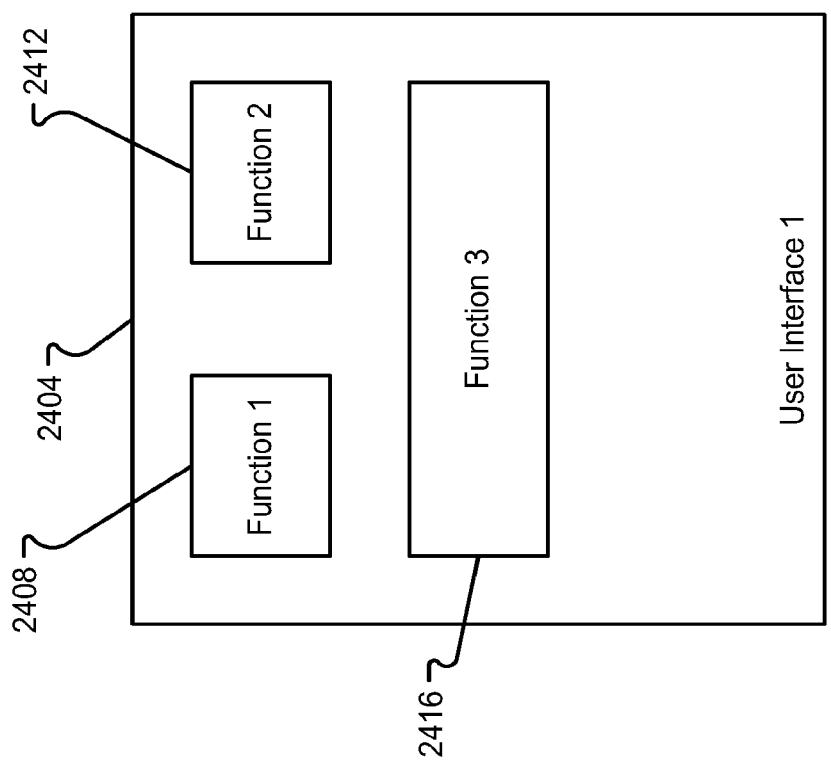
Fig. 24B
Fig. 24A

SYSTEM AND METHOD FOR ADAPTING A CONTROL FUNCTION BASED ON A USER PROFILE

CROSS REFERENCE TO RELATED APPLICATIONS

The present application claims the benefits of and priority, under 35 U.S.C. § 119(e), to U.S. Non-Provisional application Ser. No. 16/289,518, filed on Feb. 28, 2019, which is a continuation in-part of U.S. Non-Provisional application Ser. No. 14/253,321 filed on Apr. 15, 2014, entitled "User Gesture Control of Vehicle Features", which claims benefits of U.S. Provisional Application Ser. No. 61/811,981, filed on Apr. 15, 2013, entitled "Functional Specification for a Next Generation Automobile"; 61/865,954, filed on Aug. 14, 2013, entitled "Gesture Control of Vehicle Features"; 61/870,698, filed on Aug. 27, 2013, entitled "Gesture Control and User Profiles Associated with Vehicle Features"; 61/891,217, filed on Oct. 15, 2013, entitled "Gesture Control and User Profiles Associated with Vehicle Features"; 61/904,205, filed on Nov. 14, 2013, entitled "Gesture Control and User Profiles Associated with Vehicle Features"; 61/924,572, filed on Jan. 7, 2014, entitled "Gesture Control and User Profiles Associated with Vehicle Features"; and 61/926,749, filed on Jan. 13, 2014, entitled "Method and System for Providing Infotainment in a Vehicle." The entire disclosures of the applications listed above are hereby incorporated by reference, in their entirety, for all that they teach and for all purposes.

This application is also related to U.S. patent application Ser. No. 13/420,236, filed on Mar. 14, 2012, entitled, "Configurable Vehicle Console"; Ser. No. 13/420,240, filed on Mar. 14, 2012, entitled "Removable, Configurable Vehicle Console"; Ser. No. 13/462,593, filed on May 2, 2012, entitled "Configurable Dash Display"; Ser. No. 13/462,596, filed on May 2, 2012, entitled "Configurable Heads-Up Dash Display"; Ser. No. 13/679,459, filed on Nov. 16, 2012, entitled "Vehicle Comprising Multi-Operating System"; Ser. No. 13/679,234, filed on Nov. 16, 2012, entitled "Gesture Recognition for On-Board Display"; Ser. No. 13/679,412, filed on Nov. 16, 2012, entitled "Vehicle Application Store for Console"; Ser. No. 13/679,857, filed on Nov. 16, 2012, entitled "Sharing Applications/Media Between Car and Phone (Hydroid)"; Ser. No. 13/679,878, filed on Nov. 16, 2012, entitled "In-Cloud Connection for Car Multimedia"; Ser. No. 13/679,875, filed on Nov. 16, 2012, entitled "Music Streaming"; Ser. No. 13/679,676, filed on Nov. 16, 2012, entitled "Control of Device Features Based on Vehicle State"; Ser. No. 13/678,673, filed on Nov. 16, 2012, entitled "Insurance Tracking"; Ser. No. 13/678,691, filed on Nov. 16, 2012, entitled "Law Breaking/Behavior Sensor"; Ser. No. 13/678,699, filed on Nov. 16, 2012, entitled "Etiquette Suggestion"; Ser. No. 13/678,710, filed on Nov. 16, 2012, entitled "Parking Space Finder Based on Parking Meter Data"; Ser. No. 13/678,722, filed on Nov. 16, 2012, entitled "Parking Meter Expired Alert"; Ser. No. 13/678,726, filed on Nov. 16, 2012, entitled "Object Sensing (Pedestrian Avoidance/Accident Avoidance)"; Ser. No. 13/678,735, filed on Nov. 16, 2012, entitled "Proximity Warning Relative to Other Cars"; ; Ser. No. 13/678,745, filed on Nov. 16, 2012, entitled "Street Side Sensors"; Ser. No. 13/678,753, filed on Nov. 16, 2012, entitled "Car Location"; Ser. No. 13/679,441, filed on Nov. 16, 2012, entitled "Universal Bus in the Car"; Ser. No. 13/679,864, filed on Nov. 16, 2012, entitled "Mobile Hot Spot/Router/Application Share Site or Network"; Ser. No. 13/679,815, filed on Nov. 16, 2012, entitled "Universal Console Chassis for the Car"; Ser. No. 13/679,476, filed on Nov. 16, 2012, entitled "Vehicle Middleware"; Ser. No. 13/679,306, filed on Nov. 16, 2012, entitled "Method and System for Vehicle Data Collection Regarding Traffic"; Ser. No. 13/679,369, filed on Nov. 16, 2012, entitled "Method and System for Vehicle Data Collection"; Ser. No. 13/679,680, filed on Nov. 16, 2012, entitled "Communications Based on Vehicle Diagnostics and Indications"; Ser. No. 13/679,443, filed on Nov. 16, 2012, entitled "Method and System for Maintaining and Reporting Vehicle Occupant Information"; Ser. No. 13/678,762, filed on Nov. 16, 2012, entitled "Behavioral Tracking and Vehicle Applications"; Ser. No. 13/679,292, filed Nov. 16, 2012, entitled "Branding of Electrically Propelled Vehicles Via the Generation of Specific Operating Output"; Ser. No. 13/679,400, filed Nov. 16, 2012, entitled "Vehicle Climate Control"; Ser. No. 13/840,240, filed on Mar. 15, 2013, entitled "Improvements to Controller Area Network Bus"; Ser. No. 13/678,773, filed on Nov. 16, 2012, entitled "Location Information Exchange Between Vehicle and Device"; Ser. No. 13/679,887, filed on Nov. 16, 2012, entitled "In Car Communication Between Devices"); Ser. No. 13/679,842, filed on Nov. 16, 2012, entitled "Configurable Hardware Unit for Car Systems"; Ser. No. 13/679,204, filed on Nov. 16, 2012, entitled "Feature Recognition for Configuring a Vehicle Console and Associated Devices"; Ser. No. 13/679,350, filed on Nov. 16, 2012, entitled "Configurable Vehicle Console"; Ser. No. 13/679,358, filed on Nov. 16, 2012, entitled "Configurable Dash Display"; Ser. No. 13/679,363, filed on Nov. 16, 2012, entitled "Configurable Heads-Up Dash Display"; and Ser. No. 13/679,368, filed on Nov. 16, 2012, entitled "Removable, Configurable Vehicle Console". The entire disclosures of the applications listed above are hereby incorporated by reference, in their entirety, for all that they teach and for all purposes.

BACKGROUND

Whether using private, commercial, or public transport, the movement of people and/or cargo has become a major industry. In today's interconnected world, daily travel is essential to engaging in commerce. Commuting to and from work can account for a significant portion of a traveler's day. As a result, vehicle manufacturers have begun to focus on making this commute, and other journeys, more enjoyable.

Currently, vehicle manufacturers attempt to entice travelers to use a specific conveyance based on any number of features. Most of these features focus on vehicle safety or efficiency. From the addition of safety-restraints, air-bags, and warning systems to more efficient engines, motors, and designs, the vehicle industry has worked to appease the supposed needs of the traveler. Recently, however, vehicle manufactures have shifted their focus to user and passenger comfort as a primary concern. Making an individual more comfortable while traveling instills confidence and pleasure in using a given vehicle, increasing an individual's preference for a given manufacturer and/or vehicle type.

One way to instill comfort in a vehicle is to create an environment within the vehicle similar to that of an individual's home. Integrating features in a vehicle that are associated with comfort found in an individual's home can ease a traveler's transition from home to vehicle. Several manufacturers have added comfort features in vehicles such as the following: leather seats, adaptive and/or personal climate control systems, music and media players, ergonomic controls, and, in some cases, Internet connectivity. However, because these manufacturers have added features to a conveyance, they have built comfort around a vehicle and failed to build a vehicle around comfort.

SUMMARY

There is a need for a vehicle ecosystem, which can integrate both physical and mental comforts, while seamlessly communicating with current electronic devices to result in a totally intuitive and immersive user experience. These and other needs are addressed by the various aspects, embodiments, and/or configurations of the present disclosure. Also, while the disclosure is presented in terms of exemplary and optional embodiments, it should be appreciated that individual aspects of the disclosure can be separately claimed.

Embodiments include a method for receiving a gesture in a conveyance, comprising: a vehicle control system, including a processor, receiving a gesture from a user; the vehicle control system identifying the received gesture; the vehicle control system sending a verification of the received gesture to the user; the vehicle control system determining if a confirmation is received in response to the verification; and if the confirmation is received, the vehicle control system controlling a function associated with the gesture.

An aspect of the above method further comprising: if the confirmation is not received, the vehicle control system determining if the gesture should be completed; and if the gesture should be completed, the vehicle control system controlling the function associated with the gesture.

An aspect of the above method further comprises if the gesture should not be completed, the vehicle control system determining if the verification should be resent; if the verification should be resent, the vehicle control system again sending the verification; and if the verification should not be resent, receiving another gesture.

An aspect of the above method includes wherein the verification is an audible message presented to the user.

An aspect of the above method includes wherein the confirmation is a second gesture.

An aspect of the above method includes wherein the confirmation is an audible confirmation.

An aspect of the above method includes wherein the verification is a user interface message presented on a screen.

An aspect of the above method includes wherein the confirmation is a selection of a user interface device on the screen.

An aspect of the above method includes wherein the verification is a preview of the function associated with the gesture.

An aspect of the above method further comprises: the vehicle control system receiving a denial of the verification; and based on the denial, the vehicle control system not completing the function associated with the gesture.

Embodiments include a conveyance comprising: a processor operable to execute one or more modules, the modules comprising: a gesture recognition module operable to: receive a gesture from a user; identify the received gesture; a verification module operable to: send a verification of the received gesture to the user; determine if a confirmation is received in response to the verification; and a function control module operable to, if the confirmation is received, control a function associated with the gesture.

An aspect of the above conveyance includes wherein the verification module further operable to, if the confirmation is not received, determine if the gesture should be completed.

An aspect of the above conveyance includes wherein the verification module further operable to: if the gesture should not be completed, determine if the verification should be resent; if the verification should be resent, re-send the verification.

An aspect of the above conveyance includes wherein the verification is one of an audible message presented to the user, a user interface message presented on a screen, or a preview of the function associated with the gesture.

An aspect of the above conveyance includes wherein the confirmation is one of a second gesture, a selection of a user interface device on the screen, or an audible confirmation.

Embodiments include a non-transitory computer readable medium stored on a storage medium and having instructions that when executed by a processor cause the processor to perform a method, the instructions comprising: instructions to receive a gesture from a user; instructions to identify the received gesture; instructions to send a verification of the received gesture to the user; instructions to determine if a confirmation is received in response to the verification; and if the confirmation is received, instructions to control a function associated with the gesture.

An aspect of the above computer readable medium further comprises, if the confirmation is not received, instructions to determine if the gesture should be completed.

An aspect of the above computer readable medium further comprises: if the gesture should not be completed, instructions to determine if the verification should be resent; if the verification should be resent, instructions to re-send the verification.

An aspect of the above computer readable medium includes wherein the verification is one of an audible message presented to the user, a user interface message presented on a screen, or a preview of the function associated with the gesture.

An aspect of the above computer readable medium includes wherein the confirmation is one of a second gesture, a selection of a user interface device on the screen, or an audible confirmation.

Embodiments include a method for modifying features of a conveyance, comprising: a vehicle control system, including a processor, identifying a user within the conveyance; the vehicle control system retrieving characteristics associated with a user profile, which is associated with the identified user; the vehicle control system determining if at least one of the characteristics impacts the function of a vehicle; and the vehicle control system, if the at least one of the characteristics impacts the function of a vehicle, automatically changing a function based on the at least one of the characteristics.

An aspect of the above method further comprises: the vehicle control system determining if an override has been set; and if the override has been set, the vehicle control system ignoring the change to the function.

An aspect of the above method includes wherein the override is provided by the user.

An aspect of the above method includes wherein the at least one of the characteristics is an age of the user.

An aspect of the above method includes wherein, if the age is under a predetermined benchmark, the user is prohibited for accessing a function of the conveyance.

An aspect of the above method includes wherein the at least one of the characteristics is an eyesight of the user.

An aspect of the above method includes wherein, if the eyesight is under a predetermined benchmark, a user interface is modified for the user.

An aspect of the above method includes wherein the at least one of the characteristics is a logged hours of the user.

An aspect of the above method includes wherein, if the logged hours is under a predetermined benchmark, a route information is changed.

An aspect of the above method includes wherein the user is a passenger.

Embodiments include a conveyance comprising: a processor operable to execute one or more modules, the modules comprising: a user identification module operable to: identify a user within the conveyance; retrieve characteristics associated with a user profile, which is associated with the identified user; a user customization module operable to: determine if at least one of the characteristics impacts the function of a vehicle; and if the at least one of the characteristics impacts the function of a vehicle, automatically change a function based on the at least one of the characteristics.

An aspect of the above conveyance includes wherein the user customization module is further operable to: determine if an override has been set; and if the override has been set, ignore the change to the function.

An aspect of the above conveyance includes wherein the at least one of the characteristics is an age of the user, and wherein, if the age is under a predetermined benchmark, the user is prohibited for accessing a function of the conveyance.

An aspect of the above conveyance includes wherein the at least one of the characteristics is an eyesight of the user, and wherein, if the eyesight is under a predetermined benchmark, a user interface is modified for the user.

An aspect of the above conveyance includes wherein the at least one of the characteristics is a logged hours of the user, and wherein, if the logged hours is under a predetermined benchmark, a route information is changed.

Embodiments include a non-transitory computer readable medium stored on a storage medium and having instructions that when executed by a processor cause the processor to perform a method, the instructions comprising: instructions to identify a user within the conveyance; instructions to retrieve characteristics associated with a user profile, which is associated with the identified user; instructions to determine if at least one of the characteristics impacts the function of a vehicle; and if the at least one of the characteristics impacts the function of a vehicle, instructions to automatically change a function based on the at least one of the characteristics.

An aspect of the above computer readable medium further comprises: instructions to determine if an override has been set; and if the override has been set, instructions to ignore the change to the function.

An aspect of the above computer readable medium includes wherein the at least one of the characteristics is an age of the user, and wherein, if the age is under a predetermined benchmark, the user is prohibited for accessing a function of the conveyance.

An aspect of the above computer readable medium includes wherein the at least one of the characteristics is an eyesight of the user, and wherein, if the eyesight is under a predetermined benchmark, a user interface is modified for the user.

An aspect of the above computer readable medium includes wherein the at least one of the characteristics is a logged hours of the user, and wherein, if the logged hours is under a predetermined benchmark, a route information is changed.

Embodiments include a method for controlling functions of a conveyance with gestures, comprising: a vehicle control system, including a processor, receiving a gesture within the conveyance; the vehicle control system determining a location of the gesture; the vehicle control system determining an origin of the gesture based on the location of the gesture and a location of a user providing the gesture; and the vehicle control system, based on the origin of the gesture, identifying the gesture.

An aspect of the above method further comprises: determining the location of the user; and determining if the location of the user is different from the location of the gesture.

An aspect of the above method further comprises: if the location of the user and the location of the gesture is same, identifying the gesture as a first gesture.

An aspect of the above method further comprises: if the location of the user and the location of the gesture is different, identifying the gesture as a second gesture.

An aspect of the above method includes wherein the location of the user is in a first zone.

An aspect of the above method includes wherein the location of the gesture is in a second zone.

An aspect of the above method includes wherein the first gesture causes a first function to be controlled.

An aspect of the above method includes wherein the second gesture causes a second function to be controlled.

An aspect of the above method includes wherein the location of the user is in a first area.

An aspect of the above method includes wherein the location of the gesture is in a second area.

Embodiments include a conveyance comprising: a processor operable to execute one or more modules, the modules comprising: a gesture recognition module operable to: receive a gesture within the conveyance; determine a location of the gesture; determine an origin of the gesture based on the location of the gesture and a location of a user providing the gesture; and based on the origin of the gesture, identify the gesture.

An aspect of the above conveyance includes wherein the gesture recognition module is further operable to: determine the location of the user; determine if the location of the user is different from the location of the gesture; if the location of the user and the location of the gesture is same, identify the gesture as a first gesture; and if the location of the user and the location of the gesture is different, identify the gesture as a second gesture.

An aspect of the above conveyance includes wherein the location of the user is in a first zone, and wherein the location of the gesture is in a second zone.

An aspect of the above conveyance includes wherein the first gesture causes a first function to be controlled, and wherein the second gesture causes a second function to be controlled.

An aspect of the above conveyance includes wherein the location of the user is in a first area, and wherein the location of the gesture is in a second area.

Embodiments include a non-transitory computer readable medium stored on a storage medium and having instructions that when executed by a processor cause the processor to perform a method, the instructions comprising: instructions to receive a gesture within the conveyance; instructions to determine a location of the gesture; instructions to determine an origin of the gesture based on the location of the gesture and a location of a user providing the gesture; and based on the origin of the gesture, instructions to identify the gesture.

An aspect of the above computer readable medium further comprises: instructions to determine the location of the user; instructions to determine if the location of the user is different from the location of the gesture; if the location of the user and the location of the gesture is same, instructions to identify the gesture as a first gesture; and if the location of the user and the location of the gesture is different, instructions to identify the gesture as a second gesture.

An aspect of the above computer readable medium includes wherein the location of the user is in a first zone, and wherein the location of the gesture is in a second zone.

An aspect of the above computer readable medium includes wherein the first gesture causes a first function to be controlled, and wherein the second gesture causes a second function to be controlled.

An aspect of the above computer readable medium includes wherein the location of the user is in a first area, and wherein the location of the gesture is in a second area.

Embodiments include a method for controlling functions of a conveyance based on gesture focus, comprising: a vehicle control system, including a processor, receiving a gesture initiation within the conveyance; the vehicle control system identifying a focus of the gesture; the vehicle control system determining user characteristics for a user making the gesture; and the vehicle control system, based on the focus and the user characteristics, configuring a setting for the conveyance.

An aspect of the above method includes wherein the gesture is not completed.

An aspect of the above method includes wherein the focus is on a user interface.

An aspect of the above method includes wherein the vehicle control system determines which user interface has the focus.

An aspect of the above method includes wherein an appearance of the user interface changes based on the focus and before the gesture is completed.

An aspect of the above method includes wherein the appearance change is a change to the configuration of the user interface.

An aspect of the above method includes wherein at least one user-selectable button is removed from the user interface.

An aspect of the above method includes wherein a size of at least one user-selectable button is changed.

An aspect of the above method includes wherein a position of at least one user-selectable button is changed.

An aspect of the above method includes wherein a shape of at least one user-selectable button is changed.

Embodiments include a conveyance comprising: a processor operable to execute one or more modules, the modules comprising: a gesture recognition module operable to receive a gesture initiation within the conveyance; a focus module operable to: identify a focus of the gesture; determine user characteristics for a user making the gesture; and a function control module operable to, based on the focus and the user characteristics, configure a setting for the conveyance.

An aspect of the above conveyance includes wherein the gesture is not completed, and wherein the focus is on a user interface.

An aspect of the above conveyance includes wherein the vehicle control system determines which user interface has the focus, and wherein an appearance of the user interface changes based on the focus and before the gesture is completed.

An aspect of the above conveyance includes wherein the appearance change is a change to the configuration of the user interface.

An aspect of the above conveyance includes wherein the configuration change is one or more of: a user-selectable button is removed from the user interface; a size of a user-selectable button is changed; a position of a user-selectable button is changed; and a shape of a user-selectable button is changed.

Embodiments include a non-transitory computer readable medium stored on a storage medium and having instructions that when executed by a processor cause the processor to perform a method, the instructions comprising: instructions to receive a gesture initiation within the conveyance; instructions to identify a focus of the gesture; instructions to determine user characteristics for a user making the gesture; and based on the focus and the user characteristics, instructions to configure a setting for the conveyance.

An aspect of the above computer readable medium includes wherein the gesture is not completed, and wherein the focus is on a user interface.

An aspect of the above computer readable medium includes wherein the vehicle control system determines which user interface has the focus, and wherein an appearance of the user interface changes based on the focus and before the gesture is completed.

An aspect of the above computer readable medium includes wherein the appearance change is a change to the configuration of the user interface.

An aspect of the above computer readable medium includes wherein the configuration change is one or more of: a user-selectable button is removed from the user interface; a size of a user-selectable button is changed; a position of a user-selectable button is changed; and a shape of a user-selectable button is changed.

Embodiments include a method for controlling a user interface in a conveyance, comprising: a vehicle control system, including a processor, providing content on the user interface; the vehicle control system determining if a user within the conveyance should be prohibited from viewing the content; the vehicle control system determining a location of the prohibited user; and the vehicle control system modifying a display of the content to prevent viewing by the prohibited user.

An aspect of the above method includes wherein the content is a movie.

An aspect of the above method includes wherein the prohibited user is a driver.

An aspect of the above method includes wherein the prohibited user is another passenger.

An aspect of the above method includes wherein the other passenger is identified as a child.

An aspect of the above method includes wherein at least a portion of the user interface is blacked out.

An aspect of the above method includes wherein the at least a portion of the user interface is blacked out when the prohibited user looks at the user interface.

An aspect of the above method includes wherein the user interface is pivoted away from the prohibited user.

An aspect of the above method further comprises: the vehicle control system determining if the prohibited user should receive audio associated with the content; and if the prohibited user should not receive audio associated with the content, changing an audio signal to prevent listening by the prohibited user.

An aspect of the above method includes wherein a noise cancelling signal is sent to a zone associated with the prohibited user.

Embodiments include a conveyance comprising: a processor operable to execute one or more modules, the modules comprising: a media controller operable to: provide content on the user interface; modify a display of the content to prevent viewing by a user; a user customization module operable to: determine if the user within the conveyance should be prohibited from viewing the content; and determine a location of the prohibited user.

An aspect of the above conveyance includes wherein the content is a movie.

An aspect of the above conveyance includes wherein the prohibited user is one of a driver, another passenger, or a child passenger.

An aspect of the above conveyance includes wherein the display is modified by one of at least a portion of the user interface is blacked out when the prohibited user looks at the user interface or the display is pivoted away from the prohibited user.

An aspect of the above conveyance includes wherein the user customization module is further operable to: determine if the prohibited user should receive audio associated with the content; and if the prohibited user should not receive audio associated with the content, change an audio signal to prevent listening by the prohibited user, wherein a noise cancelling signal is sent to a zone associated with the prohibited user.

Embodiments include a non-transitory computer readable medium stored on a storage medium and having instructions that when executed by a processor cause the processor to perform a method, the instructions comprising: instructions to provide content on the user interface; instructions to determine if a user within the conveyance should be prohibited from viewing the content; and instructions to determine a location of the prohibited user; instructions to modify a display of the content to prevent viewing by the prohibited user.

An aspect of the above computer readable medium includes wherein the content is a movie.

An aspect of the above computer readable medium includes wherein the prohibited user is one of a driver, another passenger, or a child passenger.

An aspect of the above computer readable medium includes wherein the display is modified by one of at least a portion of the user interface is blacked out when the prohibited user looks at the user interface or the display is pivoted away from the prohibited user.

An aspect of the above computer readable medium further comprises: instructions to determine if the prohibited user should receive audio associated with the content; and if the prohibited user should not receive audio associated with the content, instructions to change an audio signal to prevent listening by the prohibited user, wherein a noise cancelling signal is sent to a zone associated with the prohibited user.

Embodiments include a method for controlling a function in a conveyance, comprising: a vehicle control system, including a processor, identifying a user within a conveyance; the vehicle control system determining a location of the user within the conveyance; the vehicle control system retrieving a user profile for the user based on the identity and the location of the user, wherein the user profile includes one or more settings associated with the user; the vehicle control system receiving an audible command from the user, wherein the audible command is one of the setting associated with the user; and the vehicle control system modifying a function of the conveyance based on the audible command.

An aspect of the above method includes wherein the location of the user is in one of two or more areas defined in the conveyance.

An aspect of the above method includes wherein a first function is controlled if the audible command is received in a first area.

An aspect of the above method includes wherein a second function is controlled if the audible command is received in a second area.

An aspect of the above method includes wherein the location of the user is in one of two or more zones defined in the conveyance.

An aspect of the above method includes wherein a third function is controlled if the audible command is received in a first zone.

An aspect of the above method includes wherein a fourth function is controlled if the audible command is received in a second zone.

An aspect of the above method includes wherein a fifth function is controlled if the audible command is received from a first user.

An aspect of the above method includes wherein a sixth function is controlled if the audible command is received in from a second user.

An aspect of the above method further comprises: the vehicle control system determining if the audible command is a search function; and if the audible command is a search function, the vehicle control system searching for another audible command based on information in the received audible command.

Embodiments include a conveyance comprising: a processor operable to execute one or more modules, the modules comprising: a user identification module operable to: identify a user within a conveyance; determine a location of the user within the conveyance; retrieve a user profile for the user based on the identity and the location of the user, wherein the user profile includes one or more settings associated with the user; a voice control module operable to: receive an audible command from the user, wherein the audible command is one of the setting associated with the user; and modify a function of the conveyance based on the audible command.

An aspect of the above conveyance includes wherein the location of the user is in one of two or more areas defined in the conveyance, wherein a first function is controlled if the audible command is received in a first area, and wherein a second function is controlled if the audible command is received in a second area.

An aspect of the above conveyance includes wherein the location of the user is in one of two or more zones defined in the conveyance, wherein a third function is controlled if the audible command is received in a first zone, and wherein a fourth function is controlled if the audible command is received in a second zone.

An aspect of the above conveyance includes wherein a fifth function is controlled if the audible command is received from a first user, and wherein a sixth function is controlled if the audible command is received in from a second user.

An aspect of the above conveyance includes wherein the voice control module is further operable to: determine if the audible command is a search function; and if the audible command is a search function, search for another audible command based on information in the received audible command.

Embodiments include a non-transitory computer readable medium stored on a storage medium and having instructions that when executed by a processor cause the processor to perform a method, the instructions comprising: instructions to identify a user within a conveyance; instructions to determine a location of the user within the conveyance; instructions to retrieve a user profile for the user based on the identity and the location of the user, wherein the user profile includes one or more settings associated with the user; instructions to receive an audible command from the user, wherein the audible command is one of the setting associated with the user; and instructions to modify a function of the conveyance based on the audible command.

An aspect of the above computer readable medium includes wherein the location of the user is in one of two or more areas defined in the conveyance, wherein a first function is controlled if the audible command is received in a first area, and wherein a second function is controlled if the audible command is received in a second area.

An aspect of the above computer readable medium includes wherein the location of the user is in one of two or more zones defined in the conveyance, wherein a third function is controlled if the audible command is received in a first zone, and wherein a fourth function is controlled if the audible command is received in a second zone.

An aspect of the above computer readable medium includes wherein a fifth function is controlled if the audible command is received from a first user, and wherein a sixth function is controlled if the audible command is received in from a second user.

An aspect of the above computer readable medium further comprises: instructions to determine if the audible command is a search function; and if the audible command is a search function, instructions to search for another audible command based on information in the received audible command.

Embodiments include a method for controlling a function in a conveyance, comprising: a vehicle control system, including a processor, identifying a user within a conveyance; the vehicle control system retrieving a user profile for the user based on the identity of the user, wherein the user profile includes one or more of a user characteristic and a user history; the vehicle control system determining, based on one or more of the user characteristic and the user history, if a change to an interaction with the user is needed; and if a change to an interaction with the user is needed, the vehicle control system configuring a user interface for the user.

An aspect of the above method further comprises: the vehicle control system suggesting the user interface change to the user; and the vehicle control system determining if the user accepts the change.

An aspect of the above method further comprises, if the user accepts the change, completing the configuration of the user interface.

An aspect of the above method includes wherein the user characteristics is a user's age and at least one application commonly used by the user.

An aspect of the above method includes wherein, when the user is driving, prohibiting access to the application on the user interface.

An aspect of the above method includes wherein the application is a social media application and will be distracting to the user.

An aspect of the above method further comprises completing the configuration change regardless of whether the user accepts the change.

An aspect of the above method includes wherein the user characteristic is a user's poor eyesight and at least one application commonly used by the user.

An aspect of the above method includes wherein the user interface presents an interface with the application differently for easier access by the user.

An aspect of the above method includes wherein at least one button to another application, not commonly used by the user, is eliminated from the user interface.

Embodiments include a conveyance comprising: a processor operable to execute one or more modules, the modules comprising: a user identification module operable to: identify a user within a conveyance; retrieve a user profile for the user based on the identity of the user, wherein the user profile includes one or more of a user characteristic and a user history; a user customization module operable to determine, based on one or more of the user characteristic and the user history, if a change to an interaction with the user is needed; and a function control module operable to change to an interaction with the user is needed, the vehicle control system configuring a user interface for the user.

An aspect of the above conveyance includes wherein the function control module is further operable to: suggest the user interface change to the user; determine if the user accepts the change; and if the user accepts the change, complete the configuration of the user interface.

An aspect of the above conveyance includes wherein the user characteristics is a user's age and at least one application commonly used by the user, wherein, when the user is driving, prohibiting access to the application on the user interface, and wherein the application is a social media application and will be distracting to the user.

An aspect of the above conveyance includes wherein the function control module is further operable to complete the configuration change regardless of whether the user accepts the change.

An aspect of the above conveyance includes wherein the user characteristic is a user's poor eyesight and at least one application commonly used by the user, wherein the user interface presents an interface with the application differently for easier access by the user, and wherein at least one button to another application, not commonly used by the user, is eliminated from the user interface.

Embodiments include a non-transitory computer readable medium stored on a storage medium and having instructions that when executed by a processor cause the processor to perform a method, the instructions comprising: instructions to identify a user within a conveyance; instructions to retrieve a user profile for the user based on the identity of the user, wherein the user profile includes one or more of a user characteristic and a user history; instructions to determine, based on one or more of the user characteristic and the user history, if a change to an interaction with the user is needed; and instructions to change to an interaction with the user is needed, the vehicle control system configuring a user interface for the user.

An aspect of the above computer readable medium further comprises: instructions to suggest the user interface change to the user; instructions to determine if the user accepts the change; and if the user accepts the change, instructions to complete the configuration of the user interface.

An aspect of the above computer readable medium includes wherein the user characteristics is a user's age and at least one application commonly used by the user, wherein, when the user is driving, prohibiting access to the application on the user interface, and wherein the application is a social media application and will be distracting to the user.

An aspect of the above computer readable medium further comprises instructions to complete the configuration change regardless of whether the user accepts the change.

An aspect of the above computer readable medium includes wherein the user characteristic is a user's poor eyesight and at least one application commonly used by the user, wherein the user interface presents an interface with the application differently for easier access by the user, and wherein at least one button to another application, not commonly used by the user, is eliminated from the user interface.

The present disclosure can provide a number of advantages depending on the particular aspect, embodiment, and/or configuration. The embodiments presented herein provide the user with an easily configured and understood system for controlling the functions of the vehicle. The interfaces can also be changed based on the identity and characteristics of the user both automatically and manually, which again makes the system more user-friendly. These and other advantages will be apparent from the disclosure.

The phrases "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The term "automatic" and variations thereof, as used herein, refer to any process or operation done without material human input when the process or operation is performed. However, a process or operation can be automatic, even though performance of the process or operation uses material or immaterial human input, if the input is received before the performance of the process or operation. Human input is deemed to be material if such input influences how the process or operation will be performed. Human input that consents to the performance of the process or operation is not deemed to be "material."

The term "automotive navigation system" can refer to a satellite navigation system designed for use in vehicles. It typically uses a GPS navigation device to acquire position data to locate the user on a road in the unit's map database. Using the road database, the unit can give directions to other locations along roads also in its database. Dead reckoning using distance data from sensors attached to the drivetrain, a gyroscope and an accelerometer can be used for greater reliability, as GPS signal loss and/or multipath can occur due to urban canyons or tunnels.

The term "bus" and variations thereof, as used herein, can refer to a subsystem that transfers information and/or data between various components. A bus generally refers to the collection communication hardware interface, interconnects, bus architecture, standard, and/or protocol defining the communication scheme for a communication system and/or communication network. A bus may also refer to a part of a communication hardware that interfaces the communication hardware with the interconnects that connect to other components of the corresponding communication network. The bus may be for a wired network, such as a physical bus, or wireless network, such as part of an antenna or hardware that couples the communication hardware with the antenna. A bus architecture supports a defined format in which information and/or data is arranged when sent and received through a communication network. A protocol may define the format and rules of communication of a bus architecture.

The terms "communication device," "smartphone," and "mobile device," and variations thereof, as used herein, can be used interchangeably and may include any type of device capable of communicating with one or more of another device and/or across a communications network, via a communications protocol, and the like. Exemplary communication devices may include but are not limited to smartphones, handheld computers, laptops, netbooks, notebook computers, subnotebooks, tablet computers, scanners, portable gaming devices, phones, pagers, GPS modules, portable music players, and other Internet-enabled and/or network-connected devices.

A "communication modality" can refer to any protocol- or standard defined or specific communication session or interaction, such as Voice-Over-Internet-Protocol ("VoIP"), cellular communications (e.g., IS-95, 1G, 2G, 3G, 3.5G, 4G, 4G/IMT-Advanced standards, 3GPP, WIMAX™, GSM, CDMA, CDMA2000, EDGE, 1xEVDO, iDEN, GPRS, HSPDA, TDMA, UMA, UMTS, ITU-R, and 5G), Bluetooth™, text or instant messaging (e.g., AIM, Blauk, eBuddy, Gadu-Gadu, IBM Lotus Sametime, ICQ, iMessage, IMVU, Lync, MXit, Paltalk, Skype, Tencent QQ, Windows Live Messenger™ or MSN Messenger™, Wireclub, Xfire, and Yahoo! Messenger™), email, Twitter (e.g., tweeting), Digital Service Protocol (DSP), and the like.

The term "communication system" or "communication network" and variations thereof, as used herein, can refer to a collection of communication components capable of one or more of transmission, relay, interconnect, control, or otherwise manipulate information or data from at least one transmitter to at least one receiver. As such, the communication may include a range of systems supporting point-to-point or broadcasting of the information or data. A communication system may refer to the collection individual communication hardware as well as the interconnects associated with and connecting the individual communication hardware. Communication hardware may refer to dedicated communication hardware or may refer a processor coupled with a communication means (i.e., an antenna) and running software capable of using the communication means to send and/or receive a signal within the communication system. Interconnect refers some type of wired or wireless communication link that connects various components, such as communication hardware, within a communication system. A communication network may refer to a specific setup of a communication system with the collection of individual communication hardware and interconnects having some definable network topography. A communication network may include wired and/or wireless network having a pre-set to an ad hoc network structure.

The term "computer-readable medium," as used herein refers to any tangible storage and/or transmission medium that participates in providing instructions to a processor for execution. Such a medium may take many forms, including but not limited to, non-volatile media, volatile media, and transmission media. Non-volatile media includes, for example, non-volatile random access memory (NVRAM), or magnetic or optical disks. Volatile media includes dynamic memory, such as main memory. Common forms of computer-readable media include, for example, a floppy disk, a flexible disk, hard disk, magnetic tape, or any other magnetic medium, magneto-optical medium, a compact disc read only memory (CD-ROM), any other optical medium, punch cards, paper tape, any other physical medium with patterns of holes, a random access memory (RAM), a programmable read only memory (PROM), and erasable programmable read only memory EPROM, a FLASH-EPROM, a solid state medium like a memory card, any other memory chip or cartridge, a carrier wave as described hereinafter, or any other medium from which a computer can read. A digital file attachment to an e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored. It should be noted that any computer readable medium that is not a signal transmission may be considered non-transitory.

The terms dash and dashboard and variations thereof, as used herein, may be used interchangeably and can be any panel and/or area of a vehicle disposed adjacent to an operator, user, and/or passenger. Dashboards may include, but are not limited to, one or more control panel(s), instrument housing(s), head unit(s), indicator(s), gauge(s), meter(s), light(s), audio equipment, computer(s), screen(s), display(s), HUD unit(s), and graphical user interface(s).

The term "module" as used herein refers to any known or later developed hardware, software, firmware, artificial intelligence, fuzzy logic, or combination of hardware and software that is capable of performing the functionality associated with that element.

The term "desktop" refers to a metaphor used to portray systems. A desktop is generally considered a "surface" that may include pictures, called icons, widgets, folders, etc. that can activate and/or show applications, windows, cabinets, files, folders, documents, and other graphical items. The icons are generally selectable to initiate a task through user interface interaction to allow a user to execute applications and/or conduct other operations.

The term "display" refers to a portion of a physical screen used to display the output of a computer to a user.

The term "displayed image" refers to an image produced on the display. A typical displayed image is a window or desktop. The displayed image may occupy all or a portion of the display.

The ten "display orientation" refers to the way in which a rectangular display is oriented for viewing. The two most common types of display orientations are portrait and landscape. In landscape mode, the display is oriented such that the width of the display is greater than the height of the display (such as a 4:3 ratio, which is 4 units wide and 3 units tall, or a 16:9 ratio, which is 16 units wide and 9 units tall). Stated differently, the longer dimension of the display is oriented substantially horizontal in landscape mode while the shorter dimension of the display is oriented substantially vertical. In the portrait mode, by contrast, the display is oriented such that the width of the display is less than the height of the display. Stated differently, the shorter dimension of the display is oriented substantially horizontal in the portrait mode while the longer dimension of the display is oriented substantially vertical. A multi-screen display can have one composite display that encompasses all the screens. The composite display can have different display characteristics based on the various orientations of the device.

The term "electronic address" can refer to any contactable address, including a telephone number, instant message handle, e-mail address, Uniform Resource Locator ("URL"), Global Universal Identifier ("GUID"), Universal Resource Identifier ("URI"), Address of Record ("AOR"), electronic alias in a database, etc., combinations thereof.

The term "gesture" refers to a user action that expresses an intended idea, action, meaning, result, and/or outcome. The user action can include manipulating a device (e.g., opening or closing a device, changing a device orientation, moving a trackball or wheel, etc.), movement of a body part in relation to the device, movement of an implement or tool in relation to the device, audio inputs, etc. A gesture may be made on a device (such as on the screen) or with the device to interact with the device.

The term "gesture capture" refers to a sense or otherwise a detection of an instance and/or type of user gesture. The gesture capture can be received by sensors in three-dimensional space. Further, the gesture capture can occur in one or more areas of a screen, for example, on a touch-sensitive display or a gesture capture region. A gesture region can be on the display, where it may be referred to as a touch sensitive display, or off the display, where it may be referred to as a gesture capture area.

The terms "infotainment" and "infotainment system" may be used interchangeably and can refer to the hardware/software products, data, content, information, and/or systems, which can be built into or added to vehicles to enhance driver and/or passenger experience. Infotainment may provide media and/or multimedia content. An example is information-based media content or programming that also includes entertainment content.

A "multi-screen application" refers to an application that is capable of producing one or more windows that may simultaneously occupy one or more screens. A multi-screen application commonly can operate in single-screen mode in which one or more windows of the application are displayed only on one screen or in multi-screen mode in which one or more windows are displayed simultaneously on multiple screens.

A "single-screen application" refers to an application that is capable of producing one or more windows that may occupy only a single screen at a time.

The terms "online community," "e-community," or "virtual community" can mean a group of people that interact via a computer network, for social, professional, educational, and/or other purposes. The interaction can use a variety of media formats, including wikis, blogs, chat rooms, Internet forums, instant messaging, email, and other forms of electronic media. Many media formats may be used in social software separately and/or in combination, including text-based chat rooms and forums that use voice, video text or avatars.

The term "satellite positioning system receiver" can refer to a wireless receiver or transceiver to receive and/or send location signals from and/or to a satellite positioning system (SPS), such as the Global Positioning System ("GPS") (US), GLONASS (Russia), Galileo positioning system (EU), Compass navigation system (China), and Regional Navigational Satellite System (India).

The term "social network service" may include a service provider that builds online communities of people, who share interests and/or activities, or who are interested in exploring the interests and/or activities of others. Social network services can be network-based and may provide a variety of ways for users to interact, such as e-mail and instant messaging services.

The term "social network" can refer to a network-based social network.

The term "screen," "touch screen," "touchscreen," or "touch-sensitive display" refers to a physical structure that enables the user to interact with the computer by touching areas on the screen and provides information to a user through a display. The touch screen may sense user contact in a number of different ways, such as by a change in an electrical parameter (e.g., resistance or capacitance), acoustic wave variations, infrared radiation proximity detection, light variation detection, and the like. In a resistive touch screen, for example, normally separated conductive and resistive metallic layers in the screen pass an electrical current. When a user touches the screen, the two layers make contact in the contacted location, whereby a change in electrical field is noted and the coordinates of the contacted location calculated. In a capacitive touch screen, a capacitive layer stores electrical charge, which is discharged to the user upon contact with the touch screen, causing a decrease in the charge of the capacitive layer. The decrease is measured, and the contacted location coordinates determined. In a surface acoustic wave touch screen, an acoustic wave is transmitted through the screen, and the acoustic wave is disturbed by user contact. A receiving transducer detects the user contact instance and determines the contacted location coordinates.

The term "window" refers to a, typically rectangular, displayed image on at least part of a display that contains or provides content different from the rest of the screen. The window may obscure the desktop. The dimensions and orientation of the window may be configurable either by another module or by a user. When the window is expanded, the window can occupy substantially all of the display space on a screen or screens.

The terms "determine," "calculate," and "compute," and variations thereof, as used herein, are used interchangeably and include any type of methodology, process, mathematical operation, or technique.

It shall be understood that the term "means," as used herein, shall be given its broadest possible interpretation in accordance with 35 U.S.C., Section 112, Paragraph 6 or other applicable law. Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

The terms "vehicle," "car," "automobile," and variations thereof may be used interchangeably herein and can refer to a device or structure for transporting animate and/or inanimate or tangible objects (e.g., persons and/or things), such as a self-propelled conveyance. A vehicle as used herein can include any conveyance or model of a conveyance, where the conveyance was originally designed for the purpose of moving one or more tangible objects, such as people, animals, cargo, and the like. The term "vehicle" does not require that a conveyance moves or is capable of movement. Typical vehicles may include but are in no way limited to cars, trucks, motorcycles, busses, automobiles, trains, railed conveyances, boats, ships, marine conveyances, submarine conveyances, airplanes, space craft, flying machines, human-powered conveyances, and the like.

The term "profile," as used herein, can refer to any data structure, data store, and/or database that includes one or more items of information associated with a vehicle, a vehicle system, a device (e.g., a mobile device, laptop, mobile phone, etc.), or a person.

The term "in communication with," as used herein, refers to any coupling, connection, or interaction using electrical signals to exchange information or data, using any system, hardware, software, protocol, or format, regardless of whether the exchange occurs wirelessly or over a wired connection.

The preceding is a simplified summary of the disclosure to provide an understanding of some aspects of the disclosure. This summary is neither an extensive nor exhaustive overview of the disclosure and its various aspects, embodiments, and/or configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and/or configurations of the disclosure are possible utilizing, alone or in combination, one or more of the features set forth above or described in detail below.

BRIEF DESCRIPTION OF THE DRAWINGS

FIG. 5B is a second block diagram of an embodiment of a vehicle interior environment separated into areas and/or zones;

FIG. 9 is a block diagram of an embodiment of a communications subsystem for a vehicle;

FIG. 22 is a block diagram of an embodiment of a vehicle systems;

FIG. 24A is a graphical representation of an embodiment of a user interface for the vehicle control system;

FIG. 24B is a graphical representation of another embodiment of a user interface for the vehicle control system;

In the appended Figs., similar components and/or features may have the same reference label. Further, various components of the same type may be distinguished by following the reference label by a letter that distinguishes among the similar components. If only the first reference label is used in the specification, the description is applicable to any one of the similar components having the same first reference label irrespective of the second reference letter or label.

DETAILED DESCRIPTION

Presented herein are embodiments of systems, devices, processes, data structures, user interfaces, etc. The embodiments may relate to an automobile and/or an automobile environment. The automobile environment can include systems associated with the automobile and devices or other systems in communication with the automobile and/or automobile systems. Furthermore, the systems can relate to communications systems and/or devices and may be capable of communicating with other devices and/or to an individual or group of individuals. Further, the systems can receive user input in unique ways. The overall design and functionality of the systems provide for an enhanced user experience making the automobile more useful and more efficient. As described herein, the automobile systems may be electrical, mechanical, electro-mechanical, software-based, and/or combinations thereof.

Figure 1:
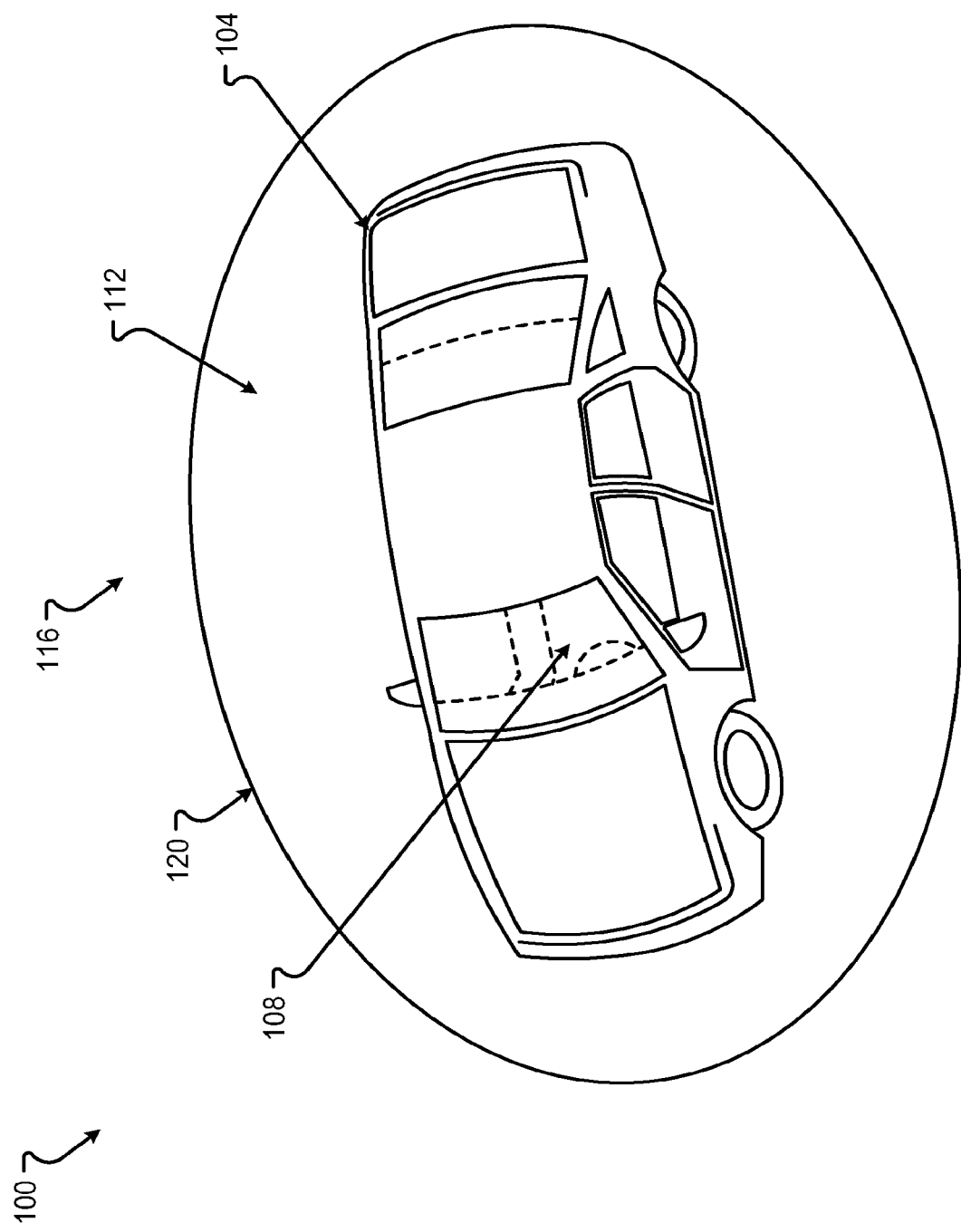
FIG. 1 depicts an embodiment of a vehicle operating environment.

A vehicle environment 100 that may contain a vehicle ecosystem is shown in FIG. 1. The vehicle environment 100 can contain areas associated with a vehicle or conveyance 104. The vehicle 104 is shown as a car but can be any type of conveyance. The environment 100 can include at least three zones. A first zone 108 may be inside a vehicle 104. The zone 108 includes any interior space, trunk space, engine compartment, or other associated space within or associated with the vehicle 104. The interior zone 108 can be defined by one or more techniques, for example, geofencing.

A second zone 112 may be delineated by line 120. The zone 112 is created by a range of one or more sensors associated with the vehicle 104. Thus, the area 112 is exemplary of the range of those sensors and what can be detected by those sensors associated with the vehicle 104. Although sensor range is shown as a fixed and continuous oval, the sensor range may be dynamic and/or discontinuous. For example, a ranging sensor (e.g., radar, lidar, ladar, etc.) may provide a variable range depending on output power, signal characteristics, or environmental conditions (e.g., rain, fog, clear, etc.). The rest of the environment includes all space beyond the range of the sensors and is represented by space 116. Thus, the environment 100 may have an area 116 that includes all areas beyond the sensor range 112. The area 116 may include locations of travel that the vehicle 104 may proceed to in the future.

Figure 2:
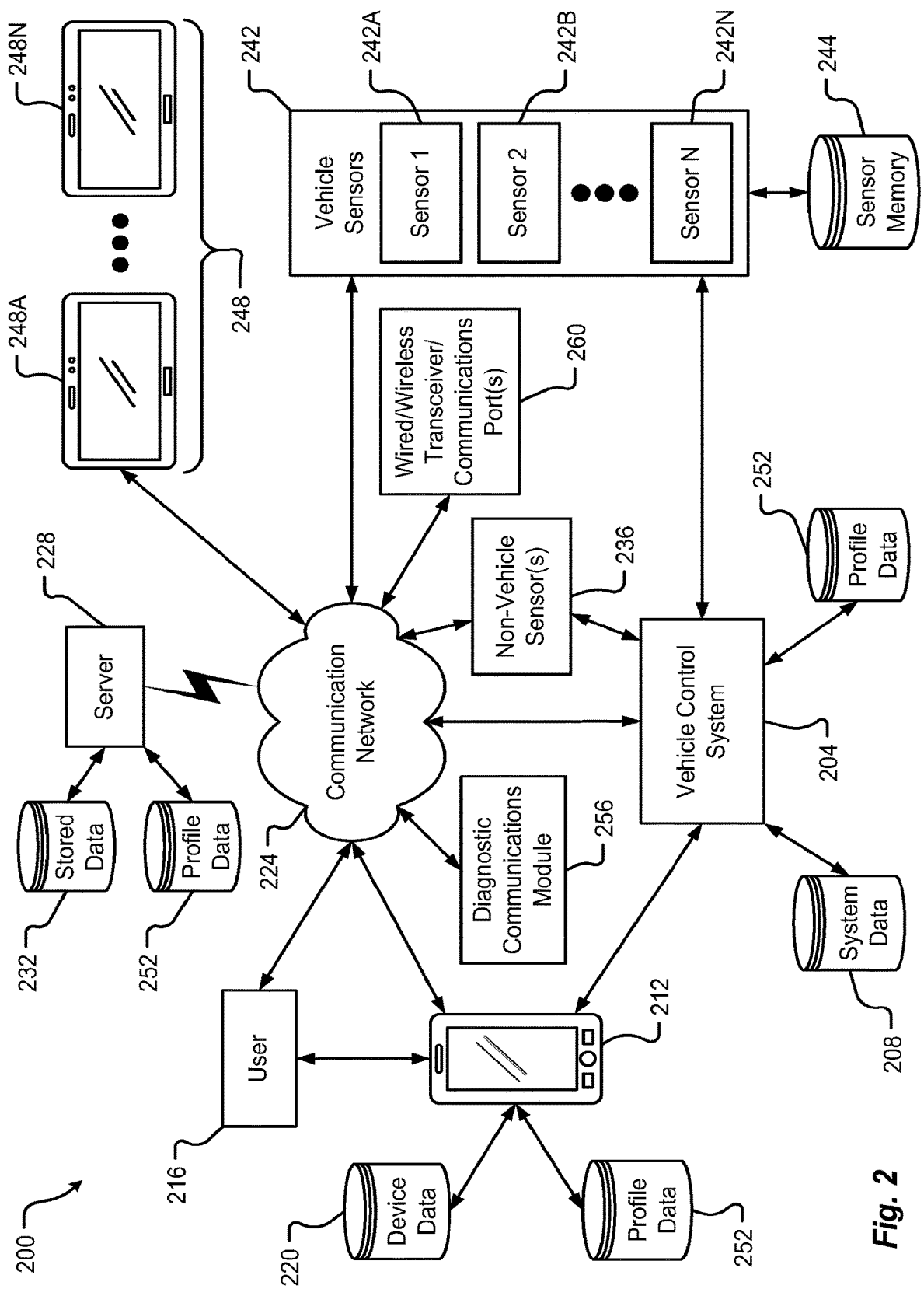
FIG. 2 is a block diagram of an embodiment of a vehicle system.

An embodiment of a vehicle system 200 is shown in FIG. 2. The vehicle system 200 may comprise hardware and/or software that conduct various operations for or with the vehicle 104. The operations can include, but are not limited to, providing information to the user 216, receiving input from the user 216, and controlling the functions or operation of the vehicle 104, etc. The vehicle system 200 can include a vehicle control system 204. The vehicle control system 204 can be any type of computing system operable to conduct the operations as described herein. An example of a vehicle control system may be as described in conjunction with FIG. 3.

The vehicle control system 204 may interact with a memory or storage system 208 that stores system data. System data 208 may be any type of data needed for the vehicle control system 204 to control effectively the vehicle 104. The system data 208 can represent any type of database or other storage system. Thus, the system data 208 can be a flat file data system, an object-oriented data system, or some other data system that may interface with the vehicle control system 204.

The vehicle control system 204 may communicate with a device or user interface 212, 248. The user interface 212, 248 may be operable to receive user input either through touch input, on one or more user interface buttons, via voice command, via one or more image sensors, or through a graphical user interface that may include a gesture capture region, as described in conjunction with the other Figs. provided herein. Further, the symbol 212, 248 can represent a device that is located or associated with the vehicle 104. The device 212, 248 can be a mobile device, including, but not limited to, a mobile telephone, a mobile computer, or other type of computing system or device that is either permanently located in or temporarily associated with, but not necessarily connected to, the vehicle 104. Thus, the vehicle control system 204 can interface with the device 212, 248 and leverage the device's computing capability to provide one or more of the features or functions as described herein.

The device or user interface 212, 248 can receive input or provide information to a user 216. The user 216 may thus interact with the vehicle control system 204 through the interface or device 212, 248. Further, the device 212, 248 may include or have access to device data 220 and/or profile data 252. The device data 220 can be any type of data that is used in conjunction with the device 212, 248 including, but not limited to, multimedia data, preferences data, device identification information, or other types of data. The profile data 252 can be any type of data associated with at least one user 216 including, but in no way limited to, bioinformatics, medical information, driving history, personal information (e.g., home physical address, business physical address, contact addresses, likes, dislikes, hobbies, size, weight, occupation, business contacts—including physical and/or electronic addresses, personal contacts—including physical and/or electronic addresses, family members, and personal information related thereto, etc.), other user characteristics, advertising information, user settings and feature preferences, travel information, associated vehicle preferences, communication preferences, historical information (e.g., including historical, current, and/or future travel destinations), Internet browsing history, or other types of data. In any event, the data may be stored as device data 220 and/or profile data 252 in a storage system similar to that described in conjunction with FIGS. 12A through 12D.

As an example, the profile data 252 may include one or more user profiles. User profiles may be generated based on data gathered from one or more of vehicle preferences (e.g., seat settings, HVAC settings, dash configurations, and the like), recorded settings, geographic location information (e.g., provided by a satellite positioning system (e.g., GPS), Wi-Fi hotspot, cell tower data, etc.), mobile device information (such as mobile device electronic addresses, Internet browsing history and content, application store selections, user settings and enabled and disabled features, and the like), private information (such as user information from a social network, user presence information, user business account, and the like), secure data, biometric information, audio information from on board microphones, video information from on board cameras, Internet browsing history and browsed content using an on board computer and/or the local area network enabled by the vehicle 104, geographic location information (e.g., a vendor storefront, roadway name, city name, etc.), and the like.

The profile data 252 may include one or more user accounts. User accounts may include access and permissions to one or more settings and/or feature preferences associated with the vehicle 104, communications, infotainment, content, etc. In one example, a user account may allow access to certain settings for a particular user, while another user account may deny access to the settings for another user, and vice versa. The access controlled by the user account may be based on at least one of a user account priority, role, permission, age, family status, a group priority (e.g., the user account priority of one or more users, etc.), a group age (e.g., the average age of users in the group, a minimum age of the users in the group, a maximum age of the users in the group, and/or combinations thereof, etc.).

For example, a user 216 may be allowed to purchase applications (e.g., software, etc.) for the vehicle 104 and/or a device associated with the vehicle 104 based on information associated with the user account. This user account information may include a preferred payment method, permissions, and/or other account information. As provided herein, the user account information may be part of the user profile and/or other data stored in the profile data 252.

As another example, an adult user (e.g., a user with an age of 18 years old and/or over, etc.) may be located in an area of a vehicle 104, such as a rear passenger area. Continuing this example a child user (e.g., a user with an age of 17 years old and/or less, etc.) may be located in the same, or close, area. In this example, the user account information in the profile data 252 associated with both the adult user and the child user may be used by the vehicle 104 in determining whether content is appropriate for the area given the age of the child user. For instance, a graphic movie containing violence (e.g., a movie associated with a mature rating, such as a Motion Picture Association of America (MPAA) rating of "R," "NC-17," etc.) may be suitable to present to a display device associated with the adult user but may not be acceptable to present to the display device if a 12-year old child user may see and/or hear the content of the movie.

The vehicle control system 204 may also communicate with or through a communication network 224. The communication network 224 can represent any type of wireless and/or wired communication system that may be included within the vehicle 104 or operable to communicate outside the vehicle 104. Thus, the communication network 224 can include a local area communication capability and a wide area communication capability. For example, the communication network 224 can include a Bluetooth® wireless system, an 802.11x (e.g., 802.11G/802.11N/802.11AC, or the like, wireless system), a CAN bus, an Ethernet network within the vehicle 104, or other types of communication networks that may function with or be associated with the vehicle 104. Further, the communication network 224 can also include wide area communication capabilities, including one or more of, but not limited to, a cellular communication capability, satellite telephone communication capability, a wireless wide area network communication capability, or other types of communication capabilities that allow for the vehicle control system 204 to communicate outside the vehicle 104.

The vehicle control system 204 may communicate through the communication network 224 to a server 228 that may be located in a facility that is not within physical proximity to the vehicle 104. Thus, the server 228 may represent a cloud computing system or cloud storage that allows the vehicle control system 204 to either gain access to further computing capabilities or to storage at a location outside of the vehicle 104. The server 228 can include a computer processor and memory and be similar to any computing system as understood to one skilled in the art.

Further, the server 228 may be associated with stored data 232. The stored data 232 may be stored in any system or by any method, as described in conjunction with system data 208, device data 220, and/or profile data 252. The stored data 232 can include information that may be associated with one or more users 216 or associated with one or more vehicles 104. The stored data 232, being stored in a cloud or in a distant facility, may be exchanged among vehicles 104 or may be used by a user 216 in different locations or with different vehicles 104. Additionally or alternatively, the server may be associated with profile data 252 as provided herein. It is anticipated that the profile data 252 may be accessed across the communication network 224 by one or more components of the system 200. Similar to the stored data 232, the profile data 252, being stored in a cloud or in a distant facility, may be exchanged among vehicles 104 or may be used by a user 216 in different locations or with different vehicles 104.

The vehicle control system 204 may also communicate with one or more sensors 236, 242, which are either associated with the vehicle 104 or communicate with the vehicle 104. Vehicle sensors 242 may include one or more sensors for providing information to the vehicle control system 204 that determine or provide information about the environment 100 in which the vehicle 104 is operating. Embodiments of these sensors may be as described in conjunction with FIGS. 6A-7B. Non-vehicle sensor 236 can be any type of sensor that is not currently associated with the vehicle 104. For example, non-vehicle sensor 236 can be sensors in a traffic system operated by a third party that provides data to the vehicle control system 204. Further, the non-vehicle sensor(s) 236 can be other types of sensors which provide information about the distant environment 116 or other information about the vehicle 104 or the environment 100. These non-vehicle sensors 236 may be operated by third parties but provide information to the vehicle control system 204. Examples of information provided by the sensors 236 and that may be used by the vehicle control system 204 may include weather tracking data, traffic data, user health tracking data, vehicle maintenance data, or other types of data, which may provide environmental or other data to the vehicle control system 204. The vehicle control system 204 may also perform signal processing of signals received from one or more sensors 236, 242. Such signal processing may include estimation of a measured parameter from a single sensor, such as multiple measurements of a range state parameter from the vehicle 104 to an obstacle, and/or the estimation, blending, or fusion of a measured state parameter from multiple sensors such as multiple radar sensors or a combination of a ladar/lidar range sensor and a radar sensor. Signal processing of such sensor signal measurements may comprise stochastic signal processing, adaptive signal processing, and/or other signal processing techniques known to those skilled in the art.

The various sensors 236, 242 may include one or more sensor memory 244. Embodiments of the sensor memory 244 may be configured to store data collected by the sensors 236, 242. For example, a temperature sensor may collect temperature data associated with a vehicle 104, user 216, and/or environment, over time. The temperature data may be collected incrementally, in response to a condition, or at specific time periods. In this example, as the temperature data is collected, it may be stored in the sensor memory 244. In some cases, the data may be stored along with an identification of the sensor and a collection time associated with the data. Among other things, this stored data may include multiple data points and may be used to track changes in sensor measurements over time. As can be appreciated, the sensor memory 244 can represent any type of database or other storage system.

The diagnostic communications module 256 may be configured to receive and transmit diagnostic signals and information associated with the vehicle 104. Examples of diagnostics signals and information may include, but is in no way limited to, vehicle system warnings, sensor data, vehicle component status, service information, component health, maintenance alerts, recall notifications, predictive analysis, and the like. Embodiments of the diagnostic communications module 256 may handle warning/error signals in a predetermined manner. The signals, for instance, can be presented to one or more of a third party, occupant, vehicle control system 204, and a service provider (e.g., manufacturer, repair facility, etc.).

Optionally, the diagnostic communications module 256 may be utilized by a third party (i.e., a party other than the user 216, etc.) in communicating vehicle diagnostic information. For instance, a manufacturer may send a signal to a vehicle 104 to determine a status associated with one or more components associated with the vehicle 104. In response to receiving the signal, the diagnostic communications module 256 may communicate with the vehicle control system 204 to initiate a diagnostic status check. Once the diagnostic status check is performed, the information may be sent via the diagnostic communications module 256 to the manufacturer. This example may be especially useful in determining whether a component recall should be issued based on the status check responses returned from a certain number of vehicles.

Wired/wireless transceiver/communications ports 260 may be included. The wired/wireless transceiver/communications ports 260 may be included to support communications over wired networks or links, for example with other communication devices, server devices, and/or peripheral devices. Examples of wired/wireless transceiver/communications ports 260 include Ethernet ports, Universal Serial Bus (USB) ports, Institute of Electrical and Electronics Engineers (IEEE) 1594, or other interface ports.

Figure 3:
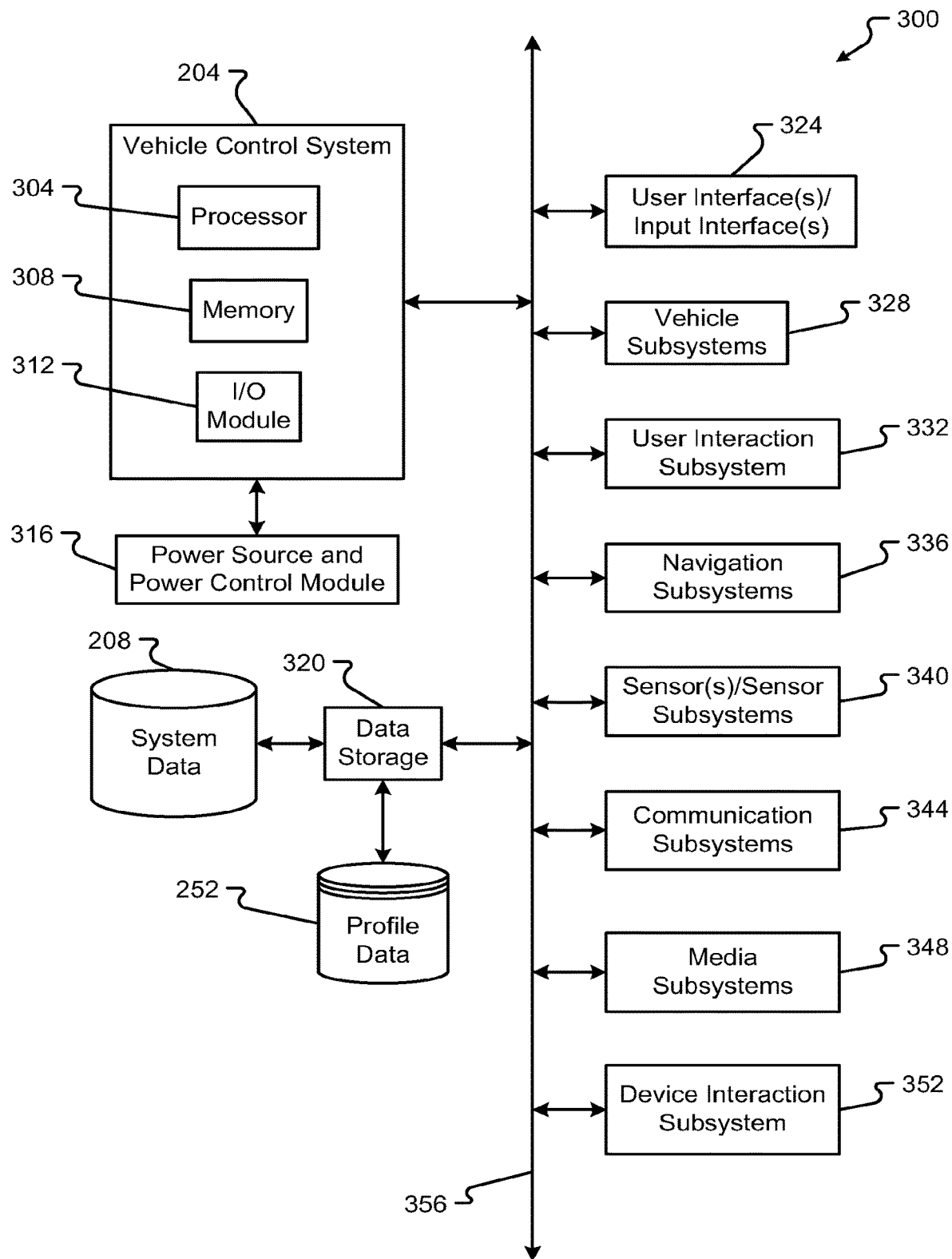
FIG. 3 is a block diagram of an embodiment of a vehicle control system environment.

An embodiment of a vehicle control environment 300 including a vehicle control system 204 may be as shown in FIG. 3. Beyond the vehicle control system 204, the vehicle control environment 300 can include one or more of, but is not limited to, a power source and/or power control module 316, a data storage module 320, user interface(s)/input interface(s) 324, vehicle subsystems 328, user interaction subsystems 332, Global Positioning System (GPS)/Navigation subsystems 336, sensor(s) and/or sensor subsystems 340, communication subsystems 344, media subsystems 348, and/or device interaction subsystems 352. The subsystems, modules, components, etc. 316-352 may include hardware, software, firmware, computer readable media, displays, input devices, output devices, etc. or combinations thereof. The system, subsystems, modules, components, etc. 204, 316-352 may communicate over a network or bus 356. This communication bus 356 may be bidirectional and perform data communications using any known or future-developed standard or protocol. An example of the communication bus 356 may be as described in conjunction with FIG. 4.

The vehicle control system 204 can include a processor 304, memory 308, and/or an input/output (I/O) module 312. Thus, the vehicle control system 204 may be a computer system, which can comprise hardware elements that may be electrically coupled. The hardware elements may include one or more central processing units (CPUs) 304; one or more components of the I/O module 312 including input devices (e.g., a mouse, a keyboard, etc.) and/or one or more output devices (e.g., a display device, a printer, etc.).

The processor 304 may comprise a general purpose programmable processor or controller for executing application programming or instructions. The processor 304 may, optionally, include multiple processor cores, and/or implement multiple virtual processors. Additionally or alternatively, the processor 304 may include multiple physical processors. As a particular example, the processor 304 may comprise a specially configured application specific integrated circuit (ASIC) or other integrated circuit, a digital signal processor, a controller, a hardwired electronic or logic circuit, a programmable logic device or gate array, a special purpose computer, or the like. The processor 304 generally functions to run programming code or instructions implementing various functions of the vehicle control system 204.

The input/output module 312 and associated ports may be included to support communications over wired or wireless networks or links, for example with other communication devices, server devices, and/or peripheral devices. Examples of an input/output module 312 include an Ethernet port, a Universal Serial Bus (USB) port, Institute of Electrical and Electronics Engineers (IEEE) 1594, or other interface.

The vehicle control system 204 may also include one or more storage devices 308. By way of example, storage devices 308 may be disk drives, optical storage devices, solid-state storage devices such as a random access memory ("RAM") and/or a read-only memory ("ROM"), which can be programmable, flash-updateable and/or the like. The vehicle control system 204 may additionally include a computer-readable storage media reader; a communications system (e.g., a modem, a network card (wireless or wired), an infra-red communication device, etc.); and working memory 308, which may include RAM and ROM devices as described above. The vehicle control system 204 may also include a processing acceleration unit, which can include a digital signal processor (DSP), a special-purpose processor, and/or the like.

The computer-readable storage media reader can further be connected to a computer-readable storage medium, together (and, optionally, in combination with storage device(s)) comprehensively representing remote, local, fixed, and/or removable storage devices plus storage media for temporarily and/or more permanently containing computer-readable information. The communications system may permit data to be exchanged with an external or internal network and/or any other computer or device described herein. Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices, and/or other machine readable mediums for storing information.

Figure 10:
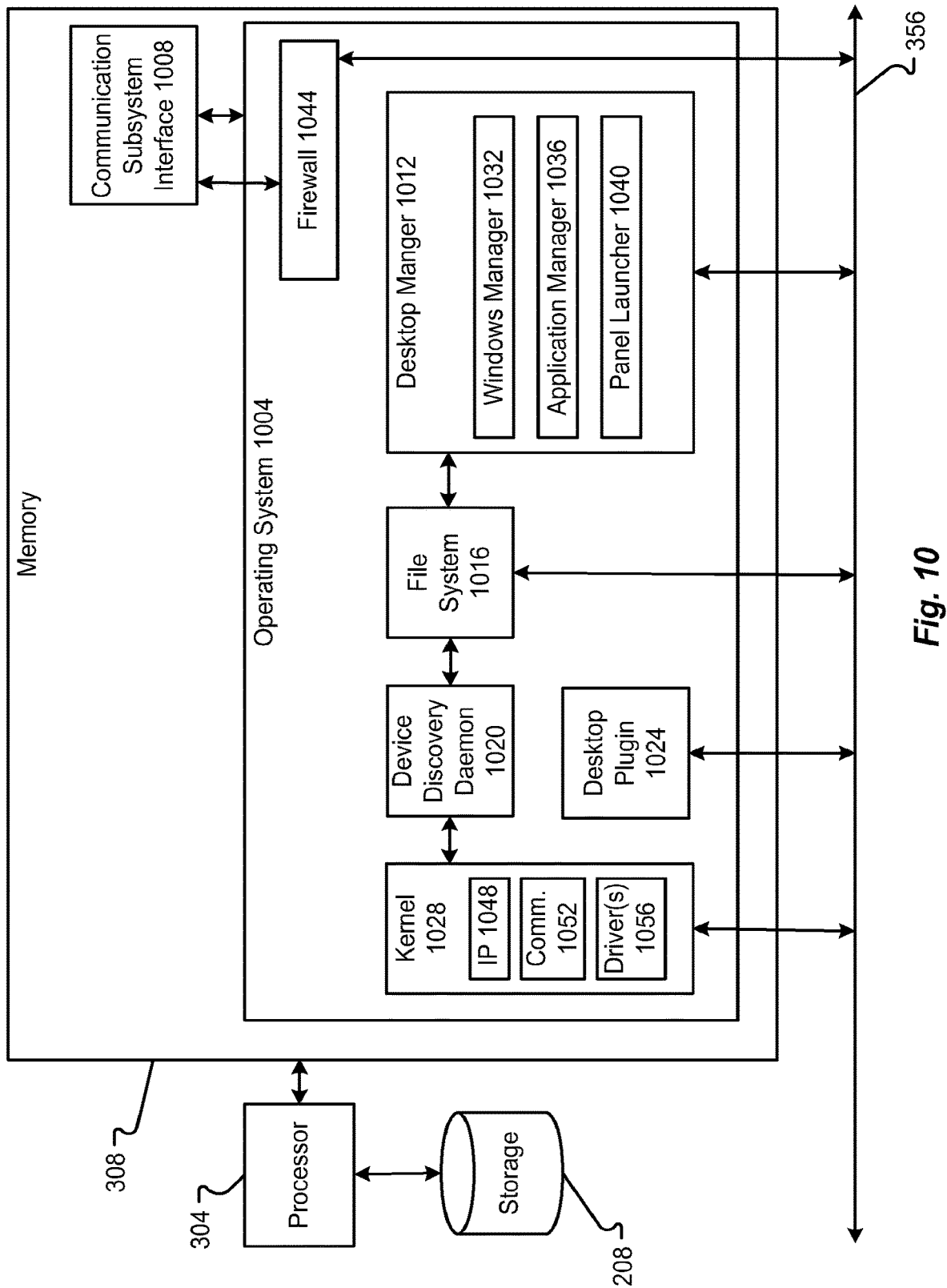
FIG. 10 is a block diagram of an embodiment of a software architecture for the vehicle control system.

The vehicle control system 204 may also comprise software elements including an operating system and/or other code, as described in conjunction with FIG. 10. It should be appreciated that alternates to the vehicle control system 204 may have numerous variations from that described herein. For example, customized hardware might also be used and/or particular elements might be implemented in hardware, software (including portable software, such as applets), or both. Further, connection to other computing devices such as network input/output devices may be employed.

The power source and/or power control module 316 can include any type of power source, including, but not limited to, batteries, alternating current sources (from connections to a building power system or power line), solar cell arrays, etc. One or more components or modules may also be included to control the power source or change the characteristics of the provided power signal. Such modules can include one or more of, but is not limited to, power regulators, power filters, alternating current (AC) to direct current (DC) converters, DC to AC converters, receptacles, wiring, other converters, etc. The power source and/or power control module 316 functions to provide the vehicle control system 204 and any other system with power.

The data storage 320 can include any module for storing, retrieving, and/or managing data in one or more data stores and/or databases. The database or data stores may reside on a storage medium local to (and/or resident in) the vehicle control system 204 or in the vehicle 104. Alternatively, some of the data storage capability may be remote from the vehicle control system 204 or automobile, and in communication (e.g., via a network) to the vehicle control system 204. The database or data stores may reside in a storage-area network ("SAN") familiar to those skilled in the art. Similarly, any necessary files for performing the functions attributed to the vehicle control system 204 may be stored locally on the respective vehicle control system 204 and/or remotely, as appropriate. The databases or data stores may be a relational database, and the data storage module 320 may be adapted to store, update, and retrieve data in response to specifically-formatted commands. The data storage module 320 may also perform data management functions for any flat file, object oriented, or other type of database or data store.

A first data store that may be part of the vehicle control environment 300 is a profile data store 252 for storing data about user profiles and data associated with the users. A system data store 208 can include data used by the vehicle control system 204 and/or one or more of the components 324-352 to facilitate the functionality described herein. The data stores 208 and/or 252 may be as described in conjunction with FIGS. 1 and/or 12A-12D.

The user interface/input interfaces 324 may be as described herein for providing information or data and/or for receiving input or data from a user. Vehicle systems 328 can include any of the mechanical, electrical, electromechanical, computer, or other systems associated with the function of the vehicle 100. For example, vehicle systems 328 can include one or more of, but is not limited to, the steering system, the braking system, the engine and engine control systems, the electrical system, the suspension, the drive train, the cruise control system, the radio, the heating, ventilation, air conditioning (HVAC) system, the windows and/or doors, etc. These systems are well known in the art and will not be described further.

Examples of the other systems and subsystems 324-352 may be as described further herein. For example, the user interface(s)/input interface(s) 324 may be as described in FIGS. 2 and 8B; the vehicle subsystems 328 may be as described in FIG. 6a et. seq.; the user interaction subsystem 332 may be as described in conjunction with the user/device interaction subsystem 817 of FIG. 8B; the Navigation subsystem 336 may be as described in FIGS. 6A and 8C; the sensor(s)/sensor subsystem 340 may be as described in FIGS. 7A and 7B; the communication subsystem 344 may be as described in FIGS. 2, 4, 5B, 5C, and 9; the media subsystem 348 may be as described in FIG. 8A; and, the device interaction subsystem 352 may be as described in FIG. 2 and in conjunction with the user/device interaction subsystem 817 of FIG. 8B.

Figure 4:
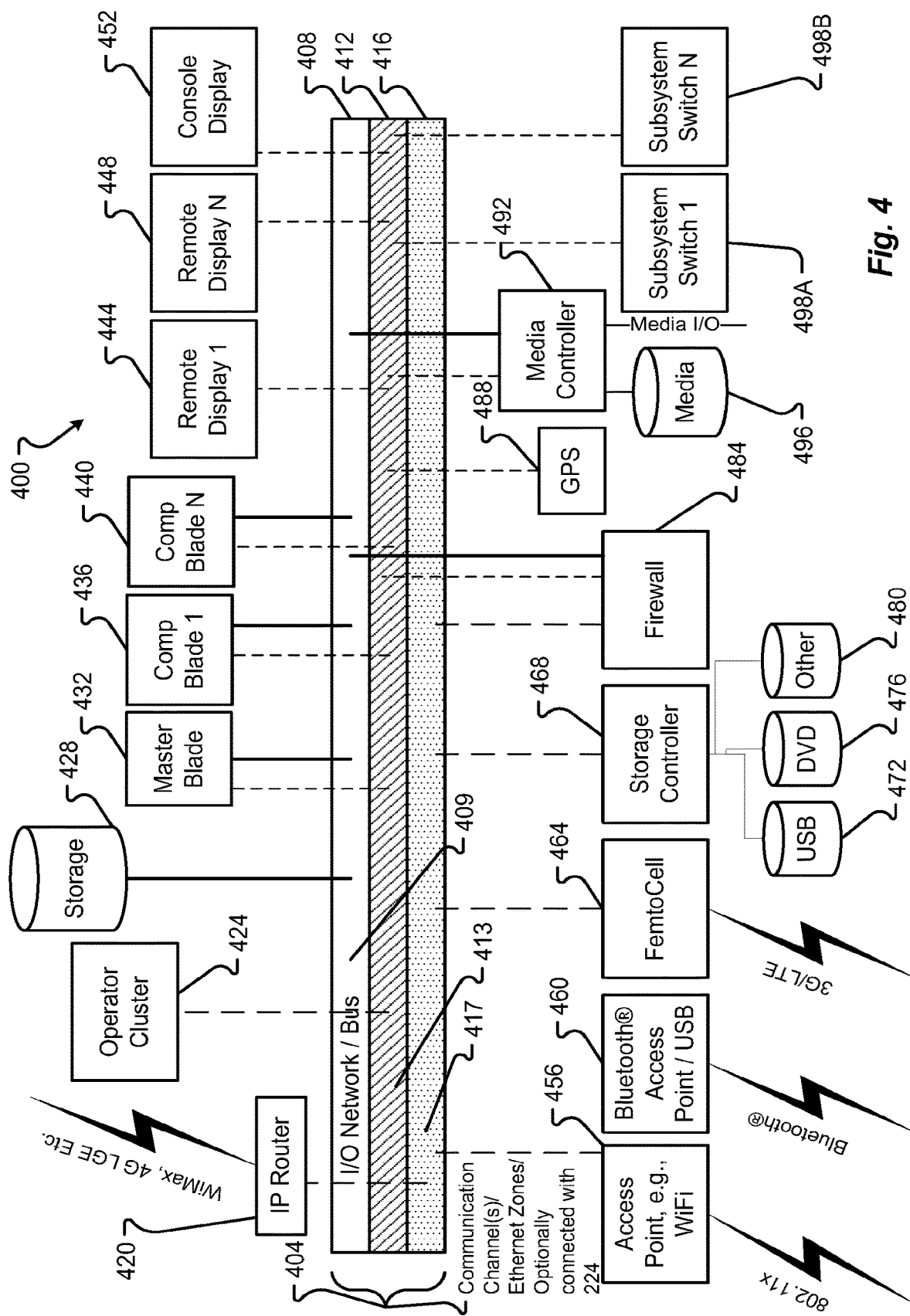
FIG. 4 is a block diagram of an embodiment of a vehicle communications subsystem.

FIG. 4 illustrates an optional communications channel architecture 400 and associated communications components. FIG. 4 illustrates some of the optional components that can be interconnected via the communication channels/zones 404. Communication channels/zones 404 can carry information on one or more of a wired and/or wireless communications link with, in the illustrated example, there being three communications channels/zones, 408, 412, and 416.

This optional environment 400 can also include an IP router 420, an operator cluster 424, one or more storage devices 428, one or more blades, such as master blade 432, and computational blades 436 and 440. Additionally, the communications channels/zones 404 can interconnect one or more displays, such as, remote display 1 444, remote display N 448, and console display 452. The communications channels/zones 404 also interconnect an access point 456, a Bluetooth® access point/USB hub 460, a Femtocell 464, a storage controller 468, that is connected to one or more of USB devices 472, DVDs 476, or other storage devices 480. To assist with managing communications within the communication channel, the environment 400 optionally includes a firewall 484 which will be discussed hereinafter in greater detail. Other components that could also share the communications channel/zones 404 include GPS 488, media controller 492, which is connected to one or more media sources 496, and one or more subsystems, such as subsystem switches 498.

Optionally, the communications channels/zones 404 can be viewed as an I/O network or bus where the communications channels are carried on the same physical media. Optionally, the communication channels 404 can be split amongst one or more physical media and/or combined with one or more wireless communications protocols. Optionally, the communications channels 404 can be based on wireless protocols with no physical media interconnecting the various elements described herein.

The environment 400 shown in FIG. 4 can include a collection of blade processors that are housed in a "crate." The crate can have a PC-style backplane connector 408 and a backplane Ethernet 408 that allows the various blades to communicate with one another using, for example, an Ethernet.

Various other functional elements illustrated in FIG. 4 can be integrated into this crate architecture with, as discussed hereinafter, various zones utilized for security. Optionally, as illustrated in FIG. 4, the backplane 404/408 can have two separate Ethernet zones that may or may not be on the same communications channel. Optionally, the zones exist on a single communications channel on the I/O network/bus 408. Optionally, the zones are actually on different communications channels, e.g., 412, 416; however, the implementation is not restricted to any particular type of configuration. Rather, as illustrated in FIG. 4, there can be a red zone 417 and a green zone 413, and the I/O backplane on the network/bus 408 that enables standard I/O operations. This backplane or I/O network/bus 408 also optionally can provide power distribution to the various modules and blades illustrated in FIG. 4. The red and green Ethernet zones, 417 and 413 respectively, can be implemented as Ethernet switches, with one on each side of the firewall 484. Two Ethernets (untrusted and trusted) are not connected in accordance with an optional embodiment. Optionally, the connector geometry for the firewall can be different for the Ethernet zones than for the blades that are a part of the system.

The red zone 417 only needs to go from the modular connector to the input side of the backplane connector of the firewall 484. While FIG. 4 indicates that there are five external red zone connectors to the firewall 484, provisions can be made for any number of ports with the connections being made at the access point 456, the Bluetooth® access point (combo controller) 460, Femtocell 464, storage controller 468, and/or firewall 484. Optionally, the external port connections can be made through a manufacturer configurable modular connector panel, and one or more of the red zone Ethernet ports could be available through a customer supplied crate which allows, for example, wired Ethernet connections from a bring-your-own-device (BYOD) to the firewall 484.

The green zone 413 goes from the output side of the firewall 484 and generally defines the trusted Ethernet. The Ethernet on the backplane 408 essentially implements an Ethernet switch for the entire system, defining the Ethernet backbone of the vehicle 104. All other modules, e.g., blades, etc., can connect to a standard backplane bus and the trusted Ethernet. Some number of switch ports can be reserved to connect to an output modular connector panel to distribute the Ethernet throughout the vehicle 104, e.g., connecting such elements as the console display 452, remote displays 444, 448, GPS 488, etc. Optionally, only trusted components, either provided or approved by the manufacturer after testing, can be attached to the green zone 413, which is by definition in the trusted Ethernet environment.

Optionally, the environment 400, shown in FIG. 4, utilizes IPv6 over Ethernet connections wherever possible. Using, for example, the Broadcom single-twisted pair Ethernet technology, wiring harnesses are simplified and data transmission speeds are maximized. However, while the Broadcom single-twisted pair Ethernet technology can be used, in general, systems and methods can work comparably well with any type of well-known Ethernet technology or other comparable communications technology.

As illustrated in FIG. 4 the I/O network/bus 408 is a split-bus concept that contains three independent bus structures:

- The red zone 417—the untrusted Ethernet environment. This zone 417 may be used to connect network devices and customer provided devices to the vehicle information system with these devices being on the untrusted side of the firewall 484.
- The green zone 413—the trusted Ethernet environment, this zone 413 can be used to connect manufacturer certified devices such as GPS units, remote displays, subsystem switches, and the like, to the vehicle network 404. Manufacturer certified devices can be implemented by vendors that allow the vehicle software system to validate whether or not a device is certified to operate with the vehicle 100. Optionally, only certified devices are allowed to connect to the trusted side of the network.

The I/O bus 409—the I/O bus may be used to provide power and data transmission to bus-based devices such as the vehicle solid state drive, the media controller blade 492, the computational blades 436, 440, and the like.

As an example, the split-bus structure can have the following minimum configuration:

Two slots for the red zone Ethernet;

One slot for built-in LTE/WiMax access 420 from the car to other network resources such as the cloud/Internet;

One slot for user devices or bring-your-own device access, this slot can implement, for example, WiFi, Bluetooth®, and/or USB connectivity 456, which can be provided in, for example, the customer crate;

One slot for combined red zone and green zone Ethernet, this slot can be reserved for the firewall controller;

Two slots for computational blades. Here the two computation blades are illustratively as shown the optional master blade and the multimedia blade or controller 492 which can be provided as standard equipment; and The expansion controller that allows the I/O bus to be extended and provides additional Ethernet switch ports for one or more of the red or green zones, which may require that the basic green zone Ethernet switch implementation will support additional ports beyond the initial three that are needed for the basic exemplary system.

It should be possible to build 8 or 16 or more Ethernet switches that allow for the expansion with existing component(s) in a straight-forward manner.

The red zone 417 can be implemented as an 8-port Ethernet switch that has three actual bus ports within the crate with the remaining five ports being available on the customer crate. The crate implements red zone slots for the firewall controller 484, the combo controller which includes WiFi, Bluetooth®, USB hub (456, 460) and the IP router 420.

The firewall controller 484 can have a dedicated slot that bridges the red zone 417, green zone 413, and uses the I/O bus for power connections. In accordance with an optional low cost implementation, the firewall 484 can be implemented by a dummy module that simply bridges the red zone 417 and the green zone 413 without necessarily providing any firewall functionality. The combo controller 460 that includes the WiFi, Bluetooth®, and USB hub can be provided for consumer device connections. This controller can also implement the IPv6 (un-routable) protocol to insure that all information is packetized for transmission via IP over the Ethernet in the I/O network/bus 408.

The combo controller 460 with the USB hub can have ports in the customer crate. The combo controller 460 can implement USB discovery functions and packetizes the information for transmission via IP over Ethernet. The combo controller 460 can also facilitate installation of the correct USB driver for the discovered device, such as a BYOD from the user. The combo controller 460 and USB hub can then map the USB address to a "local" IPv6 address for interaction with one or more of the computational blades which is generally going to be the media controller 492.

The IP router 420 can implement Internet access through a manufacturer provided service. This service can allow, for example, a manufacturer to offer value-added services to be integrated into the vehicle information systems. The existence of the manufacturer provided Internet access can also allow the "e-Call" function and other vehicle data recorder functions to be implemented. IP router 420 also allows, for example, WiMax, 4G LTE, and other connections to the Internet through a service provider that can be, for example, contracted by the manufacturer. Internally, the IP router 420 can allow cellular handset connections to the Internet through a Femtocell 464 that is part of the IP router implementation. The IP router 420, with the Femtocell 464, can also allow a cone of silence functionality to be implemented. The IP router 420 can be an optional component for a vehicle provided by, for example, the manufacturer, a dealer, or installed by a user. In the absence of the IP router 420, it is possible to connect a consumer handheld device to the I/O network/bus 408 using, for example, either WiFi or Bluetooth® 456, 460. While functionality may be somewhat reduced when using a handheld device instead of a built-in Ethernet connection, systems and methods of this invention can also work utilizing this consumer handheld device which then connects to the Internet via, for example, WiMax, 4G, 4G LTE, or the like.

Figure 5A:
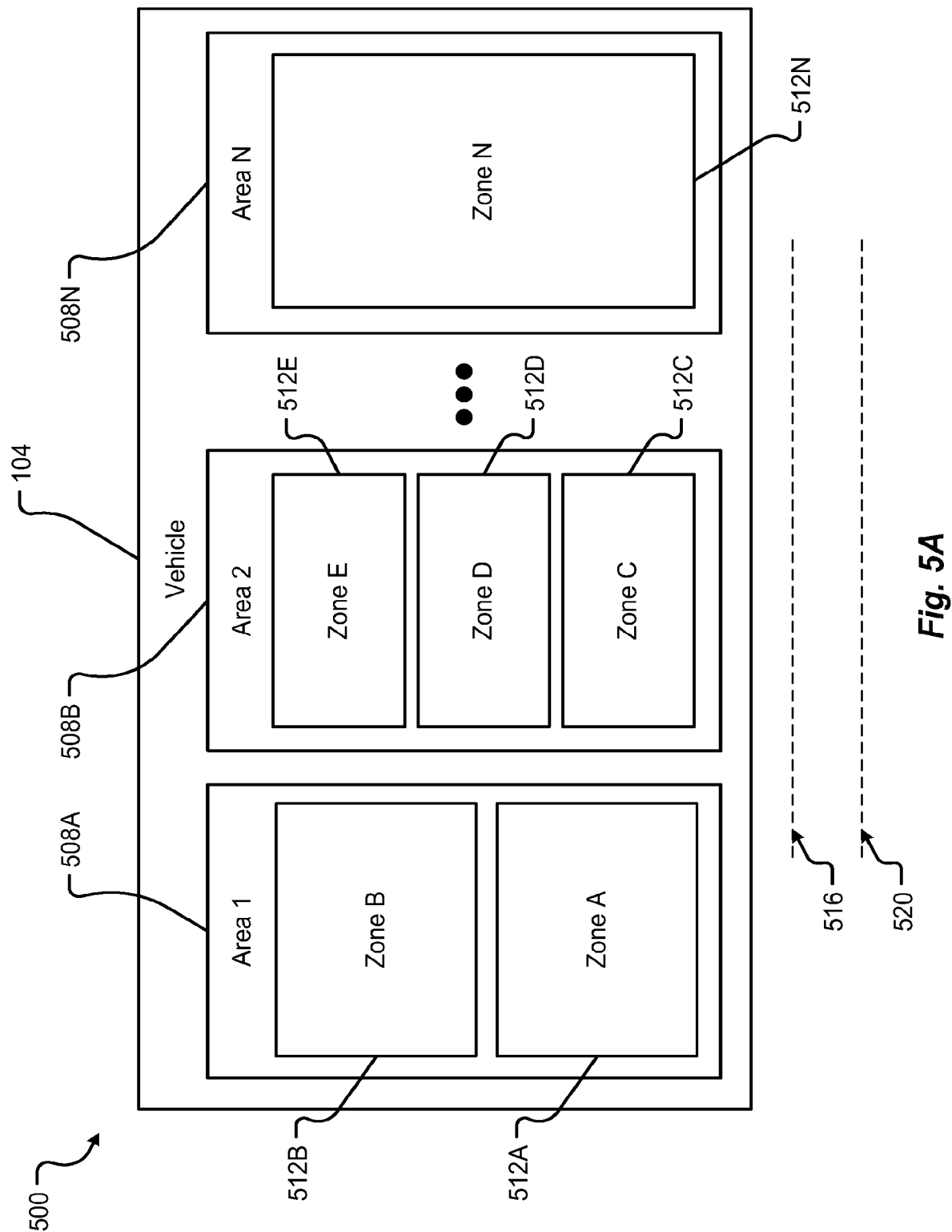
FIG. 5A is a first block diagram of an embodiment of a vehicle interior environment separated into areas and/or zones.
Figure 5C:
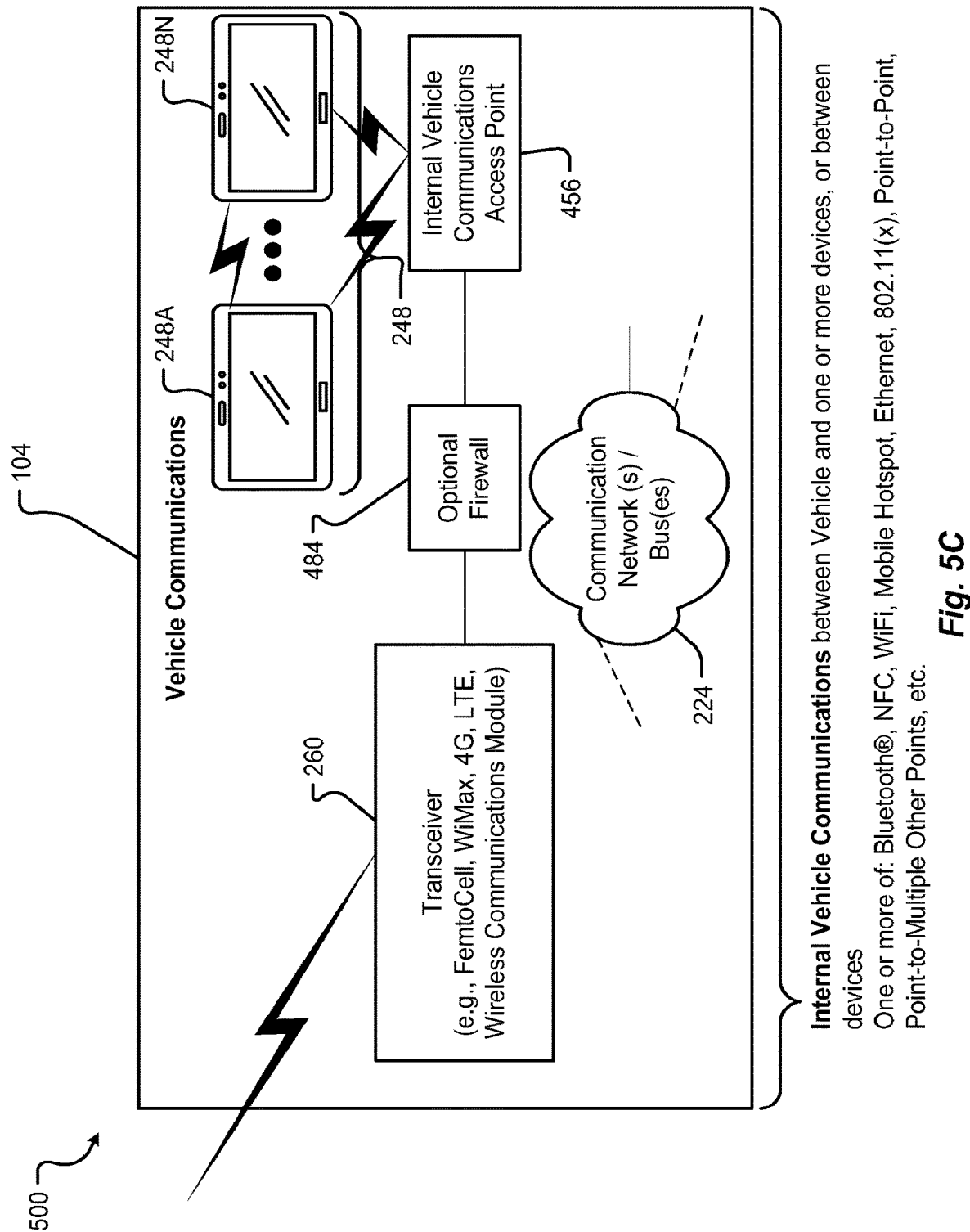
FIG. 5C is a third block diagram of an embodiment of a vehicle interior environment separated into areas and/or zones.

FIGS. 5A-5C show configurations of a vehicle 104. In general, a vehicle 104 may provide functionality based at least partially on one or more areas, zones, and distances, associated with the vehicle 104. Non-limiting examples of this functionality are provided herein below.

An arrangement or configuration for sensors within a vehicle 104 is as shown in FIG. 5A. The sensor arrangement 500 can include one or more areas 508 within the vehicle. An area can be a larger part of the environment inside or outside of the vehicle 104. Thus, area one 508A may include the area within the trunk space or engine space of the vehicle 104 and/or the front passenger compartment. Area two 508B may include a portion of the interior space 108 (e.g., a passenger compartment, etc.) of the vehicle 104. The area N, 508N, may include the trunk space or rear compartment area, when included within the vehicle 104. The interior space 108 may also be divided into other areas. Thus, one area may be associated with the front passenger's and driver's seats, a second area may be associated with the middle passengers' seats, and a third area may be associated with a rear passenger's seat. Each area 508 may include one or more sensors that are positioned or operate to provide environmental information about that area 508.

Each area 508 may be further separated into one or more zones 512 within the area 508. For example, area 1 508A may be separated into zone A 512A, and zone B 512B. Each zone 512 may be associated with a particular portion of the interior occupied by a passenger. For example, zone A 512A may be associated with a driver. Zone B 512B, may be associated with a front passenger. Each zone 512 may include one or more sensors that are positioned or configured to collect information about the environment or ecosystem associated with that zone or person.

A passenger area 508B may include more than two zones as described in conjunction with area 508A. For example, area 508B may include three zones, 512C, 512D, and 512E. These three separate zones 512C, 512D, and 512E may be associated with three passenger seats typically found in the rear passenger area of a vehicle 104. An area 508N and may include a single zone 512N as there may be no separate passenger areas but may include a single trunk area within the vehicle 104. The number of zones 512 is unlimited within the areas as the areas are also unlimited inside the vehicle 104. Further, it should be noted that there may be one or areas 508 or zones 512 that may be located outside the vehicle 104 that may have a specific set of sensors associated therewith.

Optionally, each area/access point 508, 456, 516, 520, and/or zone 512, associated with a vehicle 104, may comprise one or more sensors to determine a presence of a user 216 and/or device 212, 248 in and/or adjacent to each area 508, 456, 516, 520, and/or zone 512. The sensors may include vehicle sensors 242 and/or non-vehicle sensors 236 as described herein. It is anticipated that the sensors may be configured to communicate with a vehicle control system 204 and/or the diagnostic communications module 256. Additionally or alternatively, the sensors may communicate with a device 212, 248. The communication of sensors with the vehicle 104 may initiate and/or terminate the control of device 212, 248 features. For example, a vehicle operator may be located in a second outside area 520 associated with a vehicle 104. As the operator approaches the first outside area 516, associated with the vehicle 104, the vehicle control system 204 may determine to control features associated with one or more device 212, 248 and diagnostic communications module 256.

Optionally, the location of the device 212, 248 relative to the vehicle 104 may determine vehicle functionality and/or features to be provided and/or restricted to a user 216. By way of example, a device 212, 248 associated with a user 216 may be located at a second outside area 520 from the vehicle 104. In this case, and based at least partially on the distance of the device 212, 248 from the vehicle 104 (e.g., provided by detecting the device 212, 248 at or beyond the second outside area 520) the vehicle 104 may lock one or more features (e.g., ignition access, vehicle access, communications ability, etc.) associated with the vehicle 104. Optionally, the vehicle 104 may provide an alert based on the distance of the device 212, 248 from the vehicle 104. Continuing the example above, once the device 212, 248 reaches the first outside area 516 of the vehicle 104 at least one of the vehicle features may be unlocked. For instance, by reaching the first outside area 516, the vehicle 104 may unlock a door of the vehicle 104. In some cases, when the device is detected to be inside the vehicle 104, the various sensors 236, 242 may determine that the user 216 is in an area 508 and/or zone 512. As is further described herein, features of the vehicle 104, device 212, 248, and/or other components may be controlled based on rules stored in a memory.

FIG. 5B illustrates optional internal vehicle communications between one or more of the vehicle and one or more devices or between devices. Various communications can occur utilizing one or more Bluetooth®, NFC, WiFi, mobile hot spot, point-to-point communications, point-to-multipoint other point communications, an ad hoc network, or in general any known communications protocol over any known communications media or media-types.

Optionally, various types of internal vehicle communications can be facilitated using an access point 456 that utilizes one or more of Bluetooth®, NFC, WiFi, wireless Ethernet, mobile hot spot technology, or the like. Upon being connected with, and optionally authenticated to the access point 456, the connected device is able to communicate with one or more of the vehicle and one or more other devices that are connected to the access point 456. The type of connection to the access point 456 can be based on, for example, the zone 512, in which the device is located.

The user may identify their zone 512 in conjunction with an authentication procedure to the access point 456. For example, a driver in zone A 512A, upon authenticating to the access point 456, can cause the access point 456 to send a query to the device asking the device user in which zone 512 they are located. As discussed hereinafter, the zone 512 the user device is located in may have an impact on the type of communications, available bandwidth, the types of other devices or vehicle systems or subsystems the device could communicate with, and the like. As a brief introduction, internal communications with zone A 512A may be given preferential treatment over those communications originating from area 2 508B, which could have in itself, preferential treatment over communications originating within area N 508N.

Moreover, the device in zone A 512A can include profile information that governs the other devices that are allowed to connect to the access point 456 and what those devices have access to, how they can communicate, how much bandwidth they are allocated, and the like. While, optionally, the device associated with zone A 512A will be considered the "master" controller of the profile that governs the internal vehicle communications, it should be appreciated that this was arbitrarily chosen since it is assumed that there will always be a driver in a car that is present in zone A 512A. However, it should be appreciated the driver in zone A 512A, for example, may not have a communications device in which case a device associated with one of the other areas or zones, such as zone B 512B, area 2 508B, or area N 508N could also be associated with or control this master profile.

Optionally, various devices located within the various zones 512 can connect using, for example, ports provided by access point 456 or Bluetooth® access point/USB hub 460 as illustrated in FIG. 4. Similarly, the device(s) could connect utilizing the Femtocell 464 and optionally be directly connected via, for example, a standard Ethernet port.

As discussed, each one of the areas, area 1 508A, area 2 508B, and area N 508N, can each have associated therewith a profile that governs, for example, how many and what types of devices can connect from that area 508, bandwidth allocated to that area 508, the types of media or content available to device(s) within that area 508, the interconnection of devices within that area 508 or between areas 508, or, in general, can control any aspect of communication of an associated device with any one or more other associated devices/vehicle systems within the vehicle 104.

Optionally, area 2 508B devices can be provided with full access to multimedia and infotainment available within the vehicle 104, however, devices in area 2 508B may be restricted from any access to vehicle functions. Only devices in area 1 508A may be able to access vehicle control functions such as when "parents" are located in area 1 508A and the children are located in area 2 508B. Optionally, devices found in zone E 512E of area 2 508B may be able to access limited vehicle control functionality such as climate control within area 2. Similarly, devices in area N 508N may be able to control climate features within zone N 512N.

As will be appreciated, profiles can be established that allow management of communications within each of the areas 508, and further optionally within each of the zones 512. The profile can be granular in nature controlling not only what type of devices can connect within each zone 512, but how those devices can communicate with other devices and/or the vehicle and types of information that can be communicated.

To assist with identifying a location of a device within a zone 512, a number of different techniques can be utilized. One optional technique involves one or more of the vehicle sensors detecting the presence of an individual within one of the zones 512. Upon detection of an individual in a zone 512, communications subsystems 344 and the access point 456 can cooperate to not only associate the device within the zone 512 with the access point 456 but to also determine the location of the device within an area, and optionally within a zone 512. Once the device is established within a zone 512, a profile associated with the vehicle 104 can store information identifying that device and/or a person and optionally associating it with a particular zone 512 as a default. As discussed, there can be a master profile optionally associated with the device in zone A 512A, this master profile can govern communications with the communications subsystems 340 and where communications within vehicle 104 are to occur.

Some optional profiles are illustrated below where the Master Profile governs other device connectivity:

| Master Profile: | | | |
|---|---|---|---|
| Area 1 508A | Area 2 508B | Area N 508N | Other |
| All Communications | Allow Access to Infotainment | No Access | Master Profile acts as Firewall and Router |
| All Vehicle Controls | Allow Area 2 Climate Control | | |

| Secondary Profile (e.g. device in Zone B 512B, Area 1 508A) | | | |
|---|---|---|---|
| Area 1 508A | Area 2 508B | Area N 508N | Other |
| All Communications | Allow Access to Infotainment | Allow Access to Infotainment | Master Profile acts as Firewall and Router |
| All Vehicle Controls | Allow Area 2 Climate Control | Allow Area 2 Climate Control | |

| Secondary Profile, Option 2 | | | |
|---|---|---|---|
| Area 1 508A | Area 2 508B | Area N 508N | Other |
| All Communications | Allow Access to Infotainment, Internet | Allow Access to Infotainment | |
| All Vehicle Controls Except Driver-centric Controls | Allow Area 2 Climate Control | Allow Area 2 Climate Control | |

Some optional profiles are illustrated below where the Area/Zone governs device connectivity:

| Area 2 508B Profile: | | | |
|---|---|---|---|
| Area 1 508A | Area 2 508B | Area N 508N | Other |
| No Communications with Area 1 Devices | Allow Access to Infotainment, Allow Access to Other | | |

| Area 2 508B Profile: | | | |
|---|---|---|---|
| Area 1 508A | Area 2 508B | Area N 508N | Other |
| No Vehicle Controls | Area 2 or Zone N Devices, Internet Allow Area 2 Climate Control | | |

| Area N 508N Profile: | | | |
|---|---|---|---|
| Area 1 508A | Area 2 508B | Area N 508N | Other |
| Communications with Area 1, Zone B Device | | Allow Access to Infotainment, Allow Access to Other Area N or Zone N Devices | |
| No Vehicle Controls | | Allow Area N Climate Control | |

| Area 2 508B Profile: | | | |
|---|---|---|---|
| Area 1 508A | Area 2 508B | Area N 508N | Other |
| Media Sharing with Area 1, Zone B and Vehicle | Allow Access to Infotainment, Allow Access to Other Area 2 or Zone N Devices, Internet and Femtocell | | |
| No Vehicle Controls | | | |

Optionally, a user's device, such as a SmartPhone, can store in, for example a profile, with which zone 512 the user's device is associated. Then, assuming the user sits in the same zone 512 and area 508 as previously, the user's device can re-establish the same communications protocols with the access point 456 as were previously established.

In addition or in the alternative, the areas 508 and zones 512 can have associated therewith restrictions as to which one or more other user's devices with which users' devices can connect. For example, a first user's device can connect with any other user device in area 2 508B or area N 508N, however is restricted from connecting with a user device in area 1 508A, zone A 512A. However, the first user device may be able to communicate with another user's device that is located in area 1 508A, zone B 512B. These communications can include any type of standard communications such as sharing content, exchanging messages, forwarding or sharing multimedia or infotainment, or in general can include any communications that would ordinarily be available between two devices and/or the vehicle and vehicle systems. As discussed, there may be restrictions on the type of communications that can be sent to the device in area 1 508A, zone A 512A. For example, the user's device in area 1 508A, zone A 512A may be restricted from receiving one or more of text messages, multimedia, infotainment, or in general anything that can be envisioned as a potential distraction to the driver. Moreover, it should be appreciated that the communications between the various devices and the various zones 512 need not necessarily occur with the assistance of access point 456, but the communications could also occur directly between the device(s).

FIG. 5C outlines optional internal vehicle communications between one or more of the vehicle and one or more devices. More specifically, FIG. 5C illustrates an example of vehicle communications where the vehicle 104 is equipped with the necessary transceivers to provide a mobile hot spot functionality to any user device(s) therein, such as user devices 248A and 248N.

Optionally, and as discussed above, one or more user devices can connect to the access point 456. This access point 456 is equipped to handle communications routing to not only the communication network/buses 224 for intra-vehicle communications, but optionally can also communicate with, for example, the Internet or the cloud, in cooperation with transceiver 260. Optionally included is a firewall 484 that has the capability of not only blocking certain types of content, such as a malicious content, but can also operate to exclude certain type of communications from emanating from the vehicle 104 and transceiver 260. As will be appreciated, various profiles could be established in the firewall 484 that controls not only the type of communications that can be received at the vehicle 104, but the type of communications that can be sent from the vehicle 104.

The transceiver 260 can be any type of well-known wireless transceiver that communicates using a known communications protocol such as WiMax, 4G, 4G LTE, 3G, or the like. The user devices can communicate via, for example, WiFi link 248 with the access point 456, with the transceiver 260 providing Internet connectivity to the various user devices. As will be appreciated, there may need to be an account associated with transceiver 260 with a wireless carrier to provide data and/or voice connectivity to enable the user devices to communicate with the Internet. Typically, the account is established on a month-to-month basis with an associated fee but could also be performed based on the amount of data to be transmitted, received, or in any other manner.

Moreover, one or more of the user's devices and access point 456 can maintain profile information that governs how the user's devices are able to communicate with other devices, and optionally the Internet. Optionally, a profile can exist that only allows the user's devices to communicate with other user's devices and/or the vehicle, multimedia and/or the vehicle infotainment system, and may not be allowed access to the Internet via transceiver 260. The profile can stipulate that the user's device could connect to the Internet via transceiver 260 for a specified period of time and/or up to a certain amount of data usage. The user's device can have full access to the Internet via transceiver 260 with no limit on time or data usage which would reduce the data usage of the user's device since it is connected via WiFi to the access point 456, but however, would increase the data usage by transceiver 260, and therefore, shift the billing for that data usage to the transceiver 260 instead of the user's device. Still further, and as previously discussed, the various profiles may stipulate which user's device has priority for use of the bandwidth provided by the transceiver 260. For example, a user's device located area 1 508A, zone A 512A may be given preferential routing treatment of data above that of a user's device in zone N 512N. In this manner, for example, a driver would be given priority for Internet access above that of the passengers. This could become important, for example, when the driver is trying to obtain traffic or direction information or, for example, when the vehicle is performing a download to update various software features.

As will be appreciated, the optional firewall 484 can cooperate with the access point 456 and the various profiles that area 508 associated with the various devices within the vehicle 104 and can fully implement communications restrictions, control bandwidth limits, Internet accessibility, malicious software blocking, and the like. Moreover, the optional firewall 484 can be accessed by an administrator with one or more of these configuration settings edited through an administrator's control panel. For example, in a scenario where parents are always in area 1 508A, it may be appropriate to give all of the user's devices in area 1 508A full access to the Internet utilizing transceiver 260, however, while restricting access and/or bandwidth to any other user devices within the vehicle 104. As the user's device and profile would be known by the firewall 484, upon the user's device being associated with the access point 456, the firewall 484 and transceiver 260 can be configured to allow communications in accordance with the stored profile.

Figure 6A:
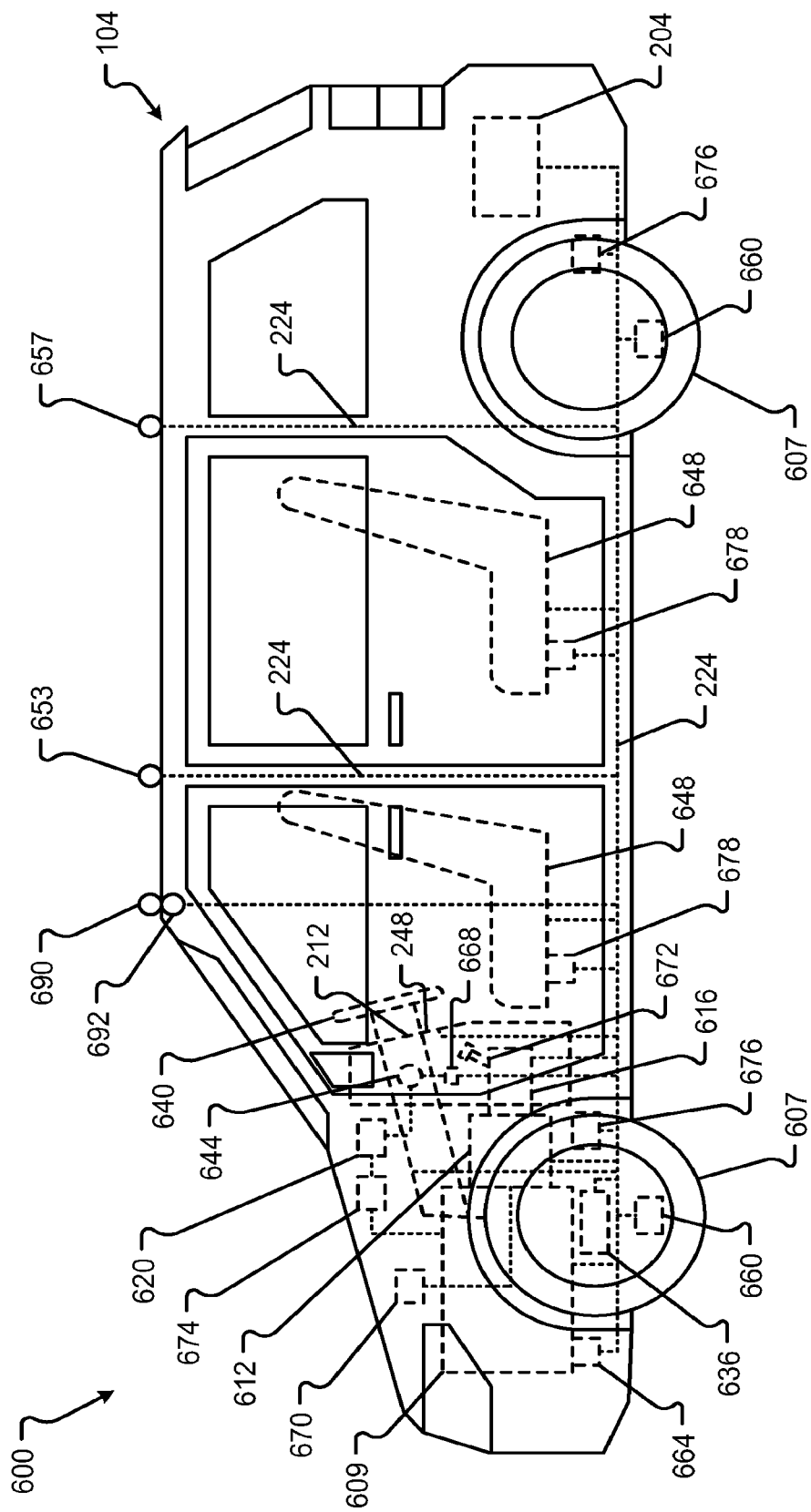
FIG. 6A depicts an embodiment of a sensor configuration for a vehicle.

A set of sensors or vehicle components 600 associated with the vehicle 104 may be as shown in FIG. 6A. The vehicle 104 can include, among many other components common to vehicles, wheels 607, a power source 609 (such as an engine, motor, or energy storage system (e.g., battery or capacitive energy storage system)), a manual or automatic transmission 612, a manual or automatic transmission gear controller 616, a power controller 620 (such as a throttle), a vehicle control system 204, the display device 212, a braking system 636, a steering wheel 640, a power source activation/deactivation switch 644 (e.g., an ignition), an occupant seating system 648, a wireless signal receiver 653 to receive wireless signals from signal sources such as roadside beacons and other electronic roadside devices, and a satellite positioning system receiver 657 (e.g., a Global Positioning System ("GPS") (US), GLONASS (Russia), Galileo positioning system (EU), Compass navigation system (China), and Regional Navigational Satellite System (India) receiver), driverless systems (e.g., cruise control systems, automatic steering systems, automatic braking systems, etc.).

The vehicle 104 can include a number of sensors in wireless or wired communication with the vehicle control system 204 and/or display device 212, 248 to collect sensed information regarding the vehicle state, configuration, and/ or operation. Exemplary sensors may include one or more of, but are not limited to, wheel state sensor 660 to sense one or more of vehicle speed, acceleration, deceleration, wheel rotation, wheel speed (e.g., wheel revolutions-per-minute), wheel slip, and the like, a power source energy output sensor 664 to sense a power output of the power source 609 by measuring one or more of current engine speed (e.g., revolutions-per-minute), energy input and/or output (e.g., voltage, current, fuel consumption, and torque) (e.g., turbine speed sensor, input speed sensor, crankshaft position sensor, manifold absolute pressure sensor, mass flow sensor, and the like), and the like, a switch state sensor 668 to determine a current activation or deactivation state of the power source activation/deactivation switch 644, a transmission setting sensor 670 to determine a current setting of the transmission (e.g., gear selection or setting), a gear controller sensor 672 to determine a current setting of the gear controller 616, a power controller sensor 674 to determine a current setting of the power controller 620, a brake sensor 676 to determine a current state (braking or non-braking) of the braking system 636, a seating system sensor 678 to determine a seat setting and current weight of seated occupant, if any) in a selected seat of the seating system 648, exterior and interior sound receivers 690 and 692 (e.g., a microphone, sonar, and other type of acoustic-to-electric transducer or sensor) to receive and convert sound waves into an equivalent analog or digital signal. Examples of other sensors (not shown) that may be employed include safety system state sensors to determine a current state of a vehicular safety system (e.g., air bag setting (deployed or underplayed) and/or seat belt setting (engaged or not engaged)), light setting sensor (e.g., current headlight, emergency light, brake light, parking light, fog light, interior or passenger compartment light, and/or tail light state (on or off)), brake control (e.g., pedal) setting sensor, accelerator pedal setting or angle sensor, clutch pedal setting sensor, emergency brake pedal setting sensor, door setting (e.g., open, closed, locked or unlocked) sensor, engine temperature sensor, passenger compartment or cabin temperature sensor, window setting (open or closed) sensor, one or more interior-facing or exterior-facing cameras or other imaging sensors (which commonly convert an optical image into an electronic signal but may include other devices for detection objects such as an electromagnetic radiation emitter/receiver that emits electromagnetic radiation and receives electromagnetic waves reflected by the object) to sense objects, such as other vehicles and pedestrians and optionally determine the distance, trajectory and speed of such objects, in the vicinity or path of the vehicle, odometer reading sensor, trip mileage reading sensor, wind speed sensor, radar transmitter/receiver output, brake wear sensor, steering/torque sensor, oxygen sensor, ambient lighting sensor, vision system sensor, ranging sensor, parking sensor, heating, venting, and air conditioning (HVAC) sensor, water sensor, air-fuel ratio meter, blind spot monitor, hall effect sensor, microphone, radio frequency (RF) sensor, infrared (IR) sensor, vehicle control system sensors, wireless network sensor (e.g., Wi-Fi and/or Bluetooth® sensor), cellular data sensor, and other sensors either future-developed or known to those of skill in the vehicle art.

In the depicted vehicle embodiment, the various sensors can be in communication with the display device 212, 248 and vehicle control system 204 via signal carrier network 224. As noted, the signal carrier network 224 can be a network of signal conductors, a wireless network (e.g., a radio frequency, microwave, or infrared communication system using a communications protocol, such as Wi-Fi), or a combination thereof. The vehicle control system 204 may also provide signal processing of one or more sensors, sensor fusion of similar and/or dissimilar sensors, signal smoothing in the case of erroneous "wild point" signals, and/or sensor fault detection. For example, ranging measurements provided by one or more RF sensors may be combined with ranging measurements from one or more IR sensors to determine one fused estimate of vehicle range to an obstacle target.

The control system 204 may receive and read sensor signals, such as wheel and engine speed signals, as a digital input comprising, for example, a pulse width modulated (PWM) signal. The processor 304 can be configured, for example, to read each of the signals into a port configured as a counter or configured to generate an interrupt on receipt of a pulse, such that the processor 304 can determine, for example, the engine speed in revolutions per minute (RPM) and the speed of the vehicle in miles per hour (MPH) and/or kilometers per hour (KPH). One skilled in the art will recognize that the two signals can be received from existing sensors in a vehicle comprising a tachometer and a speedometer, respectively. Alternatively, the current engine speed and vehicle speed can be received in a communication packet as numeric values from a conventional dashboard subsystem comprising a tachometer and a speedometer. The transmission speed sensor signal can be similarly received as a digital input comprising a signal coupled to a counter or interrupt signal of the processor 304 or received as a value in a communication packet on a network or port interface from an existing subsystem of the vehicle 104. The ignition sensor signal can be configured as a digital input, wherein a HIGH value represents that the ignition is on and a LOW value represents that the ignition is OFF. Three bits of the port interface can be configured as a digital input to receive the gear shift position signal, representing eight possible gear shift positions. Alternatively, the gear shift position signal can be received in a communication packet as a numeric value on the port interface. The throttle position signal can be received as an analog input value, typically in the range 0-5 volts. Alternatively, the throttle position signal can be received in a communication packet as a numeric value on the port interface. The output of other sensors can be processed in a similar fashion.

Other sensors may be included and positioned in the interior space 108 of the vehicle 104. Generally, these interior sensors obtain data about the health of the driver and/or passenger(s), data about the safety of the driver and/or passenger(s), and/or data about the comfort of the driver and/or passenger(s). The health data sensors can include sensors in the steering wheel that can measure various health telemetry for the person (e.g., heart rate, temperature, blood pressure, blood presence, blood composition, etc.). Sensors in the seats may also provide for health telemetry (e.g., presence of liquid, weight, weight shifts, etc.). Infrared sensors could detect a person's temperature; optical sensors can determine a person's position and whether the person has become unconscious. Other health sensors are possible and included herein.

Safety sensors can measure whether the person is acting safely. Optical sensors can determine a person's position and focus. If the person stops looking at the road ahead, the optical sensor can detect the lack of focus. Sensors in the seats may detect if a person is leaning forward or may be injured by a seat belt in a collision. Other sensors can detect that the driver has at least one hand on a steering wheel. Other safety sensors are possible and contemplated as if included herein.

Comfort sensors can collect information about a person's comfort. Temperature sensors may detect a temperature of the interior cabin. Moisture sensors can determine a relative humidity. Audio sensors can detect loud sounds or other distractions. Audio sensors may also receive input from a person through voice data. Other comfort sensors are possible and contemplated as if included herein.

Figure 6B:
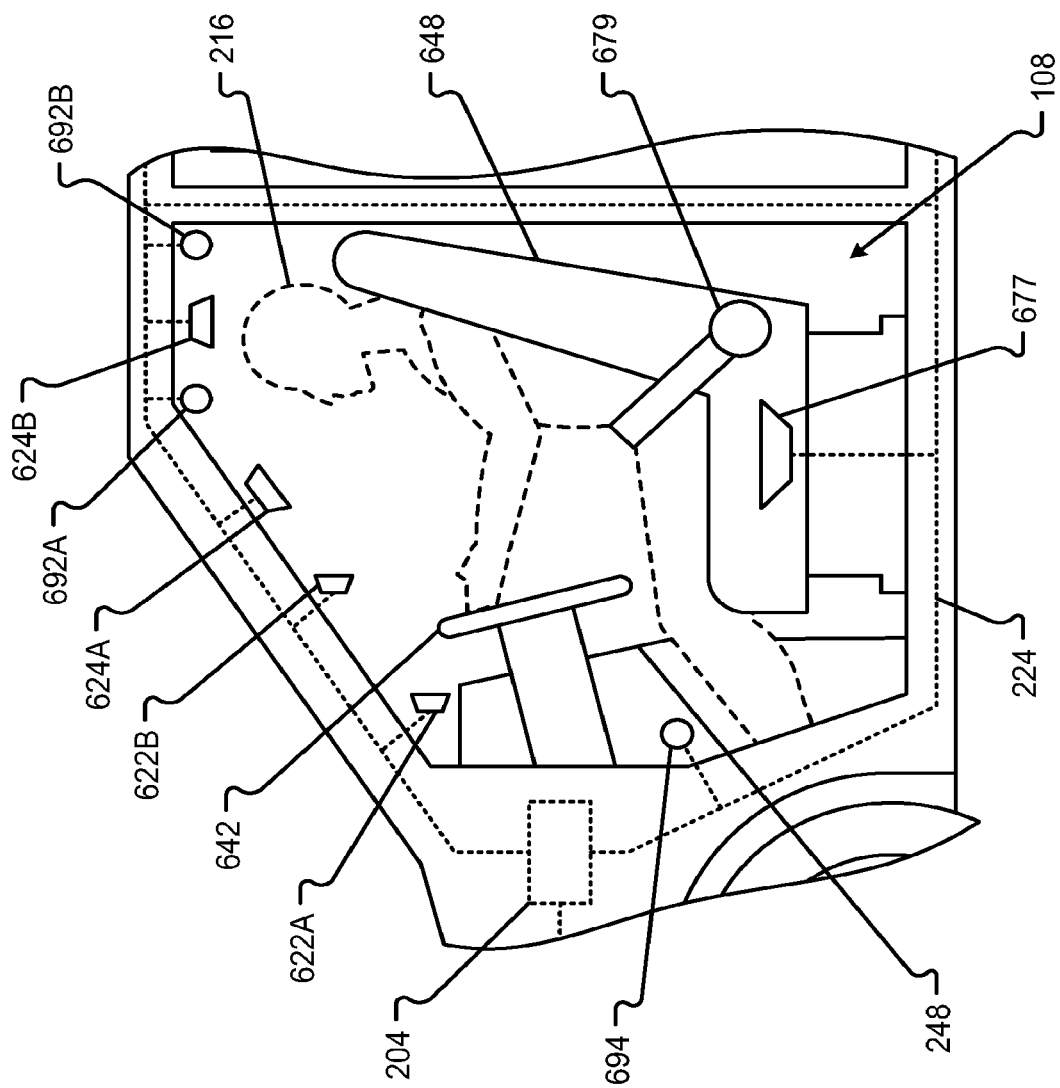
FIG. 6B depicts an embodiment of a sensor configuration for a zone of a vehicle.

FIG. 6B shows an interior sensor configuration for one or more zones 512 of a vehicle 104 optionally. Optionally, the areas 508 and/or zones 512 of a vehicle 104 may include sensors that are configured to collect information associated with the interior 108 of a vehicle 104. In particular, the various sensors may collect environmental information, user information, and safety information, to name a few. Embodiments of these sensors may be as described in conjunction with FIGS. 7A-8B.

Optionally, the sensors may include one or more of optical, or image, sensors 622A-B (e.g., cameras, etc.), motion sensors 624A-B (e.g., utilizing RF, IR, and/or other sound/image sensing, etc.), steering wheel user sensors 642 (e.g., heart rate, temperature, blood pressure, sweat, health, etc.), seat sensors 677 (e.g., weight, load cell, moisture, electrical, force transducer, etc.), safety restraint sensors 679 (e.g., seatbelt, airbag, load cell, force transducer, etc.), interior sound receivers 692A-B, environmental sensors 694 (e.g., temperature, humidity, air, oxygen, etc.), and the like.

The image sensors 622A-B may be used alone or in combination to identify objects, users 216, and/or other features, inside the vehicle 104. Optionally, a first image sensor 622A may be located in a different position within a vehicle 104 from a second image sensor 622B. When used in combination, the image sensors 622A-B may combine captured images to form, among other things, stereo and/or three-dimensional (3D) images. The stereo images can be recorded and/or used to determine depth associated with objects and/or users 216 in a vehicle 104. Optionally, the image sensors 622A-B used in combination may determine the complex geometry associated with identifying characteristics of a user 216. For instance, the image sensors 622A-B may be used to determine dimensions between various features of a user's face (e.g., the depth/distance from a user's nose to a user's cheeks, a linear distance between the center of a user's eyes, and more). These dimensions may be used to verify, record, and even modify characteristics that serve to identify a user 216. As can be appreciated, utilizing stereo images can allow for a user 216 to provide complex gestures in a 3D space of the vehicle 104. These gestures may be interpreted via one or more of the subsystems as disclosed herein. Optionally, the image sensors 622A-B may be used to determine movement associated with objects and/or users 216 within the vehicle 104. It should be appreciated that the number of image sensors used in a vehicle 104 may be increased to provide greater dimensional accuracy and/or views of a detected image in the vehicle 104.

The vehicle 104 may include one or more motion sensors 624A-B. These motion sensors 624A-B may detect motion and/or movement of objects inside the vehicle 104. Optionally, the motion sensors 624A-B may be used alone or in combination to detect movement. For example, a user 216 may be operating a vehicle 104 (e.g., while driving, etc.) when a passenger in the rear of the vehicle 104 unbuckles a safety belt and proceeds to move about the vehicle 104. In this example, the movement of the passenger could be detected by the motion sensors 624A-B. Optionally, the user 216 could be alerted of this movement by one or more of the devices 212, 248 in the vehicle 104. In another example, a passenger may attempt to reach for one of the vehicle control features (e.g., the steering wheel 640, the console, icons displayed on the head unit and/or device 212, 248, etc.). In this case, the movement (i.e., reaching) of the passenger may be detected by the motion sensors 624A-B. Optionally, the path, trajectory, anticipated path, and/or some other direction of movement/motion may be determined using the motion sensors 624A-B. In response to detecting the movement and/or the direction associated with the movement, the passenger may be prevented from interfacing with and/or accessing at least some of the vehicle control features (e.g., the features represented by icons may be hidden from a user interface, the features may be locked from use by the passenger, combinations thereof, etc.). As can be appreciated, the user 216 may be alerted of the movement/motion such that the user 216 can act to prevent the passenger from interfering with the vehicle 104 controls. Optionally, the number of motion sensors in a vehicle 104, or areas of a vehicle 104, may be increased to increase an accuracy associated with motion detected in the vehicle 104.

The interior sound receivers 692A-B may include, but are not limited to, microphones and other types of acoustic-to-electric transducers or sensors. Optionally, the interior sound receivers 692A-B may be configured to receive and convert sound waves into an equivalent analog or digital signal. The interior sound receivers 692A-B may serve to determine one or more locations associated with various sounds in the vehicle 104. The location of the sounds may be determined based on a comparison of volume levels, intensity, and the like, between sounds detected by two or more interior sound receivers 692A-B. For instance, a first interior sound receiver 692A may be located in a first area of the vehicle 104 and a second interior sound receiver 692B may be located in a second area of the vehicle 104. If a sound is detected at a first volume level by the first interior sound receiver 692A and a second, higher, volume level by the second interior sound receiver 692B in the second area of the vehicle 104, the sound may be determined to be closer to the second area of the vehicle 104. As can be appreciated, the number of sound receivers used in a vehicle 104 may be increased (e.g., more than two, etc.) to increase measurement accuracy surrounding sound detection and location, or source, of the sound (e.g., via triangulation, etc.).

Seat sensors 677 may be included in the vehicle 104. The seat sensors 677 may be associated with each seat and/or zone 512 in the vehicle 104. Optionally, the seat sensors 677 may provide health telemetry and/or identification via one or more of load cells, force transducers, weight sensors, moisture detection sensor, electrical conductivity/resistance sensor, and the like. For example, the seat sensors 677 may determine that a user 216 weighs 180 lbs. This value may be compared to user data stored in memory to determine whether a match exists between the detected weight and a user 216 associated with the vehicle 104. In another example, if the seat sensors 677 detect that a user 216 is fidgeting, or moving, in a seemingly uncontrollable manner, the system may determine that the user 216 has suffered a nervous and/or muscular system issue (e.g., seizure, etc.). The vehicle control system 204 may then cause the vehicle 104 to slow down and in addition or alternatively the automobile controller 8104 (described below) can safely take control of the vehicle 104 and bring the vehicle 104 to a stop in a safe location (e.g., out of traffic, off a freeway, etc).

Health telemetry and other data may be collected via the steering wheel user sensors 642. Optionally, the steering wheel user sensors 642 may collect heart rate, temperature, blood pressure, and the like, associated with a user 216 via at least one contact disposed on or about the steering wheel 640.

The safety restraint sensors 679 may be employed to determine a state associated with one or more safety restraint devices in a vehicle 104. The state associated with one or more safety restraint devices may serve to indicate a force observed at the safety restraint device, a state of activity (e.g., retracted, extended, various ranges of extension and/or retraction, deployment, buckled, unbuckled, etc.), damage to the safety restraint device, and more.

Environmental sensors 694, including one or more of temperature, humidity, air, oxygen, carbon monoxide, smoke, and other environmental condition sensors may be used in a vehicle 104. These environmental sensors 694 may be used to collect data relating to the safety, comfort, and/or condition of the interior space 108 of the vehicle 104. Among other things, the data collected by the environmental sensors 694 may be used by the vehicle control system 204 to alter functions of a vehicle. The environment may correspond to an interior space 108 of a vehicle 104 and/or specific areas 508 and/or zones 512 of the vehicle 104. It should be appreciate that an environment may correspond to a user 216. For example, a low oxygen environment may be detected by the environmental sensors 694 and associated with a user 216 who is operating the vehicle 104 in a particular zone 512. In response to detecting the low oxygen environment, at least one of the subsystems of the vehicle 104, as provided herein, may alter the environment, especially in the particular zone 512, to increase the amount of oxygen in the zone 512. Additionally or alternatively, the environmental sensors 694 may be used to report conditions associated with a vehicle (e.g., fire detected, low oxygen, low humidity, high carbon monoxide, etc.). The conditions may be reported to a user 216 and/or a third party via at least one communications module as provided herein.

Among other things, the sensors as disclosed herein may communicate with each other, with devices 212, 248, and/or with the vehicle control system 204 via the signal carrier network 224. Additionally or alternatively, the sensors disclosed herein may serve to provide data relevant to more than one category of sensor information including, but not limited to, combinations of environmental information, user information, and safety information to name a few.

Figure 7A:
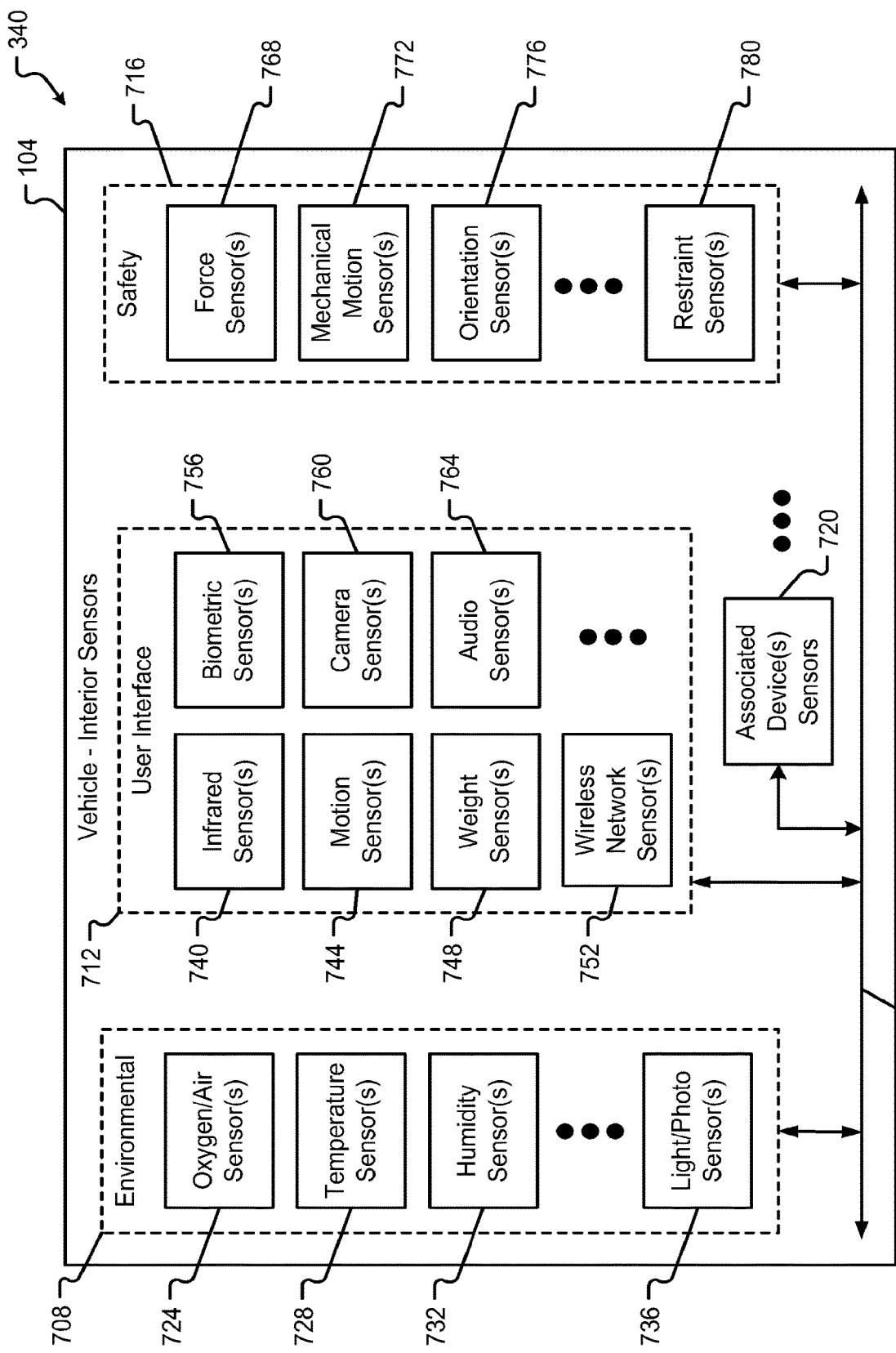
FIG. 7A is a block diagram of an embodiment of interior sensors for a vehicle.
Figure 7B:
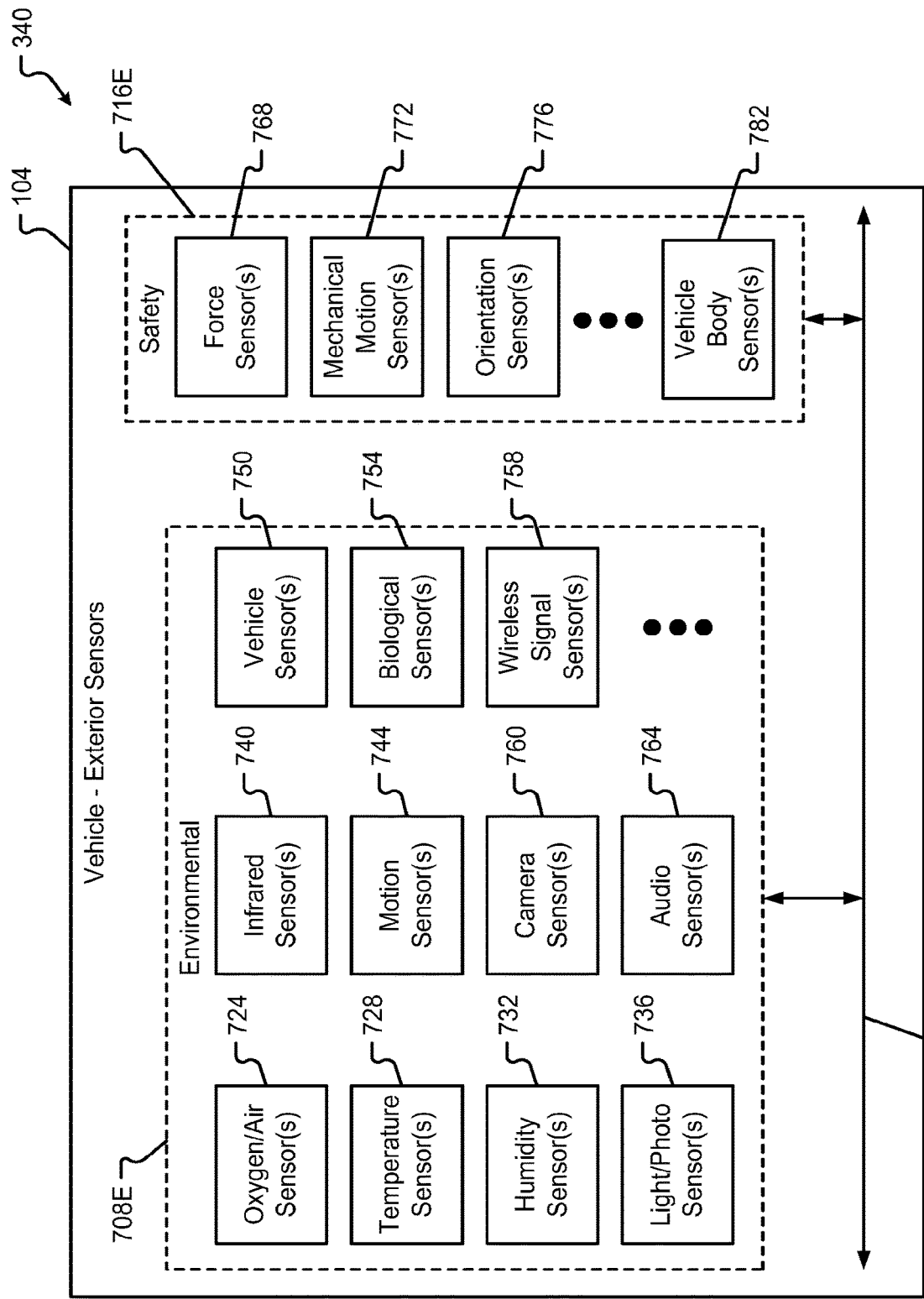
FIG. 7B is a block diagram of an embodiment of exterior sensors for a vehicle.

FIGS. 7A-7B show block diagrams of various sensors that may be associated with a vehicle 104. Although depicted as interior and exterior sensors, it should be appreciated that any of the one or more of the sensors shown may be used in both the interior space 108 and the exterior space of the vehicle 104. Moreover, sensors having the same symbol or name may include the same, or substantially the same, functionality as those sensors described elsewhere in the present disclosure. Further, although the various sensors are depicted in conjunction with specific groups (e.g., environmental 708, 708E, user interface 712, safety 716, 716E, etc.) the sensors should not be limited to the groups in which they appear. In other words, the sensors may be associated with other groups or combinations of groups and/or disassociated from one or more of the groups shown. The sensors as disclosed herein may communicate with each other, the devices 212, 248, and/or the vehicle control system 204 via one or more communications channel(s) 356.

FIG. 7A is a block diagram of an embodiment of interior sensors 340 for a vehicle 104 is provided. The interior sensors 340 may be arranged into one or more groups, based at least partially on the function of the interior sensors 340. The interior space 108 of a vehicle 104 may include an environmental group 708, a user interface group 712, and a safety group 716. Additionally or alternatively, there may be sensors associated with various devices inside the vehicle (e.g., devices 212, 248, smart phones, tablets, mobile computers, etc.)

The environmental group 708 may comprise sensors configured to collect data relating to the internal environment of a vehicle 104. It is anticipated that the environment of the vehicle 104 may be subdivided into areas 508 and zones 512 in an interior space 108 of a vehicle 104. In this case, each area 508 and/or zone 512 may include one or more of the environmental sensors. Examples of environmental sensors associated with the environmental group 708 may include, but are not limited to, oxygen/air sensors 724, temperature sensors 728, humidity sensors 732, light/photo sensors 736, and more. The oxygen/air sensors 724 may be configured to detect a quality of the air in the interior space 108 of the vehicle 104 (e.g., ratios and/or types of gasses comprising the air inside the vehicle 104, dangerous gas levels, safe gas levels, etc.). Temperature sensors 728 may be configured to detect temperature readings of one or more objects, users 216, and/or areas 508 of a vehicle 104. Humidity sensors 732 may detect an amount of water vapor present in the air inside the vehicle 104. The light/photo sensors 736 can detect an amount of light present in the vehicle 104. Further, the light/photo sensors 736 may be configured to detect various levels of light intensity associated with light in the vehicle 104.

The user interface group 712 may comprise sensors configured to collect data relating to one or more users 216 in a vehicle 104. As can be appreciated, the user interface group 712 may include sensors that are configured to collect data from users 216 in one or more areas 508 and zones 512 of the vehicle 104. For example, each area 508 and/or zone 512 of the vehicle 104 may include one or more of the sensors in the user interface group 712. Examples of user interface sensors associated with the user interface group 712 may include, but are not limited to, infrared sensors 740, motion sensors 744, weight sensors 748, wireless network sensors 752, biometric sensors 756, camera (or image) sensors 760, audio sensors 764, and more.

Infrared sensors 740 may be used to measure IR light irradiating from at least one surface, user 216, or other object in the vehicle 104. Among other things, the Infrared sensors 740 may be used to measure temperatures, form images (especially in low light conditions), identify users 216, and even detect motion in the vehicle 104.

The motion sensors 744 may be similar to the motion detectors 624A-B, as described in conjunction with FIG. 6B. Weight sensors 748 may be employed to collect data relating to objects and/or users 216 in various areas 508 of the vehicle 104. In some cases, the weight sensors 748 may be included in the seats and/or floor of a vehicle 104.

Optionally, the vehicle 104 may include a wireless network sensor 752. This sensor 752 may be configured to detect one or more wireless network(s) inside the vehicle 104. Examples of wireless networks may include, but are not limited to, wireless communications utilizing Bluetooth®, Wi-Fi™, ZigBee, IEEE 802.11, and other wireless technology standards. For example, a mobile hotspot may be detected inside the vehicle 104 via the wireless network sensor 752. In this case, the vehicle 104 may determine to utilize and/or share the mobile hotspot detected via/with one or more other devices 212, 248 and/or components associated with the vehicle 104.

Biometric sensors 756 may be employed to identify and/or record characteristics associated with a user 216. It is anticipated that biometric sensors 756 can include at least one of image sensors, IR sensors, fingerprint readers, weight sensors, load cells, force transducers, heart rate monitors, blood pressure monitors, and the like as provided herein.

The camera sensors 760 may be similar to image sensors 622A-B, as described in conjunction with FIG. 6B. Optionally, the camera sensors may record still images, video, and/or combinations thereof. The audio sensors 764 may be similar to the interior sound receivers 692A-B, as described in conjunction with FIGS. 6A-6B. The audio sensors may be configured to receive audio input from a user 216 of the vehicle 104. The audio input from a user 216 may correspond to voice commands, conversations detected in the vehicle 104, phone calls made in the vehicle 104, and/or other audible expressions made in the vehicle 104.

The safety group 716 may comprise sensors configured to collect data relating to the safety of a user 216 and/or one or more components of a vehicle 104. The vehicle 104 may be subdivided into areas 508 and/or zones 512 in an interior space 108 of a vehicle 104 where each area 508 and/or zone 512 may include one or more of the safety sensors provided herein. Examples of safety sensors associated with the safety group 716 may include, but are not limited to, force sensors 768, mechanical motion sensors 772, orientation sensors 776, restraint sensors 780, and more.

The force sensors 768 may include one or more sensors inside the vehicle 104 configured to detect a force observed in the vehicle 104. One example of a force sensor 768 may include a force transducer that converts measured forces (e.g., force, weight, pressure, etc.) into output signals.

Mechanical motion sensors 772 may correspond to encoders, accelerometers, damped masses, and the like. Optionally, the mechanical motion sensors 772 may be adapted to measure the force of gravity (i.e., G-force) as observed inside the vehicle 104. Measuring the G-force observed inside a vehicle 104 can provide valuable information related to a vehicle's acceleration, deceleration, collisions, and/or forces that may have been suffered by one or more users 216 in the vehicle 104. As can be appreciated, the mechanical motion sensors 772 can be located in an interior space 108 or an exterior of the vehicle 104.

Orientation sensors 776 can include accelerometers, gyroscopes, magnetic sensors, and the like that are configured to detect an orientation associated with the vehicle 104. Similar to the mechanical motion sensors 772, the orientation sensors 776 can be located in an interior space 108 or an exterior of the vehicle 104.

The restraint sensors 780 may be similar to the safety restraint sensors 679 as described in conjunction with FIGS. 6A-6B. These sensors 780 may correspond to sensors associated with one or more restraint devices and/or systems in a vehicle 104. Seatbelts and airbags are examples of restraint devices and/or systems. As can be appreciated, the restraint devices and/or systems may be associated with one or more sensors that are configured to detect a state of the device/system. The state may include extension, engagement, retraction, disengagement, deployment, and/or other electrical or mechanical conditions associated with the device/system.

The associated device sensors 720 can include any sensors that are associated with a device 212, 248 in the vehicle 104. As previously stated, typical devices 212, 248 may include smart phones, tablets, laptops, mobile computers, and the like. It is anticipated that the various sensors associated with these devices 212, 248 can be employed by the vehicle control system 204. For example, a typical smart phone can include, an image sensor, an IR sensor, audio sensor, gyroscope, accelerometer, wireless network sensor, fingerprint reader, and more. It is an aspect of the present disclosure that one or more of these associated device sensors 720 may be used by one or more subsystems of the vehicle system 200.

In FIG. 7B, a block diagram of an embodiment of exterior sensors 340 for a vehicle 104 is shown. The exterior sensors may include sensors that are identical, or substantially similar, to those previously disclosed in conjunction with the interior sensors of FIG. 7A. Optionally, the exterior sensors 340 may be configured to collect data relating to one or more conditions, objects, users 216, and other events that are external to the interior space 108 of the vehicle 104. For instance, the oxygen/air sensors 724 may measure a quality and/or composition of the air outside of a vehicle 104. As another example, the motion sensors 744 may detect motion outside of a vehicle 104.

The external environmental group 708E may comprise sensors configured to collect data relating to the external environment of a vehicle 104. In addition to including one or more of the sensors previously described, the external environmental group 708E may include additional sensors, such as, vehicle sensors 750, biological sensors, and wireless signal sensors 758. Vehicle sensors 750 can detect vehicles that are in an environment surrounding the vehicle 104. For example, the vehicle sensors 750 may detect vehicles in a first outside area 516, a second outside area 520, and/or combinations of the first and second outside areas 516, 520. Optionally, the vehicle sensors 750 may include one or more of RF sensors, IR sensors, image sensors, and the like to detect vehicles, people, hazards, etc. that are in an environment exterior to the vehicle 104. Additionally or alternatively, the vehicle sensors 750 can provide distance/directional information relating to a distance (e.g., distance from the vehicle 104 to the detected object) and/or a direction (e.g., direction of travel, etc.) associated with the detected object.

The biological sensors 754 may determine whether one or more biological entities (e.g., an animal, a person, a user 216, etc.) is in an external environment of the vehicle 104. Additionally or alternatively, the biological sensors 754 may provide distance information relating to a distance of the biological entity from the vehicle 104. Biological sensors 754 may include at least one of RF sensors, IR sensors, image sensors and the like that are configured to detect biological entities. For example, an IR sensor may be used to determine that an object, or biological entity, has a specific temperature, temperature pattern, or heat signature. Continuing this example, a comparison of the determined heat signature may be compared to known heat signatures associated with recognized biological entities (e.g., based on shape, locations of temperature, and combinations thereof, etc.) to determine whether the heat signature is associated with a biological entity or an inanimate, or non-biological, object.

The wireless signal sensors 758 may include one or more sensors configured to receive wireless signals from signal sources such as Wi-Fi™ hotspots, cell towers, roadside beacons, other electronic roadside devices, and satellite positioning systems. Optionally, the wireless signal sensors 758 may detect wireless signals from one or more of a mobile phone, mobile computer, keyless entry device, RFID device, near field communications (NFC) device, and the like.

The external safety group 716E may comprise sensors configured to collect data relating to the safety of a user 216 and/or one or more components of a vehicle 104. Examples of safety sensors associated with the external safety group 716E may include, but are not limited to, force sensors 768, mechanical motion sensors 772, orientation sensors 776, vehicle body sensors 782, and more. Optionally, the exterior safety sensors 716E may be configured to collect data relating to one or more conditions, objects, vehicle components, and other events that are external to the vehicle 104. For instance, the force sensors 768 in the external safety group 716E may detect and/or record force information associated with the outside of a vehicle 104. For instance, if an object strikes the exterior of the vehicle 104, the force sensors 768 from the exterior safety group 716E may determine a magnitude, location, and/or time associated with the strike.

The vehicle 104 may include a number of vehicle body sensors 782. The vehicle body sensors 782 may be configured to measure characteristics associated with the body (e.g., body panels, components, chassis, windows, etc.) of a vehicle 104. For example, two vehicle body sensors 782, including a first body sensor and a second body sensor, may be located at some distance apart. Continuing this example, the first body sensor may be configured to send an electrical signal across the body of the vehicle 104 to the second body sensor, or vice versa. Upon receiving the electrical signal from the first body sensor, the second body sensor may record a detected current, voltage, resistance, and/or combinations thereof associated with the received electrical signal. Values (e.g., current, voltage, resistance, etc.) for the sent and received electrical signal may be stored in a memory. These values can be compared to determine whether subsequent electrical signals sent and received between vehicle body sensors 782 deviate from the stored values. When the subsequent signal values deviate from the stored values, the difference may serve to indicate damage and/or loss of a body component. Additionally or alternatively, the deviation may indicate a problem with the vehicle body sensors 782. The vehicle body sensors 782 may communicate with each other, a vehicle control system 204, and/or systems of the vehicle system 200 via a communications channel 356. Although described using electrical signals, it should be appreciated that alternative embodiments of the vehicle body sensors 782 may use sound waves and/or light to perform a similar function.

Figure 8A:
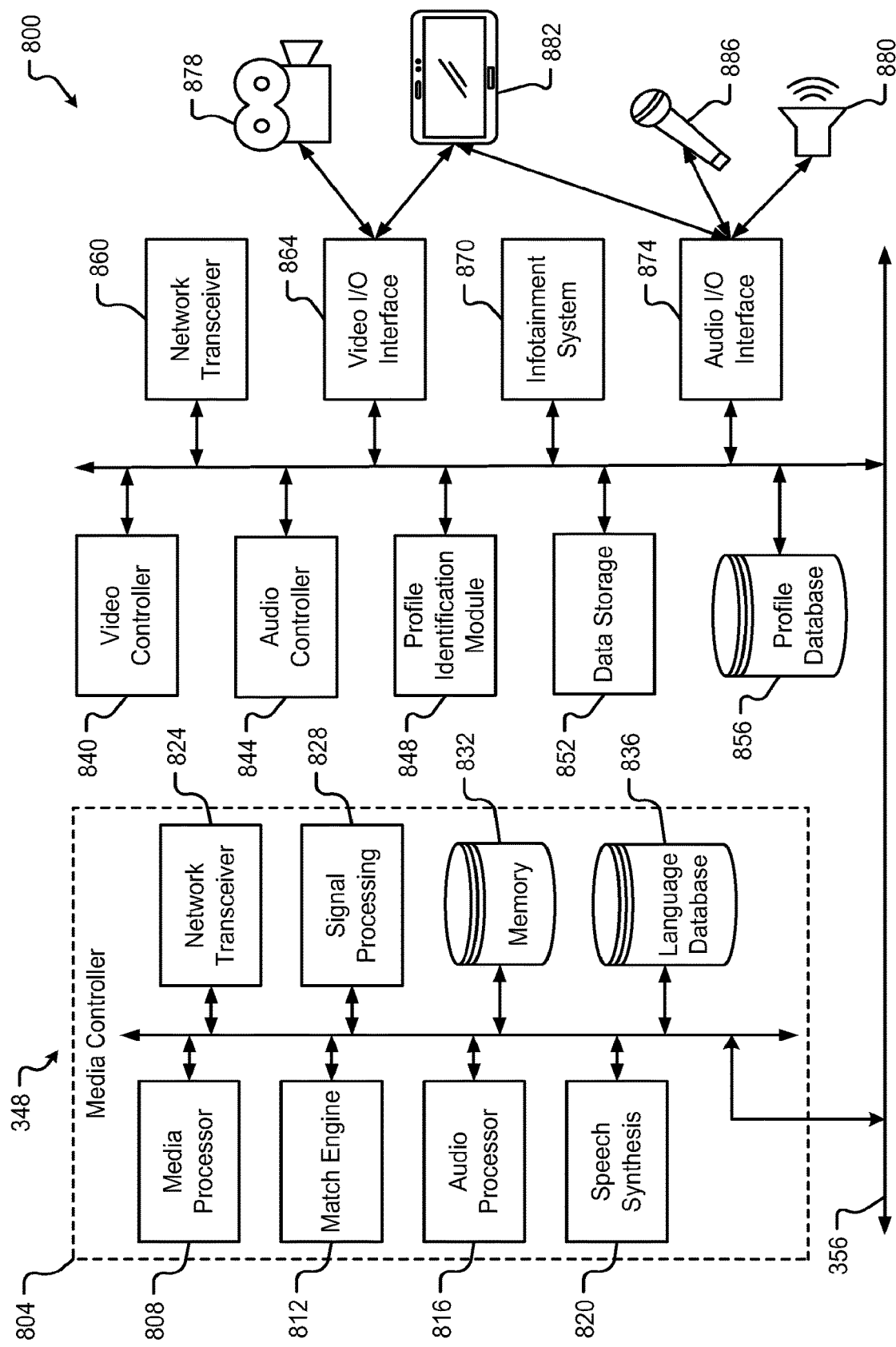
FIG. 8A is a block diagram of an embodiment of a media subsystem for a vehicle.

FIG. 8A is a block diagram of an embodiment of a media controller subsystem 348 for a vehicle 104. The media controller subsystem 348 may include, but is not limited to, a media controller 804, a media processor 808, a match engine 812, an audio processor 816, a speech synthesis module 820, a network transceiver 824, a signal processing module 828, memory 832, and a language database 836. Optionally, the media controller subsystem 348 may be configured as a dedicated blade that implements the media-related functionality of the system 200. Additionally or alternatively, the media controller subsystem 348 can provide voice input, voice output, library functions for multimedia, and display control for various areas 508 and/or zones 512 of the vehicle 104.

Optionally, the media controller subsystem 348 may include a local IP address (e.g., IPv4, IPv6, combinations thereof, etc.) and even a routable, global unicast address. The routable, global unicast address may allow for direct addressing of the media controller subsystem 348 for streaming data from Internet resources (e.g., cloud storage, user accounts, etc.). It is anticipated, that the media controller subsystem 348 can provide multimedia via at least one Internet connection, or wireless network communications module, associated with the vehicle 104. Moreover, the media controller subsystem 348 may be configured to service multiple independent clients simultaneously.

The media processor 808 may comprise a general purpose programmable processor or controller for executing application programming or instructions related to the media subsystem 348. The media processor 808 may include multiple processor cores, and/or implement multiple virtual processors. Optionally, the media processor 808 may include multiple physical processors. By way of example, the media processor 808 may comprise a specially configured application specific integrated circuit (ASIC) or other integrated circuit, a digital signal processor, a controller, a hardwired electronic or logic circuit, a programmable logic device or gate array, a special purpose computer, or the like. The media processor 808 generally functions to run programming code or instructions implementing various functions of the media controller 804.

The match engine 812 can receive input from one or more components of the vehicle system 800 and perform matching functions. Optionally, the match engine 812 may receive audio input provided via a microphone 886 of the system 800. The audio input may be provided to the media controller subsystem 348 where the audio input can be decoded and matched, via the match engine 812, to one or more functions available to the vehicle 104. Similar matching operations may be performed by the match engine 812 relating to video input received via one or more image sensors, cameras 878, and the like.

The media controller subsystem 348 may include a speech synthesis module 820 configured to provide audio output to one or more speakers 880, or audio output devices, associated with the vehicle 104. Optionally, the speech synthesis module 820 may be configured to provide audio output based at least partially on the matching functions performed by the match engine 812.

As can be appreciated, the coding/decoding, the analysis of audio input/output, and/or other operations associated with the match engine 812 and speech synthesis module 820, may be performed by the media processor 808 and/or a dedicated audio processor 816. The audio processor 816 may comprise a general purpose programmable processor or controller for executing application programming or instructions related to audio processing. Further, the audio processor 816 may be similar to the media processor 808 described herein.

The network transceiver 824 can include any device configured to transmit and receive analog and/or digital signals. Optionally, the media controller subsystem 348 may utilize a network transceiver 824 in one or more communication networks associated with the vehicle 104 to receive and transmit signals via the communications channel 356. Additionally or alternatively, the network transceiver 824 may accept requests from one or more devices 212, 248 to access the media controller subsystem 348. One example of the communication network is a local-area network (LAN). As can be appreciated, the functionality associated with the network transceiver 824 may be built into at least one other component of the vehicle 104 (e.g., a network interface card, communications module, etc.).

The signal processing module 828 may be configured to alter audio/multimedia signals received from one or more input sources (e.g., microphones 886, etc.) via the communications channel 356. Among other things, the signal processing module 828 may alter the signals received electrically, mathematically, combinations thereof, and the like.

The media controller 804 may also include memory 832 for use in connection with the execution of application programming or instructions by the media processor 808, and for the temporary or long term storage of program instructions and/or data. As examples, the memory 832 may comprise RAM, DRAM, SDRAM, or other solid state memory.

The language database 836 may include the data and/or libraries for one or more languages, as are used to provide the language functionality as provided herein. In one case, the language database 836 may be loaded on the media controller 804 at the point of manufacture. Optionally, the language database 836 can be modified, updated, and/or otherwise changed to alter the data stored therein. For instance, additional languages may be supported by adding the language data to the language database 836. In some cases, this addition of languages can be performed via accessing administrative functions on the media controller 804 and loading the new language modules via wired (e.g., USB, etc.) or wireless communication. In some cases, the administrative functions may be available via a vehicle console device 248, a user device 212, 248, and/or other mobile computing device that is authorized to access administrative functions (e.g., based at least partially on the device's address, identification, etc.).

One or more video controllers 840 may be provided for controlling the video operation of the devices 212, 248, 882 associated with the vehicle. Optionally, the video controller 840 may include a display controller for controlling the operation of touch sensitive screens, including input (touch sensing) and output (display) functions. Video data may include data received in a stream and unpacked by a processor and loaded into a display buffer. In this example, the processor and video controller 840 can optimize the display based on the characteristics of a screen of a display device 212, 248, 882. The functions of a touch screen controller may be incorporated into other components, such as a media processor 808 or display subsystem.

The audio controller 844 can provide control of the audio entertainment system (e.g., radio, subscription music service, multimedia entertainment, etc.), and other audio associated with the vehicle 104 (e.g., navigation systems, vehicle comfort systems, convenience systems, etc.). Optionally, the audio controller 844 may be configured to translate digital signals to analog signals and vice versa. As can be appreciated, the audio controller 844 may include device drivers that allow the audio controller 844 to communicate with other components of the system 800 (e.g., processors 816, 808, audio I/O 874, and the like).

The system 800 may include a profile identification module 848 to determine whether a user profile is associated with the vehicle 104. Among other things, the profile identification module 848 may receive requests from a user 216, or device 212, 228, 248, to access a profile stored in a profile database 856 or profile data 252. Additionally or alternatively, the profile identification module 848 may request profile information from a user 216 and/or a device 212, 228, 248, to access a profile stored in a profile database 856 or profile data 252. In any event, the profile identification module 848 may be configured to create, modify, retrieve, and/or store user profiles in the profile database 856 and/or profile data 252. The profile identification module 848 may include rules for profile identification, profile information retrieval, creation, modification, and/or control of components in the system 800.

By way of example, a user 216 may enter the vehicle 104 with a smart phone or other device 212. In response to determining that a user 216 is inside the vehicle 104, the profile identification module 848 may determine that a user profile is associated with the user's smart phone 212. As another example, the system 800 may receive information about a user 216 (e.g., from a camera 878, microphone 886, etc.), and, in response to receiving the user information, the profile identification module 848 may refer to the profile database 856 to determine whether the user information matches a user profile stored in the database 856. It is anticipated that the profile identification module 848 may communicate with the other components of the system to load one or more preferences, settings, and/or conditions based on the user profile. Further, the profile identification module 848 may be configured to control components of the system 800 based on user profile information.

Optionally, data storage 852 may be provided. Like the memory 832, the data storage 852 may comprise a solid state memory device or devices. Alternatively or in addition, the data storage 852 may comprise a hard disk drive or other random access memory. Similar to the data storage 852, the profile database 856 may comprise a solid state memory device or devices.

An input/output module 860 and associated ports may be included to support communications over wired networks or links, for example with other communication devices, server devices, and/or peripheral devices. Examples of an input/output module 860 include an Ethernet port, a Universal Serial Bus (USB) port, CAN Bus, Institute of Electrical and Electronics Engineers (IEEE) 1594, or other interface. Users may bring their own devices (e.g., Bring Your Own Device (BYOD), device 212, etc.) into the vehicle 104 for use with the various systems disclosed. Although most BYOD devices can connect to the vehicle systems (e.g., the media controller subsystem 348, etc.) via wireless communications protocols (e.g., Wi-Fi™, Bluetooth®, etc.) many devices may require a direct connection via USB, or similar. In any event, the input/output module 860 can provide the necessary connection of one or more devices to the vehicle systems described herein.

A video input/output interface 864 can be included to receive and transmit video signals between the various components in the system 800. Optionally, the video input/output interface 864 can operate with compressed and uncompressed video signals. The video input/output interface 864 can support high data rates associated with image capture devices. Additionally or alternatively, the video input/output interface 864 may convert analog video signals to digital signals.

The infotainment system 870 may include information media content and/or entertainment content, informational devices, entertainment devices, and the associated programming therefor. Optionally, the infotainment system 870 may be configured to handle the control of one or more components of the system 800 including, but in no way limited to, radio, streaming audio/video devices, audio devices 880, 882, 886, video devices 878, 882, travel devices (e.g., GPS, navigational systems, etc.), wireless communication devices, network devices, and the like. Further, the infotainment system 870 can provide the functionality associated with other infotainment features as provided herein.

An audio input/output interface 874 can be included to provide analog audio to an interconnected speaker 880 or other device, and to receive analog audio input from a connected microphone 886 or other device. As an example, the audio input/output interface 874 may comprise an associated amplifier and analog to digital converter. Alternatively or in addition, the devices 212, 248 can include integrated audio input/output devices 880, 886 and/or an audio jack for interconnecting an external speaker 880 or microphone 886. For example, an integrated speaker 880 and an integrated microphone 886 can be provided, to support near talk, voice commands, spoken information exchange, and/or speaker phone operations.

Among other things, the system 800 may include devices that are part of the vehicle 104 and/or part of a device 212, 248 that is associated with the vehicle 104. For instance, these devices may be configured to capture images, display images, capture sound, and present sound. Optionally, the system 800 may include at least one of image sensors/cameras 878, display devices 882, audio input devices/microphones 886, and audio output devices/speakers 880. The cameras 878 can be included for capturing still and/or video images. Alternatively or in addition, image sensors 878 can include a scanner or code reader. An image sensor/camera 878 can include or be associated with additional elements, such as a flash or other light source. In some cases, the display device 882 may include an audio input device and/or an audio output device in addition to providing video functions. For instance, the display device 882 may be a console, monitor, a tablet computing device, and/or some other mobile computing device.

Figure 8B:
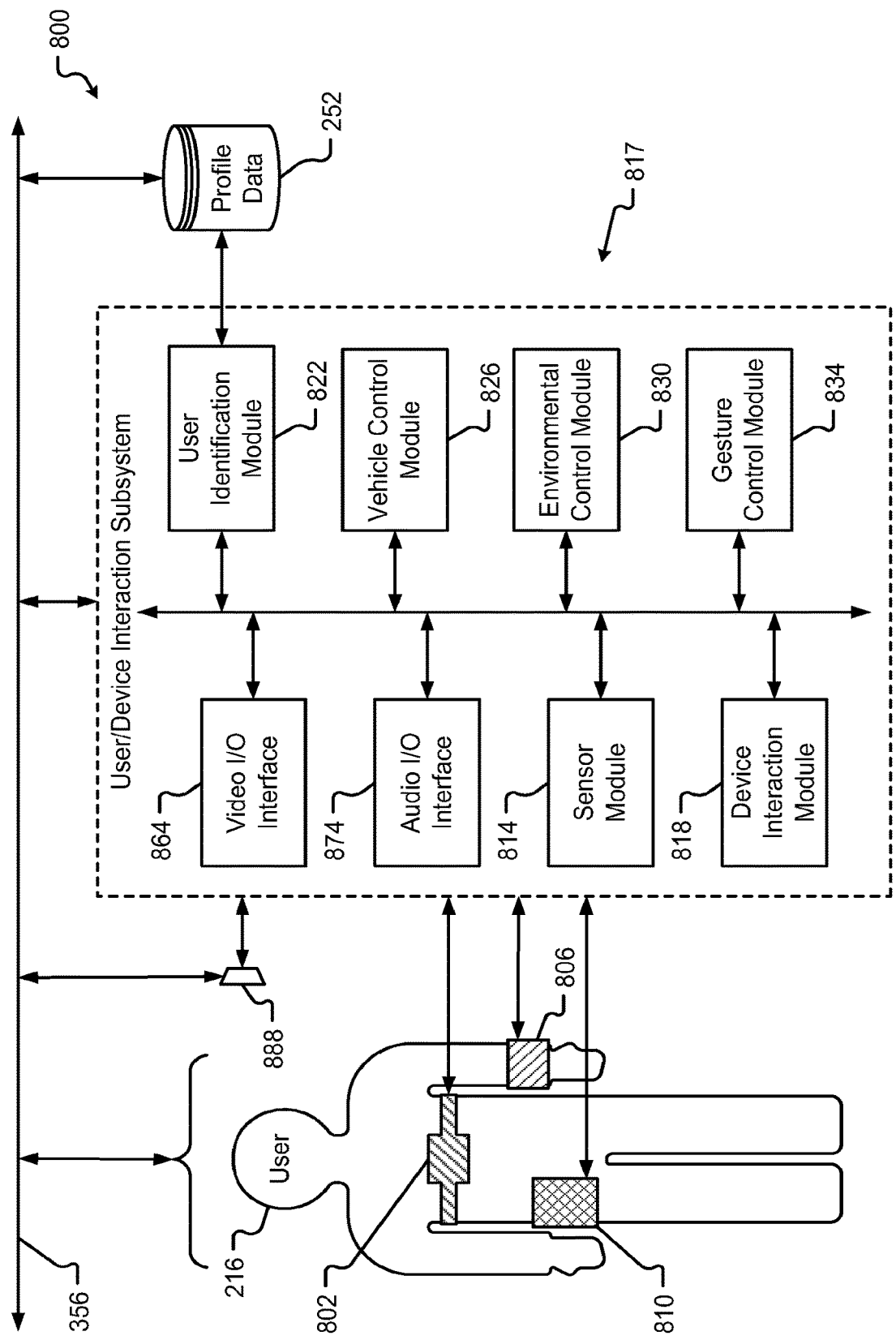
FIG. 8B is a block diagram of an embodiment of a user and device interaction subsystem for a vehicle.

FIG. 8B is a block diagram of an embodiment of a user/device interaction subsystem 817 in a vehicle system 800. The user/device interaction subsystem 817 may comprise hardware and/or software that conduct various operations for or with the vehicle 104. For instance, the user/device interaction subsystem 817 may include at least one user interaction subsystem 332 and device interaction subsystem 352 as previously described. These operations may include, but are not limited to, providing information to the user 216, receiving input from the user 216, and controlling the functions or operation of the vehicle 104, etc. Among other things, the user/device interaction subsystem 817 may include a computing system operable to conduct the operations as described herein.

Optionally, the user/device interaction subsystem 817 can include one or more of the components and modules provided herein. For instance, the user/device interaction subsystem 817 can include one or more of a video input/output interface 864, an audio input/output interface 874, a sensor module 814, a device interaction module 818, a user identification module 822, a vehicle control module 826, an environmental control module 830, and a gesture control module 834. The user/device interaction subsystem 817 may be in communication with other devices, modules, and components of the system 800 via the communications channel 356.

The user/device interaction subsystem 817 may be configured to receive input from a user 216 and/or device via one or more components of the system. By way of example, a user 216 may provide input to the user/device interaction subsystem 817 via wearable devices 802, 806, 810, video input (e.g., via at least one image sensor/camera 878, etc.) audio input (e.g., via the microphone, audio input source, etc.), gestures (e.g., via at least one image sensor 878, motion sensor 888, etc.), device input (e.g., via a device 212, 248 associated with the user, etc.), combinations thereof, and the like.

The wearable devices 802, 806, 810 can include heart rate monitors, blood pressure monitors, glucose monitors, pedometers, movement sensors, wearable computers, and the like. Examples of wearable computers may be worn by a user 216 and configured to measure user activity, determine energy spent based on the measured activity, track user sleep habits, determine user oxygen levels, monitor heart rate, provide alarm functions, and more. It is anticipated that the wearable devices 802, 806, 810 can communicate with the user/device interaction subsystem 817 via wireless communications channels or direct connection (e.g., where the device docks, or connects, with a USB port or similar interface of the vehicle 104).

A sensor module 814 may be configured to receive and/or interpret input provided by one or more sensors in the vehicle 104. In some cases, the sensors may be associated with one or more user devices (e.g., wearable devices 802, 806, 810, smart phones 212, mobile computing devices 212, 248, and the like). Optionally, the sensors may be associated with the vehicle 104, as described in conjunction with FIGS. 6A-7B.

The device interaction module 818 may communicate with the various devices as provided herein. Optionally, the device interaction module 818 can provide content, information, data, and/or media associated with the various subsystems of the vehicle system 800 to one or more devices 212, 248, 802, 806, 810, 882, etc. Additionally or alternatively, the device interaction module 818 may receive content, information, data, and/or media associated with the various devices provided herein.

The user identification module 822 may be configured to identify a user 216 associated with the vehicle 104. The identification may be based on user profile information that is stored in profile data 252. For instance, the user identification module 822 may receive characteristic information about a user 216 via a device, a camera, and/or some other input. The received characteristics may be compared to data stored in the profile data 252. Where the characteristics match, the user 216 is identified. As can be appreciated, where the characteristics do not match a user profile, the user identification module 822 may communicate with other subsystems in the vehicle 104 to obtain and/or record profile information about the user 216. This information may be stored in a memory and/or the profile data storage 252.

The vehicle control module 826 may be configured to control settings, features, and/or the functionality of a vehicle 104. In some cases, the vehicle control module 826 can communicate with the vehicle control system 204 to control critical functions (e.g., driving system controls, braking, accelerating, etc.) and/or noncritical functions (e.g., driving signals, indicator/hazard lights, mirror controls, window actuation, etc.) based at least partially on user/device input received by the user/device interaction subsystem 817.

The environmental control module 830 may be configured to control settings, features, and/or other conditions associated with the environment, especially the interior environment, of a vehicle 104. Optionally, the environmental control module 830 may communicate with the climate control system (e.g. changing cabin temperatures, fan speeds, air direction, etc.), oxygen and/or air quality control system (e.g., increase/decrease oxygen in the environment, etc.), interior lighting (e.g., changing intensity of lighting, color of lighting, etc.), an occupant seating system 648 (e.g., adjusting seat position, firmness, height, etc.), steering wheel 640 (e.g., position adjustment, etc.), infotainment/entertainment system (e.g., adjust volume levels, display intensity adjustment, change content, etc.), and/or other systems associated with the vehicle environment. Additionally or alternatively, these systems can provide input, set-points, and/or responses, to the environmental control module 830. As can be appreciated, the environmental control module 830 may control the environment based at least partially on user/device input received by the user/device interaction subsystem 817.

The gesture control module 834 is configured to interpret gestures provided by a user 216 in the vehicle 104. Optionally, the gesture control module 834 may provide control signals to one or more of the vehicle systems 300 disclosed herein. For example, a user 216 may provide gestures to control the environment, critical and/or noncritical vehicle functions, the infotainment system, communications, networking, and more. Optionally, gestures may be provided by a user 216 and detected via one or more of the sensors as described in conjunction with FIGS. 6B-7A. As another example, one or more motion sensors 888 may receive gesture input from a user 216 and provide the gesture input to the gesture control module 834. Continuing this example, the gesture input is interpreted by the gesture control module 834. This interpretation may include comparing the gesture input to gestures stored in a memory. The gestures stored in memory may include one or more functions and/or controls mapped to specific gestures. When a match is determined between the detected gesture input and the stored gesture information, the gesture control module 834 can provide a control signal to any of the systems/subsystems as disclosed herein.

Figure 8C:
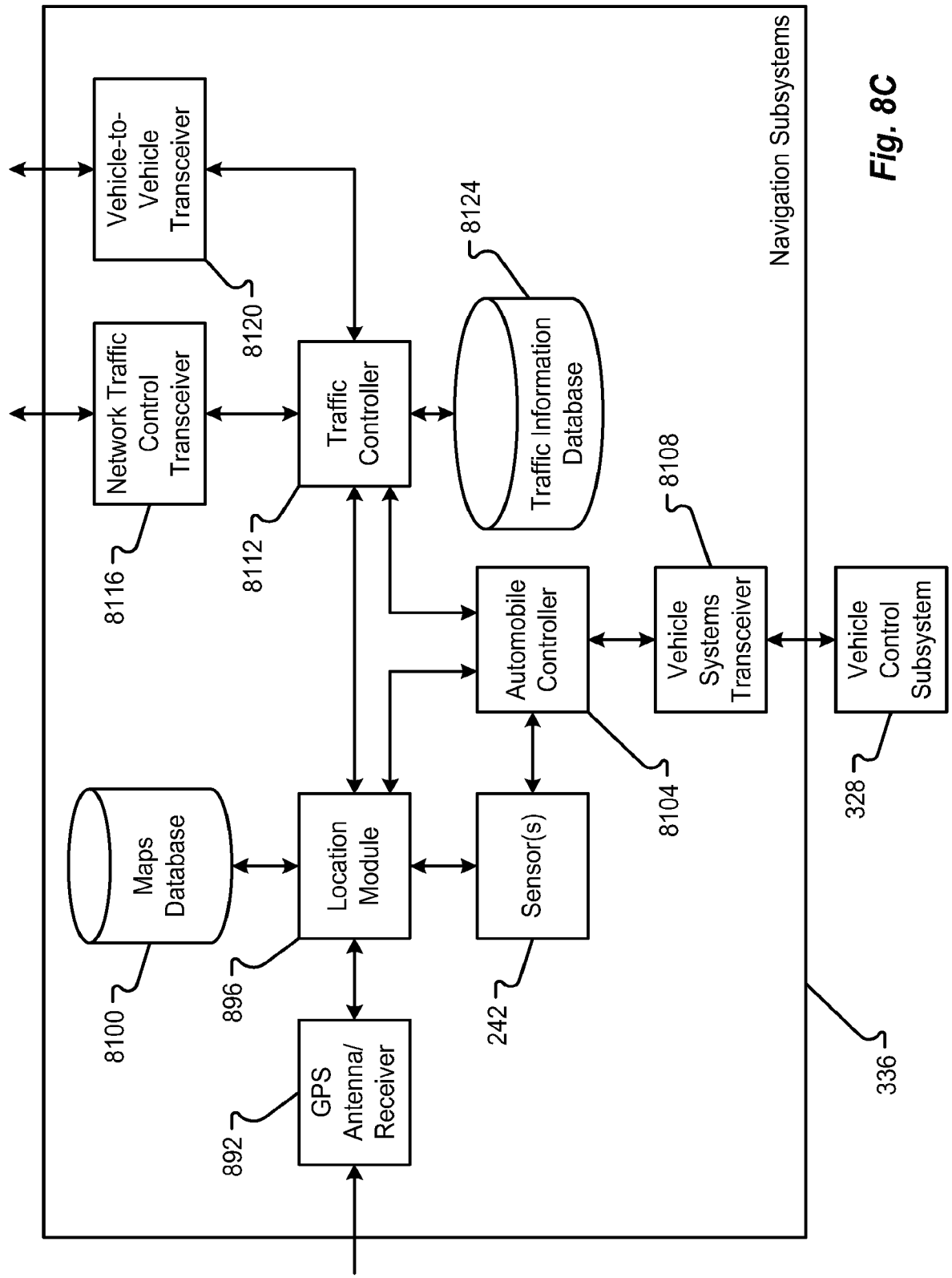
FIG. 8C is a block diagram of an embodiment of a Navigation subsystem for a vehicle.

FIG. 8C illustrates a GPS/Navigation subsystem(s) 336. The Navigation subsystem(s) 336 can be any present or future-built navigation system that may use location data, for example, from the Global Positioning System (GPS), to provide navigation information or control the vehicle 104. The Navigation subsystem(s) 336 can include several components or modules, such as, one or more of, but not limited to, a GPS Antenna/receiver 892, a location module 896, a maps database 8100, an automobile controller 8104, a vehicle systems transceiver 8108, a traffic controller 8112, a network traffic transceiver 8116, a vehicle-to-vehicle transceiver 8120, a traffic information database 8124, etc. Generally, the several components or modules 892-8124 may be hardware, software, firmware, computer readable media, or combinations thereof.

A GPS Antenna/receiver 892 can be any antenna, GPS puck, and/or receiver capable of receiving signals from a GPS satellite or other navigation system, as mentioned hereinbefore. The signals may be demodulated, converted, interpreted, etc. by the GPS Antenna/receiver 892 and provided to the location module 896. Thus, the GPS Antenna/receiver 892 may convert the time signals from the GPS system and provide a location (e.g., coordinates on a map) to the location module 896. Alternatively, the location module 896 can interpret the time signals into coordinates or other location information.

The location module 896 can be the controller of the satellite navigation system designed for use in automobiles. The location module 896 can acquire position data, as from the GPS Antenna/receiver 892, to locate the user or vehicle 104 on a road in the unit's map database 8100. Using the road database 8100, the location module 896 can give directions to other locations along roads also in the database 8100. When a GPS signal is not available, the location module 896 may apply dead reckoning to estimate distance data from sensors 242 including one or more of, but not limited to, a speed sensor attached to the drive train of the vehicle 104, a gyroscope, an accelerometer, etc. GPS signal loss and/or multipath can occur due to urban canyons, tunnels, and other obstructions. Additionally or alternatively, the location module 896 may use known locations of Wi-Fi hotspots, cell tower data, etc. to determine the position of the vehicle 104, such as by using time difference of arrival (TDOA) and/or frequency difference of arrival (FDOA) techniques.

The maps database 8100 can include any hardware and/or software to store information about maps, geographical information system information, location information, etc. The maps database 8100 can include any data definition or other structure to store the information. Generally, the maps database 8100 can include a road database that may include one or more vector maps of areas of interest. Street names, street numbers, house numbers, and other information can be encoded as geographic coordinates so that the user can find some desired destination by street address. Points of interest (waypoints) can also be stored with their geographic coordinates. For example, a point of interest may include speed cameras, fuel stations, public parking, and "parked here" (or "you parked here") information. The map database contents can be produced or updated by a server connected through a wireless system in communication with the Internet, even as the vehicle 104 is driven along existing streets, yielding an up-to-date map.

An automobile controller 8104 can be any hardware and/or software that can receive instructions from the location module 896 or the traffic controller 8112 and operate the vehicle 104. The automobile controller 8104 receives this information and data from the sensors 242 to operate the vehicle 104 without driver input. Thus, the automobile controller 8104 can drive the vehicle 104 along a route provided by the location module 896. The route may be adjusted by information sent from the traffic controller 8112. Discrete and real-time driving can occur with data from the sensors 242. To operate the vehicle 104, the automobile controller 8104 can communicate with a vehicle systems transceiver 8108.

The vehicle systems transceiver 8108 can be any present or future-developed device that can comprise a transmitter and/or a receiver, which may be combined and can share common circuitry or a single housing. The vehicle systems transceiver 8108 may communicate or instruct one or more of the vehicle control subsystems 328. For example, the vehicle systems transceiver 8108 may send steering commands, as received from the automobile controller 8104, to an electronic steering system, to adjust the steering of the vehicle 100 in real time. The automobile controller 8104 can determine the effect of the commands based on received sensor data 242 and can adjust the commands as need be. The vehicle systems transceiver 8108 can also communicate with the braking system, the engine and drive train to speed or slow the car, the signals (e.g., turn signals and brake lights), the headlights, the windshield wipers, etc. Any of these communications may occur over the components or function as described in conjunction with FIG. 4.

A traffic controller 8112 can be any hardware and/or software that can communicate with an automated traffic system and adjust the function of the vehicle 104 based on instructions from the automated traffic system. An automated traffic system is a system that manages the traffic in a given area. This automated traffic system can instruct cars to drive in certain lanes, instruct cars to raise or lower their speed, instruct a car to change their route of travel, instruct cars to communicate with other cars, etc. To perform these functions, the traffic controller 8112 may register the vehicle 104 with the automated traffic system and then provide other information including the route of travel. The automated traffic system can return registration information and any required instructions. The communications between the automated traffic system and the traffic controller 8112 may be received and sent through a network traffic transceiver 8116.

The network traffic transceiver 8116 can be any present or future-developed device that can comprise a transmitter and/or a receiver, which may be combined and can share common circuitry or a single housing. The network traffic transceiver 8116 may communicate with the automated traffic system using any known or future-developed, protocol, standard, frequency, bandwidth range, etc. The network traffic transceiver 8116 enables the sending of information between the traffic controller 8112 and the automated traffic system.

The traffic controller 8112 can also communicate with another vehicle, which may be in physical proximity (i.e., within range of a wireless signal), using the vehicle-to-vehicle transceiver 8120. As with the network traffic transceiver 8116, the vehicle-to-vehicle transceiver 8120 can be any present or future-developed device that can comprise a transmitter and/or a receiver, which may be combined and can share common circuitry or a single housing. Generally, the vehicle-to-vehicle transceiver 8120 enables communication between the vehicle 104 and any other vehicle. These communications allow the vehicle 104 to receive traffic or safety information, control or be controlled by another vehicle, establish an alternative communication path to communicate with the automated traffic system, establish a node including two or more vehicle that can function as a unit, etc. The vehicle-to-vehicle transceiver 8120 may communicate with the other vehicles using any known or future-developed, protocol standard, frequency, bandwidth range, etc.

The traffic controller 8112 can control functions of the automobile controller 8104 and communicate with the location module 896. The location module 896 can provide current location information and route information that the traffic controller 8112 may then provide to the automated traffic system. The traffic controller 8112 may receive route adjustments from the automated traffic system that are then sent to the location module 896 to change the route. Further, the traffic controller 8112 can also send driving instructions to the automobile controller 8104 to change the driving characteristics of the vehicle 104. For example, the traffic controller 8112 can instruct the automobile controller 8104 to accelerate or decelerate to a different speed, change lanes, or perform another driving maneuver. The traffic controller 8112 can also manage vehicle-to-vehicle communications and store information about the communications or other information in the traffic information database 8124.

The traffic information database 8124 can be any type of database, such as relational, hierarchical, object-oriented, and/or the like. The traffic information database 8124 may reside on a storage medium local to (and/or resident in) the vehicle control system 204 or in the vehicle 104. The traffic information database 8124 may be adapted to store, update, and retrieve information about communications with other vehicles or any active instructions from the automated traffic system. This information may be used by the traffic controller 8112 to instruct or adjust the performance of driving maneuvers.

FIG. 9 illustrates an optional communications architecture where, the host device 908 may include one more routing profiles, permission modules, and rules that control how communications within the vehicle 104 are to occur. This communications architecture can be used in conjunction with the routing tables, rules and permissions associated with access point 456 and optional firewall 484, or can be in lieu thereof. For example, the host device 908 acts as a mobile hot spot to one or more other devices within vehicle 104, such as, other device 1 912, other device 2 916, other device 3 920, and other device N 924. Optionally, one or more of the other devices 912 can communicate directly with the host device 908 which then provides Internet access to those devices 912 via the device 908. The host device 908 can act as a mobile hot spot for any one or more of the other devices 912, which may not need to communicate over the network/communications buses 224/404, but could instead connect directly to the host device 908 via, for example, NFC, Bluetooth®, WiFi, or the like. When the device 908 is acting as the host device, the device 908 can include one or more routing profiles, permissions, rules modules, and can also act as a firewall for the various inter and intra vehicle communications.

As will be appreciated, there could be alternative host devices, such as, host 904 which could also act as, for example, a co-host in association with device 908. Optionally, one or more of the routing profile, permission information, and rules could be shared between the co-host devices 904, 908, both of those devices being usable for Internet access for one or more of the other devices, 912-924. As will be appreciated, the other devices 912-924 need not necessarily connect to one or more of host device 908 and the other device 904 via a direct communications link, but could also interface with those devices 904, 908 utilizing the network/communications buses 224/404 associated with the vehicle 100. As previously discussed, one or more of the other devices can connect to the network/communications buses 224/404 utilizing the various networks and/or buses discussed herein which would therefore enable, for example, regulation of the various communications based on the Ethernet zone that the other device 912 is associated with.

An embodiment of one or more modules that may be associated with the vehicle control system 204 may be as shown in FIG. 10. The modules can include a communication subsystem interface 1008 in communication with an operating system 1004. The communications may pass through a firewall 1044. The firewall 1044 can be any software that can control the incoming and outgoing communications by analyzing the data packets and determining whether the packets should be allowed through the firewall, based on applied rule set. A firewall 1044 can establish a "barrier" between a trusted, secure internal network and another network (e.g., the Internet) that is not assumed to be secure and trusted.

In some situations, the firewall 1044 may establish security zones that are implemented by running system services and/or applications in restricted user groups and accounts. A set of configuration files and callbacks may then be linked to an IP table firewall. The IP table firewall can be configured to notify a custom filter application at any of the layers of the Ethernet packet. The different users/group rights to access the system may include: system users, which may have exclusive right over all device firewall rules and running software; a big-brother user, which may have access to on board device (OBD) control data and may be able to communicate with the vehicle subsystem 328 and may be able to alter the parameters in the vehicle control system 204; a dealer user, which can have rights to read OBD data for diagnostics and repairs; a dashboard user, which can have rights to launch dashboard applications and/or authenticate guest users and change their permissions to trusted/friend/family, and can read but cannot write into OBD diagnostic data; a world wide web (WWW) data user, which can have HTTP rights to respond to HTTP requests (the HTTP requests also can target different user data, but may be filtered by default user accounts); a guest user, which may have no rights; a family/friend user, which may have rights to play media from the media subsystem 348 and/or to stream media to the media subsystem 348.

The operating system 1004 can be a collection of software that manages computer hardware resources and provides common services for applications and other programs. The operating system 1004 may schedule time-sharing for efficient use of the system. For hardware functions, such as input, output, and memory allocation, the operating system 1004 can act as an intermediary between applications or programs and the computer hardware. Examples of operating systems that may be deployed as operating system 1004 include Android, BSD, iOS, Linux, OS X, QNX, Microsoft Windows, Windows Phone, IBM z/OS, etc.

The operating system 1004 can include one or more sub-modules. For example, a desktop manager 1012 can manage one or more graphical user interfaces (GUI) in a desktop environment. Desktop GUIs can help the user to easily access and edit files. A command-line interface (CLI) may be used if full control over the operating system (OS) 1004 is required. The desktop manager 1012 is described further hereinafter.

A kernel 1028 can be a computer program that manages input/output requests from software and translates them into data processing instructions for the processor 304 and other components of the vehicle control system 204. The kernel 1028 is the fundamental component of the operating system 1004 that can execute many of the functions associated with the OS 1004.

The kernel 1028 can include other software functions, including, but not limited to, driver(s) 1056, communication software 1052, and/or Internet Protocol software 1048. A driver 1056 can be any computer program that operates or controls a particular type of device that is attached to a vehicle control system 204. A driver 1056 can communicate with the device through the bus 356 or communications subsystem 1008 to which the hardware connects. When a calling program invokes a routine in the driver 1056, the driver 1056 may issue one or more commands to the device. Once the device sends data back to the driver 1056, the driver 1056 may invoke routines in the original calling program. Drivers can be hardware-dependent and operating-system-specific. Driver(s) 1056 can provide the interrupt handling required for any necessary asynchronous time-dependent hardware interface.

The IP module 1048 can conduct any IP addressing, which may include the assignment of IP addresses and associated parameters to host interfaces. The address space may include networks and sub-networks. The IP module 1048 can perform the designation of network or routing prefixes and may conduct IP routing, which transports packets across network boundaries. Thus, the IP module 1048 may perform all functions required for IP multicast operations.

The communications module 1052 may conduct all functions for communicating over other systems or using other protocols not serviced by the IP module 1048. Thus, the communications module 1052 can manage multicast operations over other busses or networks not serviced by the IP module 1048. Further, the communications module 1052 may perform or manage communications to one or more devices, systems, data stores, services, etc. that are in communication with the vehicle control system 204 or other subsystems through the firewall 1044. Thus, the communications module 1052 can conduct communications through the communication subsystem interface 1008.

A file system 1016 may be any data handling software that can control how data is stored and retrieved. The file system 1016 can separate the stored data into individual pieces, and giving each piece a name, can easily separate and identify the pieces of data. Each piece of data may be considered a "file". The file system 1016 can construct data structure and logic rules used to manage the information and the identifiers for the information. The structure and logic rules can be considered a "file system."

A device discovery daemon 1020 may be a computer program that runs as a background process that can discover new devices that connect with the network 356 or communication subsystem 1008 or devices that disconnect from the network 356 or communication subsystem 1008. The device discovery daemon 1020 can ping the network 356 (the local subnet) when the vehicle 104 starts, when a vehicle door opens or closes, or upon the occurrence of other events. Additionally or alternatively, the device discovery daemon 1020 may force Bluetooth®, USB, and/or wireless detection. For each device that responds to the ping, the device discovery daemon 1020 can populate the system data 208 with device information and capabilities, using any of one or more protocols, including one or more of, but not limited to, IPv6 Hop-by-Hop Option (HOPOPT), Internet Control Message Protocol (ICMP), Internet Group Management Protocol (IGMP), Gateway-to-Gateway Protocol (GGP), Internet Protocol (IP), Internet Stream Protocol (ST), Transmission Control Protocol (TCP), Exterior Gateway Protocol (EGP), CHAOS, User Datagram Protocol (UDP), etc.

For example, the device discovery daemon 1020 can determine device capabilities based on the opened ports the device exposes. If a camera exposes port 80, then the device discovery daemon 1020 can determine that the camera is using a Hypertext Transfer Protocol (HTTP). Alternatively, if a device is supporting Universal Plug and Play (UPnP), the system data 208 can include more information, for example, a camera control universal resource locator (URL), a camera zoom URL, etc. When a scan stops, the device discovery daemon 1020 can trigger a dashboard refresh to ensure the user interface reflects the new devices on the desktop.

A desktop manager 1012 may be a computer program that manages the user interface of the vehicle control system 204. The desktop environment may be designed to be customizable and allow the definition of the desktop configuration look-and-feel for a wide range of appliances or devices from computer desktops, mobile devices, computer tablets, etc. Launcher(s), panels, desktop areas, the desktop background, notifications, panes, etc., can be configured from a dashboard configuration file managed by the desktop manager 1012. The graphical elements in which the desktop manager 1012 controls can include launchers, the desktop, notification bars, etc.

The desktop may be an area of the display where the applications are running. The desktop can have a custom background. Further, the desktop may be divided into two or more areas. For example, the desktop may be divided into an upper half of a display and a lower half of the display. Each application can be configured to run in a portion of the desktop. Extended settings can be added to the desktop configuration file, such that, some objects may be displayed over the whole desktop or in custom size out of the context of the divided areas.

The notification bar may be a part of a bar display system, which may provide notifications by displaying, for example, icons and/or pop-up windows that may be associated with sound notifications. The notification mechanism can be designed for separate plug-ins, which run in separate processes and may subscribe to a system Intelligent Input Bus (IBUS)/D-BUS event service. The icons on the notifications bar can be accompanied with application short-cuts to associated applications, for example, a Bluetooth® manager, a USB manager, radio volume and or tone control, a security firewall, etc.

The desktop manager 1012 may include a windows manager 1032, an application launcher 1036, and/or a panel launcher 1040. Each of these components can control a different aspect of the user interface. The desktop manager 1012 can use a root window to create panels that can include functionality for one or more of, but not limited to: launching applications, managing applications, providing notifications, etc.

The windows manager 1032 may be software that controls the placement and appearance of windows within a graphical user interface presented to the user. Generally, the windows manager 1032 can provide the desktop environment used by the vehicle control system 204. The windows manager 1032 can communicate with the kernel 1028 to interface with the graphical system that provides the user interface(s) and supports the graphics hardware, pointing devices, keyboard, touch-sensitive screens, etc. The windows manager 1032 may be a tiling window manager (i.e., a window manager with an organization of the screen into mutually non-overlapping frames, as opposed to a coordinate-based stacking of overlapping objects (windows) that attempts to fully emulate the desktop metaphor). The windows manager 1032 may read and store configuration files, in the system data 208, which can control the position of the application windows at precise positions.

An application manager 1036 can control the function of any application over the lifetime of the process. The process or application can be launched from a panel launcher 1040 or from a remote console. The application manager 1036 can intercept the process name and may take appropriate action to manage that process. If the process is not running, the application manager 1036 can load the process and may bring the process to a foreground in a display. The application manager 1036 may also notify the windows manager 1032 to bring the associated window(s) to a top of a window stack for the display. When a process starts from a shell or a notification out of the context of the desktop, the application manager 1036 can scan files to match the process name with the entry name provided. When a match is found, the application manager 1036 can configure the process according to a settings file.

In some situations, the application manager 1036 may restrict an application as singleton (i.e., restricts the instantiation of a class to one object). If an application is already running and the application manager 1036 is asked to run the application again, the application manager 1036 can bring the running process to a foreground on a display. There can be a notification event exchange between the windows manager 1032 and the application manager 1036 for activating the appropriate window for the foreground process. Once an application is launched, the application may not be terminated or killed. The application can be sent to the background, except, possibly, for some applications (e.g., media player, Bluetooth®, notifications, etc.), which may be given a lowest process priority.

The panel launcher 1040 can be a widget configured to be placed along a portion of the display. The panel launcher 1040 may be built from desktop files from a desktop folder. The desktop folder location can be configured by a configuration file stored in system data 208. The panel launcher 1040 can allow for the launching or executing of applications or processes by receiving inputs from a user interface to launch programs.

A desktop plugin 1024 may be a software component that allows for customization of the desktop or software interface through the initiation of plug-in applications.

One or more gestures used to interface with the vehicle control system 204 may be as described in conjunction with FIG. 11A through 11K. FIGS. 11A through 11H depict various graphical representations of gesture inputs that may be recognized by the devices 212, 248. The gestures may be performed not only by a user's body part, such as a digit, but also by other devices, such as a stylus, that may be sensed by the contact sensing portion(s) of a screen associated with the device 212, 248. In general, gestures are interpreted differently, based on where the gestures are performed (either directly on a display or in a gesture capture region). For example, gestures in a display may be directed to a desktop or application, and gestures in a gesture capture region may be interpreted as for the system.

With reference to FIGS. 11A-11H, a first type of gesture, a touch gesture 1120, is substantially stationary on a portion (e.g., a screen, a display, etc.) of a device 212, 248 for a selected length of time. A circle 1128 represents a touch or other contact type received at particular location of a contact sensing portion of the screen. The circle 1128 may include a border 1132, the thickness of which indicates a length of time that the contact is held substantially stationary at the contact location. For instance, a tap 1120 (or short press) has a thinner border 1132A than the border 1132B for a long press 1124 (or for a normal press). The long press 1124 may involve a contact that remains substantially stationary on the screen for longer time period than that of a tap 1120. As will be appreciated, differently defined gestures may be registered depending upon the length of time that the touch remains stationary prior to contact cessation or movement on the screen.

Figure 11A:
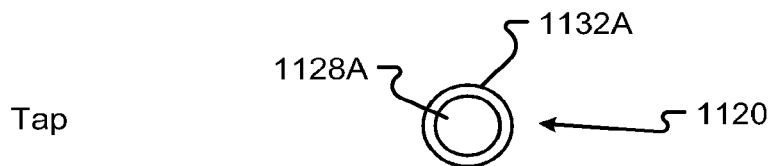
FIG. 11A is a graphical representation of an embodiment of a gesture that a user may perform to provide input to a vehicle control system.
Figure 11B:
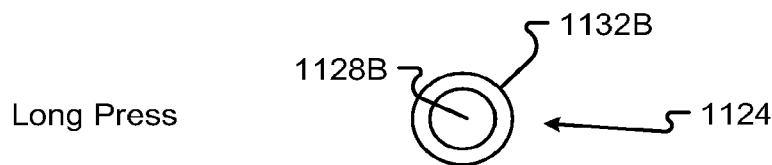
FIG. 11B is a graphical representation of an embodiment of a gesture that a user may perform to provide input to a vehicle control system.
Figure 11C:
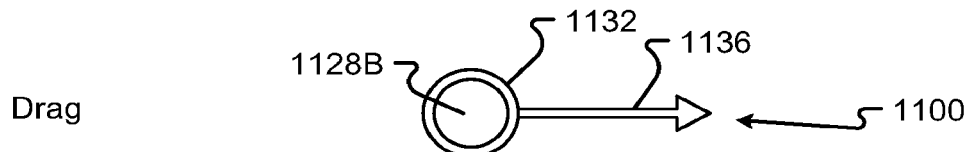
FIG. 11C is a graphical representation of an embodiment of a gesture that a user may perform to provide input to a vehicle control system.

With reference to FIG. 11C, a drag gesture 1100 on the screen is an initial contact (represented by circle 1128) with contact movement 1136 in a selected direction. The initial contact 1128 may remain stationary on the screen for a certain amount of time represented by the border 1132. The drag gesture typically requires the user to contact an icon, window, or other displayed image at a first location followed by movement of the contact in a drag direction to a new second location desired for the selected displayed image. The contact movement need not be in a straight line but have any path of movement so long as the contact is substantially continuous from the first to the second locations.

Figure 11D:
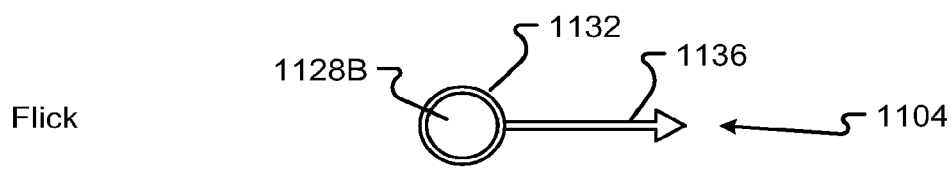
FIG. 11D is a graphical representation of an embodiment of a gesture that a user may perform to provide input to a vehicle control system.

With reference to FIG. 11D, a flick gesture 1104 on the screen is an initial contact (represented by circle 1128) with truncated contact movement 1136 (relative to a drag gesture) in a selected direction. A flick may have a higher exit velocity for the last movement in the gesture compared to the drag gesture. The flick gesture can, for instance, be a finger snap following initial contact. Compared to a drag gesture, a flick gesture generally does not require continual contact with the screen from the first location of a displayed image to a predetermined second location. The contacted displayed image is moved by the flick gesture in the direction of the flick gesture to the predetermined second location. Although both gestures commonly can move a displayed image from a first location to a second location, the temporal duration and distance of travel of the contact on the screen is generally less for a flick than for a drag gesture.

Figure 11E:
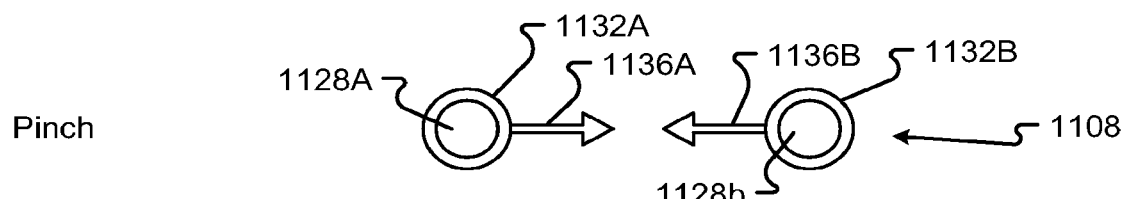
FIG. 11E is a graphical representation of an embodiment of a gesture that a user may perform to provide input to a vehicle control system.

With reference to FIG. 11E, a pinch gesture 1108 on the screen is depicted. The pinch gesture 1108 may be initiated by a first contact 1128A to the screen by, for example, a first digit and a second contact 1128B to the screen by, for example, a second digit. The first and second contacts 1128A,B may be detected by a common contact sensing portion of a common screen, by different contact sensing portions of a common screen, or by different contact sensing portions of different screens. The first contact 1128A is held for a first amount of time, as represented by the border 1132A, and the second contact 1128B is held for a second amount of time, as represented by the border 1132B. The first and second amounts of time are generally substantially the same, and the first and second contacts 1128A,B generally occur substantially simultaneously. The first and second contacts 1128A,B generally also include corresponding first and second contact movements 1136A,B, respectively. The first and second contact movements 1136A,B are generally in opposing directions. Stated another way, the first contact movement 1136A is towards the second contact 1136B, and the second contact movement 1136B is towards the first contact 1136A. More simply stated, the pinch gesture 1108 may be accomplished by a user's digits touching the screen in a pinching motion.

Figure 11F:
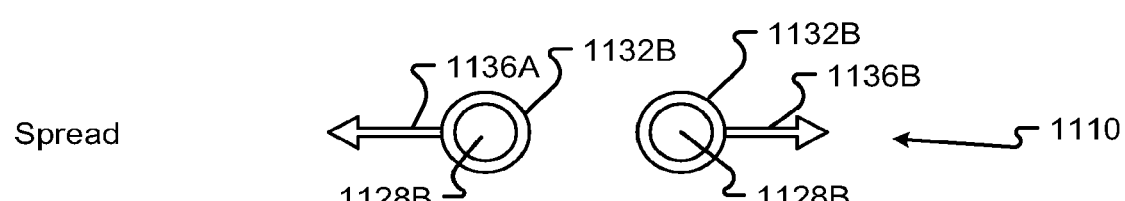
FIG. 11F is a graphical representation of an embodiment of a gesture that a user may perform to provide input to a vehicle control system.

With reference to FIG. 11F, a spread gesture 1110 on the screen is depicted. The spread gesture 1110 may be initiated by a first contact 1128A to the screen by, for example, a first digit, and a second contact 1128B to the screen by, for example, a second digit. The first and second contacts 1128A,B may be detected by a common contact sensing portion of a common screen, by different contact sensing portions of a common screen, or by different contact sensing portions of different screens. The first contact 1128A is held for a first amount of time, as represented by the border 1132A, and the second contact 1128B is held for a second amount of time, as represented by the border 1132B. The first and second amounts of time are generally substantially the same, and the first and second contacts 1128A,B generally occur substantially simultaneously. The first and second contacts 1128A,B generally also include corresponding first and second contact movements 1136A,B, respectively. The first and second contact movements 1136A,B are generally in an opposing direction. Stated another way, the first and second contact movements 1136A,B are away from the first and second contacts 1128A,B. More simply stated, the spread gesture 1110 may be accomplished by a user's digits touching the screen in a spreading motion.

Figure 11G:
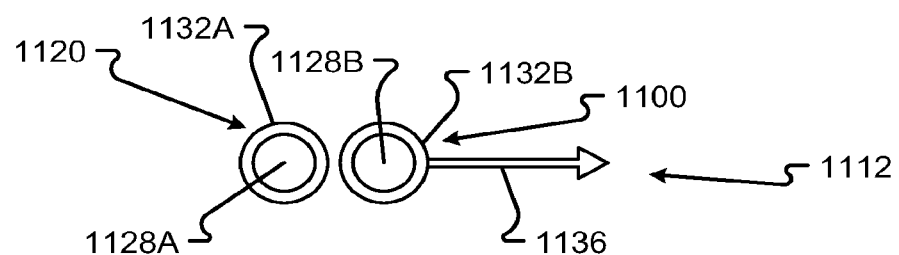
FIG. 11G is a graphical representation of an embodiment of a gesture that a user may perform to provide input to a vehicle control system.
Figure 11H:
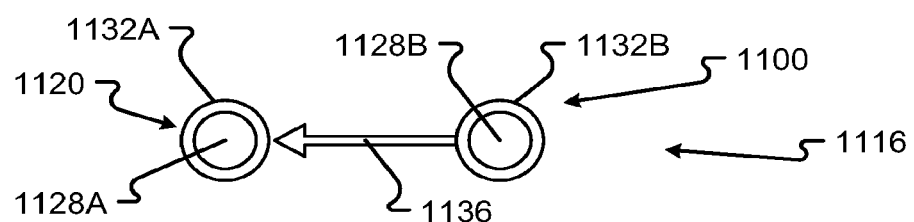
FIG. 11H is a graphical representation of an embodiment of a gesture that a user may perform to provide input to a vehicle control system.

The above gestures may be combined in any manner, such as those shown by FIGS. 11G and 11H, to produce a determined functional result. For example, in FIG. 11G a tap gesture 1120 is combined with a drag or flick gesture 1112 in a direction away from the tap gesture 1120. In FIG. 11H, a tap gesture 1120 is combined with a drag or flick gesture 1116 in a direction towards the tap gesture 1120.

The functional result of receiving a gesture can vary depending on a number of factors, including a state of the vehicle 104, display, or screen of a device, a context associated with the gesture, or sensed location of the gesture, etc. The state of the vehicle 104 commonly refers to one or more of a configuration of the vehicle 104, a display orientation, and user and other inputs received by the vehicle 104. Context commonly refers to one or more of the particular application(s) selected by the gesture and the portion(s) of the application currently executing, whether the application is a single- or multi-screen application, and whether the application is a multi-screen application displaying one or more windows. A sensed location of the gesture commonly refers to whether the sensed set(s) of gesture location coordinates are on a touch sensitive display or a gesture capture region of a device 212, 248, whether the sensed set(s) of gesture location coordinates are associated with a common or different display, or screen, or device 212, 248, and/or what portion of the gesture capture region contains the sensed set(s) of gesture location coordinates.

A tap, when received by a touch sensitive display of a device 212, 248, can be used, for instance, to select an icon to initiate or terminate execution of a corresponding application, to maximize or minimize a window, to reorder windows in a stack, and/or to provide user input such as by keyboard display or other displayed image. A drag, when received by a touch sensitive display of a device 212, 248, can be used, for instance, to relocate an icon or window to a desired location within a display, to reorder a stack on a display, or to span both displays (such that the selected window occupies a portion of each display simultaneously). A flick, when received by a touch sensitive display of a device 212, 248 or a gesture capture region, can be used to relocate a window from a first display to a second display or to span both displays (such that the selected window occupies a portion of each display simultaneously). Unlike the drag gesture, however, the flick gesture is generally not used to move the displayed image to a specific user-selected location but to a default location that is not configurable by the user.

The pinch gesture, when received by a touch sensitive display or a gesture capture region of a device 212, 248, can be used to minimize or otherwise increase the displayed area or size of a window (typically when received entirely by a common display), to switch windows displayed at the top of the stack on each display to the top of the stack of the other display (typically when received by different displays or screens), or to display an application manager (a "pop-up window" that displays the windows in the stack). The spread gesture, when received by a touch sensitive display or a gesture capture region of a device 212, 248, can be used to maximize or otherwise decrease the displayed area or size of a window, to switch windows displayed at the top of the stack on each display to the top of the stack of the other display (typically when received by different displays or screens), or to display an application manager (typically when received by an off-screen gesture capture region on the same or different screens).

The combined gestures of FIG. 11G, when received by a common display capture region in a common display or screen of a device 212, 248, can be used to hold a first window location constant for a display receiving the gesture while reordering a second window location to include a window in the display receiving the gesture. The combined gestures of FIG. 11H, when received by different display capture regions in a common display or screen of a device 212, 248 or in different displays or screens of one more devices 212, 248, can be used to hold a first window location for a display receiving the tap part of the gesture while reordering a second window location to include a window in the display receiving the flick or drag gesture. Although specific gestures and gesture capture regions in the preceding examples have been associated with corresponding sets of functional results, it is to be appreciated that these associations can be redefined in any manner to produce differing associations between gestures and/or gesture capture regions and/or functional results.

Figure 11I:
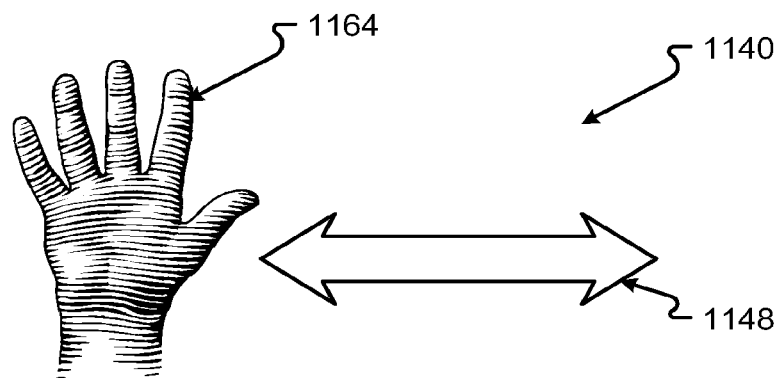
FIG. 11I is a graphical representation of an embodiment of a gesture that a user may perform to provide input to a vehicle control system.
Figure 11J:
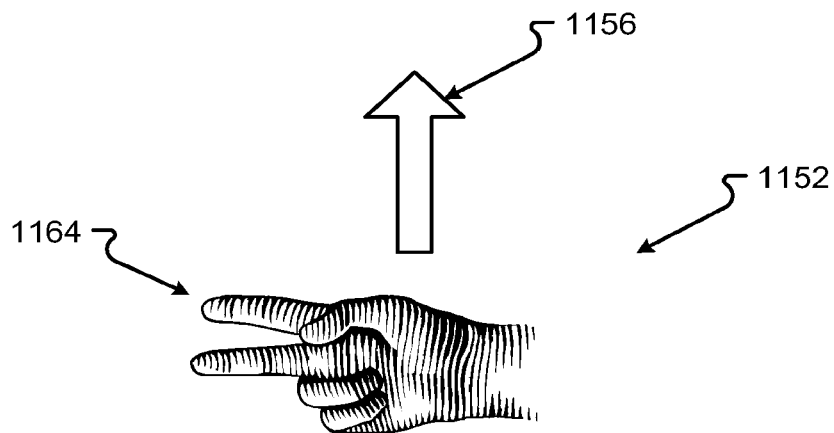
FIG. 11J is a graphical representation of an embodiment of a gesture that a user may perform to provide input to a vehicle control system.
Figure 11K:
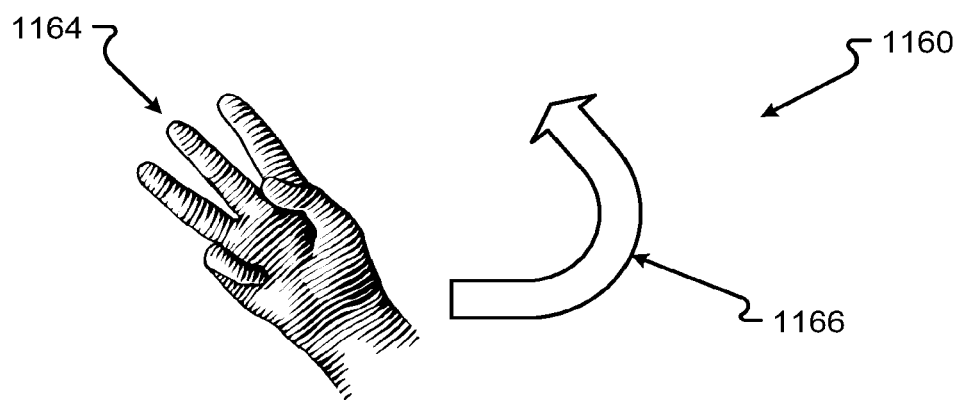
FIG. 11K is a graphical representation of an embodiment of a gesture that a user may perform to provide input to a vehicle control system.

Gestures that may be completed in three-dimensional space and not on a touch sensitive screen or gesture capture region of a device 212, 248 may be as shown in FIGS. 11I-11K. The gestures may be completed in an area where a sensor, such as an optical sensor, infrared sensor, or other type of sensor, may detect the gesture. For example, the gesture 1140 in FIG. 11I may be executed by a person when the person opens their hand 1164 and moves their hand in a back and forth direction 1148 as a gesture 1140 to complete some function with the vehicle 104. For example gesture 1140 may change the station of the radio in the vehicle 104. The sensors 242 may both determine the configuration of the hand 1164 and the vector of the movement. The vector and hand configuration can be interpreted to mean certain things to the vehicle control system 204 and produce different results.

In another example of a gesture 1152 in FIG. 11I, a user may configure their hand 1164 to extend two fingers and move the hand 1164 in an up and down operation 1156. This gesture 1152 may control the volume of the radio or some other function. For instance, this gesture 1152 may be configured to place the vehicle in a "valet" mode to, among other things, restrict access to certain features associated with the vehicle. Again, the sensors 242 may determine how the person has configured their hand 1164, and the vector of the movement. In another example of a gesture 1160 shown in FIG. 11K, a user may extend their middle three fingers at an angle that is substantially 45° for vertical from straight vertical and circle the hand in a counter-clockwise motion 1166. This gesture 1160 may cause the automobile to change the heat setting or do some other function. As can be understood by one skilled in the art, the configurations of the hand and the types of movement are variable. Thus, the user may configure the hand 1164 in any way imaginable and may also move that hand 1164 in any direction with any vector in three-dimensional space.

The gestures 1140, 1152, 1160, as shown in FIGS. 11I-11K, may occur in a predetermined volume of space within the vehicle 104. For example, a sensor may be configured to identify such gestures 1140, 1152, 1160 between the front passenger's and front driver's seats over a console area within the passenger compartment of the vehicle 104. The gestures 1140, 1152, 1160 may be made within area 1 508A between zones A 512A and B 512B. However, there may be other areas 508 where a user may use certain gestures, where sensors 242 may be able to determine a certain function is desired. Gestures that may be similar but used in different areas within the vehicle 104 may cause different functions to be performed. For example, the gesture 1140 in FIG. 11I, if used in zone E 512E, may change the heat provided in zone E 512E, but may change the station of a radio if used in zone A 512A and/or zone B 512B. Further, the gestures may be made with other body parts or, for example, different expressions of a person's face and may be used to control functions in the vehicle 104. Also, the user may use two hands in some circumstances or do other types of physical movements that can cause different reactions in the vehicle 104.

FIGS. 12A-12D show various embodiments of a data structure 1200 to store different settings. The data structure 1200 may include one or more of data files or data objects 1204, 1250, 1270, 1280. Thus, the data structure 1200 may represent different types of databases or data storage, for example, object-oriented data bases, flat file data structures, relational database, or other types of data storage arrangements. Embodiments of the data structure 1200 disclosed herein may be separate, combined, and/or distributed. As indicated in FIGS. 12A-12D, there may be more or fewer portions in the data structure 1200, as represented by ellipses 1244. Further, there may be more or fewer files in the data structure 1200, as represented by ellipses 1248.

Figure 12A:
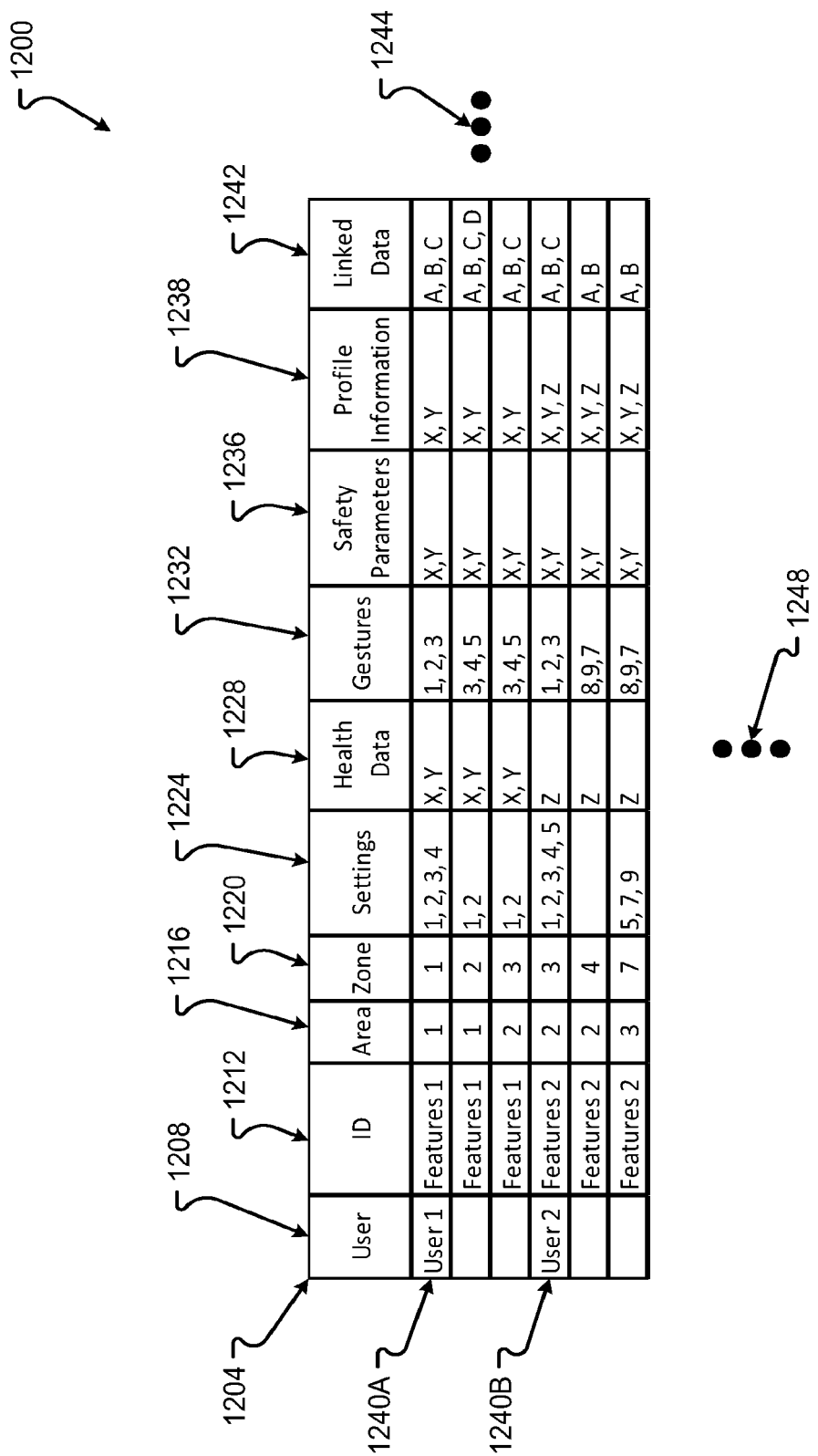
FIG. 12A is a diagram of an embodiment of a data structure for storing information about a user of a vehicle.

Referring to FIG. 12A, a first data structure is shown. The data file 1204 may include several portions 1208-1242 representing different types of data. Each of these types of data may be associated with a user, as shown in portion 1208.

There may be one or more user records 1240 and associated data stored within the data file 1204. As provided herein, the user can be any person that uses or rides within the vehicle or conveyance 104. The user may be identified in portion 1212. For the vehicle 104, the user may include a set of one or more features that may identify the user. These features may be the physical characteristics of the person that may be identified by facial recognition or some other type of system. In other situations, the user may provide a unique code to the vehicle control system 204 or provide some other type of data that allows the vehicle control system 204 to identify the user. The features or characteristics of the user are then stored in portion 1212.

Each user, identified in portion 1208, may have a different set of settings for each area 508 and/or each zone 512 within the vehicle 104. Thus, each set of settings may also be associated with a predetermined zone 512 or area 508. The zone 512 is stored in portion 1220, and the area 508 is stored in portion 1216.

One or more settings may be stored in portion 1224. These settings 1224 may be the configurations of different functions within the vehicle 104 that are specified by or for that user. For example, the settings 1224 may be the position of a seat, the position of a steering wheel, the position of accelerator and/or brake pedals, positions of mirrors, a heating/cooling setting, a radio setting, a cruise control setting, or some other type of setting associated with the vehicle 104. Further, in vehicles adapted to have a configurable console or a configurable dash or heads-up display, the settings 1224 may also provide for how that heads-up display, dash, or console are configured for this particular user.

Each setting 1224 may be associated with a different area 508 or zone 512. Thus, there may be more settings 1224 for when the user is the driver and in zone A 512A, 512A, of area 1, 508A. However, there may be similar settings 1224 among the different zones 512 or areas 508 as shown in portion 1224. For example, the heating or radio settings for the user may be similar in every zone 512.

The sensors 242 within the vehicle 104 may be able to either obtain or track health data in portion 1228. Health data 1228 may include any type of physical characteristic associated with the user. For example, a heart rate, a blood pressure, a temperature, or other types of heath data may be obtained and stored in portion 1228. The user may have this health data tracked over a period of time to allow for statistical analysis of the user's health while operating the vehicle 104. In this way, if some function of the user's health deviates from a norm (e.g., a baseline measurement, average measurements taken over time, and the like), the vehicle 104 may be able to determine there is a problem with the person and react to that data.

One or more gestures may be stored in portion 1232. Thus, the gestures used and described in conjunction FIG. 11A through 11K may be configurable. These gestures may be determined or created by the user and stored in portion 1132. A user may have different gestures for each zone 512 or area 508 within the vehicle. The gestures that do certain things while driving may do other things while in a different area 508 of the vehicle 104. Thus, the user may use a first set of gestures while driving and a second set while a passenger. Further, one or more users may share gestures as shown in portion 1232. Each driver may have a common set of gestures that they use in zone A 512A, 512A. Each of these gestures may be determined or captured and then stored with their characteristics (e.g., vector, position of gesture, etc.) in portion 1232.

One or more sets of safety parameters may be stored in portion 1236. Safety parameters 1236 may be common operating characteristics for this driver/passenger or for all drivers/passengers that if deviated from may determine there is a problem with the driver/passenger or the vehicle 104. For example, a certain route may be taken repeatedly and an average speed or mean speed may be determined. If the mean speed deviates by some number of standard deviations, a problem with the vehicle 104 or the user may be determined. In another example, the health characteristics or driving experience of the user may be determined. If the user drives in a certain position where their head occupies a certain portion of three-dimensional space within the vehicle 104, the vehicle control system 204 may determine that the safety parameter includes the users face or head being within this certain portion of the vehicle interior space. If the user's head deviates from that interior space for some amount of time, the vehicle control system 204 can determine that something is wrong with the driver and change the function or operation of the vehicle 104 to assist the driver. This may happen, for example, when a user falls asleep at the wheel. If the user's head droops and no longer occupies a certain three dimensional space, the vehicle control system 204 can determine that the driver has fallen asleep and may take control of the operation of the vehicle 204 and the automobile controller 8104 may steer the vehicle 204 to the side of the road. In other examples, if the user's reaction time is too slow or some other safety parameter is not nominal, the vehicle control system 204 may determine that the user is inebriated or having some other medical problem. The vehicle control system 204 may then assume control of the vehicle to ensure that the driver is safe.

Information corresponding to a user and/or a user profile may be stored in the profile information portion 1238. For example, the profile information 1238 may include data relating to at least one of current data, historical data, a user preference, user habit, user routine, observation, location data (e.g., programmed and/or requested destinations, locations of parking, routes traveled, average driving time, etc.), social media connections, contacts, brand recognition (e.g., determined via one or more sensors associated with the vehicle 104, a device 212, 248, etc.), audible recording data, text data, email data, political affiliation, preferred retail locations/sites (e.g., physical locations, web-based locations, etc.), recent purchases, behavior associated with the aforementioned data, and the like. The data in the profile information portion 1238 may be stored in one or more of the data structures 1200 provided herein. As can be appreciated, these one or more data structures may be stored in one or more memory locations. Examples of various memory locations are described in conjunction with FIG. 2.

One or more additional data fields may be stored in the linked data portion 1242 as data and/or locations of data. The linked data 1242 may include at least one of pointers, addresses, location identification, data source information, and other information corresponding to additional data associated with the data structure 1200. Optionally, the linked data portion 1242 may refer to data stored outside of a particular data structure 1200. For example, the linked data portion 1242 may include a link/locator to the external data. Continuing this example, the link/locator may be resolved (e.g., via one or more of the methods and/or systems provided herein, etc.) to access the data stored outside of the data structure 1200. Additionally or alternatively, the linked data portion 1242 may include information configured to link the data objects 1204 to other data files or data objects 1250, 1270, 1280. For instance, the data object 1204 relating to a user may be linked to at least one of a device data object 1250, a vehicle system data object 1270, and a vehicle data object 1280, to name a few.

Figure 12B:
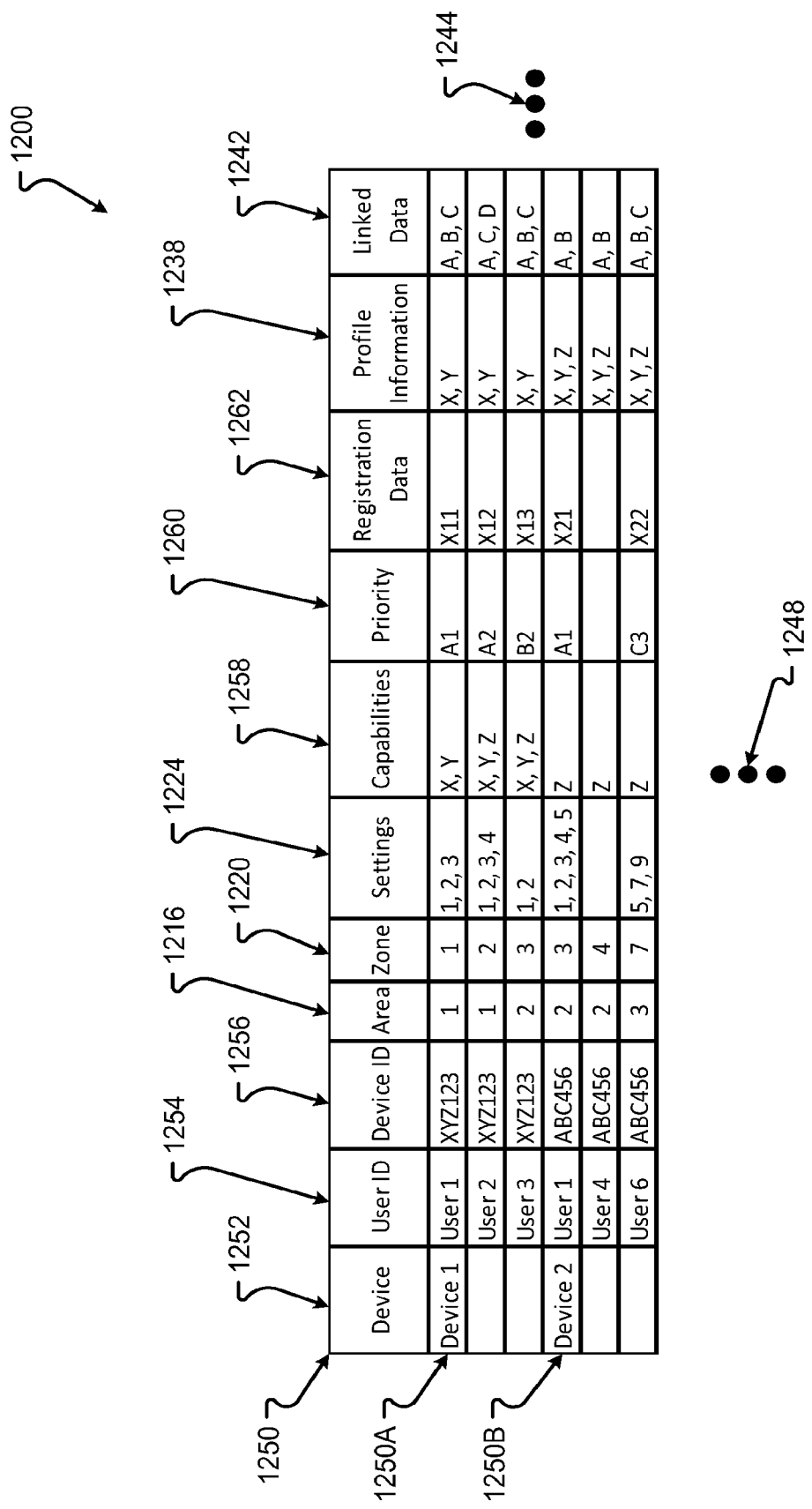
FIG. 12B is a diagram of an embodiment of a data structure for storing information about a device associated with or in a vehicle.

An embodiment of a data structure 1200 to store information associated with one or more devices is shown in FIG. 12B. The data file 1250 may include several portions 1216-1262 representing different types of data. Each of these types of data may be associated with a device, as shown in portion 1252.

There may be one or more device records 1250 and associated data stored within the data file 1250. As provided herein, the device may be any device that is associated with the vehicle 104. For example, a device may be associated with a vehicle 104 when that device is physically located within the interior space 108 of the vehicle 104. As another example, a device may be associated with a vehicle 104 when the device registers with the vehicle 104. Registration may include pairing the device with the vehicle 104 and/or one or more of the vehicle systems (e.g., as provided in FIG. 3). In some cases, the registration of a device with a vehicle 104 may be performed manually and/or automatically. An example of automatic registration may include detecting, via one or more of the vehicle systems, that a device is inside the vehicle 104. Upon detecting that the device is inside the vehicle 104, the vehicle system may identify the device and determine whether the device is or should be registered. Registration may be performed outside of a vehicle 104 via providing a unique code to the vehicle 104 and/or at least one of the vehicle systems.

The device may be identified in portion 1256. Among other things, the device identification may be based on the hardware associated with the device (e.g., Media Access Control (MAC) address, Burned-In Address (BIA), Ethernet Hardware Address (EHA), physical address, hardware address, and the like).

Optionally, a device may be associated with one or more users. For example, a tablet and/or graphical user interface (GUI) associated with the vehicle 104 may be used by multiple members of a family. For instance, the GUI may be located in a particular area 508 and/or zone 512 of the vehicle 104. Continuing this example, when a family member is located in the particular area 508 and/or zone 512, the device may include various settings, features, priorities, capabilities, and the like, based on an identification of the family member. The user may be identified in portion 1254. For the device, the user identification portion 1254 may include a set of one or more features that may identify a particular user. These features may be the physical characteristics of the person that may be identified by facial recognition, or some other type of system, associated with the device and/or the vehicle 104. Optionally, the user may provide a unique code to the device, or provide some other type of data, that allows the device to identify the user. The features or characteristics of the user are then stored in portion 1254.

Each device identified in the device identification portion 1256 may have a different set of settings for each area 508 and/or each zone 512, and/or each user of the device. Thus, each set of settings may also be associated with a predetermined zone 512, area 508, and/or user. The zone 512 is stored in portion 1220 and the area 508 is stored in portion 1216.

One or more settings may be stored in portion 1224. These settings 1224 may be similar and/or identical to those previously described. Further, the settings 1224 may also provide for how a device is configured for a particular user. Each setting 1224 may be associated with a different area 508 or zone 512. Thus, there may be more restrictive settings 1224 (e.g., restricted multimedia, texting, limited access to device functions, and the like) for the device when the user is the driver and in zone A 512A, 512A, of area 1, 508A. However, when the user is in another zone 512 or area 508, for example, where the user is not operating a vehicle 104, the settings 1224 may provide unrestricted access to one or more features of the device (e.g., allowing texting, multimedia, etc.).

Optionally, the capabilities of a device may be stored in portion 1258. Examples of device capabilities may include, but are not limited to, a communications ability (e.g., via wireless network, EDGE, 3G, 4G, LTE, wired, Bluetooth®, Near Field Communications (NFC), Infrared (IR), etc.), hardware associated with the device (e.g., cameras, gyroscopes, accelerometers, touch interface, processor, memory, display, etc.), software (e.g., installed, available, revision, release date, etc.), firmware (e.g., type, revision, etc.), operating system, system status, and the like. Optionally, the various capabilities associated with a device may be controlled by one or more of the vehicle systems provided herein. Among other things, this control allows the vehicle 104 to leverage the power and features of various devices to collect, transmit, and/or receive data.

One or more priorities may be stored in portion 1260. The priority may correspond to a value, or combination of values, configured to determine how a device interacts with the vehicle 104 and/or its various systems. The priority may be based on a location of the device (e.g., as stored in portions 1216, 1220). A default priority can be associated with each area 508 and/or zone 512 of a vehicle 104. For example, the default priority associated with a device found in zone 1 512A of area 1 508A (e.g., a vehicle operator position) may be set higher than an (or the highest of any) alternative zone 512 or area 508 of the vehicle 104. Continuing this example, the vehicle 104 may determine that, although other devices are found in the vehicle, the device, having the highest priority, controls features associated with the vehicle 104. These features may include vehicle control features, critical and/or non-critical systems, communications, and the like. Additionally or alternatively, the priority may be based on a particular user associated with the device. Optionally, the priority may be used to determine which device will control a particular signal in the event of a conflict.

Registration data may be stored in portion 1262. As described above, when a particular device registers with a vehicle 104, data related to the registration may be stored in the registration data portion 1262. Such data may include, but is not limited to, registration information, registration codes, initial registration time, expiration of registration, registration timers, and the like. Optionally, one or more systems of the vehicle 104 may refer to the registration data portion 1262 to determine whether a device has been previously registered with the vehicle 104. As shown in FIG. 12B, User 4 of Device 2 has not been registered. In this case, the registration data field 1262, for this user, may be empty, contain a null value, or other information/indication that there is no current registration information associated with the user.

Additionally or alternatively, the data structure 1200 may include a profile information portion 1238 and/or a linked data portion 1242. Although the profile information portion 1238 and/or the linked data portion 1242 may include different information from that described above, it should be appreciated that the portions 1238, 1242 may be similar, or identical, to those as previously disclosed.

Figure 12C:
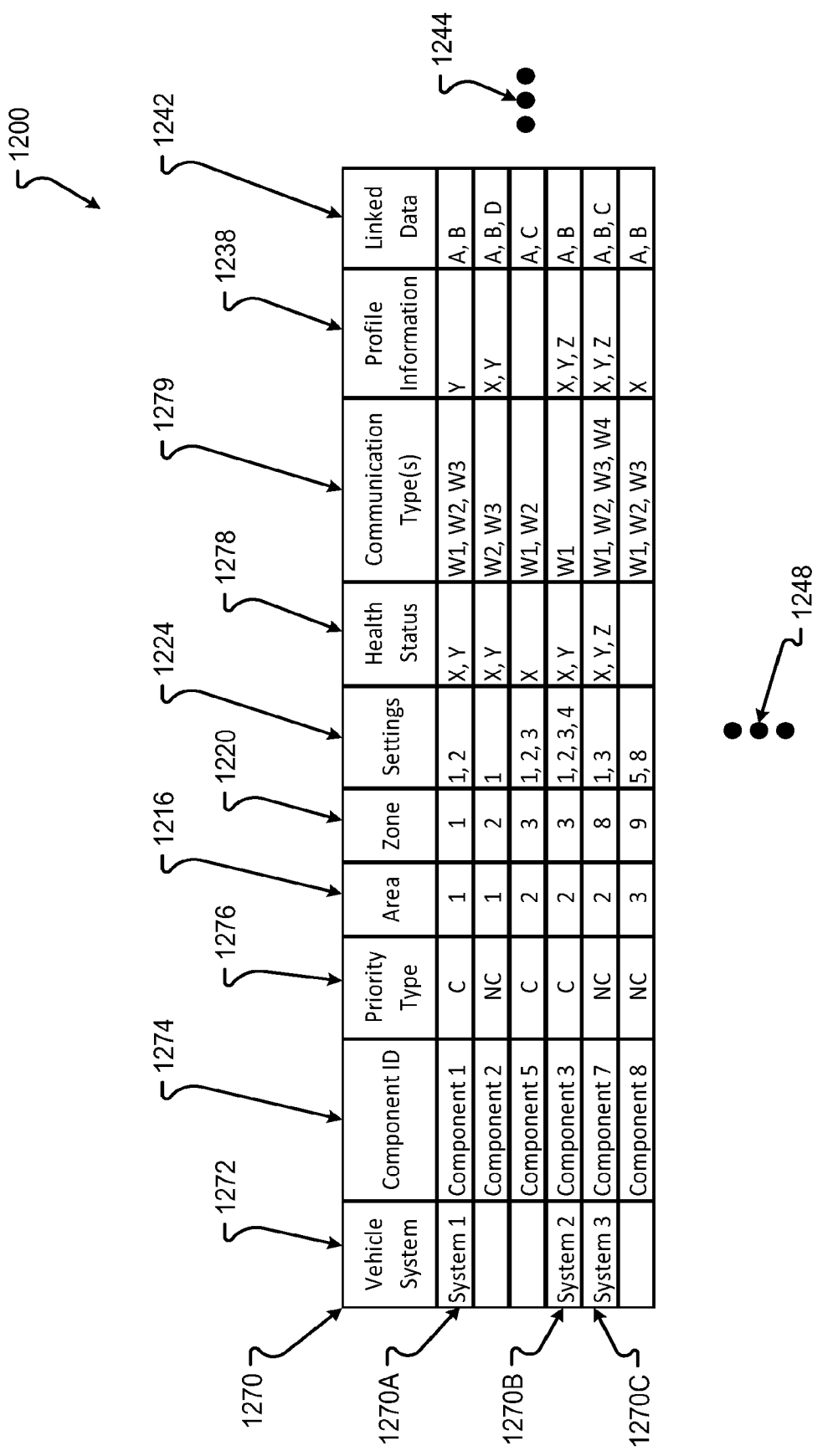
FIG. 12C is a diagram of an embodiment of a data structure for storing information about a system of a vehicle.

An embodiment of a data structure 1200 to store information associated with one or more vehicle systems is shown in FIG. 12C. The data file 1270 may include several portions 1216-1279 representing different types of data. Each of these types of data may be associated with a vehicle system, as shown in portion 1272.

There may be one or more system records 1270 and associated data stored within the data file 1270. As provided herein, the vehicle systems may be any system and/or subsystem that is associated with the vehicle 104. Examples of various systems are described in conjunction with FIG. 3 and other related Figs. (e.g., systems 324-352, etc.). One example of a system associated with the vehicle 104 is the vehicle control system 204. Other systems may include communications subsystems 344, vehicle subsystems 328, and media subsystems 348, to name a few. It should be appreciated that the various systems may be associated with the interior space 108 and/or the exterior of the vehicle 104.

Each system may include one or more components. The components may be identified in portion 1274. Identification of the one or more components may be based on hardware associated with the component. This identification may include hardware addresses similar to those described in conjunction with the devices of FIG. 12B. Additionally or alternatively, a component can be identified by one or more signals sent via the component. Such signals may include an Internet Protocol (IP), or similar, address as part of the signal. Optionally, the signal may identify the component sending the signal via one or more of a header, a footer, a payload, and/or an identifier associated with the signal (e.g., a packet of a signal, etc.).

Each system and/or component may include priority type information in portion 1276. Among other things, the priority type information stored in portion 1276 may be used by the various methods and systems provided herein to differentiate between critical and non-critical systems. Non-limiting examples of critical systems may correspond to those systems used to control the vehicle 104, such as, steering control, engine control, throttle control, braking control, and/or navigation informational control (e.g., speed measurement, fuel measurement, etc.) Non-critical systems may include other systems that are not directly related to the control of the vehicle 104. By way of example, non-critical systems may include media presentation, wireless communications, comfort settings systems (e.g., climate control, seat position, seat warmers, etc.), and the like. Although examples of critical and/or non-critical systems are provided above, it should be appreciated that the priority type of a system may change (e.g., from critical to non-critical, from non-critical to critical, etc.) depending on the scenario. For instance, although the interior climate control system may be classified as a non-critical system at a first point in time, it may be subsequently classified as a critical system when a temperature inside/outside of the vehicle 104 is measured at a dangerous level (e.g., sub-zero Fahrenheit, greater than 90-degrees Fahrenheit, etc.). As such, the priority type may be associated with temperature conditions, air quality, times of the day, condition of the vehicle 104, and the like.

Each system may be associated with a particular area 508 and/or zone 512 of a vehicle 104. Among other things, the location of a system may be used to assess a state of the system and/or provide how the system interacts with one or more users of the vehicle 104. As can be appreciated each system may have a different set of settings for each area 508 and/or each zone 512, and/or each user of the system. Thus, each set of settings may also be associated with a predetermined zone 512, area 508, system, and/or user. The zone 512 is stored in portion 1220 and the area 508 is stored in portion 1216.

One or more settings may be stored in portion 1224. These settings 1224 may be similar and/or identical to those previously described. Further, the settings 1224 may also provide for how a system is configured for a particular user. Each setting 1224 may be associated with a different area 508 or zone 512. For instance, a climate control system may be associated with more than one area 508 and/or zone 512. As such, a first user seated in zone 1 512A of area 1 508A may store settings related to the climate control of that zone 512A that are different from other users and/or zones 512 of the vehicle 104. Optionally, the settings may not be dependent on a user. For instance, specific areas 508 and/or zones 512 of a vehicle 104 may include different, default, or the same settings based on the information stored in portion 1224.

The various systems and/or components may be able to obtain or track health status data of the systems and/or components in portion 1278. The health status 1278 may include any type of information related to a state of the systems. For instance, an operational condition, manufacturing date, update status, revision information, time in operation, fault status, state of damage detected, inaccurate data reporting, and other types of component/system health status data may be obtained and stored in portion 1278.

Each component and/or system may be configured to communicate with users, systems, servers, vehicles, third parties, and/or other endpoints via one or more communication type. At least one communication ability and/or type associated with a system may be stored in the communication type portion 1279. Optionally, the communication types contained in this portion 1279 may be ordered in a preferential order of communication types. For instance, a system may be configured to preferably communicate via a wired communication protocol over one or more wired communication channels (e.g., due to information transfer speeds, reliability, and the like). However, in this instance, if the one or more wired communication channels fail, the system may transfer information via an alternative communication protocol and channel (e.g., a wireless communication protocol and wireless communication channel, etc.). Among other things, the methods and systems provided herein may take advantage of the information stored in the communication type portion 1279 to open available communication channels in the event of a communication channel failure, listen on other ports for information transmitted from the systems, provide a reliability rating based on the number of redundant communication types for each component, and more. Optionally, a component or system may be restricted from communicating via a particular communication type (e.g., based on rules, traffic, critical/non-critical priority type, and the like). In this example, the component or system may be forced by the vehicle control system 204 to use an alternate communication type where available, cease communications, or store communications for later transfer.

Additionally or alternatively, the data structure 1200 may include a profile information portion 1238 and/or a linked data portion 1242. Although the profile information portion 1238 and/or the linked data portion 1242 may include different information from that described above, it should be appreciated that the portions 1238, 1242 may be similar, or identical, to those as previously disclosed.

Figure 12D:
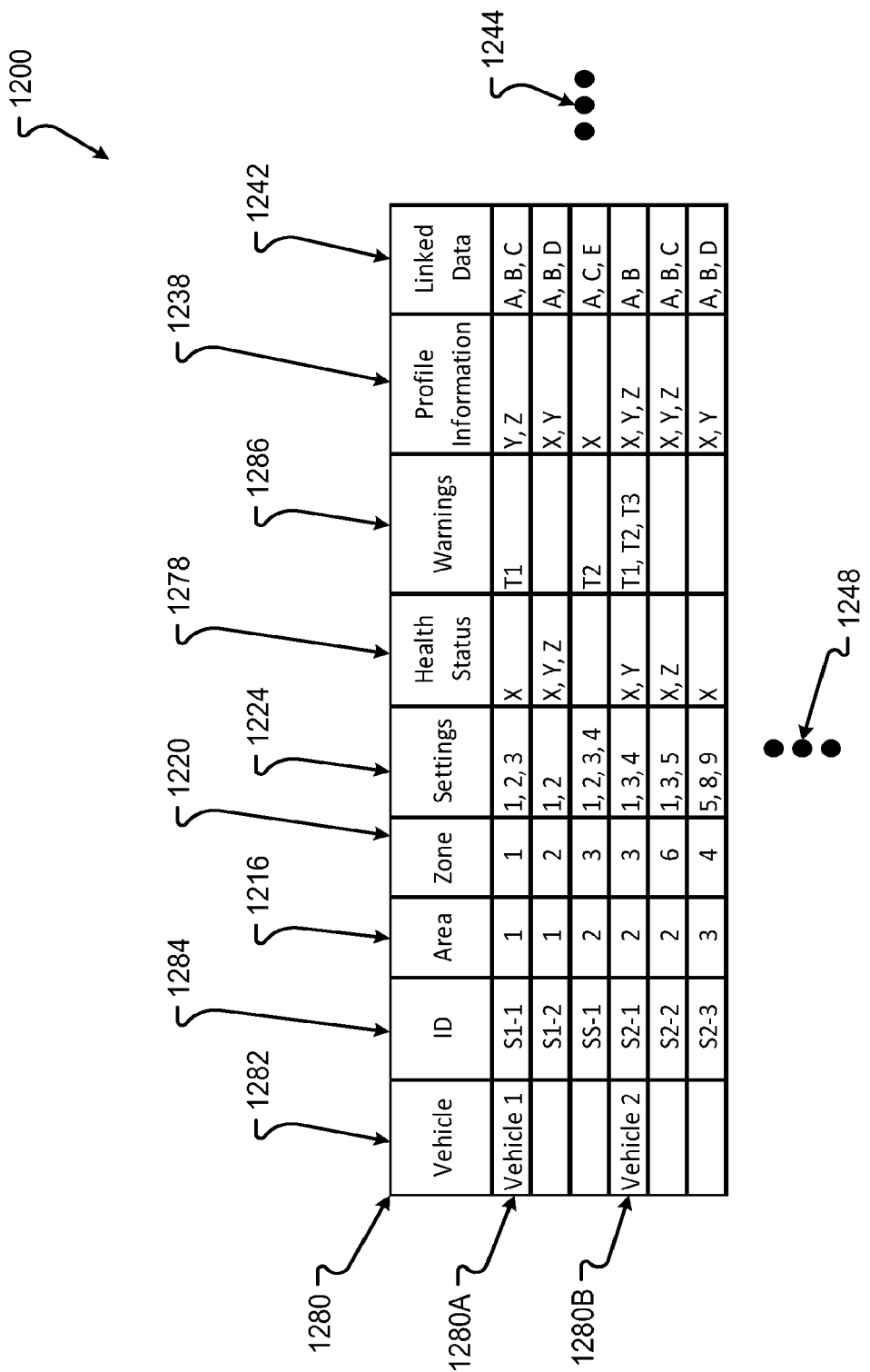
FIG. 12D is a diagram of an embodiment of a data structure for storing information about a vehicle.

Referring now to FIG. 12D, a data structure 1200 is shown optionally. The data file 1280 may include several portions 1216-1286 representing different types of data. Each of these types of data may be associated with a vehicle, as shown in portion 1282.

There may be one or more vehicle records 1280 and associated data stored within the data file 1282. As provided herein, the vehicle 104 can be any vehicle or conveyance 104 as provided herein. The vehicle 104 may be identified in portion 1282. Additionally or alternatively, the vehicle 104 may be identified by one or more systems and/or subsystems. The various systems of a vehicle 104 may be identified in portion 1284. For example, various features or characteristics of the vehicle 104 and/or its systems may be stored in portion 1284. Optionally, the vehicle 104 may be identified via a unique code or some other type of data that allows the vehicle 104 to be identified.

Each system may be associated with a particular area 508 and/or zone 512 of a vehicle 104. Among other things, the location of a system may be used to assess a state of the system and/or provide how the system interacts with one or more users of the vehicle 104. As can be appreciated each system may have a different set of settings for each area 508 and/or each zone 512, and/or each user of the system. Thus, each set of settings may also be associated with a predetermined zone 512, area 508, system, and/or user. The zone 512 is stored in portion 1220 and the area 508 is stored in portion 1216.

One or more settings may be stored in portion 1224. These settings 1224 may be similar and/or identical to those previously described. Further, the settings 1224 may also provide for how a vehicle and/or its systems are configured for one or more users. Each setting 1224 may be associated with a different area 508 or zone 512. Optionally, the settings may not be dependent on a particular user. For instance, specific areas 508 and/or zones 512 of a vehicle 104 may include different, default, or the same settings based on the information stored in portion 1224.

The various systems and/or components may be able to obtain or track health status data of the systems and/or components in portion 1278. The health status 1278 may include any type of information related to a state of the systems. For instance, an operational condition, manufacturing date, update status, revision information, time in operation, fault status, state of damage detected, inaccurate data reporting, and other types of component/system health status data may be obtained and stored in portion 1278.

One or more warnings may be stored in portion 1286. The warnings data 1286 may include warning generated by the vehicle 104, systems of the vehicle 104, manufacturer of the vehicle, federal agency, third party, and/or a user associated with the vehicle. For example, several components of the vehicle may provide health status information (e.g., stored in portion 1278) that, when considered together, may suggest that the vehicle 104 has suffered some type of damage and/or failure. Recognition of this damage and/or failure may be stored in the warnings data portion 1286. The data in portion 1286 may be communicated to one or more parties (e.g., a manufacturer, maintenance facility, user, etc.). In another example, a manufacturer may issue a recall notification for a specific vehicle 104, system of a vehicle 104, and/or a component of a vehicle 104. It is anticipated that the recall notification may be stored in the warning data field 1286. Continuing this example, the recall notification may then be communicated to the user of the vehicle 104 notifying the user of the recall issued by the manufacturer.

Additionally or alternatively, the data structure 1200 may include a profile information portion 1238 and/or a linked data portion 1242. Although the profile information portion 1238 and/or the linked data portion 1242 may include different information from that described above, it should be appreciated that the portions 1238, 1242 may be similar, or identical, to those as previously disclosed.

Figure 13:
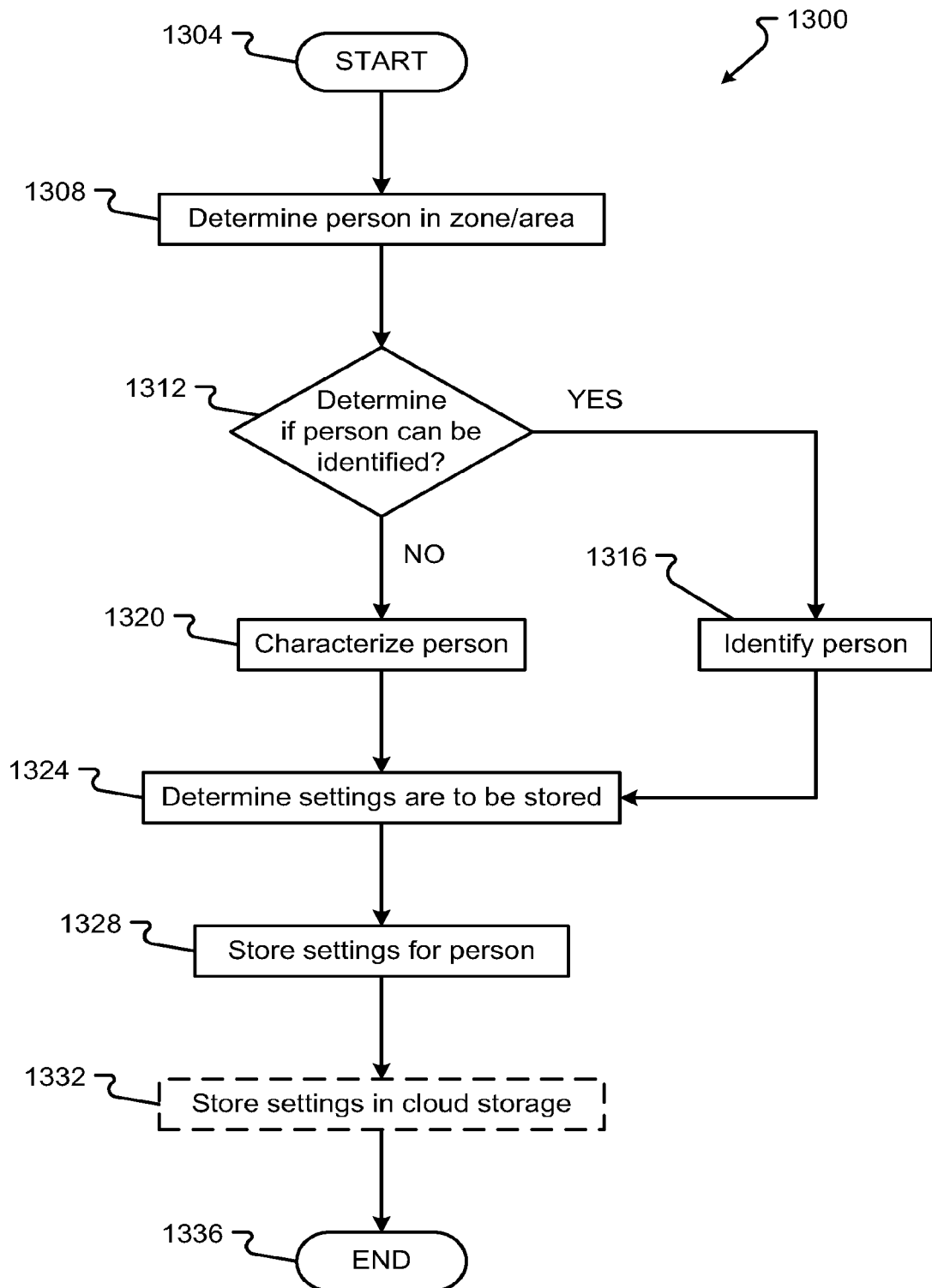
FIG. 13 is a flow or process diagram of a method for storing one or more settings associated with a user.

An embodiment of a method 1300 for storing settings for a user 216 associated with vehicle 104 is shown in FIG. 13. While a general order for the steps of the method 1300 is shown in FIG. 13, the method 1300 can include more or fewer steps or can arrange the order of the steps differently than those shown in FIG. 13. Generally, the method 1300 starts with a start operation 1304 and ends with an end operation 1336. The method 1300 can be executed as a set of computer-executable instructions executed by a computer system and encoded or stored on a computer readable medium. Hereinafter, the method 1300 shall be explained with reference to the systems, components, modules, software, data structures, user interfaces, etc. described in conjunction with FIGS. 1-12.

A person may enter the vehicle space 108. One or more sensors 242 may then identify that a person is sitting within the vehicle 104, in step 1308. For example, sensors 242 in a seat, may determine that some new amount of weight has been registered. The amount of weight may fall within predetermined parameters (e.g., over a threshold, in a specific range, etc.). This weight may then be determined to be a person by one or more optical or other sensors 242. The vehicle control system 204 may then determine that a person is in a certain zone 512 or area 508. For example, the sensors 242 may send signals to the vehicle controls system 204 that an event has occurred. This information may be sent to the vehicle control system processor 304 to determine the zone 512 and area 508 where the event occurred. Further, the vehicle control system 204 may then identify the person, in step 1312.

The vehicle control system 204 can receive the information from the sensors 242 and use that information to search the database 1200 that may be stored within the system data 208. The sensor data may be compared to ID characteristics 1212 to determine if the person has already been identified. The vehicle control system 204 may also send the characteristic data from the sensors to the communication network 224 to a server 228 to compare the sensor data to stored data 232 that may be stored in a cloud system. The person's features can be compared to stored features 1212 to determine if the person in the vehicle 104 can be identified.

If the person has been identified previously and their characteristics stored in portion 1212, the method 1300 proceeds YES to step 1316 where that person may be identified. In identifying a person, the information associated with that person 1240 may be retrieved and provided to the vehicle control system 204 for further action. If a person cannot be identified by finding their sensor characteristics in portion 1212, the method 1300 proceeds NO to step 1320. In step 1320, the vehicle control system 204, using an application, may create a new record in table 1200 for the user. This new record may store a user identifier and their characteristics 1212. It may also store the area 508 and zone 512 in data portions 1216 and 1220. The new record may then be capable of receiving new settings data for this particular user. In this way, the vehicle 104 can automatically identify or characterize a person so that settings may be established for the person in the vehicle 104.

The input module 312 may then determine if settings are to be stored, in step 1324. Settings might be any configuration of the vehicle 104 that may be associated with the user. The determination may be made after receiving a user input from the user. For example, the user may make a selection on a touch sensitive display indicating that settings currently made are to be stored. In other situations, a period of time may elapse after the user has made a configuration. After determining that the user is finished making changes to the settings, based on the length of the period of time since the setting was established, the vehicle control system 204 can save the setting. Thus, the vehicle control system 204 can make settings automatically based on reaching a steady state for settings for user.

The vehicle control system 204 may then store the settings for the person, in step 1328. The user interaction subsystem 332 can make a new entry for the user 1208 in data structure 1204. The new entry may be either a new user or a new settings listed in 1224. The settings may be stored based on the area 508 and zone 512. As explained previously, the settings can be any kind of configuration of the vehicle 104 that may be associated with the user in that area 508 and the zone 512.

The settings may also be stored in cloud storage, in step 1332. Thus, the vehicle control system 204 can send the new settings to the server 228 to be stored in storage 232. In this way, these new settings may be ported to other vehicles for the user. Further, the settings in storage system 232 may be retrieved, if local storage does not include the settings in storage system 208.

Additionally or alternatively, the settings may be stored in profile data 252. As provided herein, the profile data 252 may be associated with one or more devices 212, 248, servers 228, vehicle control systems 204, and the like. Optionally, the settings in profile data 252 may be retrieved in response to conditions. For instance, the settings may be retrieved from at least one source having the profile data if local storage does not include the settings in storage system 208. As another example, a user 216 may wish to transfer settings stored in profile data 252 to the system data 208. In any event, the retrieval and transfer of settings may be performed automatically via one or more devices 204, 212, 248, associated with the vehicle 104.

Figure 14:
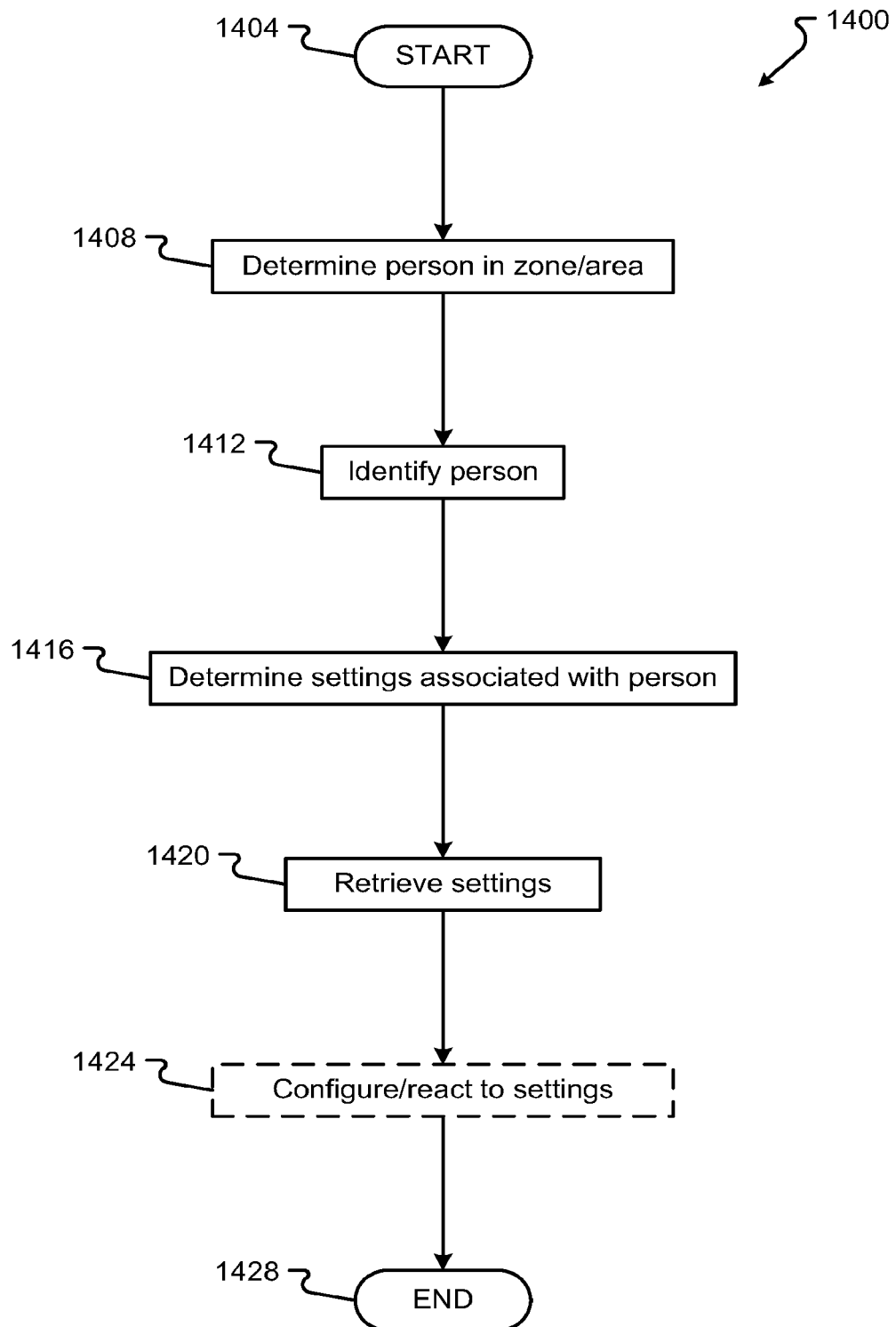
FIG. 14 is a flow or process diagram of a method for establishing one or more settings associated with a user.

An embodiment of a method 1400 to configure the vehicle 104 based on stored settings is shown in FIG. 14. A general order for the steps of the method 1400 is shown in FIG. 14. Generally, the method 1400 starts with a start operation 1404 and ends with an end operation 1428. The method 1400 can include more or fewer steps or can arrange the order of the steps differently than those shown in FIG. 14. The method 1400 can be executed as a set of computer-executable instructions executed by a computer system and encoded or stored on a computer readable medium. Hereinafter, the method 1400 shall be explained with reference to the systems, components, modules, software, data structures, user interfaces, etc. described in conjunction with FIGS. 1-13.

The vehicle control system 204 can determine if a person is in a zone 512 or area 508, in step 1408. This determination may be made by receiving data from one or more sensors 242. The vehicle 104 can use facial recognition, weight sensors, heat sensors, or other sensors to determine whether a person is occupying a certain zone 512.

Using the information from the sensors 242, the vehicle control system 204 can identify the person, in step 1412. The vehicle control system 204 can obtain characteristics for the user currently occupying the zone 512 and compare those characteristics to the identifying features in portion 1212 of data structure 1204. Thus, the settings in portion 1224 may be retrieved by identifying the correct zone 512, area 508, and characteristics for the user.

The vehicle control system 204 can first determine if there are settings associated with the identified person for that zone 512 and/or area 508, in step 1416. After identifying the user by matching characteristics with the features in portion 1212, the vehicle control system 204 can determine if there are settings for the user for the area 1216 and zone 1220 the user currently occupies. If there are settings, then the vehicle control system 204 can make the determination that there are settings in portion 1224, and the vehicle control system 204 may then read and retrieve those settings, in step 1420. The settings may be then used to configure or react to the presence of the user, in step 1424. Thus, these settings may be obtained to change the configuration of the vehicle 104, for example, how the position of the seats or mirrors are set, how the dash, console, or heads up display is configured, how the heat or cooling is configured, how the radio is configured, or how other different configurations are made.

Figure 15:
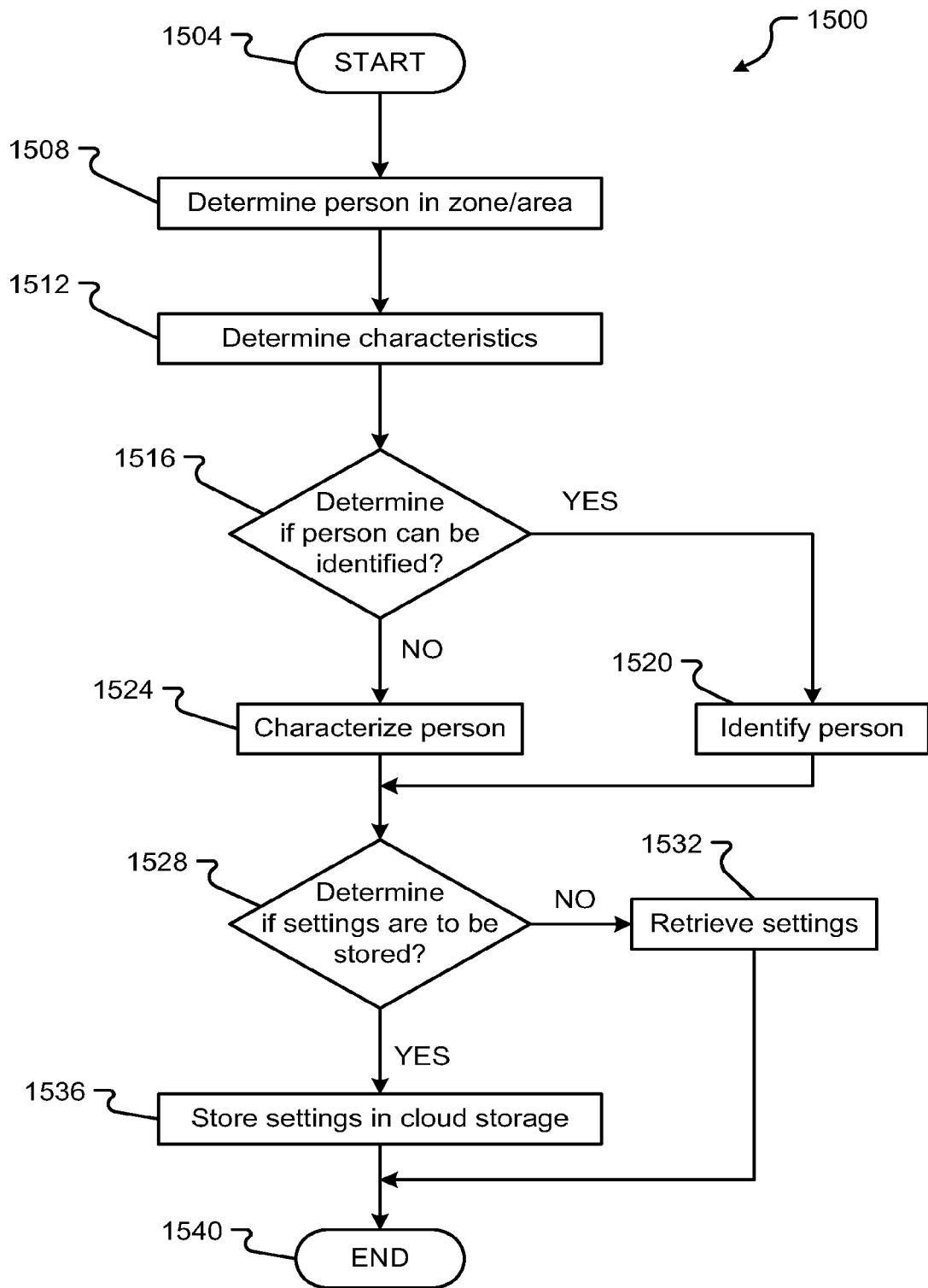
FIG. 15 is a flow or process diagram of a method for storing one or more settings associated with a user.

Embodiments of a method 1500 for storing settings in cloud storage are shown in FIG. 15. A general order for the steps of the method 1500 is shown in FIG. 15. Generally, the method 1500 starts with a start operation 1504 and ends with an end operation 1540. The method 1500 can include more or fewer steps or can arrange the order of the steps differently than those shown in FIG. 15. The method 1500 can be executed as a set of computer-executable instructions executed by a computer system and encoded or stored on a computer readable medium. Hereinafter, the method 1500 shall be explained with reference to the systems, components, modules, software, data structures, user interfaces, etc. described in conjunction with FIGS. 1-14.

The vehicle control system 204 can determine if a person is in a zone 512 or area 508, in step 1508. As explained previously, the vehicle control system 204 can receive vehicle sensor data from vehicle sensors 242 that show a person has occupied a zone 512 or an area 508 of the vehicle 104. Using the vehicle sensor data, the vehicle control system 204 can determine characteristics of the person, in step 1512. These characteristics are compared to the features in portion 1212 of the data structure 1204. From this comparison, the vehicle control system 204 can determine if the person is identified within the data structure 1204, in step 1516. If there is a comparison and the person can be identified, the method 1500 proceeds YES to step 1520. However, if the person cannot be identified, the method 1500 proceeds NO, to step 1524.

In step 1520, the person is identified in portion 1208 by the successful comparison of the characteristics and the features. It should be noted that there may be a degree of variability between the characteristics and the features in portion 1212. Thus, the comparison may not be an exact comparison but may use methods known in the art to make a statistically significant comparison between the characteristics received from the sensors 242 and the features stored in portion 1212. In step 1524, the characteristics received from sensors 242 are used to characterize the person. In this way, the received characteristics may be used as an ID, in portion 1212, for a new entry for a new user in portion 1208.

The user may make one or more settings for the vehicle 104. The vehicle control system 204 may determine if the settings are to be stored, in step 1528. If the settings are to be stored, the method 1500 proceeds YES to step 1536. If the settings are not to be stored or if there are no settings to be stored, the method 1500 proceeds NO to step 1532. In step 1532, the vehicle control system 204 can retrieve the settings in the portion 1224 of the data structure 1204. Retrieval of the settings may be as described in conjunction with FIG. 14. If settings are to be stored, the vehicle control system 204 can send those settings to server 228 to be stored in data storage 232, in step 1536. Data storage 232 acts as cloud storage that can be used to retrieve information on the settings from other vehicles or from other sources. Thus, the cloud storage 232 allows for permanent and more robust storage of user preferences for the settings of the vehicle 104.

Figure 16:
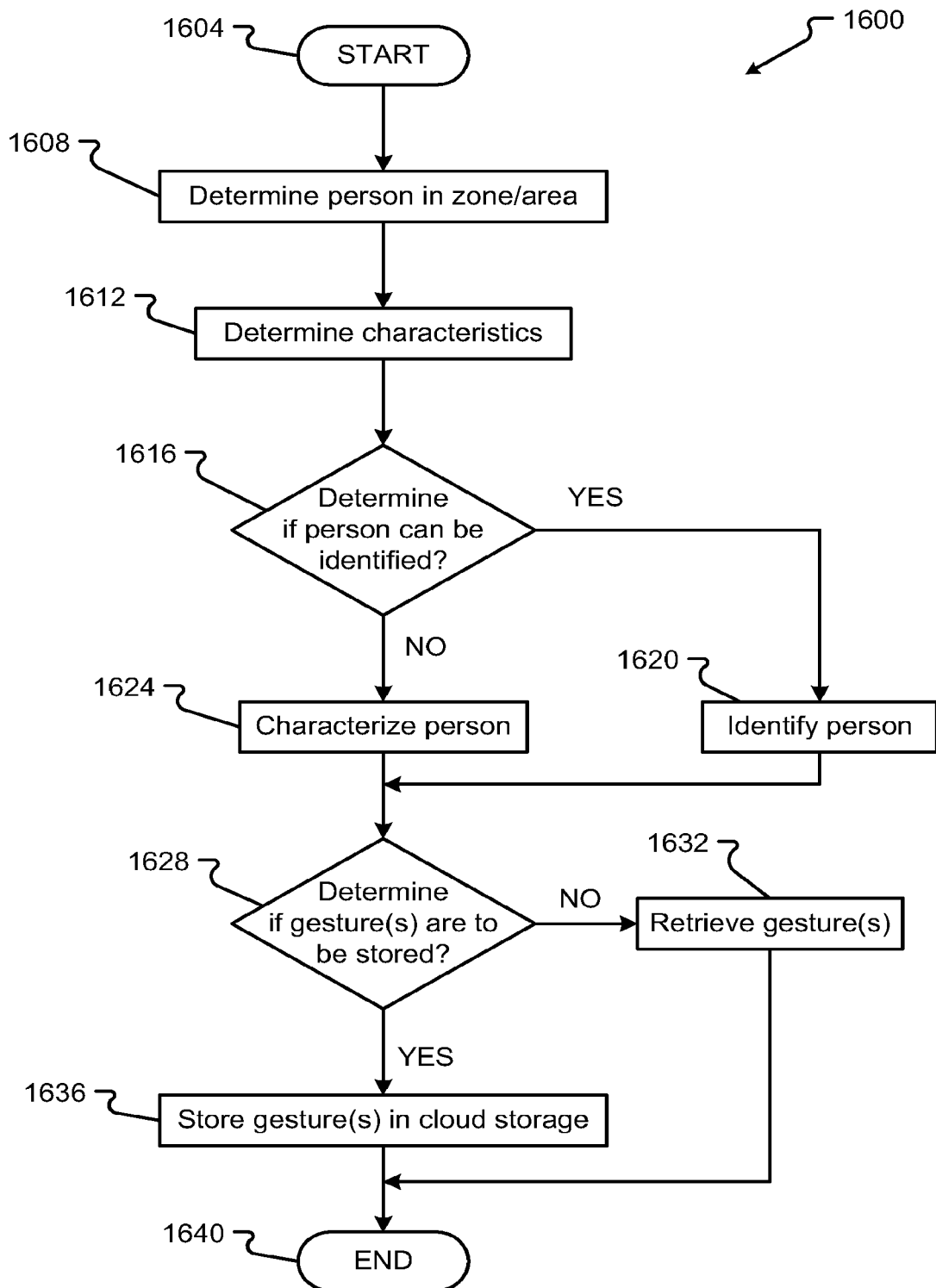
FIG. 16 is a flow or process diagram of a method for storing one or more gestures associated with a user.

An embodiment of a method 1600 for storing gestures associated with the user is shown in FIG. 16. A general order for the steps of the method 1600 is shown in FIG. 16. Generally, the method 1600 starts with a start operation 1604 and ends with an end operation 1640. The method 1600 can include more or fewer steps or can arrange the order of the steps differently than those shown in FIG. 16. The method 1600 can be executed as a set of computer-executable instructions executed by a computer system and encoded or stored on a computer readable medium. Hereinafter, the method 1600 shall be explained with reference to the systems, components, modules, software, data structures, user interfaces, etc. described in conjunction with FIGS. 1-15.

Vehicle control system 204 may receive sensor data from sensors 242 to determine a person is occupying a zone 512 in an area 508 of the vehicle 104, in step 1608. The sensor data may provide characteristics for the person, in step 1612. The vehicle control system 204 may then use the characteristics to determine if the person can be identified, in step 1616. The vehicle control system 204 may compare the characteristics to the features in portion 1212 for the people having been recognized and having data associated therewith. If a comparison is made between the characteristics and the features in portion 1212, the person can be identified, and the method 1600 proceeds YES to step 1620. If there is no comparison, the method 1600 may proceed NO to step 1624. In step 1620, the person may be identified by the vehicle control system 204. Thus, the person's features and associated data record 1240 may be determined and the user identified in portion 1208. If the person is not identified, the vehicle control system 204 can characterize the person in step 1624 by establishing a new record in data structure 1204 using the characteristics, received from the sensors 242, for the features in portion 1212.

Thereinafter, the vehicle control system 204 may determine if gestures are to be stored and associated with the user, in step 1628. The vehicle control system 204 may receive user input on a touch sensitive display or some other type of gesture capture region which acknowledges that the user wishes to store one or more gestures. Thus, the user may create their own gestures such as those described in conjunction with FIGS. 11A-11K. These gestures may then be characterized and stored in data structure 1204. If there are gestures to be stored, the method 1600 proceeds YES to step 1636. If gestures are not to be stored the method 1600 may proceed NO to step 1632.

In step 1632, the vehicle control system 204 can retrieve current gestures from portion 1232, which are associated with user 1240. These gestures may be used then to configure how the vehicle 104 will react if a gesture is received. If gestures are to be stored, the vehicle control system 204 may store characteristics, in step 1636, as received from sensor 242 or from one more user interface inputs. These characteristics may then be used to create the stored gestures 1232, in data structure 1204. The characteristics may include what the gesture looks like or appears and also what affect the gesture should have. This information may then be used to change the configuration or operation of the vehicle 104 based on the gesture if it is received at a later time.

Figure 17:
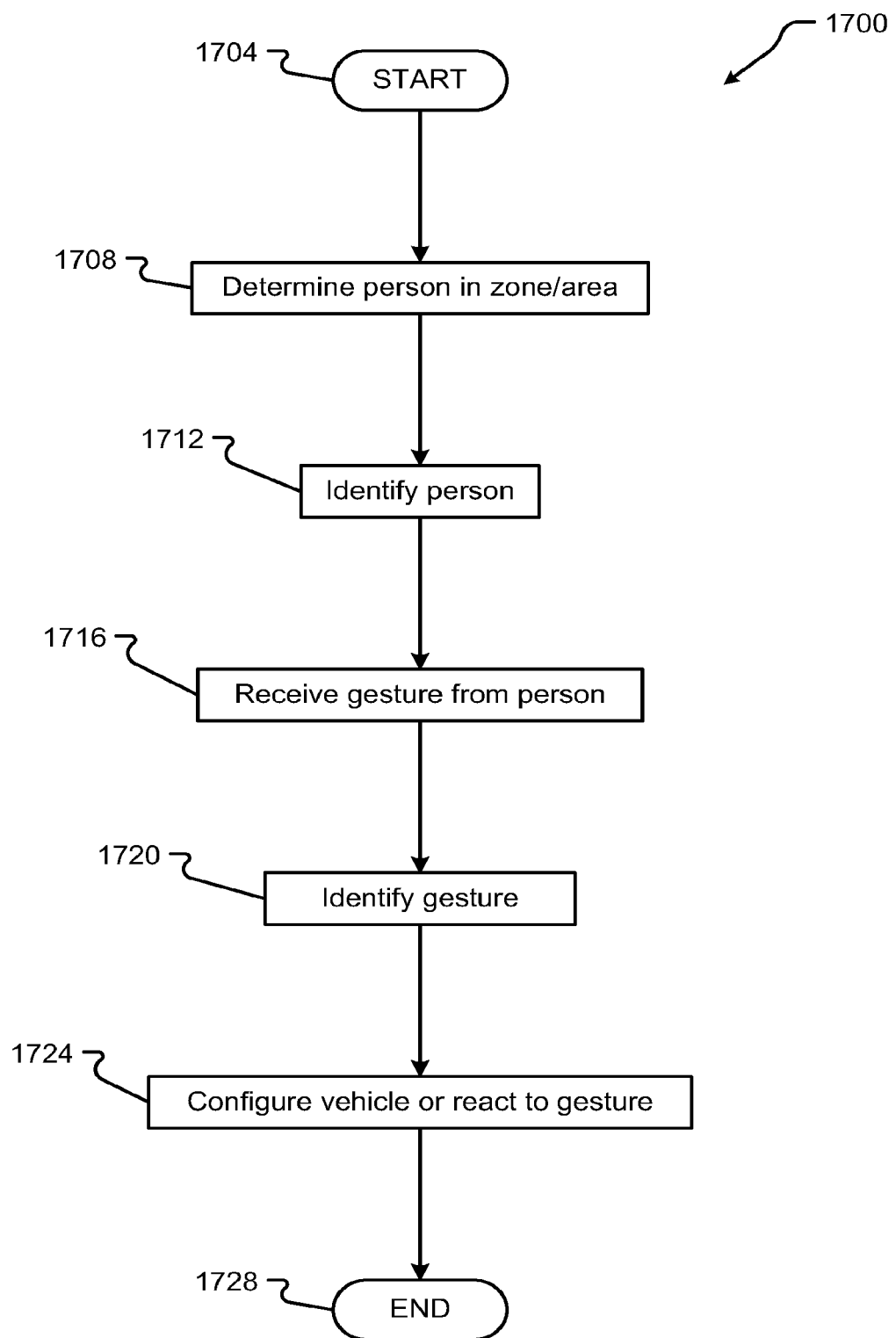
FIG. 17 is a flow or process diagram of a method for reacting to a gesture performed by a user.

An embodiment of a method 1700 for receiving a gesture and configuring the vehicle 104 based on the gesture may be as provided in FIG. 17. A general order for the steps of the method 1700 is shown in FIG. 17. Generally, the method 1700 starts with a start operation 1704 and ends with an end operation 1728. The method 1700 can include more or fewer steps or can arrange the order of the steps differently than those shown in FIG. 17. The method 1700 can be executed as a set of computer-executable instructions executed by a computer system and encoded or stored on a computer readable medium. Hereinafter, the method 1700 shall be explained with reference to the systems, components, modules, software, data structures, user interfaces, etc. described in conjunction with FIGS. 1-16.

A vehicle control system 204 can receive sensor data from vehicle sensors 242. The vehicle sensor data can be used by the vehicle control system 204 to determine that a person is in a zone 512 or area 508, in step 1708. The vehicle sensor data may then be used to compare against feature characteristics 1212 to identify a person, in step 1712. The vehicle control system 204 thereinafter may receive a gesture, in step 1716. The gesture may be perceived by vehicle sensors 242 or received in a gesture capture region. The gesture may be as described in conjunction with FIGS. 11A-11K. Upon receiving the gesture, the vehicle control system 204 can compare the gesture to gesture characteristics in portion 1232, in step 1720. The comparison may be made so that a statistically significant correlation between the sensor data or gesture data and the gesture characteristic 1232 is made. Upon identifying the gesture, the vehicle control system 204 can configure the vehicle 104 and/or react to the gesture, in step 1724. The configuration or reaction to the gesture may be as prescribed in the gesture characteristic 1232.

Figure 18:
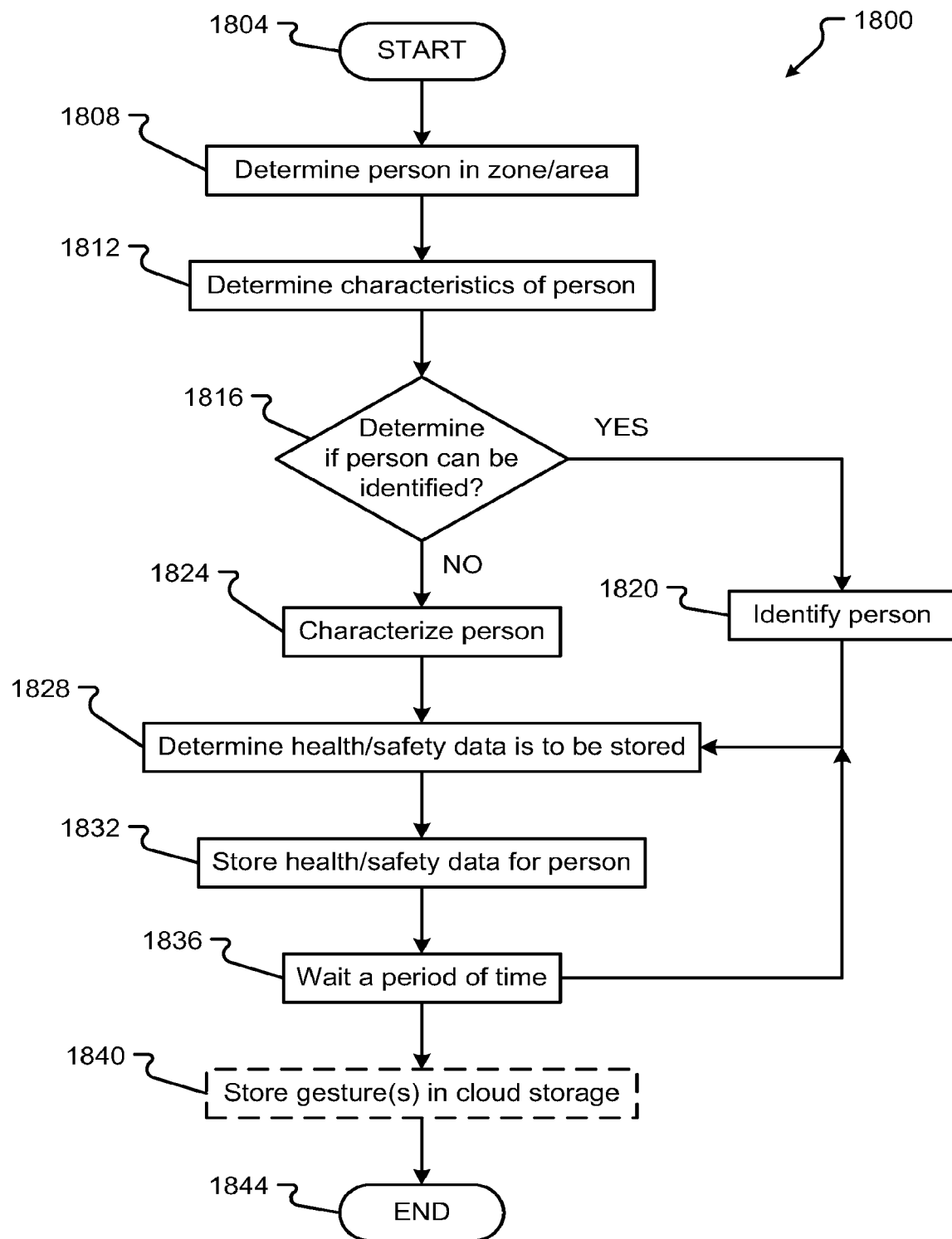
FIG. 18 is a flow or process diagram of a method for storing health data associated with a user.

An embodiment of a method 1800 for storing health data may be as shown in FIG. 18. A general order for the steps of the method 1800 is shown in FIG. 18. Generally, the method 1800 starts with a start operation 1804 and ends with an end operation 1844. The method 1800 can include more or fewer steps or can arrange the order of the steps differently than those shown in FIG. 18. The method 1800 can be executed as a set of computer-executable instructions executed by a computer system and encoded or stored on a computer readable medium. Hereinafter, the method 1800 shall be explained with reference to the systems, components, modules, software, data structures, user interfaces, etc. described in conjunction with FIGS. 1-17.

Vehicle control system 204 can receive sensor data from sensors 242. The sensor data may be used to determine that a person is in a zone 512 or area 508, in step 1808. The sensor data may then be used to determine characteristics of the person, in step 1812. From the characteristics, the vehicle control system 204 can determine if a person may be identified in data structure 1204, in step 1816. If it is determined that the person can be identified in step 1816, the method 1800 proceeds YES to step 1820. If the person cannot be identified, the method 1800 proceeds NO to step 1824. A person may be identified by matching the characteristics of a person from the sensor data to the features shown in portion 1212. If these comparisons are statistically significant, the person may be identified in portion 1208, in step 1820. However, if the person is not identified in portion 1208, the vehicle control system 204 can characterize the person using the vehicle sensor data, in step 1824. In this way, the vehicle control system 204 can create a new record for a new user in data structure 1204.

Thereinafter, the vehicle control system 204 may receive health and/or safety data from the vehicle sensors 242, in step 1828. The vehicle control system 204 can determine if the health or safety data is to be stored, in step 1832. The determination is made as to whether or not there is sufficient health data or safety parameters, in portion 1228 and 1236, to provide a reasonable baseline data pattern for the user 1240. If there is data to be received and stored, the vehicle control system 204 can store the data for the person in portions 1228 and 1236 of the data structure 1204, in step 1832.

The vehicle control system 204 may then wait a period of time, in step 1836. The period of time may be any amount of time from seconds to minutes to days. Thereinafter, the vehicle control system 204 can receive new data from vehicle sensors 242, in step 1828. Thus, the vehicle control system 204 can receive data periodically and update or continue to refine the health data and safety parameters in data structure 1204. Thereinafter, the vehicle control system 204 may optionally store the health and safety data in cloud storage 232 by sending it through the communication network 224 to the server 228, in step 1840.

Figure 19:
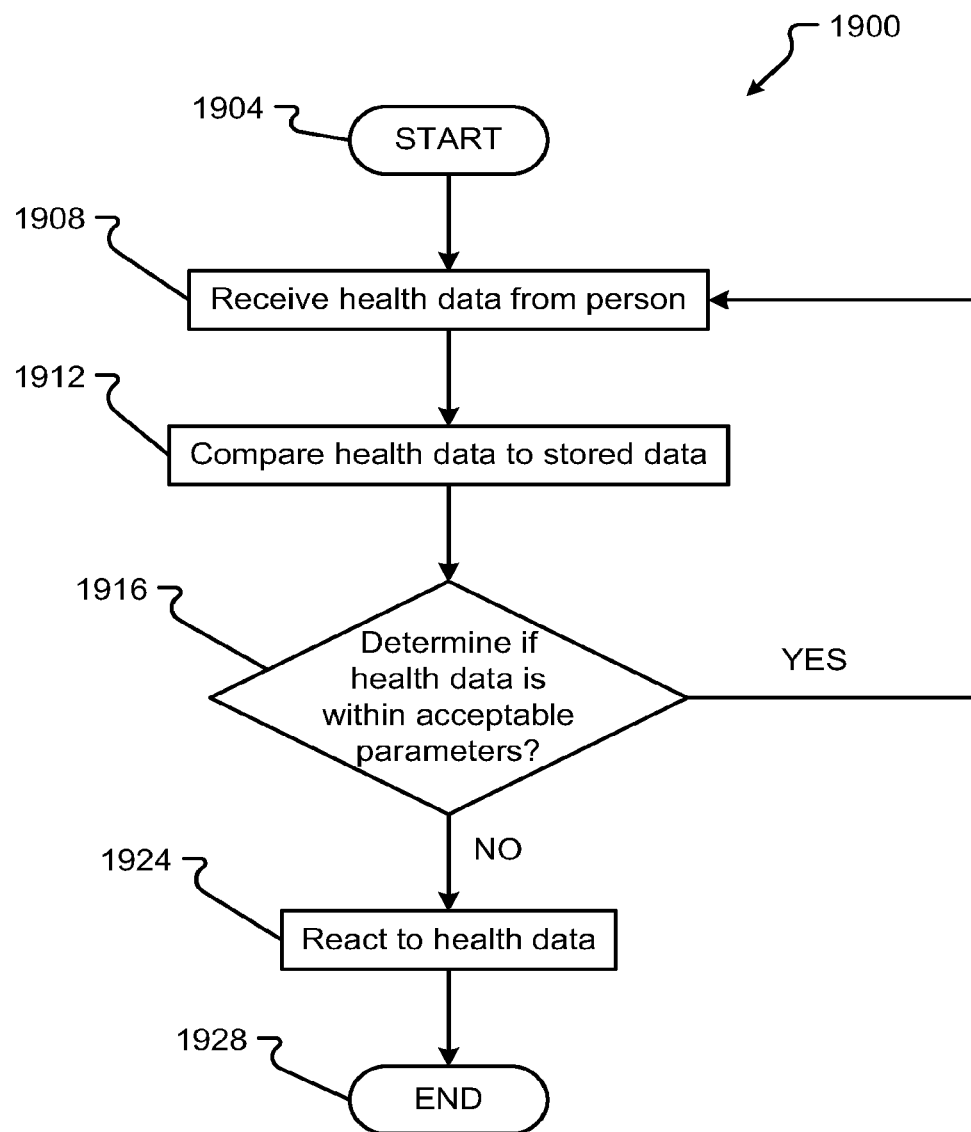
FIG. 19 is a flow or process diagram of a method for reacting to a gesture performed by a user.

An embodiment of a method 1900 for monitoring the health of a user may be as shown in FIG. 19. A general order for the steps of the method 1900 is shown in FIG. 19. Generally, the method 1900 starts with a start operation 1904 and ends with an end operation 1928. The method 1900 can include more or fewer steps or can arrange the order of the steps differently than those shown in FIG. 19. The method 1900 can be executed as a set of computer-executable instructions executed by a computer system and encoded or stored on a computer readable medium. Hereinafter, the method 1900 shall be explained with reference to the systems, components, modules, software, data structures, user interfaces, etc. described in conjunction with FIGS. 1-18.

The vehicle control system 204 can receive health data from sensors 242. The health data may be received in step 1908. The vehicle control system 204 may then compare the received health data to stored health parameters in portion 1228 or portion 1236, in step 1912. The comparison may check if there is statistically significant separation or disagreement between the received health data and the stored health data. Thus, the vehicle control system 204 can make a health comparison of the user based on a baseline of health data previously stored. A statistically significant comparison may include determining if there are any parameters more than three standard deviations from the average or norm, any parameter that is increasing or decreasing over a period of eight different measurements, a measurement that is more than two standard deviations from the norm more than three measurements consecutively, or other types of statistical comparisons.

If the vehicle control system 204 determines that measured health parameter does deviate from the norm, the vehicle control system 204 can determine whether the health data is within acceptable limits, in step 1916. If the health data is within acceptable limits, the method 1900 proceeds YES back to receiving new health data, in step 1908. In this way, the health data is periodically or continually monitored to ensure that the driver is in a healthy state and able to operate the vehicle. If the health data is not within acceptable parameters, the method 1900 may proceed NO to step 1924 where the vehicle control system 204 may react to the change in the health data. The reaction may include any measure to provide for the safety of the user, such as stopping the vehicle, beginning to drive the vehicle, driving the vehicle to a new location, such as a hospital, waking the driver with an alarm or other noise, or performing some other function that may help maintain the health or safety of the user.

The health data received may be a reaction from the driver. For example, the driver may call for help or ask the vehicle for assistance. For example, the driver or passenger may say that they are having a medical emergency and ask the car to perform some function to help. The function to help may include driving the person to a hospital or stopping the car and calling for emergency assistance.

Figure 20:
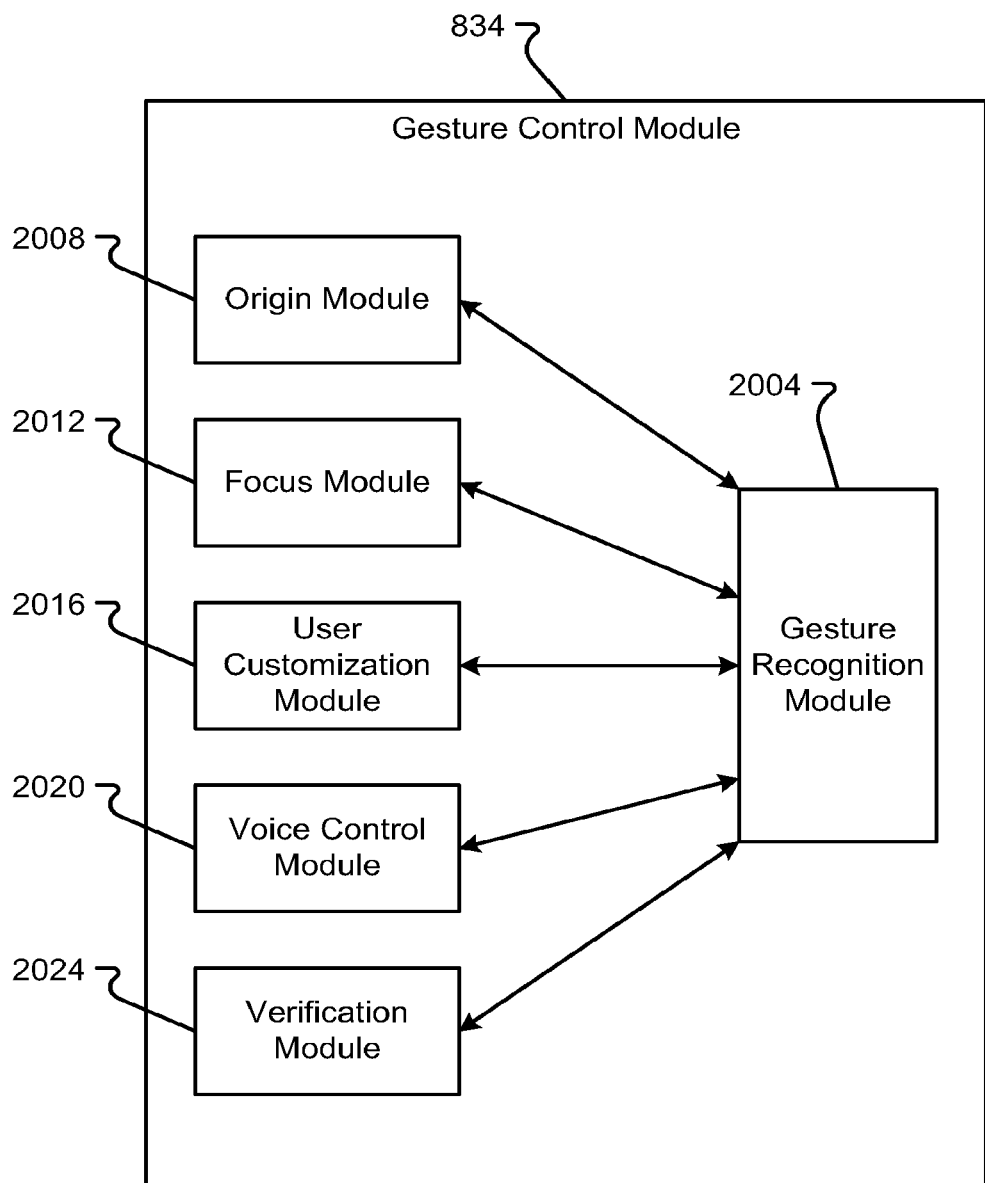
FIG. 20 is a block diagram of an embodiment of a gesture control module.

An embodiment of a gesture control module 834 is shown in FIG. 20. The gesture control module 834 may be hardware, software, or a combination of hardware and software. In one situation, the gesture control module 834 may be part of the user and device interaction subsystem 352, which is described in conjunction with FIGS. 3 and 8B. In other situations, the gesture control module 834 may be a desktop plug-in 1024, as described in conjunction with FIG. 10.

The gesture control module 834 can include one or more modules. The module may include one or more of, but are not limited to, an origin module 2008, a focus module 2012, a user customization module 2016, a voice control module 2020, a verification module 2024, and/or a gesture recognition module 2004. Each of these different modules may be described hereinafter. It should be noted that the modules 2004 through 2024 appear to be included with the gesture control module 834, but may be separate functions embodied in another part of the vehicle control 204.

The origin module 2008 is generally operable to determine the origin of a gesture. The origin of the gesture may be the same as the location of the person providing the gesture, or may be a different zone 512, a different area 508, a different location within a zone 512 or area 508, or on a console 248 that is near the person. Generally, the origin module 2008 receives vehicle sensor data from one or more vehicle sensors 242. The vehicle sensors 242 may be as described in conjunction with FIG. 2 and FIGS. 6A through 7B. Based on which sensors provide information, the origin module 2008 can identify and determine where the gesture is provided. For example, if two sensors, within a first zone 512A, determine that a gesture has been made, the origin module 2008 may be able to determine that the gesture originates in zone A 512A. It may be possible for the origin module 2008 to determine a location of the gesture within a zone 512 or area 508. Thus, beyond just determining that the gesture happened within the more general zone 512 or area 508, the origin module 2008 can determine that the gesture occurred within a particular quadrant or portion of a zone 512 or area 508.

The origin module 2008 may also determine that the gesture occurred in a zone 512 or area 508 that is different from where a person making the gesture is located. For example, if the origin module 2008 determines that a gesture occurred within zone B 512B, but no occupant currently is occupying that zone 512B, the origin module 2008 can determine that the gesture originated in a zone 512 separate from zone A 512A in which the person is occupying.

Further, the origin module 2008 may determine upon which console or user interface device 248 on the user interface of the vehicle 248 in which the gesture originates. With gestures that includes a tactile input on a touch screen or other electromechanical device, the origin module 2008 can determine upon which console or device input the gesture originated. Gestures may also be given as other types of inputs that may not have a specific device or console 248, but may be input by a device, such as a mobile device, may be input onto a surface and then recognized by one or more sensors, may be input either verbally or through other types of physical interaction, or may be input by other different means or methods. Regardless, the origin module 2008 can determine where the gesture is made.

A focus module 2012, similar to an origin module 2008, can determine the place upon which a user desires interaction. Unlike the origin module 2008, the focus module 2012 can determine to which input device a user wishes to interact before that interaction occurs. For example, if a user begins to lean or move an arm towards a device console 248A, the focus module 2012 may determine, in varying degrees of certainty, to which console or other input device the user desires to interact.

As such, the focus module 2012, similar to the origin module 2008, can obtain sensor data from sensors, as described in conjunction with FIGS. 2 and 6A through 7B. From the sensor data, the focus module 2012 can determine a location within one or more zones 512 or areas 508 within the vehicle that a person occupies. When the user within the zone 512 or area 508 desires to make an interaction, the person may begin to move or make a physical indication of desiring to enter a gesture. The movement may be viewed by the focus module 2012 and interpreted as having a target for a gesture or input. The focus module may then determine where that target is and provide that information to a gesture recognition module 2004.

A user customization module 2016 can change the way in which gestures may be received by the vehicle control system 204. A user customization module 2016 can update or enact gesture preferences, as delineated by a user profile 1200, as described in conjunction with FIG. 12A. The gesture preferences may be specific to an area 1216 or zone 1220. The gestures 1232 can be different for each zone 512 or area 508, and may be different if the user makes a gesture while occupying one zone 512 or area 508 but makes the gesture in a different zone 512 or area 508. Further, a user customization module 2016 can also update audio and/or other inputs that the user may be able to make. The customization information may be obtained from the user identification module 822, which interfaces with the profile data 252. The user customization module 2016 may provide the customization information to the gesture recognition module 2004.

A voice control module 2020 may receive and interpret any type of audio or voice inputs from the user. Thus, if the user makes a statement in the vehicle interior, the statement may be received by a microphone, as described in conjunction with FIGS. 6A and 6B. The received signal information may be sent to the voice control module 2020 through an audio interface 874. The information may then be interpreted based on profiles 1200, described in conjunction with FIG. 12A. If the voice command is determined to be a command to change a function of a vehicle or other interaction with the vehicle control system 204, the voice command or its subsequent interpretation may be sent to the gesture recognition module 2004.

A verification module 2024 may be provided that can output a verification of the gesture received. The gesture recognition module 2004, after receiving information from one or more of the modules 2008 through 2020, may determine the gesture desired by the user and send that information to the verification module 2024. The verification module 2024 may then provide a name or other indication of what gesture was received through an audio interface 874 to one or more speakers, as described in conjunction with FIGS. 6A and 6B. There may be other verifications possible, such as displays of information on a heads-up display or other console that may indicate which gesture was received.

In other situations, the verification module 2024 can give a preview of the gesture function. For example, if the user desires to turn on the cabin lights and states "turn on cabin lights," the verification module 2024 can turn on the cabin lights for a finite period of time, for example 5 seconds, and then turn the cabin lights off.

The verification module 2024 may also be able to receive any confirmation from the user that the gesture as verified is the gesture desired by the user. For example, if the verification module 2024 states that the user desired to turn on cabin lights, the verification module 2024 can provide an audio verification that states "turn on cabin lights," the user can reply by saying "yes," "yes, please," or some other type of audio or other gesture input. If the user does confirm that the gesture is correct, the verification module 2024 may send this information to the gesture recognition module 2004 to enact the function or change desired by the user as confirmed by the verification module 2024.

The gesture recognition module 2004 receives information from the origin module 2008, focus module 2012, the user customization module 2016, the vehicle control module 2020, and/or the verification module 2024. With interactions with the modules 2008 through 2024, the recognition module 2004 can interpret which gesture, as may be indicated within the user profile data described in conjunction with FIG. 12A, the user desires to enact. Once the gesture is recognized and interpreted correctly, verified, and/or confirmed, the gesture recognition module 2004 can send information to the vehicle control module 826 to enact whatever type of gesture the user has provided.

Figure 21:
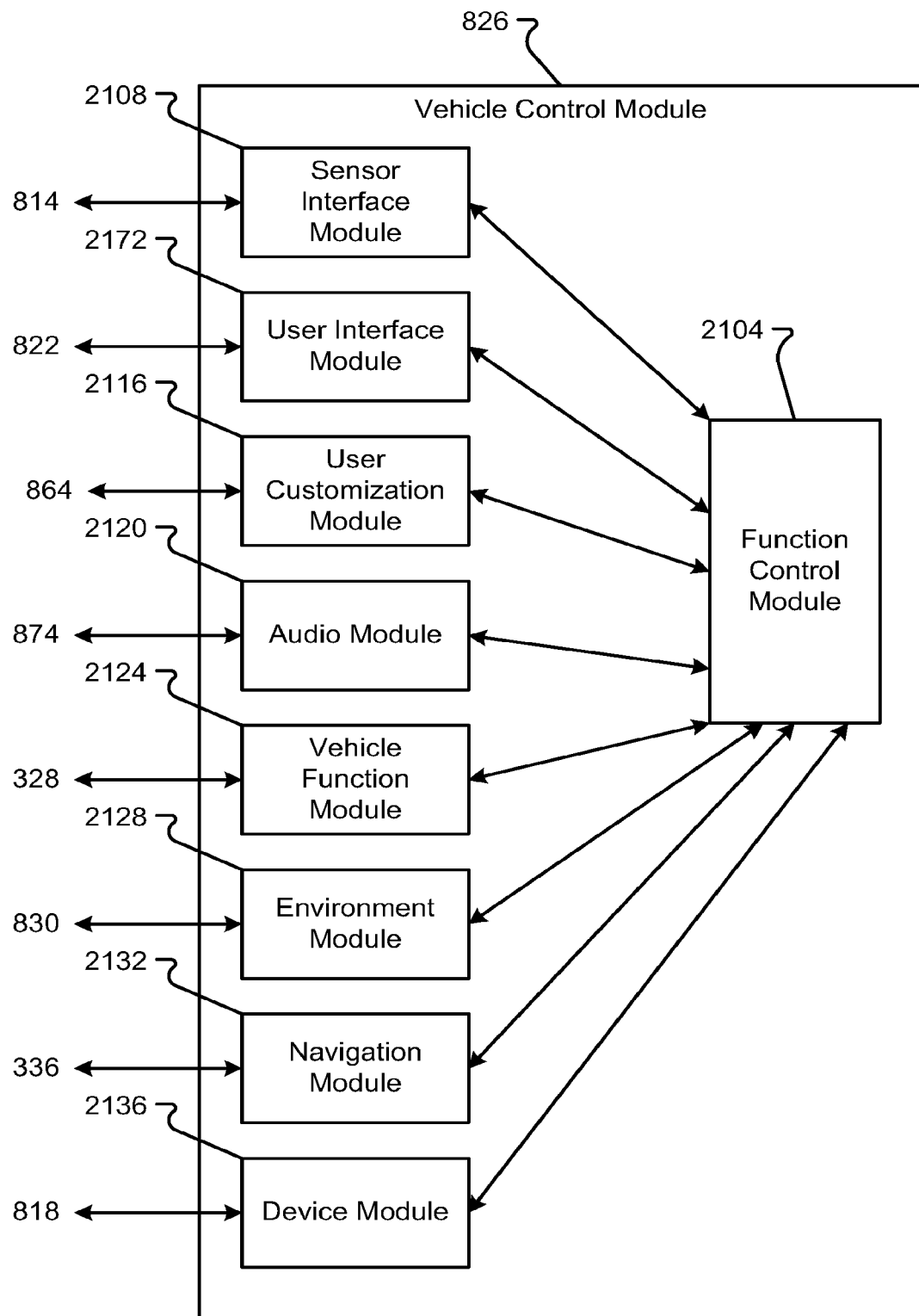
FIG. 21 is a block diagram of an embodiment of a vehicle control module.

An example of the vehicle control module 826 is shown in FIG. 21. The vehicle control module 826 can be any hardware, software, combination of hardware or software, or other electrical or code-based systems. The vehicle control module 826 may be part of the user device and interaction subsystem 817, as described in FIG. 8B. In other situations, for example, the vehicle control module 826 may be a separate function embodied in a different system within the vehicle control system 204 or a separate function embodied in separate hardware and/or software. In other examples, the vehicle control module 826 may be a software system or application provided as a desktop plug-in 1024, as described in conjunction with FIG. 10. The vehicle control module 826 may have one or more modules 2104 through 2136, as described hereinafter.

A function control module 2104 may receive information to control one more functions of a vehicle. Based on information from a gesture recognition module 834, the function control module 2104 may change one or more of the vehicle functions or settings, as prescribed in the user profile data described in conjunction with FIGS. 12A through 12D. The vehicle functions controlled by the function control module 2104 may be as listed and described in conjunction with FIG. 22.

To communicate or control the vehicle functions, the function control module 2104 may communicate and interact with one or more modules 2108 through 2136. A sensor interface module 2108 may communicate with the sensor module 814, which can communicate with one or more sensors, as described in conjunction with FIGS. 2 and 6A through 7B. The sensor interface module 2108 can communicate, translate, or interpret any information from the one or more sensors. The sensor information may be provided to the function control module 2104 to change the function of one or more of the functions of the vehicle. Further, the function control module 2104 may also adjust or change the interaction or tune the one or more sensors based on activity or other information. Thus, the function control module 2104 may interact through the sensor interface module 2108 to turn on or turn off sensors, change how the sensors function, or do other tasks.

The user customization module 2172 may communicate with the user identification module 822. The user identification module 822 may provide profile data from profile database 252, which may be as described in conjunction with FIGS. 12A through 12D. The user profile information 1200 may provide settings 1224, profile information 1238, or other information to the function control module 2104. Based on the profile information, the function control module 2104 may change the function of one more vehicles settings, such as the display of one more interfaces 248 or other types of devices, displays, consoles, or other vehicle functions that provide information to or retrieve information from a user.

While not illustrated, a vehicle control system for adapting a control function based on a user profile is provided. The vehicle control system may customize a control function output based on the control function request and a user's profile data. More particularly, certain characteristics from the user's profile may be parsed from the profile based on its relationship or threshold-grade relevance to the control function request (effect). Based on the parsed characteristics, a control function module may re-write a control function command for a customized control function output. For instance, an elderly user (occupant or vehicle operator) may request a display of information on the user interface display. The vehicle control system may parse specifically for characteristics related to the users age or vision (eye-sight) from the user profile (by a user-profile module), and as a result, the control function module may re-write (adapt) the control function command of displaying the information on the user interface display with at least one of larger, colored, or bolded font to account for the user's poor vision.

The vehicle control system/method for adapting a control function based on a user profile may comprise: a gesture recognition module; a user profile module; a function control module; a processor; a non-transitory storage element coupled to the processor; encoded instructions stored in the non-transitory storage element, wherein the encoded instructions when implemented by the processor, configure the system to: identify a user; retrieve a user profile for the identified user; receive at a gesture recognition module, an input indicating a gesture from the user; identify a control function request corresponding to the gesture input; send a verification of the control function request; and receive at a function control module characteristics parsed from the user profile that effect the control function request by the user profile module to adapt a control function command for an adapted control function output by the function control module. The user input or control function input may be at least one of an audible input, gesture-based input, scroll-down menu of entries, or text input. In some embodiments, the user may be identified by at least one of a biometric sensed input, user entered, user selected, user profile created, user profile selected, or user profile crawled.

A user interface (UI) module 2116 may communicate with a video input/output interface 864 to receive or output video information. The user interface module 2116 may also communicate with the function control module 2104 to change the function of one or more displays 248. Further, the UI module 2116 may also change a heads-up display or any type of visual environment output that affects the user.

Similarly, the audio module 2120 can interact with the audio input/output interface 874 to change the function of one or more audio outputs/inputs. The audio module 2120 may also output any type of communication from a function control module 2104 for provision to a user through a speaker 880 or other output.

The function control module 2104 can change or modify the one or more vehicle functions through vehicle function module 2124. The vehicle function module 2124 may communicate with one or more vehicle subsystems 328, which may be as described in conjunction with FIG. 3. Further, the vehicle subsystems 328 may be as described in conjunction with FIG. 22. This vehicle function module 2124 is operable to communicate through one or more communication pathways as described in conjunction with FIG. 4 to change the function of one or more of the vehicle settings or systems.

The function control module 2104 may also communicate through an environment module 2128 to an environmental control module 830. Through these communications, the function control module 2104 can change the environment for a user. The environment may include heating, air conditioning, lighting or other types of conditions which change how the vehicle functions for the user.

The function control module 2104 can also communicate through a navigation module 2132 to navigation subsystem 396, as described in conjunction with FIG. 8C. Navigation subsystems 336 may change how the vehicle provides route information or possibly how the vehicle steers or controls itself from an origination point to a destination point. The function control module 2104 can provide or communicate with the navigation module 2132 to change how the navigation subsystem 396 functions.

The function control module 2104 may also communicate with the device module 2136 to change the interaction parameters by communicating with the device interaction module 818. In this way, the function control module 2104 may change how a device may be accessed or operated within a vehicle.

One or more different vehicle subsystems that may be controlled by a function control module 2104 may be as described in conjunction and as shown in FIG. 22. Here, the different systems listed may be as understood in the art. For example, the vehicle systems may include one or more of, but are not limited to, an ignition 2202, a transmission function 2204, braking function 2206, an acceleration function 2208, one or more doors 2210, a hood 2212, a trunk 2214, one or more windows 2116, a tire pressure system 2220, one or more locks 2222, a cruise control function 2224, a parking system 2226, a steering function 2228, one or more alarms 2230, a wiper system 2232, a headlight or exterior light system 2234, an interior lighting system 2236, one or more mirrors 2238, a sunroof 2240, a convertible top 2242, or other systems that may be associated with a vehicle. There may be more or fewer systems control by the function control module as represented by ellipses 2298. These vehicle systems may be as understood in the art.

An ignition system 2202 may be any system that turns on or turns off the vehicle or starts or turns off the motor.

The transmission system 2204 may be any system that can change gears or change the function of the transmission within the vehicle.

A braking system 2206 can be any system that causes the deceleration of the vehicle or engages brakes or an emergency brake for the vehicle.

An acceleration system 2208 can be any system that causes the vehicle to accelerate or maintain a speed. Acceleration systems 2208 may include a gas pedal, acceleration pedal, or any electronic system that may change the speed of the vehicle.

The doors 2210, hood 2212, trunk 2214, and windows 2216 may be any system that can open a portal or part of a car. These systems can unlock, lock, open, or possibly close any of these different parts of the car.

A tire pressure system 2220 may be any system that monitors or possibly deflates or inflates the tires or spare tire of a vehicle.

A lock system 2220 may be any system that can lock or unlock any of the doors, trunk, hood, or other parts of the car.

A cruise control 2224 may be any system that controls the automated driving system or systems that cause a cruise control to be engaged, disengaged, or changed.

A parking system 2226 can be any system that does automatic parking or may help or provide information when parking a vehicle. The parking system 2226 may include any brakes or other systems that may be engaged once the car is parked.

A steering system 2228 may be any system that controls the steering wheel of a car or any electronics or other electromechanical devices which may be used instead of a steering wheel.

An alarm system 2230 may be any system that changes or controls the function of alarms. For example, the alarms can include a key left in the ignition alarm, lights remain on, proximity warnings, blind spot warnings, backing up warnings, or other types of alarms that may be provided by the vehicle.

A wipers function 2232 may be any system that controls, turns on, turns off, or changes the operation of the windshield wipers, headlight wipers, rear windshield wiper, or other types of wipers that may be used in a car. The wipers subsystem 2232 may also control any other devices, functions, or processes that can change or modify the function of any windshield, window, or other type of transparent surface. For example, if the car uses a sonar or ultrasonic sound system to clear rain from the windshield, the wiper system 2232 may control that operation.

A headlights, exterior lights subsystem 2234 may be any system that controls the headlights, tail lights, braking lights and reverse lights, or any type of lights that may exist on the exterior the vehicle. The system 2234 may control both the on/off function and any type of high beam or other change to the lights.

The interior lighting system 2236 may be any system that controls the cabin lights, foot-well lights, door puddle lights, or any type of lights that may exist on the interior of the vehicle. Interior lighting system 2236 may control the on/off function and any other change to the interior lights including dimming or changing of the color of the interior lights.

The mirror subsystem 2232 can include any type of system that controls the driver's side and passenger side rear view mirror, the rear view mirror in the interior of the car, or any backup system that may provide information for looking to the rear of the vehicle. The mirror system 2232 may adjust the positioning or functioning of these mirrors including auto-dimming or any other type of process that changes how the mirror operates.

The sunroof subsystem 2240 may control the function of the sunroof or moon roof in the vehicle. The sunroof subsystem 2240 may open, close, tilt, change the covering, or complete other types of operations of the sunroof.

A convertible subsystem 2242 may control or operate the convertible top, which may be automated and include systems to open or close the convertible top.

Figures 23A, 23B:
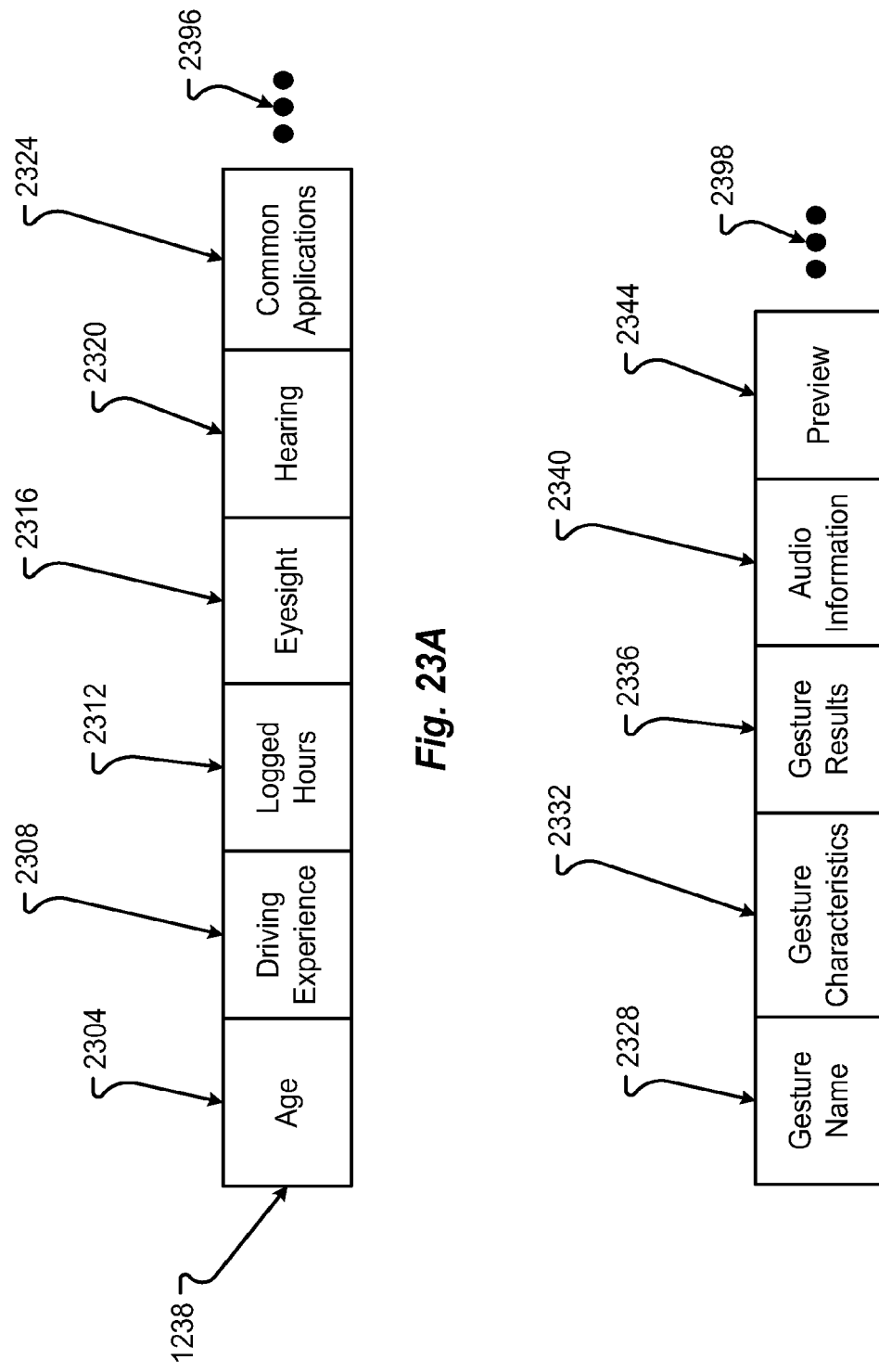
FIG. 23A is a diagram of an embodiment of a data structure for storing profile information.
FIG. 23B is a diagram of an embodiment of a data structure for storing gesture information.

An embodiment of profile information 1238, which may be part of a profile database 252, as described in conjunction with FIG. 12A through FIG. 12D, may be as shown in FIG. 23A. The profile information 1238 may have one or more fields. There may be more or fewer fields than those shown in FIG. 23A, as represented by ellipses 2396. The fields within the profile information 1238 can include one or more of, but are not limited to, an age field 2304, a driving experience field 2308, a logged hours field 2312, an eyesight field 2316, a hearing field 2320, and/or a common applications field 2324.

An age field 2304 may include an age or date of birth for a user. The age may be provided in years, months, days, or other increments that indicate how long the person has been alive.

The driving experience field 2308 can include the number of years, days, months, etc. that a user has been driving. In one example, the driving experience 2308 may be determined by a first driver's license issue date. The driving experience may then be determined by the number of years, days, or other period of time between the first issue date of the driver's license and the current date. Driving experience 2308 may also be provided by a user.

Driving experience 2308 can also include one or more situations in which a user has been driving. For example, the driving experience 2308 may indicate a positive indication of or number of minutes, hours, or other periods of time in which different types of conditions the driver has encountered. For example, the driving conditions can include snowy conditions, rainy conditions, sleeting conditions, poor visibility, nighttime conditions, sunset conditions, or other types the conditions encountered while driving. The driving experience field 2308 can provide indications of whether or not a driver may require assistance or have functions of vehicle change based on which environment the user is currently driving.

A logged hours field 2312 can include a number of hours a person has been in this vehicle or all vehicles driven. The logged hours 2312 can give an indication of the amount of driving experience. The logged hours 2312 can also be broken into subcategories based on the driving experience data 2308. Thus, the driving experience data 2308 and logged hours field 2312 may be linked by pointers or other information that indicates a driving situation or driving experience/condition 2308 and a number of logged hours for that driving experience in the logged hours field 2312. As such, between the driving experience 2308 and the logged hours 2312 fields, an indication of the ability of the driver may be determined.

The eyesight 2316 and the hearing 2320 fields can give an indication of a disability for user. The eyesight field 2316 may have an indication that the user wears glasses or contacts or may have, based on past experiences, indicated that the driver has trouble seeing in certain conditions. For example, if a user drives slower during a type of driving experience indicated in driving experience 2308, the vehicle control system 204 may determine that the person's eyesight or hearing is poor and requires a change in the operation of the vehicle. The eyesight field 2316 may also indicate other types of eyesight problems beyond just poor eyesight, such as, colorblindness, blind spots, poor peripheral vision, or other eyesight issues that may be deduced from the type of driving done by the user. The hearing field 2320 may also indicate the ability for a user to hear both types of sounds, the decibel level of sounds the user can hear or cannot hear, whether users are able to hear during certain types of background noise, etc. Thus, the hearing field 2320, like the eyesight field 2316, provides information as to how the user functions in different types of conditions.

A common applications field 2324 can include any type of software application on a device or used by a user in the car or on a device. These common applications 2324 also may have an indication of how often the user uses an application or accesses that application while driving in different conditions or how often the application is used as a passenger. A common applications field 2324 may include the applications listed hierarchically based on amount of usage. As such, the vehicle control system 204 can access the applications more quickly for a particular user based on frequency of use by that user.

An embodiment of gesture information 1232, as provided in the profile database 252 and described in conjunction with FIGS. 12A through 12D, may be as shown in FIG. 23B. The information provided in the gesture information 1232 can provide information for a gesture and the associated function that the gesture may invoke. The gesture information 1232 can be standardized, as each person may use the same gesture to affect the function, or may be user-created and may include the information provided from a user for certain functions. There may be a single set of information for each type of gesture. The gesture information 1232 can provide any type of characteristics for the gesture that may be as described in conjunction with FIGS. 11A through 11K. The gesture information 1232 can include one or more of, but are not limited to, a gesture name field 2328, a gesture characteristics field 2332, a gesture results field 2336, an audio information field 2340, a preview field 2344, etc. There may be more or fewer fields than those shown in FIG. 23B, as represented by ellipses 2398.

A gesture name field 2328 can include a name of the gesture. The gesture name 2328 may be, for example, a one word or several word description of the gesture. For example, the gesture name 2328 for turning the radio volume up may include the words "radio," "volume," and "up." The gesture name 2328 may be unique and provide both an indication to the database 252 and to the user of what gesture is being requested or completed.

Gesture characteristics field 2332 can include any of the characteristics used to determine or identify one of the gestures in FIGS. 11A through 11K The gesture characteristics 2332 information can include any type of vocal, visual, or tactile information received by the vehicle control system 204. For example, a hand gesture in 3D space may include a configuration for a hand and a type or vector of movement that is required by the vehicle control system 2004. Any of this gesture characteristics 2332 information may be stored in the gesture characteristics field 2332.

A gesture results field 2336 can include any information for the function or what type of process is required after receiving the gesture. Thus, if the user provides a gesture recognized by gesture characteristics 2332, the result 2336 should be some function performed. For example, if the user provides a gesture for turning the radio volume up, the gesture results field 2338 can include any of the functions or processes required for turning up or increasing the volume of the radio and how much of the volume should be increased.

Audio information field 2340 may be any information provided back to the user to verify the gesture and/or may be any data about a verbal command that may be associated with the gesture/function. The audio information 2340 may also include other verification parameters that may be visual. For example, if the user desires to turn the volume up on the radio, the information 2340 can include the verification response, such as, "radio volume up," which may be spoken to the user through one or more speakers 880. The audio information 2340 may also include any type of confirmation required by the user to enact the function of the gesture. For example, if the user is required to say "correct," "yes," or "enact" to cause the radio volume up gesture to be enacted, the audio information 2340 includes that response that as required by the user. The audio information field 2340 may also include any kind of visual response that may be provided to a heads up display or other display. This visual information may also include verification information, such as, a button selection or other type of interaction that is required by the user to verify the gesture.

A preview field 2344 includes any characteristics or information required to preview the gesture results 2336 for a gesture. For example, if the user provides a radio volume up gesture, the preview field 2344 may include a preview of turning a radio volume up for a specified and predetermined amount of time. For example, the volume of the radio may go up by 10% for 5 seconds. Thus, instead of having an audio or visual verification, the user can verify the command by the preview. If the preview is not correct, the user can provide information or a response for denying or confirming the command. If confirmed, the gesture results 2336 may mimic what was provided by the preview 2344.

Embodiments of different user interfaces that may be provided on display 248 are shown in FIGS. 24A and 24B.

A first user interface 2404A may include three buttons for a first function 2408, a second function 2412, a third function 2416. The user interface 2404A can include different function buttons or user interface devices 2408 through 2416, as shown in FIG. 24A for receiving input from a user. The buttons 2408 through 2416 or user interface devices may be selectable by a user on a touch screen device or other console. The function buttons 2408 through 2416 can each have a different function associated the button 2408 through 2416. Each of the buttons 2408 through 2416 may have a different color, shape, location, or configuration visually for the user. For example, function buttons 2408 and 2412 are square, large, and at the top of the screen 2404A. A function button 2416 may be in the middle of the screen, may be rectangular, and may be larger than the first two function buttons 2408 and 2412. Each of the different configurations may be changed based on user data or interactions with the user.

A second user interface 2404B (which may provide an interface for the same application or process) is shown in FIG. 24B. Here, the buttons 2408 through 2432 may have changed based on different settings and interactions with the user. For example, function buttons 2408 through 2416 are now located at the top of the screen, are square, and are much smaller than shown in 2404A. Further, more function buttons 2420, 2424, 2428, and 2432 have been added to the user interface 2404B. For example, function button 2424 is not provided on the user interface of 2404A. Further, function buttons 2428 and 2432 are round and located the bottom of the user interface.

Both user interfaces 2404A and 2404B may be associated with a common application that may be executed by the vehicle control system 204. Thus, the common application may have different user interfaces, which may be changed based on device settings 1224, profile information 1238, or an interaction parameter, as determined by the vehicle control system 2004. Further, one user interface 2404A may be provided to a first user, while a second user interface 2404B may be provided to a second user. Further, these different user interfaces 2404A, 2404B may be provided to the different people while those people are in the vehicle operating the same console 248. Thus, depending on which user is using the console 248 at which time, the user interface 2404 may change. It should be noted that any type of visual, audio, tactile, configuration of a user interface, or other interaction configurations may be changed by the vehicle control system.

Figure 25:
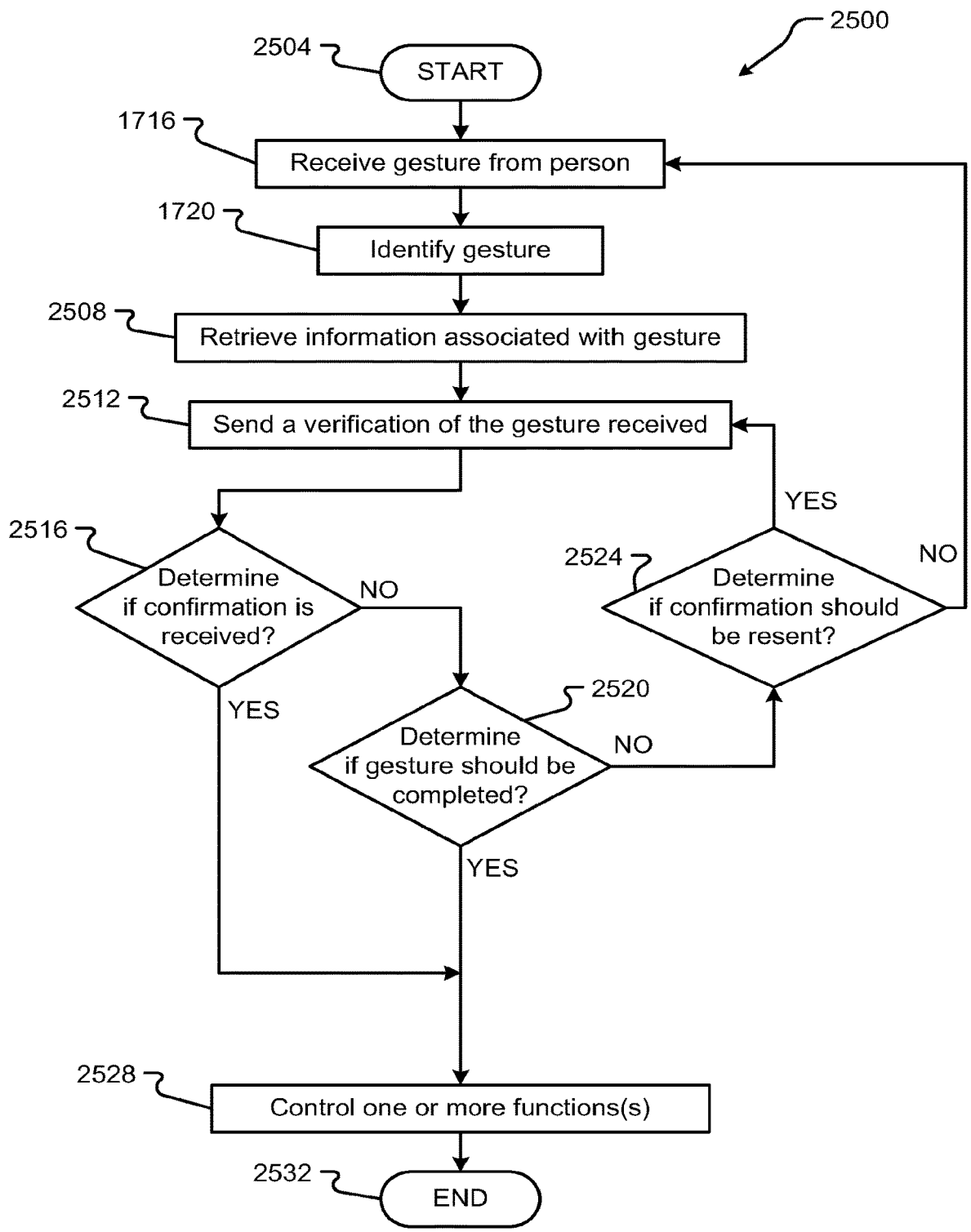
FIG. 25 is a flow or process diagram of a method for verifying a received gesture.

An embodiment of the method 2500 for receiving a gesture or other input may be as shown in FIG. 25. A general order for the steps of the method 2500 is shown in FIG. 25. Generally, the method 2500 starts with a start operation 2504 and ends with an end operation 2532. The method 2500 can include more or fewer steps or can arrange the order of the steps differently than those shown in FIG. 25. The method 2500 can be executed as a set of computer-executable instructions executed by a computer system and encoded or stored on a computer readable medium. Hereinafter, the method 2500 shall be explained with reference to the systems, components, modules, software, data structures, user interfaces, etc. described in conjunction with FIGS. 1-24.

A receive step 1716, which may be as described in conjunction with FIG. 17, may receive a gesture. The gesture may be provided to a gesture recognition module 2004. The gesture recognition module 2004 may also receive a voice input or other type of input into a display 248. The gesture recognition module 2004 may then identify the gesture, in step 1720, which may be as described in conjunction with FIG. 17. Once the gesture is identified, the gesture information may be provided from the database, as described in conjunction with FIG. 23B, to a verification module 2024.

The verification module 2024 may retrieve the gesture information, in step 2508. The information may be retrieved from information sent by the gesture recognition module 2004 or by information that is accessed through the profile database 252, as described in conjunction with FIG. 23B. The gesture information can include any kind of characteristics or information 2332-2344 required by the verification module 2024 to send a verification to the user.

The verification module 2024 may then retrieve the audio or visual information from field 2340 or the preview or other type of information from field 2344 to send the verification, in step 2512. Here, the verification module 2024 may provide an audio verification output to an audio input/output interface 874 to send to one more speakers 880. This audio output can include the name of the gesture 2328 or other information that may be provided in the data field 2340. For example, if the user provided a gesture that is recognized as turning all the interior lights on, the verification module 2024 may provide an audio output that states "all interior lights on" through the speaker 880. The verification module 2024 may access the media controller 348 to signal the speech synthesis module 820 to provide a voice-like audio output that states "all interior lights on" through the audio input/output interface 874 to the speakers 880. In this way, a synthesized human voice may state what gesture was recognized by the gesture recognition module 2004.

In other examples, the verification module 2024 can provide a visual indication of the gesture as recognized. For example, a verification message may be displayed on a display 248 on the head unit or one of the consoles 248. For example, a message "all interior lights on," in text, may be displayed on one of the user interfaces 248. In other situations, a symbolic character, such as a flashing light bulb, may be presented that indicates the gesture requested was that all interior lights be turned on. The visual indication may be provided on one more the visual user interfaces 248 and may include some type of confirmation button or user interface device that may be selected to confirm that verified gesture is associated with the correct function desired by the user. In still other examples, another user interface device may be provided that states that the verified gesture is incorrect.

In other examples, the verification module 2024 may provide a preview, as described in preview field 2344. A preview of all the interior lights on may require the verification module 2024 to send a signal to the function control module 2104 to control, through the vehicle function module 2024, a vehicle subsystem 328. The vehicle function control module 2104 can send a "lights on" signal to the interior lights system 2236 to turn on the interior lights for some definite and predetermined amount of time. For example, the interior lights system 2236 may turn on the interior lights for a period of 5 seconds. The preview may then be presented with the either an audio or visual confirmation request. For example, one more user interface devices may be presented on one or more user interfaces 248 that may be selected by the user to either confirm or to deny that the preview is associated with the correct function. An audio indication may also be provided asking whether the preview was correct.

A user may then provide either a confirmation or a denial to the verification module 2024 of whether the verified gesture is correct. The verification module 2024 can determine if a confirmation is received, in step 2516. Here, the verification module 2024 may receive a signal through the audio input/output interface 874, video input/output interface 864, a video controller 840, an audio controller 844, other system that controls the input side of the devices 248. Thus, a module can send a signal back to the verification module 2024 to indicate whether a user selectable device, confirming the verification, was selected. Further, the audio input/output interface 874 may receive a signal from a microphone 886 that can be sent to the verification module 2024, And in still other examples, one or more sensors, as described in conjunction with FIG. 6A through 7B, may determine if a confirmation gesture is received by the user. Regardless, some type of user action may be perceived and sent to the verification module 2024. If the user has confirmed the gesture as recognized, the method 2500 proceeds YES to step 2528. However, if no confirmation or a denial is received, the method 2500 may proceed NO to step 2520.

In step 2520, the verification module 2024 can determine whether to complete the function associated with the gesture. For example, if the user provides no confirmation, but a confirmation is assumed if no confirmation occurs after a predetermined period of time, for example 5 seconds, the gesture may still be completed. As such, the user may acquiesce to a function without interaction. Thus, no confirmation or no interaction from user may be a confirmation. If the gesture is to be completed, the method 2500 proceeds YES to step 2528. However, if the gesture is not to be completed, the method 2500 may proceed NO to step 2524.

In some situations, the verification module 2024 may determine to resend the verification message, in step 2524. For example, if no confirmation is received and the gesture is not to be completed unless a confirmation is indicated, the verification module 2024 may require at least some type of confirmation. As such, if the verification is to be resent, the method 2500 proceeds YES back to step 2512 where the verification module 2024 may resend the verification message either visually, audibly, tactilely, by vibration, or through another type of signal. The verification module 2024 may then wait for a period of time to determine if the confirmation is sent. The verification module 2024 may resend the verification message some predetermined number of times before determining that the gesture is denied or is not confirmed. If the verification is not to be resent, the method 2500 proceeds NO back to receive step 1716, where the gesture may be resent, and the user may try and input the gesture again and have the gesture re-recognized because the verified gesture was either wrong or inadvertent.

In step 2528, the verification module 2024 confirms that the gesture was recognized accurately and sends that indication back to the gesture recognition module 2004. The gesture recognition module 2004 may then send a signal to the function control module 2104 to complete a function associated with the gesture. The function control module 2104 may then enact any type of function associated with that gesture. The signal sent from the gesture recognition module 2004 can provide either the gesture or the function information. If the function control module 2104 receives the gesture information, the function control module 2104 may look up the function associated with that gesture in a database, as described in conjunction with FIG. 23B. As such, the function control module 2104 may retrieve the gesture results information 2336 and enact the function required by the gesture.

Figure 26:
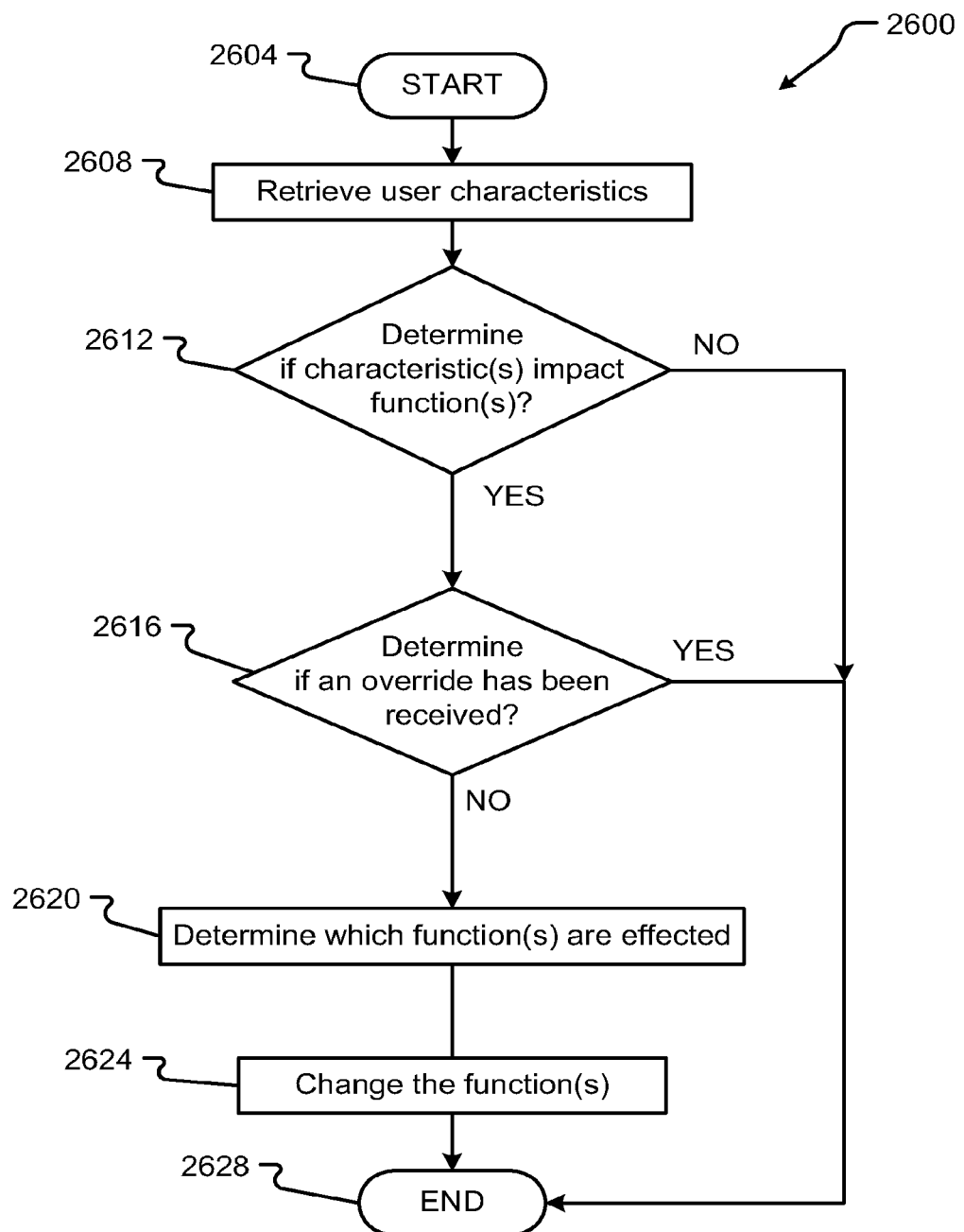
FIG. 26 is a flow or process diagram of a method for change vehicle functions based on user characteristic(s)

An embodiment of a method 2600 for changing the function of a vehicle based on user characteristics is as shown in FIG. 26. A general order for the steps of the method 2600 is shown in FIG. 26. Generally, the method 2600 starts with a start operation 2604 and ends with an end operation 2628. The method 2600 can include more or fewer steps or can arrange the order of the steps differently than those shown in FIG. 26. The method 2600 can be executed as a set of computer-executable instructions executed by a computer system and encoded or stored on a computer readable medium. Hereinafter, the method 2600 shall be explained with reference to the systems, components, modules, software, data structures, user interfaces, etc. described in conjunction with FIGS. 1-25.

The user identification module 822 can retrieve user characteristics, settings, profile information, etc., in step 2608. The retrieval of settings from a user profile 1200 may be as described in FIG. 14 through FIG. 19. Thus, FIG. 26 may be a further addendum to customization of the vehicle based on user profile 1200. Here, the user may be recognized as described previously in FIGS. 14 through 19. The user identification module 822 may then retrieve user characteristics, in step 2608. The user identification module 822 may retrieve the information as described in conjunction with FIG. 23A. This information may then be sent to the user customization module 2172.

The user customization module 2172 may then access the characteristic(s), as described in conjunction with FIG. 23A, to determine if any of the characteristics may impact the function of the vehicle, in step 2612. Here, the user customization module 2112 may use one more rules to determine if any of the characteristics are over or under a benchmark or within an area of concern. The rules may include quantitative or qualitative assessments of the different characteristics. For example, if the user's age 2304 is below a predetermined age, for example, age 20, the user customization module 2172 may determine that that characteristic requires some type of customization or change to a function of the vehicle.

The user customization module 2172, if determining that the characteristic does impact a function, may then retrieve any type of the settings 1224 that may be required or needed to address that characteristic. The settings information may then be sent to a function control module 2104. Thus, if the characteristics do impact a function of the vehicle, the method 2600 proceeds YES to step 2616. However, if no characteristic does affect a function of a vehicle, the method 2600 proceeds NO to end step 2628.

The function control module 2104 or the user customization module 2172 may then determine if there was an override, in step 2616. An override may be a user-provided or an automatic override that eliminates the adjustment of any of the vehicle functions based on user characteristics. The override, if set, may require the function control module 2104 or the user customization module 2172 to ignore or not adopt any of the settings provided in field 1224. If there an override set or enacted, method 2600 proceeds YES to end step 2628. However, if no override is provided, method 2600 proceeds NO to step 2620.

The function control module 2104 may then determine which functions are affected by the characteristics, in step 2620. Here, the function control module 2104 may retrieve settings 1224 that are associated with the changes based on the characteristics. In other situations, the function control module 2104 may access a standardized set of changes required based on a characteristic. For example, if a person's eyesight is poor, the standardized set of functions that are changed are to increase the size, vibrancy, and accessibility of any of the controls provided on a user interface 248. Other changes may be associated with other different characteristics.

The function control module 2104 then proceeds to change those functions, in step 2624. Here, the function control module 2104 may send one more commands or control signals through one more modules 2116 through 2136 to change the functions of the vehicle. The different functions may then be modified to control user interfaces, vehicle functions, or other types of processes, functions, or means that modify how the vehicle interacts with the user or how the vehicle operates. The changes may include gesture preferences, vehicles settings, infotainment system controls, climate control settings, access and manipulation of the dashboard, console functions or layouts, or one or more vehicles subsystems.

An example includes changing access to vehicle features or functions based on the user's age 2204, driving experience 2308, logged hours 2312, or other characteristic. For example, a user may have an age 2304 that is under some benchmark (the user is 16 and under the benchmark age of 20) that causes one or more vehicle functions to be changed. For example, the function control module 2104 may receive further information from the sensor data sensor module 814 that three people are within the car. The laws of the state may require the function control module 2104 to prohibit a teenage driver from having more than one passenger within the car. As such, the ignition system 2202 may be disengaged and not allow the user to turn on the car based on the number of passengers and their age characteristic 2304.

In another example, one or more distractions may be eliminated based on a user profile or other condition currently being encountered by the vehicle. As such, the function control module 2104 may receive information from sensor module 814 and compare that to characteristics, as described in conjunction with FIG. 23A. For example, the user may have a limited amount of driving experience indicated in fields 2308 or 2312 and is driving in a dangerous condition or at high speed, the function control module 2104 may then limit the amount of information in one or more vehicle user interfaces to provide for a less distracting environment. For example, the head unit or dashboard may be changed to present only information which is critical, for example, speed warnings or other types of critical information. As such, the user has to view the limited information only for a short amount of time, compared to a normal dashboard display, to see what is critical to their current driving situation.

Further, if a distraction may be inevitable when the convertible top is open (such as when it is raining), the convertible systems 2242 may be limited such that the user's environment is more contained and outside distractions are not possible. Further, if there's a type of situation which may cause the user to be distracted if the convertible top is open, the convertible systems 2242 may be disabled. Further, the radio operations may be changed such that channels may be restricted or the amount of volume provided is lowered. Thus, if the user is less experienced, the user's amount of radio interaction may be changed such that the user maintains a lower volume of the radio and has fewer channels to select.

An Internet access may be restricted for drivers under a certain age or under a certain amount of experience. As such, if the vehicle is operable to access the Internet, the access may be restricted to one more passengers within the vehicle and may not be accessible to the driver. Further, applications may be restricted based on age or other information. For example, if a game is presented but is a game only for people who are 17 years old or older, a passenger in the rear of the vehicle that is under such an age may be restricted from playing that game. Further, the applications store may be limited to people with access to purchase applications. As such, passengers in the back that are not old enough to access or do not have the correct identity to access the applications may restricted from any applications store. As such, distractions may be changed for the driver and for any passenger based on information in the profile 1238.

These examples also connote that the profile permissions 1238 can also change how vehicle functions are provided to passengers and drivers. The function vehicle control module 2104 can also change how a transmission system 2204 is used based on information in the database 1238. For example, if there's a law against high speed acceleration, or the user has less driving experience, the transmission may restrict higher gears or may change the ability to speed or accelerate the car based on gear changes. As such, the car's function when driving may be changed based on characteristics.

The function control module 2104 may also interact with the navigation system 336 through the navigation module 2132. Thus, based on characteristics provided in information shown in FIG. 23A, the type of navigation or route information provided may change. For example, a younger driver may only be provided with routes that are safer, have lower traffic, and prevent interaction with heavy traffic scenarios. As such, the user is less likely to get in situations where their driving experience 2308, logged hours 2312, or age 2308 have not prepared them. For an older driver that may have poor eyesight, as indicated in field 2316, or poor hearing is indicated in field 2320, the routes may be provided that have better lighting or other conditions for that user. Further, the user may be provided with routes that limit the exposure to heavy traffic, pedestrian walkways, wildlife, or other situations that require a quicker reaction time that may be determined in the driving experience section 2308. Further, based on the time and the driving experience 2308, the maps may be included with live traffic data when necessary. Further, the mapping utility can also suggest that a user wait for some period of time before starting the vehicle or beginning their route based on the current traffic conditions associated therewith in comparison to their experience or logged hours. Further, the user may be prevented from continuing a route or starting a route based on the traffic conditions or other information if the characteristics indicate that that user may not be able to handle the current conditions, such as bad weather or heavy traffic.

Figure 27:
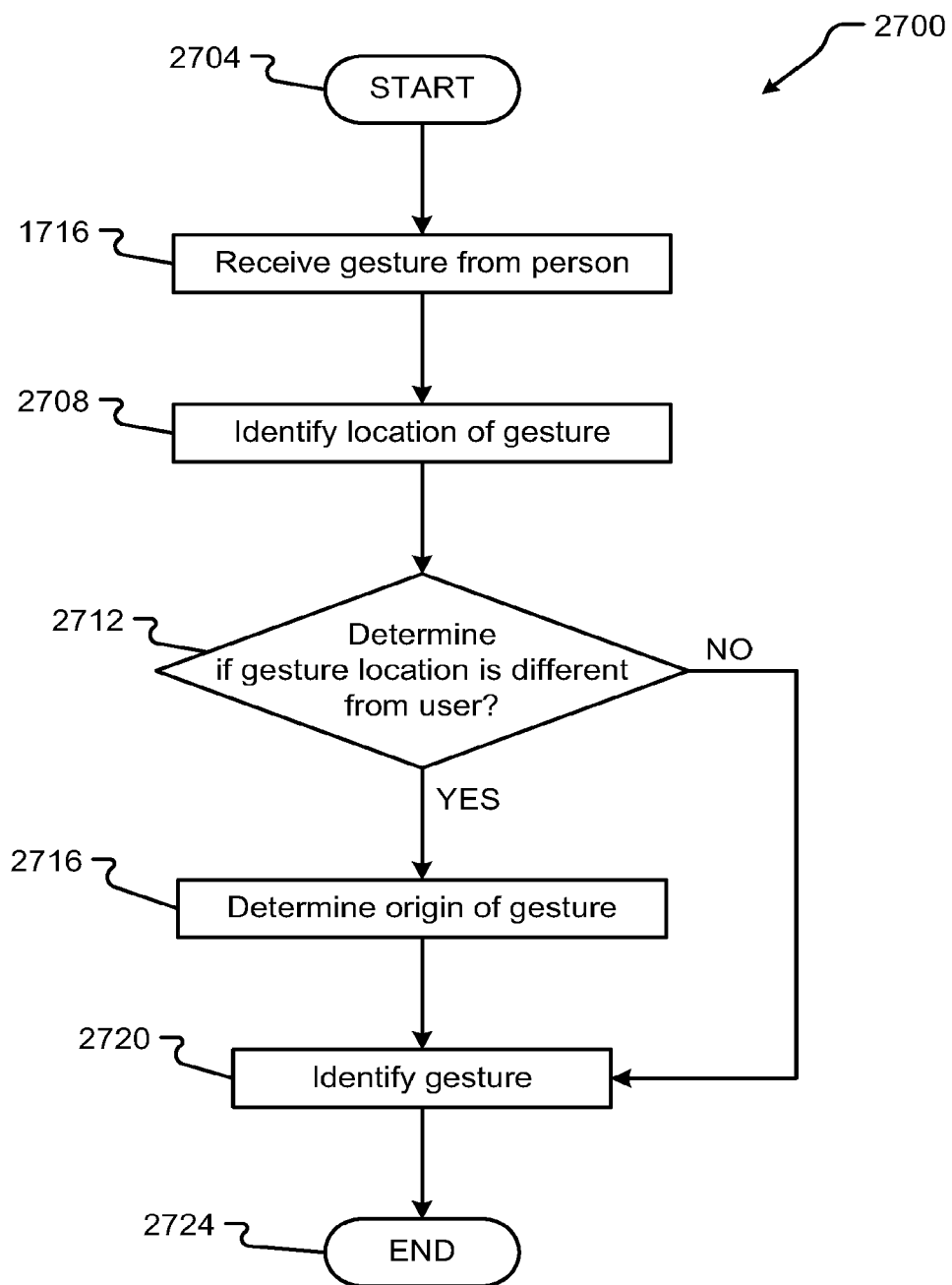
FIG. 27 is a flow or process diagram of a method for receiving a gesture in at a different point of origin.

A method 2700 for receiving a gesture may be as shown in FIG. 27. A general order for the steps of the method 2700 is shown in FIG. 27. Generally, the method 2700 starts with a start operation 2704 and ends with an end operation 2724. The method 2700 can include more or fewer steps or can arrange the order of the steps differently than those shown in FIG. 27. The method 2700 can be executed as a set of computer-executable instructions executed by a computer system and encoded or stored on a computer readable medium. Hereinafter, the method 2700 shall be explained with reference to the systems, components, modules, software, data structures, user interfaces, etc. described in conjunction with FIGS. 1-26.

The gesture may be received, in step 716. The reception of a gesture may be as described in conjunction with FIG. 17. The origin module 2008 can receive information from one or more sensors through a sensor module 814. The sensors may be described in conjunction with FIGS. 6A through 7B. The sensor module 814 can provide the information to the origin module 2008 to determine a location of a gesture, in step 2708. To determine the location, the origin module 2008 can determine in which zone 512, area 508, or location within a zone 512 of a vehicle interior the gesture is received. Thus, if one or more sensors associated with specific zone 512A identify that gesture as being provided within zone A 512A, the origin module 2008 can determine that the location of the gesture is in zone A 512A. However, other sensors may determine that the gesture is received in zone B 512 B, or in other zones 512C through 512N of the vehicle.

The origin module 2008 may then determine if the location of the received gesture is different from the user providing the gesture, in step 2712. Thus, the origin module 2008 may receive information from the user identification module 822 or sensor module 814 to determine a location of one more passengers within the zones 512A through 512N. For example, the origin module 2008 may determine there's only a single person in the vehicle and is seated within zone A 512A. The gesture may be received in zone B 512B, which is different from the location of user that made the gesture. In other examples, the origin module 2008 may use other information to determine that the user providing the gesture is in a different location within the vehicle. For example, one or more sensors may provide information to sensor module 814 that indicates an occupant may be reaching out of one zone into another zone to provide the gesture. For example, as a passenger in zone D 512D reaches into the front passenger area 508A and provides a gesture in 512B, the sensor module 814 may provide information that the person's body or arm stretches out of zone D and into zone B. Thus, the origin module 2008 may user pattern recognition to identify a gesture when the user reaches. The origin module 2008 may interpret any of this information to determine that the user may be in different location than the location of the gesture. Based on the location of the gesture and location the user, the origin module 2008 may send information to the gesture recognition module 2004 of the origin and location of the gesture.

The gesture recognition module 2004 may then determine the origin of the gesture based on the information provided by the origin module 2008. The gesture recognition module 2004 can use the origin of the gesture to look up gesture information from the profile 1200, as described in conjunction with FIGS. 12A-12D.

The gesture recognition module 2004 may then identify a gesture, in step 2720. The identification of the gesture, in step 2720, may be similar to that as described in step 1720 of FIG. 17. However, in this situation, the gesture recognition module 2004 may use the origin of the gesture and location of the user as factors in determining which gesture was received. For example, a user may make a gesture within zone A 512A that may mean a first function is desired. However, if that same gesture is made by the user in zone B 512B, that gesture may require a different function. Thus, although the user is located in one zone, for example, zone A 512A, gestures the user makes may have different meaning if made in a separate zone 512 from which the user is occupying. For example, a user in zone D 512D may make a first gesture to change the content of a display provided in zone D or in area 2 508B. However, if that same gesture is made in zone B 512B, from that occupant in zone D 512D, the function associated with the gesture is different.

In this way, the number of gestures, available to control functions, is expanded. Further, gestures within another zone 512 may be prohibited based on the location of the user and where the gesture was made. For example, a user in zone D 512D may not be able to provide any gestures in zone A 512A, as those gestures may be detrimental or hazardous. As such, occupants in zone D 512D may be prohibited or blocked from making gestures in area 508A or zone A 512A. The gesture recognition module 2004 can determine the location of the gesture, but also all the location of the user to determine the origin of that gesture to determine if the gesture should be recognized at all.

Figure 28:
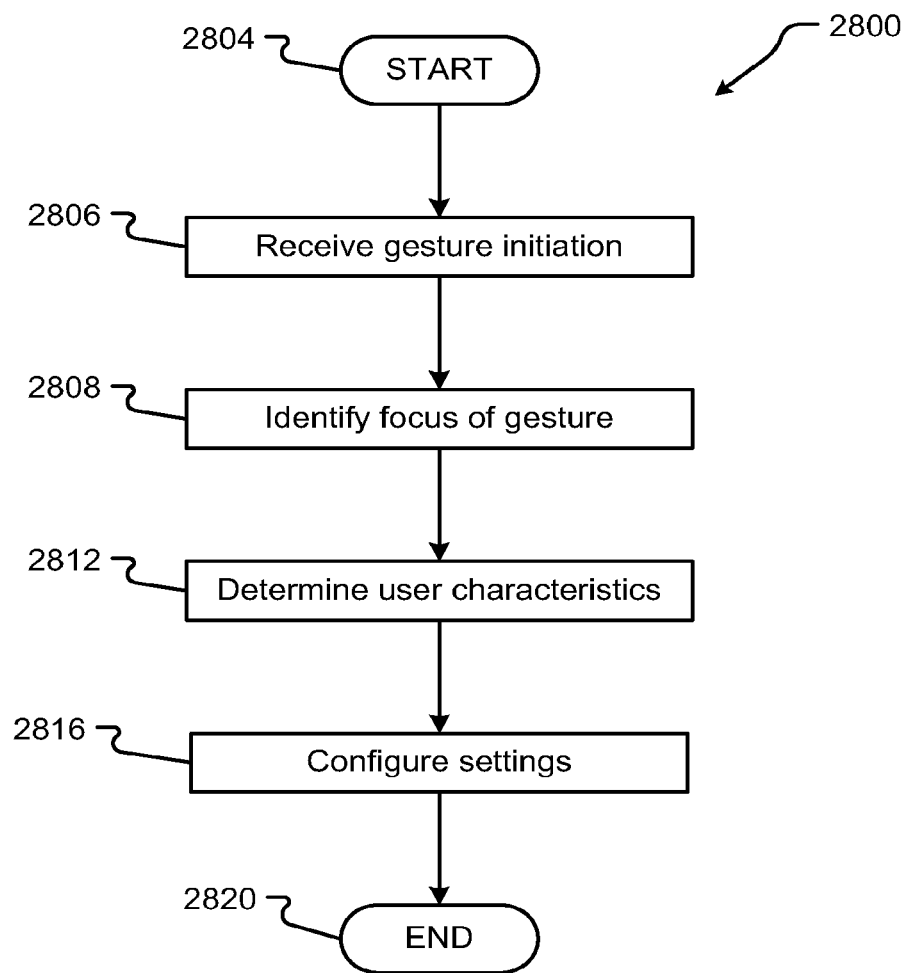
FIG. 28 is a flow or process diagram of a method for changing a vehicle setting based on a gesture focus.

An embodiment of a method 2800 for changing the functions of the vehicle based on the focus of a user is shown in FIG. 28. A general order for the steps of the method 2800 is shown in FIG. 28. Generally, the method 2800 starts with a start operation 2804 and ends with an end operation 2820. The method 2800 can include more or fewer steps or can arrange the order of the steps differently than those shown in FIG. 28. The method 2800 can be executed as a set of computer-executable instructions executed by a computer system and encoded or stored on a computer readable medium. Hereinafter, the method 2800 shall be explained with reference to the systems, components, modules, software, data structures, user interfaces, etc. described in conjunction with FIGS. 1-27.

A gesture control module 834 may receive a gesture initiation, in step 2806. A gesture initiation may be the beginning of a type of gesture but may not be a completion of the gesture. A gesture initiation may be preceded by one more other gestures or may be preceded by a physical movement or interaction of the user with the vehicle. For example, if a user in zone A 512A reaches for a console in the center of a head unit, the gesture recognition module 2004 may determine that a gesture is being initiated.

The focus module 2012 can receive sensor information from sensors, as described in conjunction with FIGS. 6A and 7B that are sent to a sensor module 814. The focus module 2012 can determine that a gesture is being initiated. Pattern recognition or other information may be used to determine that the gesture is being initiated on an interface 248 or in three dimensional space, as described with gestures in FIGS. 11A through 11K.

Upon determining that a gesture is being initiated, the focus module 2012 can then determine a target or focus of the gesture for the user, in step 2808. For example, if the user is reaching for a user interface 2408, the focus module 2012 may determine by a vector or a physical positioning of an arm, finger, or other physical part of the user 2016 to which display 248 the user is reaching or with which the user is attempting to interact. In other situations, the user may reach into a three dimensional space used for three dimensional gestures or may reach for or into some other type of input area. The focus module 2012 may determine by the movement or interaction of the user (which may be determined from past interactions with this user) to which system or interface the user is focusing. The information of the focus may be provided from the focus module 2012 to the gesture recognition module 2004.

The gesture recognition module 2004 may then send information about user interface 248 or other system the user is focusing upon to the function control module 2104. The function control module 2104 may then determine one more user characteristics, in step 2812. The user characteristics may be described in profile information 1200, as described in FIGS. 12A through 12D. Further, the user characteristics may also include any kind of current environmental information (e.g., the current driving conditions, cabin conditions, etc.) associated with the user. For example, the information can include which zone 512 the user currently occupies, what device the user is currently using, the interaction the user is currently making within the vehicle 104. These user characteristics may then be studied by the function control module 2104 to determine if one more settings may be changed.

In step 2816, the function control module 2104 may control one or more of the settings of a system based on the focus. The changes to the settings may be made before the user interacts with the system allowing the user less distraction or easier access to certain functions of a system based on the gesture initiation. For example, the function control module 2104 may change the configuration or display of the user interfaces, as described in FIGS. 24A and 24B, based on the user characteristics and a gesture focus. For example, if a driver in zone A 512A is initiating a gesture to a center console 2408, the user interface 2404A may be changed as shown in FIG. 24A. As such, fewer buttons are provided and those buttons are easily selectable or provided because the driver has less time to be distracted or less time to take their focus off of the road.

Thus, the focus module 2012 can determine that the interaction with this interface 2404 is being initiated. The function control module 2104 based on this determination can then change the interface from that shown in FIG. 24B to that shown in 24A to allow the user to focus on the important functions they may wish to select. Other changes may be made to vehicle systems or controls settings based on what the focus of the user is before the user provides the initial gesture.

Figure 29:
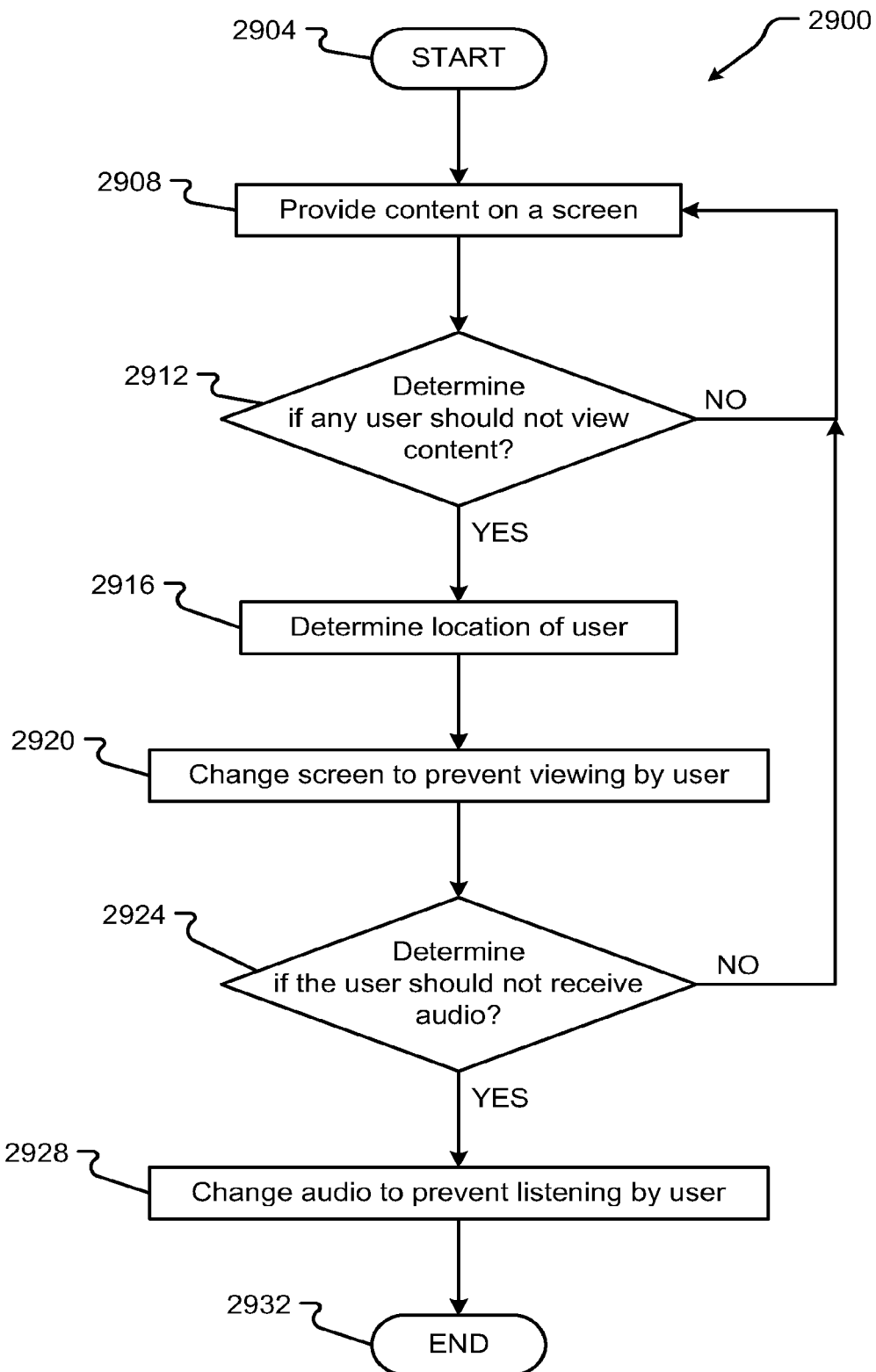
FIG. 29 is a flow or process diagram of a method for changing the function of a screen to prevent viewing by a user.

An embodiment of the method 2900 for preventing access by the user to one more user interfaces based on the current conditions of the user within the vehicle 104 is shown in FIG. 29. A general order for the steps of the method 2900 is shown in FIG. 29. Generally, the method 2900 starts with a start operation 2904 and ends with an end operation 2932. The method 2900 can include more or fewer steps or can arrange the order of the steps differently than those shown in FIG. 29. The method 2900 can be executed as a set of computer-executable instructions executed by a computer system and encoded or stored on a computer readable medium. Hereinafter, the method 2900 shall be explained with reference to the systems, components, modules, software, data structures, user interfaces, etc. described in conjunction with FIGS. 1-28.

A media controller 348 or other system may provide content on one or more user interfaces 248, in step 2908. For example, a passenger in zone B 512B may be viewing a video on a center console 248, as provided by a media controller 348. Information about the video may be provided, from the media controller 348, to a UI module 2116 of the vehicle control module 826. Then, the information may then be provided by a function control module 2104 to a user customization module 2172. The user customization module 2172 may then access profile data 252 or sensor data provided from sensor module 814.

With the provided information, the user customization module 2172 can determine if there is a driver or passenger who should not view and/or hear the current content provided in the user interface 248, in step 2912. For example, the driver that is operating the vehicle in zone A 512A may be prohibited from viewing the video content provided to occupants in zone B 512B, based on state law or simply for safety reasons. As such, the user customization module 2172 may determine that the driver should not see or hear the content being provided to the passenger in zone B 512B. In other situations, a passenger in zone E 512E may be viewing video or the other information which is meant for adults. As such, if a child is determined to be in zone C 512C, the video or content should be prohibited from being seen by the child in zone C 512C. As such, if it is determined that a user should not see, hear, or be able to interact with the content provided, the method 2900 proceeds YES to step 2916. However, if it is determined that the user can see, hear, or interact with the content, the method 2900 proceeds NO back to step 2908 where that content is provided.

The user customization module 2172 may then access sensor information from sensor module 814. From that information, the user customization module 2172 can determine the location of the user that should not interact or view the content, in step 2916. This location information may then be sent to the function control module 2104.

The function control module 2104 may then change at least a portion of the user interface or other device or system to prevent viewing of or interaction with the content by the prohibited user, in step 2920. For example, the function control module 2104 may instruct the media controller 348 to change the video output through the video I/O interface 864 to the screen 248. The change may include blacking out one or more portions of the screen to prevent the prohibited user from seeing the video. The function control module 2104 may determine from sensor information provided by the sensor module 814 every time the user moves their eyes to look to the video. If the user does attempt to view the video, the video will be blacked out for all occupants. As such, the user will not be provided content, and therefore, does not attempt to view the video.

In other situations, an electromechanical pivot may be used so that the screen is pivoted away from the prohibited user and will not allow that occupant to see the video screen at an angle that allows them to view the video. In other situations, one or more types of electromechanical or electrical systems may be used to polarize the signal or change the viewing parameters of the screen such that the prohibited user is unable to view the video when looking at the screen but the visual signal is still sent to the other user(s). As such, the change in the screen, in step 2920, prevents the user who is prohibited from viewing the content from actually viewing the information on the screen or viewing the screen at all.

The function control module 2104 may also receive a signal from user customization module 2172 as to whether the prohibited user is also prohibited from listening to any of the audio associated with the content. Thus, the user customization module 2172 can also determine if audio is not to be provided, in step 2924. The profile data or the type of content being provided may indicate whether the audio should be provided. For example, if a movie is being viewed, the soundtrack to the movie can be distracting for a driver in zone A 512A. As such, the audio may not be desired in that zone 512A. As such, the user customization module 2172 may send a signal to the function control module 2104 to not provide the audio in zone 512A. If the user customization module 2172 determines that no audio is to be provided, the method 2900 proceeds YES to step 2928. However, if the user customization module 2172 determines the audio is not distracting or can be provided to all occupants, the method 2900 proceeds NO back to step 2908 to provide the content.

In step 2928, the function control module 2104 can change the audio conditions for the prohibited user. For example, the function control module 2104 can send a signal or information to the audio I/O interface 874 to control one more speakers 880. The speakers may change the direction of sound to limit sound that may leak into the zone of the prohibited user. Thus, the speakers 880 may be changed electrically or physically to direct sound only to a certain area 508B or 508A or into a specific zone 512A through 512N. In other situations, noise canceling technology may be used to project a noise canceling signal from speakers 880 into the prohibited user's zone 512. As such, the noise canceling signal actually creates a cone or an area of silence around the person within that zone. Regardless, the function control module 2104 can control systems to change how the user receives audio within that zone 512 or area 508.

In other situations, the passengers in the other zones may be required to use headphones or other systems that prevent audio from being projected across the speakers. There are many ways to control the video and audio content within a car; these systems are controlled by the function control module 2104 to prohibit one or more users within the vehicle from viewing content if that content is unfit or unsuitable for the current situation.

Figure 30:
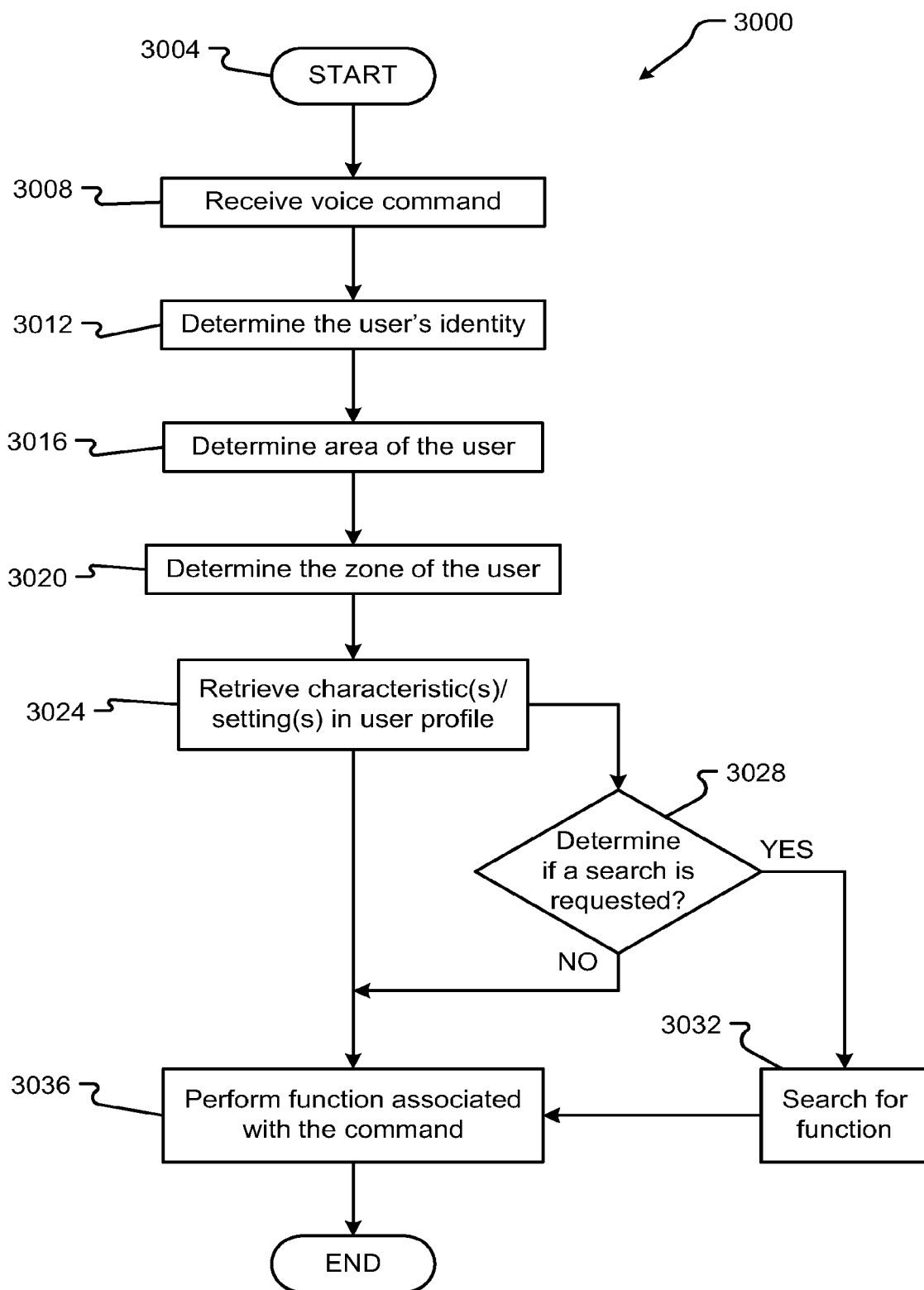
FIG. 30 is a flow or process diagram of a method for receiving a voice command.

An embodiment of a method 3000 for receiving voice commands in the vehicle environment is shown in FIG. 30. A general order for the steps of the method 3000 is shown in FIG. 30. Generally, the method 3000 starts with a start operation 3004 and ends with an end operation 3040. The method 3000 can include more or fewer steps or can arrange the order of the steps differently than those shown in FIG. 30. The method 3000 can be executed as a set of computer-executable instructions executed by a computer system and encoded or stored on a computer readable medium. Hereinafter, the method 3000 shall be explained with reference to the systems, components, modules, software, data structures, user interfaces, etc. described in conjunction with FIGS. 1-29.

A voice control module 2020 may interface with a sensor module 814 to receive voice commands, in step 3008. The audio signal is received, by a microphone 886, and provided through the audio I/O interface 874 to the voice control module 2020. The voice command can then be interpreted by the voice control module 2020.

A user identification module 822 can identify a user within the vehicle, in step 3012. The identification of the user may be as described in conjunction with FIGS. 13 through 19. Further, the user identification module 822 can receive sensor information from the sensor module 814 to determine an area 508 in which the person or user occupies, in step 3016, and determine the zone 512 which the user occupies, in step 3020. The detection of which area 508 and zone 512 the user is in may be as described in conjunction with FIGS. 13 through 19.

Based on the identity of the user, the user identification module 822 may then retrieve characteristics or settings in a user profile 1200 and profile data 252, in step 3024. The characteristics and settings of the profile 1200 may be as described in conjunction with FIGS. 12A and 23A. This information may be retrieved as described in conjunction with FIGS. 13 through 19. The settings or profile data may be as described in conjunction with the FIGS. 12A, 23A, and 23B, and may indicate one or more different audio commands that are associated with the user.

Each user may have a customizable set of audio settings that the user can provide and store, as described in conjunction FIGS. 13 through 19. Further, there may be a standard set of audio commands that any user may use within the vehicle. Each audio command may be associated with an area 508 and/or a zone 512. Thus, a first command used in zone A 512A may cause of a first function to be controlled or process to be executed, while that same audio command used in zone E 512E may have a different function or process executed. As such, based on the area 508 or zone 512, upon which the user occupies, the audio commands may cause different processes or functions to be executed.

One audio command that may be completed is a search. Thus, the user may search for a function or command audibly. The voice control module 2020 can determine if a search is being conducted, in step 3028. A search may be one type of command that can be used anywhere within the vehicle. Thus, the voice control module 2020 may search for gesture or voice information in field 2340 to determine if a search command is being executed. If a search command is not being executed, the method proceeds NO to step 3028. However, if a search is being conducted, the method 3000 proceeds YES to step 3032 where the voice control module 2012 provides the search information to the gesture recognition module 2004. The gesture recognition module 2004 may then instruct the media controller 348 or the vehicle control module 826 to provide a search function, in step 3032. Information about the search function may be included and then used to identify another function.

The vehicle control module 826 may then perform the function based on the verbal communication(s), in step 3032. Thus, if the voice command is identified, the information is sent to the function control module 2104. The function control module 2104 may perform the function based on the received information, in step 3032. In this way, the voice command can be used for the vehicle systems, as described in conjunction with FIG. 22.

Figure 31:
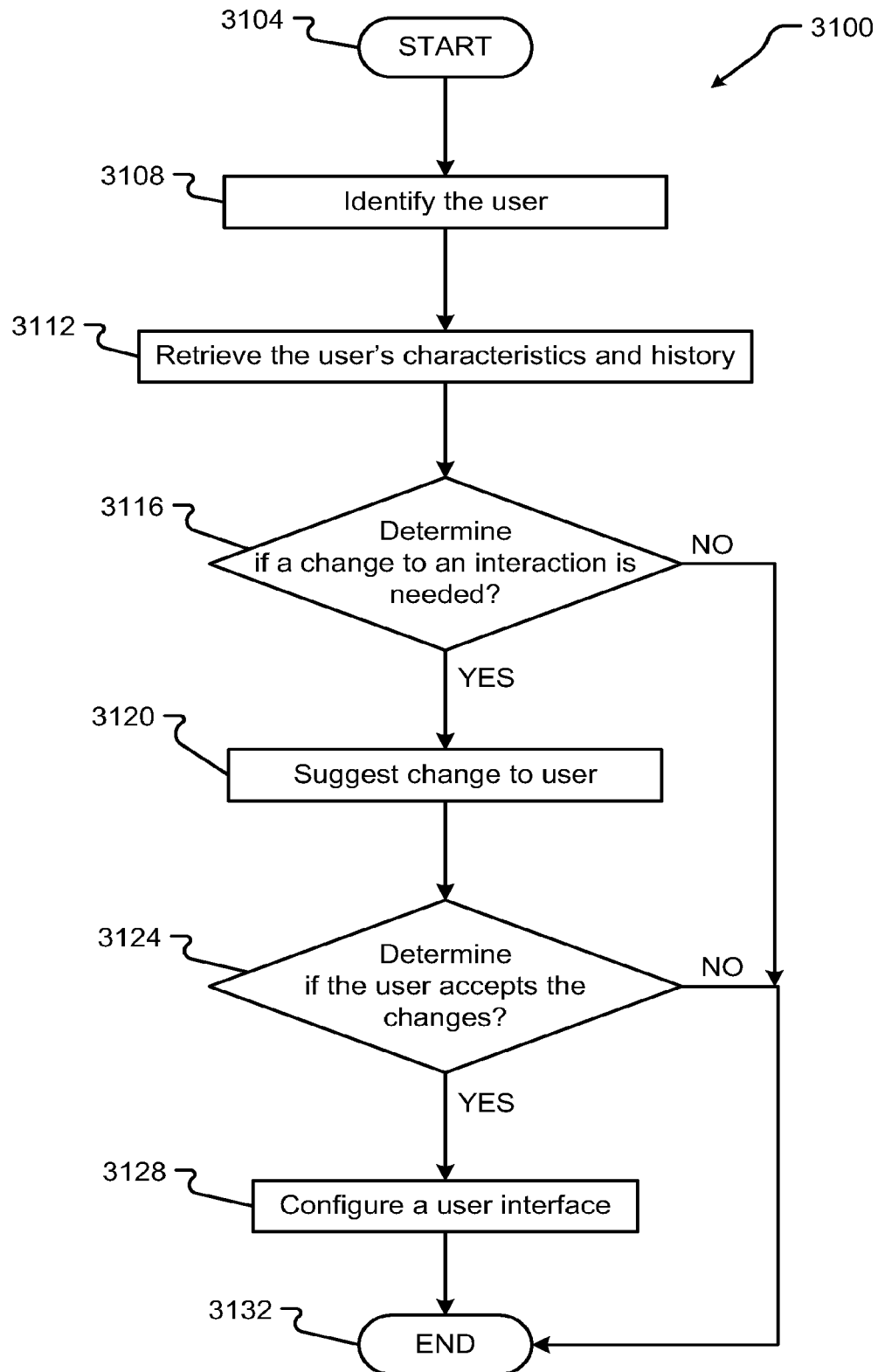
FIG. 31 is a flow or process diagram of a method for changing a system interaction based on user characteristics.

An embodiment 3100 of configuring user interactions based on user characteristics and user history is shown in FIG. 31. A general order for the steps of the method 3100 is shown in FIG. 31. Generally, the method 3100 starts with a start operation 3104 and ends with an end operation 3132. The method 3100 can include more or fewer steps or can arrange the order of the steps differently than those shown in FIG. 31. The method 3100 can be executed as a set of computer-executable instructions executed by a computer system and encoded or stored on a computer readable medium. Hereinafter, the method 3100 shall be explained with reference to the systems, components, modules, software, data structures, user interfaces, etc. described in conjunction with FIGS. 1-30.

The user interaction module 822 may identify a user, in step 3108. Here, the user action module 822 may identify the user as explained in FIGS. 13 through 19. The user identification module 822 may then retrieve characteristics of the user and/or the user history from profile data 252, in step 3112. The user identification module 822 may retrieve this information as described in conjunction with FIGS. 13 through 19. The characteristics may be the characteristics as described in conjunction with FIGS. 12A through 12D or the information as described in conjunction with FIG. 23A. Further, the history or information of the user may also include common applications accessed or used by the user during other periods of operating a vehicle or riding within the vehicle, as provided in the common applications field 2324. Thus, the common applications field 2324 can provide a history of access to what applications, for how long, and in what situations. This information may be provided by the user in identification module 8222 to the vehicle control module 826.

The user customization module 8172 may receive the information and determine if a change to an interaction interface associated with the user may be required, in step 3116. Thus, the characteristics such as age, driving experience, other information described in conjunction with FIG. 23A, the common applications, and the current situation of the vehicle, as indicated by sensor module 814, may be input into the user customization module 2172. The user customization module 2172 can determine if a change may be necessary to a user interface 248 or other user interaction within the system. If a change is determined to be needed, the method 3100 proceeds YES to step 3120. However, if no change is needed, the method 3100 may proceed NO to end step 3132.

In step 3120, the user customization module 2172 may provide the information about the suggested changes to the function control module 2104. The function control module may then instruct the verification module 2024 or the gesture recognition module 2004 to suggest the change. The verification module 2024 may suggest a change by making an audio, visual, or tactile suggestion or by making a preview for the user.

The verification module 2024 may then receive or detect if the user accepts the changes, in step 3124. It should be noted that it is not necessary to suggest that the changes be made, the changes may be made automatically without input from the user—made automatically without the user being able to accept or deny the changes. If the user does accept the changes in step 3124, the method proceeds YES to step 3128. However, if the user does not accept the changes, the method 3100 proceeds NO to step 3132. The verification module 2024 can receive the acceptance of the changes and provide that confirmation through the gesture recognition module 2004 to the function control module 2104. Here, the function control module 2104 may then send commands through the user interface module 2116 to change the function of one or more user interfaces 2408 or other systems controlled by the video I/O interface 864, audio I/O interface 874, etc. The configuration of the UI may be completed in step 3128.

As an example, the user customization module 2172 may determine the user's age, gender, type of applications used, type of email program, what other activity the user partakes in while inside the vehicle. The user customization module 2172 may also determine how the user typically digests information. For example, if the user has poor eyesight or their age may indicate difficulties reading information on the screen if the screen is too crowded. The information may be presented in an altered configuration. For example, the senior citizen with poor eyesight requires to access a GPS application (which is the only application this user ever accesses). The GPS application may be presented in the user interface with larger icons that are easily selectable for the driver. For example, as shown in FIGS. 24A and 24B, GPS application may include function buttons F1 through F3 shown in user interface 2404A. However, in a standard user interface shown in FIG. 2424B, other function buttons for other different applications may be presented. However, those application buttons may be eliminated in a simplified screen shown in FIG. 24A with only the GPS user interface selectable devices 2408 through 2416 shown in the interface 2404. The buttons may be changed to make them more easily selectable by the user.

In another example, the passenger or driver may be a teenager. The teenager may have several applications they wish to access, such as Facebook and Twitter. However, if the teenage driver is attempting to access the user interface with these types of applications while driving, those application buttons may also be eliminated, preventing distractions from the teenage driver. Thus, the user interface shown in FIG. 24B may include a Facebook button 2420 and/or a Twitter button 2424 that are eliminated when user interface 2404A is presented to the user. Depending on the common applications used by the user, their age, and other characteristics, the user interface 2404 may be changed to better provide an easily interactive user interface for the user based on the characteristics.

The exemplary systems and methods of this disclosure have been described in relation to configurable vehicle consoles and associated devices. However, to avoid unnecessarily obscuring the present disclosure, the preceding description omits a number of known structures and devices. This omission is not to be construed as a limitation of the scopes of the claims. Specific details are set forth to provide an understanding of the present disclosure. It should however be appreciated that the present disclosure may be practiced in a variety of ways beyond the specific detail set forth herein.

Furthermore, while the exemplary aspects, embodiments, options, and/or configurations illustrated herein show the various components of the system collocated, certain components of the system can be located remotely, at distant portions of a distributed network, such as a LAN and/or the Internet, or within a dedicated system. Thus, it should be appreciated, that the components of the system can be combined in to one or more devices, such as a Personal Computer (PC), laptop, netbook, smart phone, Personal Digital Assistant (PDA), tablet, etc., or collocated on a particular node of a distributed network, such as an analog and/or digital telecommunications network, a packet-switch network, or a circuit-switched network. It will be appreciated from the preceding description, and for reasons of computational efficiency, that the components of the system can be arranged at any location within a distributed network of components without affecting the operation of the system. For example, the various components can be located in a switch such as a PBX and media server, gateway, in one or more communications devices, at one or more users' premises, or some combination thereof. Similarly, one or more functional portions of the system could be distributed between a telecommunications device(s) and an associated computing device.

Furthermore, it should be appreciated that the various links connecting the elements can be wired or wireless links, or any combination thereof, or any other known or later developed element(s) that is capable of supplying and/or communicating data to and from the connected elements. These wired or wireless links can also be secure links and may be capable of communicating encrypted information. Transmission media used as links, for example, can be any suitable carrier for electrical signals, including coaxial cables, copper wire and fiber optics, and may take the form of acoustic or light waves, such as those generated during radio-wave and infra-red data communications.

Also, while the flowcharts have been discussed and illustrated in relation to a particular sequence of events, it should be appreciated that changes, additions, and omissions to this sequence can occur without materially affecting the operation of the disclosed embodiments, configuration, and aspects.

A number of variations and modifications of the disclosure can be used. It would be possible to provide for some features of the disclosure without providing others.

It should be appreciated that the various processing modules (e.g., processors, vehicle systems, vehicle subsystems, modules, etc.), for example, can perform, monitor, and/or control critical and non-critical tasks, functions, and operations, such as interaction with and/or monitoring and/or control of critical and non-critical on board sensors and vehicle operations (e.g., engine, transmission, throttle, brake power assist/brake lock-up, electronic suspension, traction and stability control, parallel parking assistance, occupant protection systems, power steering assistance, self-diagnostics, event data recorders, steer-by-wire and/or brake-by-wire operations, vehicle-to-vehicle interactions, vehicle-to-infrastructure interactions, partial and/or full automation, telematics, navigation/SPS, multimedia systems, audio systems, rear seat entertainment systems, game consoles, tuners (SDR), heads-up display, night vision, lane departure warning, adaptive cruise control, adaptive headlights, collision warning, blind spot sensors, park/reverse assistance, tire pressure monitoring, traffic signal recognition, vehicle tracking (e.g., LoJack™) dashboard/instrument cluster, lights, seats, climate control, voice recognition, remote keyless entry, security alarm systems, and wiper/window control). Processing modules can be enclosed in an advanced EMI-shielded enclosure containing multiple expansion modules. Processing modules can have a "black box" or flight data recorder technology, containing an event (or driving history) recorder (containing operational information collected from vehicle on board sensors and provided by nearby or roadside signal transmitters), a crash survivable memory unit, an integrated controller and circuitry board, and network interfaces.

Critical system controller(s) can control, monitor, and/or operate critical systems. Critical systems may include one or more of (depending on the particular vehicle) monitoring, controlling, operating the ECU, TCU, door settings, window settings, blind spot monitor, monitoring, controlling, operating the safety equipment (e.g., airbag deployment control unit, collision sensor, nearby object sensing system, seat belt control unit, sensors for setting the seat belt, etc.), monitoring and/or controlling certain critical sensors such as the power source controller and energy output sensor, engine temperature, oil pressure sensing, hydraulic pressure sensors, sensors for headlight and other lights (e.g., emergency light, brake light, parking light, fog light, interior or passenger compartment light, and/or tail light state (on or off)), vehicle control system sensors, wireless network sensor (e.g., Wi-Fi and/or Bluetooth sensors, etc.), cellular data sensor, and/or steering/torque sensor, controlling the operation of the engine (e.g., ignition, etc.), head light control unit, power steering, display panel, switch state control unit, power control unit, and/or brake control unit, and/or issuing alerts to a user and/or remote monitoring entity of potential problems with a vehicle operation.

Non-critical system controller(s) can control, monitor, and/or operate non-critical systems. Non-critical systems may include one or more of (depending on the particular vehicle) monitoring, controlling, operating a non-critical system, emissions control, seating system controller and sensor, infotainment/entertainment system, monitoring certain non-critical sensors such as ambient (outdoor) weather readings (e.g., temperature, precipitation, wind speed, and the like), odometer reading sensor, trip mileage reading sensor, road condition sensors (e.g., wet, icy, etc.), radar transmitter/receiver output, brake wear sensor, oxygen sensor, ambient lighting sensor, vision system sensor, ranging sensor, parking sensor, heating, venting, and air conditioning (HVAC) system and sensor, water sensor, air-fuel ratio meter, hall effect sensor, microphone, radio frequency (RF) sensor, and/or infrared (IR) sensor.

It is an aspect of the present disclosure that one or more of the non-critical components and/or systems provided herein may become critical components and/or systems, and/or vice versa, depending on a context associated with the vehicle.

Optionally, the systems and methods of this disclosure can be implemented in conjunction with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein can be used to implement the various aspects of this disclosure. Exemplary hardware that can be used for the disclosed embodiments, configurations and aspects includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein.

In yet another embodiment, the disclosed methods may be readily implemented in conjunction with software using object or object-oriented software development environments that provide portable source code that can be used on a variety of computer or workstation platforms. Alternatively, the disclosed system may be implemented partially or fully in hardware using standard logic circuits or VLSI design. Whether software or hardware is used to implement the systems in accordance with this disclosure is dependent on the speed and/or efficiency requirements of the system, the particular function, and the particular software or hardware systems or microprocessor or microcomputer systems being utilized.

In yet another embodiment, the disclosed methods may be partially implemented in software that can be stored on a storage medium, executed on programmed general-purpose computer with the cooperation of a controller and memory, a special purpose computer, a microprocessor, or the like. In these instances, the systems and methods of this disclosure can be implemented as program embedded on personal computer such as an applet, JAVA® or COI script, as a resource residing on a server or computer workstation, as a routine embedded in a dedicated measurement system, system component, or the like. The system can also be implemented by physically incorporating the system and/or method into a software and/or hardware system.

Although the present disclosure describes components and functions implemented in the aspects, embodiments, and/or configurations with reference to particular standards and protocols, the aspects, embodiments, and/or configurations are not limited to such standards and protocols. Other similar standards and protocols not mentioned herein are in existence and are considered to be included in the present disclosure. Moreover, the standards and protocols mentioned herein and other similar standards and protocols not mentioned herein are periodically superseded by faster or more effective equivalents having essentially the same functions. Such replacement standards and protocols having the same functions are considered equivalents included in the present disclosure.

The present disclosure, in various aspects, embodiments, and/or configurations, includes components, methods, processes, systems and/or apparatus substantially as depicted and described herein, including various aspects, embodiments, configurations embodiments, subcombinations, and/or subsets thereof. Those of skill in the art will understand how to make and use the disclosed aspects, embodiments, and/or configurations after understanding the present disclosure. The present disclosure, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving ease and\or reducing cost of implementation.

The foregoing discussion has been presented for purposes of illustration and description. The foregoing is not intended to limit the disclosure to the form or forms disclosed herein. In the foregoing Detailed Description for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

This application is also related to PCT Patent Application Nos. PCT/US14/34092, filed on Apr. 15, 2014, entitled, "Building Profiles Associated with Vehicle Users"; PCT/US14/34099, filed on Apr. 15, 2014, entitled "Access and Portability of User Profiles Stored as Templates"; PCT/US14/34087, filed on Apr. 15, 2014, entitled "User Interface and Virtual Personality Presentation Based on User Profile"; PCT/US14/34088, filed on Apr. 15, 2014, entitled "Creating Targeted Advertising Profiles Based on User Behavior"; PCT/US14/34232, filed on Apr. 15, 2014, entitled "Behavior Modification via Altered Map Routes Based on User Profile Information"; PCT/US14/34098, filed on Apr. 15, 2014, entitled "Vehicle Location-Based Home Automation Triggers"; PCT/US14/34108, filed on Apr. 15, 2014, entitled "Vehicle Initiated Communications with Third Parties via Virtual Personalities"; PCT/US14/34101, filed on Apr. 15, 2014, entitled "Vehicle Intruder Alert Detection and Indication"; PCT/US14/34103, filed on Apr. 15, 2014, entitled "Driver Facts Behavior Information Storage System"; PCT/US14/34114, filed on Apr. 15, 2014, entitled "Synchronization Between Vehicle and User Device Calendar"; PCT/US14/34125, filed on Apr. 15, 2014, entitled "User Gesture Control of Vehicle Features"; PCT/US14/34254, filed on Apr. 15, 2014, entitled "Central Network for the Automated Control of Vehicular Traffic"; and PCT/US14/34194, filed on Apr. 15, 2014, entitled "Vehicle-Based Multimode Discovery". The entire disclosures of the applications listed above are hereby incorporated by reference, in their entirety, for all that they teach and for all purposes.

Examples of the processors as described herein may include, but are not limited to, at least one of Qualcomm® Snapdragon® 800 and 801, Qualcomm® Snapdragon® 610 and 615 with 4G LTE Integration and 64-bit computing, Apple® A7 processor with 64-bit architecture, Apple® M7 motion coprocessors, Samsung® Exynos® series, the Intel® Core™ family of processors, the Intel® Xeon® family of processors, the Intel® Atom™ family of processors, the Intel Itanium® family of processors, Intel® Core® i5-4670K and i7-4770K 22 nm Haswell, Intel® Core® i5-3570K 22 nm Ivy Bridge, the AMD® FX™ family of processors, AMD® FX-4300, FX-6300, and FX-8350 32 nm Vishera, AMD® Kaveri processors, Texas Instruments® Jacinto C6000™ automotive infotainment processors, Texas Instruments® OMAP™ automotive-grade mobile processors, ARM® Cortex™-M processors, ARM® Cortex-A and ARM926EJ-S™ processors, other industry-equivalent processors, and may perform computational functions using any known or future-developed standard, instruction set, libraries, and/or architecture.

I claim:

1. A vehicle comprising:
    a cabin;
    a plurality of sensors positioned at different locations in the cabin and configured to capture images of a gesture in a predetermined three-dimensional (3D) space in the cabin;
    a gesture database that stores gesture characteristics and maps gestures to vehicle functions;
    a processing device;
    a storage device storing instructions that, when executed by the processing device, cause the vehicle to perform operations comprising:
        receiving images from the plurality of sensors;
        constructing combined image data based on the images from the plurality of sensors;
        generating depth data of a portion of a user in the cabin;
        identifying a gesture initiation based at least in part on the depth data;
        determining a target vehicle subsystem based on the gesture initiation;
        determining a first gesture based at least in part on the depth data;
        identifying, using the gesture database, a control command associated with the first gesture;
        generating a control signal based on the identified control command; and
        transmitting the control signal to the target vehicle subsystem, wherein the target vehicle subsystem performs a vehicle function associated with the control command.

2. The vehicle of claim 1, wherein the plurality of sensors include at least one of optical sensors, infrared sensors, motions sensors, still image cameras, or video cameras.

3. The vehicle of claim 1, wherein determining the first gesture comprises:
    determining a configuration of a hand of the user;
    determining a vector of movement of the hand; and
    comparing the configuration and the vector with the gesture characteristics in the gesture database.

4. The vehicle of claim 1, wherein the predetermined 3D space includes an area between a front driver seat and a front passenger seat over a console area.

5. The vehicle of claim 1, wherein the operations further comprises:
   determining an origin of the first gesture based on the combined image data.

6. The vehicle of claim 1, wherein the operations further comprises:
   determining an input device with which the first gesture is intended to interact.

7. The vehicle of claim 1, wherein the operations further comprises:
   generating a notification that confirms receipt of the first gesture.

8. The vehicle of claim 7, wherein the notification is an audible message indicating the control command associated with the first gesture.

9. The vehicle of claim 1, wherein the gesture database include standardized gestures.

10. The vehicle system of claim 1, wherein the combined image data includes at least one of a stereo image or a three-dimensional image.

11. The vehicle of claim 1, wherein the vehicle subsystem includes a vehicle infotainment system.

12. The vehicle of claim 11, wherein the vehicle function associated with the control command includes at least one of an infotainment system power on and off, a volume adjustment, or a radio station scan.

13. The vehicle of claim 1, wherein the vehicle subsystem includes a vehicle climate control system.

14. The vehicle of claim 13, wherein the vehicle function associated with the control command includes at least one of a climate control power on and off, a temperature control, or a fan speed control.

15. The vehicle of claim 1, wherein the vehicle subsystem includes a vehicle lighting control system.

16. The vehicle of claim 15, wherein the vehicle function associated with the control command includes at least one of a room light power on and off, a room light bright adjustment, a room light color adjustment, or an exterior light power on and off.

17. The vehicle of claim 1, wherein the vehicle subsystem includes a vehicle operation system.

18. The vehicle of claim 1, wherein the images from the plurality of sensors include sensor data generated by the plurality of sensors, and wherein constructing the combined image data includes constructing combined sensor data based on the sensor data from the plurality of sensors.

19. A method for controlling a vehicle, comprising:
   receiving images from a plurality of sensors positioned at different locations in a cabin, wherein the plurality of sensors are configured to capture images of a gesture in a predetermined three-dimensional (3D) space in the cabin;
   constructing combined image data based on the images from the plurality of sensors;
   generating depth data of a portion of a user in the cabin;
   identifying a gesture initiation based at least in part on the depth data;
   determining a target vehicle subsystem based on the gesture initiation;
   determining a first gesture based at least in part on the depth data;
   identifying, using a gesture database, a control command associated with the first gesture, wherein the gesture database stores gesture characteristics and maps the first gesture and other gestures to vehicle functions;
   generating a control signal based on the identified control command; and
   transmitting the control signal to the target vehicle subsystem, wherein the target vehicle subsystem performs a vehicle function associated with the control command.

20. The method of claim 19, wherein the predetermined 3D space includes an area between a front driver seat and a front passenger seat over a console area.

21. The method of claim 19, wherein receiving the images from the plurality of sensors includes receiving sensor data from the plurality of sensors, and
   wherein constructing combined image data includes constructing combined sensor data based on the sensor data from the plurality of sensors.

\* \* \* \* \*